US010765698B2

(12) United States Patent
Vournakis et al.

(10) Patent No.: US 10,765,698 B2
(45) Date of Patent: Sep. 8, 2020

(54) TREATMENT OF DISEASE WITH POLY-N-ACETYLGLUCOSAMINE NANOFIBERS

(71) Applicant: Marine Polymer Technologies, Inc., Burlington, MA (US)

(72) Inventors: John N. Vournakis, Charleston, SC (US); Sergio Finkielsztein, Newton, MA (US)

(73) Assignee: Marine Polymer Technologies, Inc., Burlington, MA (US)

( * ) Notice: Subject to any disclaimer, the term of this patent is extended or adjusted under 35 U.S.C. 154(b) by 0 days.

(21) Appl. No.: 15/457,576

(22) Filed: Mar. 13, 2017

(65) Prior Publication Data

US 2017/0304354 A1 Oct. 26, 2017

Related U.S. Application Data

(63) Continuation of application No. 14/111,703, filed as application No. PCT/US2012/033782 on Apr. 16, 2012, now abandoned.

(60) Provisional application No. 61/476,237, filed on Apr. 15, 2011.

(51) Int. Cl.
| | |
|---|---|
| *A61K 31/726* | (2006.01) |
| *A61K 9/14* | (2006.01) |
| *A61K 9/00* | (2006.01) |
| *A61K 47/18* | (2017.01) |
| *A61K 9/02* | (2006.01) |
| *A61K 9/06* | (2006.01) |
| *A61K 9/08* | (2006.01) |
| *A61K 9/10* | (2006.01) |
| *A61F 13/00* | (2006.01) |
| *A61P 17/02* | (2006.01) |
| *A61P 17/06* | (2006.01) |
| *A61K 38/00* | (2006.01) |

(52) U.S. Cl.
CPC ...... *A61K 31/726* (2013.01); *A61F 13/00017* (2013.01); *A61K 9/0014* (2013.01); *A61K 9/0024* (2013.01); *A61K 9/0092* (2013.01); *A61K 9/02* (2013.01); *A61K 9/06* (2013.01); *A61K 9/08* (2013.01); *A61K 9/10* (2013.01); *A61K 9/14* (2013.01); *A61K 47/18* (2013.01); *A61P 17/02* (2018.01); *A61P 17/06* (2018.01); *A61K 38/00* (2013.01)

(58) Field of Classification Search
CPC . A61F 13/00017; A61K 31/726; A61K 38/00; A61K 9/0014; A61K 9/02; A61K 9/06; A61K 9/08; A61K 9/10; A61K 9/14; A61L 15/28; A61L 15/44; A61L 26/0066; A61L 27/54
See application file for complete search history.

(56) References Cited

U.S. PATENT DOCUMENTS

| | | |
|---|---|---|
| 3,988,411 A | 10/1976 | Capozza |
| 3,989,535 A | 11/1976 | Capozza |
| 4,068,757 A | 1/1978 | Casey |
| 4,195,175 A | 3/1980 | Peniston et al. |
| 4,378,017 A | 3/1983 | Kosugi et al. |
| 4,394,373 A | 7/1983 | Malette et al. |
| 4,532,134 A | 7/1985 | Malette et al. |
| 4,575,519 A | 3/1986 | Kifune et al. |
| 4,605,623 A | 8/1986 | Malette et al. |
| 4,699,135 A | 10/1987 | Motosugi et al. |
| 4,749,620 A | 6/1988 | Rha et al. |
| 4,803,168 A | 2/1989 | Jarvis, Jr. |
| 4,895,724 A | 1/1990 | Cardinal et al. |
| 4,942,129 A | 7/1990 | Goosen et al. |
| 5,008,116 A | 4/1991 | Cahn |
| 5,057,540 A | 10/1991 | Kensil et al. |
| 5,071,977 A | 12/1991 | Cassels et al. |
| 5,093,319 A | 3/1992 | Higham et al. |
| 5,116,747 A | 5/1992 | Moo-Young et al. |
| 5,219,749 A | 6/1993 | Bouriotis et al. |
| 5,229,123 A | 7/1993 | Masubuchi et al. |
| 5,252,468 A | 10/1993 | Fujishima et al. |
| 5,447,505 A | 9/1995 | Valentine et al. |
| 5,457,141 A | 10/1995 | Matsuda et al. |
| 5,510,102 A | 4/1996 | Cochrum |
| 5,529,914 A | 6/1996 | Hubbell et al. |
| 5,541,186 A | 7/1996 | Breu et al. |
| 5,550,110 A | 8/1996 | Cody et al. |
| 5,571,821 A | 11/1996 | Chan et al. |
| 5,573,934 A | 11/1996 | Hubbell et al. |
| 5,622,834 A | 4/1997 | Vournakis et al. |
| 5,623,064 A | 4/1997 | Vournakis et al. |
| 5,624,679 A | 4/1997 | Vournakis et al. |
| 5,635,493 A | 6/1997 | Vournakis et al. |

(Continued)

FOREIGN PATENT DOCUMENTS

| | | |
|---|---|---|
| CA | 2072395 | 1/1993 |
| DE | 19821598 | 11/1999 |

(Continued)

OTHER PUBLICATIONS

Neurath (Nature Reviews, 2017, vol. 14, pp. 269-278).*

(Continued)

*Primary Examiner* — Mark V Stevens
(74) *Attorney, Agent, or Firm* — Jones Day

(57) ABSTRACT

This application relates to compositions comprising shortened fibers of poly-N-acetylglucosamine and/or a derivative thereof ("sNAG nanofibers") and the use of such compositions in the treatment of disease.

37 Claims, 31 Drawing Sheets

Figure 1A:
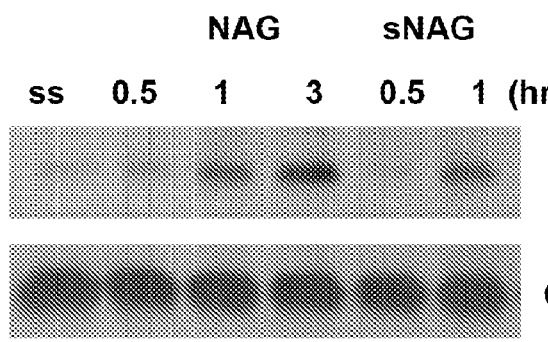

Specification includes a Sequence Listing.

(56) References Cited

U.S. PATENT DOCUMENTS

| | | | |
|---|---|---|---|
| 5,641,752 A | 6/1997 | Cody et al. | |
| 5,658,943 A | 8/1997 | Berryman et al. | |
| 5,686,115 A | 11/1997 | Vournakis et al. | |
| 5,731,298 A | 3/1998 | Reinmullet et al. | |
| 5,804,594 A | 9/1998 | Murad et al. | |
| 5,811,416 A | 9/1998 | Chwalisz et al. | |
| 5,846,952 A | 12/1998 | Vournakis et al. | |
| 5,858,350 A | 1/1999 | Vournakis et al. | |
| 5,871,985 A | 2/1999 | Aebischer et al. | |
| 5,916,907 A | 6/1999 | Bird | |
| 6,046,179 A * | 4/2000 | Murch | A61K 9/0031 514/62 |
| 6,063,911 A | 5/2000 | Vournakis et al. | |
| 6,080,866 A | 6/2000 | Spurr | |
| 6,162,241 A | 12/2000 | Coury et al. | |
| 6,599,720 B2 | 7/2003 | Vournakis et al. | |
| 6,610,668 B2 | 8/2003 | Vournakis et al. | |
| 6,630,459 B2 | 10/2003 | Vournakis et al. | |
| 6,649,599 B2 | 11/2003 | Vournakis et al. | |
| 6,686,342 B2 | 2/2004 | Vournakis et al. | |
| 6,743,783 B1 | 6/2004 | Vournakis et al. | |
| 6,864,245 B2 | 3/2005 | Vournakis et al. | |
| 7,037,983 B2 | 5/2006 | Huang et al. | |
| 7,041,657 B2 | 5/2006 | Vournakis et al. | |
| 7,115,588 B2 | 10/2006 | Vournakis et al. | |
| 7,140,882 B2 | 11/2006 | Ito | |
| 7,157,079 B2 | 1/2007 | Nielsen et al. | |
| 7,285,266 B2 | 10/2007 | Vournakis et al. | |
| 7,307,157 B2 | 12/2007 | Yoshii et al. | |
| 7,371,403 B2 | 5/2008 | McCarthy et al. | |
| 7,691,832 B2 | 4/2010 | Haty | |
| 7,704,522 B2 | 4/2010 | Morgan | |
| 7,931,637 B2 | 4/2011 | Vournakis et al. | |
| 8,152,750 B2 | 4/2012 | Vournakis et al. | |
| 8,232,242 B2 | 7/2012 | Kjaer et al. | |
| 8,232,248 B2 | 7/2012 | Kjaer et al. | |
| 8,481,512 B2 | 7/2013 | Vournakis et al. | |
| 8,802,083 B2 | 8/2014 | Vournakis et al. | |
| 8,802,621 B2 | 8/2014 | Kjaer et al. | |
| 8,835,408 B2 | 9/2014 | Vournakis et al. | |
| 8,858,964 B2 | 10/2014 | Vournakis et al. | |
| 8,859,528 B2 | 10/2014 | Vournakis et al. | |
| 8,871,247 B2 | 10/2014 | Finkielsztein et al. | |
| 8,992,453 B2 | 3/2015 | Vournakis et al. | |
| 9,139,663 B2 | 9/2015 | Finkielsztein et al. | |
| 9,139,664 B2 | 9/2015 | Finkielsztein et al. | |
| 9,198,928 B2 | 12/2015 | Vournakis et al. | |
| 9,279,010 B2 | 3/2016 | Kjaer et al. | |
| 9,320,653 B2 | 4/2016 | Vournakis et al. | |
| 9,642,871 B2 | 5/2017 | Vournakis et al. | |
| 10,206,938 B2 | 2/2019 | Vournakis et al. | |
| 10,383,971 B2 | 8/2019 | Finkielsztein et al. | |
| 2001/0055807 A1 | 5/2001 | Vournakis et al. | |
| 2002/0019367 A1 | 2/2002 | Vournakis et al. | |
| 2002/0091101 A1 | 7/2002 | Vournakis et al. | |
| 2002/0106792 A1 | 8/2002 | Vournakis et al. | |
| 2003/0078234 A1 | 4/2003 | Vournakis et al. | |
| 2003/0104020 A1 | 6/2003 | Davison et al. | |
| 2003/0144347 A1 * | 7/2003 | Ryback | A61K 31/18 514/459 |
| 2003/0212040 A1 | 11/2003 | Vournakis et al. | |
| 2004/0087015 A1 | 5/2004 | Vournakis et al. | |
| 2004/0091493 A1 | 5/2004 | Perrier et al. | |
| 2004/0220140 A1 * | 11/2004 | Vournakis | A01N 1/02 514/54 |
| 2004/0237970 A1 | 12/2004 | Vournakis et al. | |
| 2004/0243043 A1 | 12/2004 | McCarthy et al. | |
| 2004/0254244 A1 * | 12/2004 | Kono | A61K 31/192 514/559 |
| 2005/0004072 A1 | 1/2005 | Vournakis et al. | |
| 2005/0075597 A1 | 4/2005 | Vournakis et al. | |
| 2005/0113773 A1 | 5/2005 | Yoshii et al. | |
| 2006/0051432 A1 | 3/2006 | Morgan et al. | |
| 2006/0105049 A1 | 5/2006 | Fernandes et al. | |
| 2006/0172000 A1 | 8/2006 | Cullen et al. | |
| 2007/0021703 A1 | 1/2007 | McCarthy | |
| 2007/0036846 A1 | 2/2007 | Tsang | |
| 2007/0072826 A1 | 3/2007 | Vournakis et al. | |
| 2007/0085059 A1 | 4/2007 | Mora-Gutierrez et al. | |
| 2007/0093416 A1 | 4/2007 | Igarashi et al. | |
| 2007/0105815 A1 | 5/2007 | Vournakis et al. | |
| 2007/0237812 A1 | 10/2007 | Patel et al. | |
| 2008/0026064 A1 | 1/2008 | Vournakis et al. | |
| 2008/0207561 A1 | 8/2008 | Utecht et al. | |
| 2008/0299147 A1 | 12/2008 | Dillon et al. | |
| 2009/0117175 A1 * | 5/2009 | Finkielsztein | A61L 26/0066 424/445 |
| 2009/0130186 A1 | 5/2009 | McCarthy et al. | |
| 2009/0247737 A1 | 10/2009 | Wiley et al. | |
| 2009/0247738 A1 | 10/2009 | Vournakis et al. | |
| 2009/0318383 A1 | 12/2009 | Vournakis et al. | |
| 2010/0016230 A1 | 1/2010 | Kjaer et al. | |
| 2010/0016231 A1 | 1/2010 | Kjaer et al. | |
| 2010/0016232 A1 | 1/2010 | Kjaer et al. | |
| 2010/0021514 A1 | 1/2010 | Fugmann | |
| 2010/0040694 A1 | 2/2010 | Nah et al. | |
| 2010/0086613 A1 | 4/2010 | Wu et al. | |
| 2010/0105139 A1 | 4/2010 | Spanjaard et al. | |
| 2010/0150960 A1 | 6/2010 | Schlom et al. | |
| 2010/0323986 A1 | 12/2010 | Vournakis et al. | |
| 2011/0251139 A1 | 10/2011 | Kjaer et al. | |
| 2012/0220958 A1 | 8/2012 | Vournakis et al. | |
| 2012/0309678 A1 | 12/2012 | Kjaer et al. | |
| 2012/0309686 A1 | 12/2012 | Kjaer et al. | |
| 2013/0028980 A1 | 1/2013 | Vournakis et al. | |
| 2013/0129789 A1 | 5/2013 | Vournakis et al. | |
| 2013/0287853 A1 | 10/2013 | Vournakis et al. | |
| 2013/0288999 A1 | 10/2013 | Vournakis et al. | |
| 2013/0337037 A1 | 12/2013 | Finkielsztein et al. | |
| 2014/0051849 A1 | 2/2014 | Finkielsztein et al. | |
| 2014/0127310 A1 | 5/2014 | Vournakis et al. | |
| 2014/0135258 A1 | 5/2014 | Kjaer et al. | |
| 2014/0350449 A1 | 11/2014 | Vournakis et al. | |
| 2014/0363673 A1 | 12/2014 | Minami et al. | |
| 2015/0024014 A1 | 1/2015 | Finkielsztein et al. | |
| 2015/0118281 A1 | 4/2015 | Vournakis et al. | |
| 2015/0140045 A1 | 5/2015 | Vournakis et al. | |
| 2016/0030465 A1 | 2/2016 | Finkielsztein et al. | |
| 2016/0193379 A1 | 7/2016 | Finkielsztein et al. | |
| 2016/0235774 A1 | 8/2016 | Vournakis et al. | |
| 2017/0128382 A1 | 5/2017 | Vournakis et al. | |
| 2018/0099003 A1 | 4/2018 | Vournakis et al. | |
| 2018/0360868 A1 | 12/2018 | Finkielsztein et al. | |
| 2019/0060348 A1 | 2/2019 | Finkielsztein et al. | |
| 2019/0247410 A1 | 8/2019 | Vournakis et al. | |

FOREIGN PATENT DOCUMENTS

| | | |
|---|---|---|
| EP | 0 392 396 | 10/1990 |
| EP | 0 426 368 | 5/1991 |
| EP | 0543572 | 5/1993 |
| EP | 0 544 000 | 6/1993 |
| EP | 0731812 | 9/1996 |
| EP | 1139752 | 10/2001 |
| EP | 1306390 | 5/2003 |
| FR | 2736835 | 1/1997 |
| GB | 2220211 | 1/1990 |
| GB | 1038367 | 8/1996 |
| JP | 55-152705 | 11/1980 |
| JP | 56-131639 | 10/1981 |
| JP | 56-133344 | 10/1981 |
| JP | 58-088424 | 5/1983 |
| JP | 58-220899 | 12/1983 |
| JP | 60-025003 | 2/1985 |
| JP | 60-208302 | 10/1985 |
| JP | 60-215003 | 10/1985 |
| JP | 61-253065 | 11/1986 |
| JP | 62-288602 | 12/1987 |
| JP | 63-503466 | 12/1988 |
| JP | 01-167301 | 7/1989 |
| JP | 02-006501 | 1/1990 |
| JP | 02-225539 | 9/1990 |
| JP | 02-235905 | 9/1990 |
| JP | 02-240101 | 9/1990 |

(56) References Cited

FOREIGN PATENT DOCUMENTS

| | | |
|---|---|---|
| JP | 03-167201 | 7/1991 |
| JP | 03-204812 | 9/1991 |
| JP | 04-041422 | 2/1992 |
| JP | 04-126701 | 4/1992 |
| JP | A-H04-371161 | 12/1992 |
| JP | 05-025289 | 2/1993 |
| JP | 05-032702 | 2/1993 |
| JP | 05-051465 | 3/1993 |
| JP | 05-502267 | 4/1993 |
| JP | 05-235905 | 9/1993 |
| JP | 05-271094 | 10/1993 |
| JP | A-H04-102458 | 4/1995 |
| JP | 9-506126 | 6/1997 |
| JP | 2002-512195 | 4/2002 |
| JP | 2003-128704 | 5/2003 |
| JP | 2003-160602 | 6/2003 |
| JP | 2004-211101 | 7/2004 |
| JP | 2005-509059 | 4/2005 |
| JP | 2005-281239 | 10/2005 |
| JP | 2006-518764 | 8/2006 |
| JP | 2008-019264 | 1/2008 |
| JP | 2010-518917 | 6/2010 |
| NZ | 277662 | 4/1998 |
| WO | WO 1987/07618 | 12/1987 |
| WO | WO 92/03480 | 3/1992 |
| WO | WO 1992/04408 | 3/1992 |
| WO | WO 93/08799 | 5/1993 |
| WO | WO 93/09176 | 5/1993 |
| WO | WO 93/12875 | 7/1993 |
| WO | WO 94/03483 | 2/1994 |
| WO | WO 95/15343 | 6/1995 |
| WO | WO 96/11927 | 4/1996 |
| WO | WO 96/19459 | 6/1996 |
| WO | WO 96/39122 | 12/1996 |
| WO | WO 97/08169 | 3/1997 |
| WO | WO 97/37987 | 10/1997 |
| WO | WO 00/36918 | 6/2000 |
| WO | WO 02/063961 | 8/2002 |
| WO | WO 03/042251 | 5/2003 |
| WO | WO 2004/024196 | 3/2004 |
| WO | WO 04/060172 | 7/2004 |
| WO | WO 04/076637 | 9/2004 |
| WO | WO 05/027993 | 3/2005 |
| WO | WO 05/063311 | 7/2005 |
| WO | WO 2006/066752 | 6/2006 |
| WO | WO 2007/059605 | 5/2007 |
| WO | WO 2007/109812 | 9/2007 |
| WO | WO 2007/109813 | 9/2007 |
| WO | WO-2008048076 A1 * 4/2008 ......... A61K 31/7028 | |
| WO | WO 2008/103345 | 8/2008 |
| WO | WO 2009/095456 | 8/2009 |
| WO | WO 2011/130646 | 10/2011 |
| WO | WO 2011/140638 | 11/2011 |
| WO | WO 2012/061803 | 5/2012 |
| WO | WO 2012/142581 | 10/2012 |
| WO | WO 2014/165302 | 10/2014 |

OTHER PUBLICATIONS

U.S. Appl. No. 09/875,846, filed Jun. 6, 2001, Vournakis et al.
'Activity of human beta-defensin 3 against metallo-beta-lactamase-producing Pseudomonas aeruginosa strains' [online] Kazakos et al., European Society of Clinical Microbiology and Infectious Diseases [retrieved on Sep. 12, 2013]. Retrieved from the Internet <URL: http://www.blackwellpublishing.com/eccmid17/abstract.asp?id=56248>.
Aebischer, P. et al., 1993, "Cell Encapsulation for the Nervous System," in *Fundamentals of Animal Cell Encapsulation and Immobilization*, CRC Press, pp. 197-224.
ASTM Committee F04 on Medical and Surgical Materials and Devices, 2001, "Designation F2103-01: Standard Guide for Characterization and Testing of Chitosan Salts as Starting Materials Intended for Use in Biomedical and Tissue-Engineered Medical Product Applications," ASTM International, pp. 1-8.
Austin, P.R. and Sennett, S., 1986, "Dry Chitosan Salts and Complexes of Aliphatic Carboxylic Acids," in *Chitin in Nature and Technology*, Muzzarelli et al., eds., Plenum Press, New York, pp. 279-286.
Azuma, 2012, "alpha-Chitin Nanofibrils Improve Inflammatory and Fibrosis Responses in Inflammatory Bowel Disease Mice Model," Carbohydrate Polymers 90:197-200.
Azuma, 2012, "Beneficial and Preventive Effect of Chitin Nanofibrils in a Dextran Sulfate Sodium-induced Acute Ulcerative Colitis Model," Carbohydrate Polymers 87:1399-1403.
Battistini, B. et al., 1993, "Growth Regulatory Properties of Endothelins," Peptides, 14:385-399.
Bell, K.M. et al., 1995, "Effect of Endothelin-1 and Sarafotoxin S6c on Blood Flow in a Rat Tumor," J. Cardiovasc. Pharmacol., 26(Suppl. 3):S222-S225.
Berkeley, R.C.W. et al., 1979, "Chitin, Chitosan and their Degradative Enzymes," in *Microbial Polysaccharides and Polysaccharases*, Berkeley et al., eds., Academic Press, pp. 205-216.
Bissett, 2006, "Glucosamine: an Ingredient with Skin and Other Benefits," J. Cosm. Dermatol. 5:309-315.
Blackwell, J. et al., 1967, "Chitin Fibers of the Diatoms Thalassiosira fluviatilis and Cyclotella cryptica," J. Mol. Biol., 28:383-385.
Blackwell, J., 1988, "Physical Methods for the Determination of Chitin Structure and Conformation," Meth. Enz., 161:435-442.
Bodmeier, R. et al., 1989, "A Novel Approach to the Oral Delivery of Micro- or Nanoparticles," Pharm. Res., 6(5):413-417.
Carreno-Gomez, B. & Duncan, R., 1997, "Evaluation of the Biological Properties of Soluble Chitosan and Chitosan Microspheres," Int. J. Pharma., 148:231-240.
Chhabra, 2004, "Antimicrobial and antioxidant properties of chitosan," Thesis Submitted to the Graduate Faculty of the University of Georgia for Master of Science Degree, Athens, Georgia.
Choi, W.-S. et al., 2002, "Preparation of Chitosan Oligomers by Irradiation," Polym. Degrad. Stab., 78:533-538.
Clozel, M. et al., 1994, "Pharmacological Characterization of Bosentan, a New Potent Orally Active Nonpeptide Endothelin Receptor Antagonist," J. Pharmacol. Exp. Ther., 270(1): 228-235.
Dai et al., 2009, "Chitosan acetate bandage as a topical antimicrobial dressing for infected burns," Antimicrobial Agents and Chemotherapy, 53(2):393-400.
Davis, M. and Preston, J.F., 1981, "A Simple Modified Carbodiimide Method for Conjugation of Small Molecular Weight Compounds to Immunoglobulin G with Minimal Protein Crosslinking," Anal. Biochem. 116:402-407.
Diaz-Visurraga et al., 2010, "Lethal effect of chitosan-Ag (I) films on *Staphylococcus aureus* as evaluated by electron microscopy," J Applied Microbiol. 108:633-646.
Ding et al., 2014, "Emerging Chitin and Chitosan Nanofibrous Materials for Biomedical Applications," Nanoscale 6:9477-9493.
Domard, A., 1986, "Circular Dichroism Study on N-acetyl-glucosamine Oligomers," Int. J. Macromol. 8:243-246.
Dong, C. and Rogers, J.A., 1991, "Polymer-coated Liposomes: Stability and Release of ASA from Carboxymethyl Chitin Coated Liposomes," Journal of Controlled Release 17:217-224.
Falk, M. et. al., 1966, "Studies on Chitin (β-(1-4)-linked 2-acetamido-2-deoxy-D-glucan) Fibers of the Diatom Thalassiosira fluviatilis hustedt," Can. J. Chem. 44: 2269-2281.
Fischer et al., 2004, "Comparison of Structural and Hemostatic Properties of the Poly-N-Acetyl Glucosamine Syvek Patch with Products Containing Chitosan," Microsc. Res. Tech. 63:168-174.
Fischer et al., 2005, "Synergistic Platelet Integrin Signaling and Factor XII activation in poly-N-acetyl Glucosamine Fiber-mediated hemostasis," Biomaterials 26:5433-5443.
Fischer et al., 2006, "Hemostatic Properties of Glucosamine-based Materials," Journal of Biomedical Materials Research 80A: 167-174.
Fujimoto et al., 2006, "Antibacterial effects of Chitosan solution® against Legionella Pneumophila, *Escherichia coli*, and *Staphylococcus aureus*," Intl J Food Microbiol. 112:96-101.
Gomez-Garre, D. et al., 1996, "An Orally Active $ET_A/ET_B$ Receptor Antagonist Ameliorates Proteinuria and Glomerular Lesions in Rats with Proliferative Nephritis," Kidney Intl. 50:962-972.

(56) References Cited

OTHER PUBLICATIONS

Goodwin, A.T. et al., 1998, "Role of Endogenous Endothelin in the Regulation of Basal Coronary Tone in the Rat," J. Physiol. 511(2):549-557.

Groboillot, A.F. et al., 1993, "Membrane Formation by Interfacial Cross-linking of Chitosan for Microencapsulation of *Lactococcus lactis*," Biotech. and Bioeng. 42(10):1157-1163.

Halaban, R., 1996, "Growth Factors and Melanomas," Seminars in Oncology 23:673-681.

Hirano, S. et al., 1976, "Selective N-acylation of Chitosan," Carbohydrate Research 47:315-320.

Hirano, S. et al., 1981, "SEM Ultrastructure Studies of N-acyl- and N-benzylidene-chitosan and Chitosan Membranes," J. Biomed. Mat. Res. 15:903-911.

Hirano, S. et al., 1990, "The Regulation of Serum Cholesterol Level by Oral Administration of Chitosan in Rabbits," Proceedings of the International Symposium of Chitin Derivatives in Life Sciences, Oct. 5-7, pp. 115-120.

Hirano, S., 1989, "Production and Application of Chitin and Chitosan in Japan," in *Chitin and Chitosan*, Skjak-Braek, Anthosen, and Sanford, eds. Elsevier Science Publishing Co., pp. 37-43.

Hirsch et al., 2009, "Human beta-defensin-3 promotes wound healing in infected diabetic wounds," J Gene Med. 11(3):220-228.

Hocher, B. et al., 1997, "The Paracrine Endothelial System: Pathophysiology and Implications in Clinical Medicine," Eur. J. Chem. Clin. Biochem. 35:175-189.

Howell, et al., 2007, "Antiviral Activity of Human Beta-defensin 3 against vaccinia virus," J. Allergy and Clini. Immuno. 119(4):1022-25.

Huang, Y.C. et al., 2005, "Pulmonary Inflammation Caused by Chitosan Microparticles," J. Biomed. Mater. Res. Part A 75(2):283-287.

Hwang, C. et al., 1985, "Encapsulation with Chitosan: Transmembrane Diffusion of Proteins in Capsules," in *Chitin in Nature and Technology*, Muzzareli, R. et al., eds., Plenum Press, pp. 389-396.

IBA Industrial, 2007, "IBA Solutions in Cancer Diagnosis, Therapy. Sterilization and Ionization Solutions for Hygiene and Safety. Material Applications," retrieved Feb. 7, 2007 from: http://www.iba-worldwide.com/industrial/applications/material/index.php.

Ishihara, M. et al., 2002, "Photocrosslinkable Chitosan as a Dressing for Wound Occlusion and Accelerator in Healing Process," Biomaterials 23:833-840.

Jiang, Y. et al., 2009, "Expression of mouse beta-defensin-3 in MDCK cells and its anti-influenza-virus activity," Arch Virol. 154(4):639-47.

Johnson, R.S. et al, 1992, "In Vivo Tissue Response to Implanted Chitosan Glutamate," in *Advances in Chitin and Chitosan*, Brine, C.J. et al., eds., Elsevier Publishers, Ltd., pp. 3-8.

Kenny, B. et al., 1997, "Pharmacological Options in the Treatment of Benign Prostatic Hyperplasia," J. Medicinal Chem. 40:1293-1315.

Kikuchi, K. et al., 1996, "Decreased $ET_B$ Receptor Expression in Human Metastatic Melanoma Cells," Biochem. Biophys. Res. Comm. 219:734-739.

Komai, T. et al., 1986, "Biomedical Evaluation of Acylated Chitins as Coating Materials," in *Chitin in Nature and Technology*, Muzzarelli et al., eds., Plenum Press, New York, pp. 497-506.

Kurita, K. and Inoue, S., 1989, "Preparation of Indo-chitins and Graft Copolymerization onto the Derivatives," in *Chitin and Chitosan*, Skjak-Braek et al, Elsevier Science Publishing Co., Inc., pp. 365-372.

Kurita, K. et al., 1990, "Preparations of Soluble Chitin Derivatives and the Modifications to Branched Chitins," Polym. Prep. (Am. Chem. Soc., Div. Polym. Chem.) 31:624-625.

Lindner et al., 2011, "Anti-bacterial effects of poly-N-acetylglucosamine nanofibers in cutaneous wound healing: requirement for Akt1," PLoS ONE 6(4):E18996. DOI: 10.1371/JOURNAL.PONE.0018996.

Liu et al., 2001, "Antibacterial action of chitosan and carboxymethylated chitosan," Journal of Applied Polymer Science 79:1324-1335.

Liu et al., 2004, "Chitosan kills bacteria through cell membrane damage," Intl J Food Microbiol. 95:147-155.

Lundblad, R. et al., 1996, "Granulocyte Colony-Stimulating Factor Improves Survival Rate and Reduces Concentrations of Bacteria, Endotoxin, Tumor Necrosis Factor, and Endothelin-1 in Fulminant Intra-Abdominal Sepsis in Rats," Crit. Care Med. 24:820-826.

Lüscher, T.F. and Wenzel, R.R., 1995, "Endothelin and Endothelin Antagonists: Pharmacology and Clinical Implications," in *Mediators in the Cardiovascular System: Regional Ischemia*, Birkhäuser Verlag, Basel, Switzerland, pp. 237-253.

Mann, M. et al., 2006, "Unsaturated N-Acetyl-D-Glucosaminuronic Acid Glycosides as Inhibitors of Influenza Virus Sialidase," Glycoconj J. 23(1-2):127-33.

Maresch, G. et al., 1989, "Hydroxypropylation of Chitosan," in *Chitin and Chitosan*, Skjak-Braek, Anthosen, and Sanford, eds., Elsevier Science Publishing Co., pp. 389-395.

Markewitz, B.A. et al., 1995, "Endothelin-1 Synthesis, Receptors, and Signal Transduction in Alveolar Epithelium: Evidence for an Autocrine Role," Am. J. Physiol. 268:L192-L200.

Mateo, A.O. and De Artiñano, M.A., 1997, "Highlights on Endothelins: A Review," Pharmacol. Res. 36(5):339-351.

Matsuhashi, S. and Kume, T., 1997, "Enhancement of Antimicrobial Activity of Chitosan by Irradiation," J. Sci. Food Agric. 73:237-241.

Matthew, H.W. et al., 1993, "Complex Coacervate Microcapsules for Mammalian Cell Culture and Artificial Organ Development," BioTechnol. Prog. 9(5):510-519.

McCurdy, J.D., 1992, "FDA and the Use of Chitin and Chitosan Derivatives," in Advances in *Chitin and Chitosan*, Brine, C.J. et al., eds., Elsevier Publishers, Ltd., pp. 659-662.

McLachlan and Craigne, 1966, "Chitin Fibers in Cyclotella cryptica and Growth of C. cryptica and Thalassiosira fluviatilis," Some Contemp. Stud. Mar. Sci., pp. 511-517.

McLachlan, A.G. et al., 1965, "Studies on the Chitin (chitin: poly-N-acetylglucosamine) Fibers of the Diatom *Thalassiosira fluviatilis* hustedt," Can. J. Botany 43 :707-713.

Mezzana, 2008, "Clinical Efficacy of a New Chitin Nanofibrils-based Gel in Wound Healing," Acta Chirurgiae Plasticae 50(3):81-84.

Middleton, J.C. and Tipton, A.J., 1998, "Materials: Synthetic Biodegradable Polymers as Medical Devices," retrieved Feb. 7, 2007 from: http://www.devicelink.com/mpb/archive/98/03/002.html.

Min, B.-M. et al., 2004, "Chitin and Chitosan Nanofibers: Electrospinning of Chitin and Deacetylation of Chitin Nanofibers," Polymer 45:7137-7142.

Minami, S. et al., 1996, "Chitosan-Inducing Hemorrhagic Pneumonia in Dogs," Carb. Polymers. 29:241-246.

Mireles, C. et al., 1992, "Complex Formation of Chitosan and Naturally Occurring Polyanion," in *Advances in Chitin and Chitosan*, Brine, C.J. et al., eds., Elsevier Publishers, Ltd., pp. 506-515.

Moraitis, S. et al., 1997, "Endothelin Expression and Responsiveness in Human Ovarian Carcinoma Cell Lines," Eur. J. Cancer 33:661-668.

Morbidelli, L. et al., 1995, "Proliferation and Migration of Endothelial Cells is Promoted by Endothelins via Activation of $ET_B$ Receptors," Am. J. Physiol. 269:H686-H695.

Morganti & Morganti, 2008, "Chitin Nanofibrils for Advanced Cosmeceuticals," Clinics in Dermatology 26:334-340.

Morganti et al., 2011, "Transforming Nanostructured Chitin from Crustacean Waste into Beneficial Health Products: a Must for our Society," Nanotechnology, Science and Applications 4:123-129.

Nelson, J.B. et al., 1996, "Endothelin-1 Production and Decreased Endothelin B Receptor Expression in Advanced Prostate Cancer," Cancer Res. 56:663-668.

Nishi, N. et al., 1986, "Preparation and Characterization of Phosphorylated Chitin and Chitosan," in *Chitin in Nature and Technology*, Muzzarelli et al., Plenum Press, New York, pp. 297-299.

No et al., 2002, "Antibacterial Activity of Chitosans and Chitosan Oligomers with Different Molecular Weights," Intl J Food Microbiol. 74:65-72.

Noguchi, J. et al., 1969, "Chitosan Epichlorohydrin Anion Exchange Resin with Primary Amines as Absorption Site," Kogyo Kagaku Zasshi 72:796-799.

(56) References Cited

OTHER PUBLICATIONS

Obara, K. et al., 2005, "Acceleration of Wound Healing in Healing-Impaired db/db Mice with a Photocrosslinkable Chitosan Hydrogel Containing Fibroblast Growth Factor-2," Wound Repair Regen. 13(4):390-397.
Ohlstein, E.H. et al., 1996, "Endothelin Receptors: Receptor Classification, Novel Receptor Antagonists, and Potential Therapeutic Targets," Medicinal Res. Rev. 16:365-390.
Oikawa, T. et al., 1994, "Production of Endothelin-1 and Thrombomodulin by Human Pancreatic Cancer Cells," Br. J. Cancer 69:1059-1064.
Parris, R.J. and Webb, D.L., 1997, "The Endothelin System in Cardiovascular Physiology and Pathophysiology," Vascular Med. 2:31-43.
Patel, K.V. and Schrey, M.P., 1995, "Human Breast Cancer Cells Contain a Phosphoramidon-Sensitive Metalloproteinase which Can Process Exogenous Big Endothelin-1 to Endothelin-1: A Proposed Mitogen for Human Breast Fibroblasts," Brit. J. Cancer 71:442-447.
Paul, W. and Sharma, C.P., 2004, "Chitosan and Aiginate Wound Dressings: A Short Review," Trends Biomater. Artif. Organs 18(1):18-23.
Perkins et al., 2010, "Poly-N-acetylglucosamine nanofibers from a marine diatom promote wound healing and defensin expression in an AKT1-dependent manner," Abstracts of Papers American Chemical Society 239:527.
Pietramaggiori et al., 2008, "Effects of poly-N-acetyl glucosamine (pGlcNAc) patch on wound healing in db/db mouse," The Journal of Trauma Injury, Infection, and Critical Care 64(3):803-808.
Polk, A. et al., 1994, "Controlled Release of Albumin from Chitosan-alginate Microcapsules," J. Pharma. Sci. 83(2):178-185.
Rabea et al., 2003, "Chitosan as antimicrobial agent: applications and mode of action," BioMacromolecules, American Chemical Society 4(6):1457-1465.
Reid, K. et al., 1996, "Multiple Roles for Endothelin in Melanocyte Development: Regulation of Progenitor Number and Stimulation of Differentiation," Development 122:3911-3919.
Rosiak, J. et al., 1992, "Radiation Sterilization of Chitosan Sealant for Vascular Prostheses," J. Radioan. and Nucl. Chem. 159(1):87-96.
Roux, S. et al., 1997, "Ro 61/1790, a New Hydrosoluble Endothelin Antagonist: General Pharmacology and Effects on Experimental Cerebral Vasospasm," J. Pharm. Exp. Ther. 283(3):1110-1118.
Sangui Biotech Witten, 2004, "New Wounds Pads Based on Chitosan and Chitosan-Glucan-Complex," SanguiBioTech GmbH, pp. 1-5.
Scherer et al., 2009, "Poly-N-Acetyl glucosamine nanofibers," Annals of Surgery 250(2):322-330.
Schorigin, P. and Hait, E., 1934, "Über die Nitrierung von Chitin," Chem. Ber. 67:1712-1714.
Schweiger, R.G., 1972, "Polysaccharide Sulfates I. Cellulose Sulfate with a High Degree of Substitution," Carbohydrate Res. 21:219-228.
Shichiri, M. et al., 1991, "Endothelin-1 is an Autocrine/Paracrine Growth Factor for Human Cancer Cell Lines," J. Clin. Invest. 87:1867-1871.
Staros, J.V. et al., 1986, "Enhancement by N-hydroxysulfosuccinate of Water Soluble Carbodiimide Mediated Coupling Reactions," Anal. Biochem. 156:220-222.
Suzuki, N. et al., 1989, "Production of Endothelin-1 and Big-Endothelin-1 by Tumor Cells with Epithelial-Like Morphology," J. Biochem. 106:736-741.
Tanaka, Y. et al., 1997, "Effects of Chitin and Chitosan Particles on BALB/c Mice by Oral and Parenteral Administration," Biomaterials 18(8):591-595.
Technical Insights, Inc., 1989, "Barriers to Commercialization," Ch. 4 in *Chitin and Chitosan: Specialty Biopolymers for Foods, Medicine, and Industry*, Technical Insights, Inc., Ft. Lee, NJ.
Thanoo, B.C. et al., 1992, "Cross-linked Chitosan Microspheres: Preparation and Evaluation as a Matrix for the Controlled Release of Pharmaceuticals," J. Pharm. Pharmacol. 44:283-286.
Tokura, S. et al., 1983, "Studies on Chitin VIII. Some properties of Water Soluble Chitin Derivatives," Polym. J. 15:485-489.
TSI Mason Laboratories, 1995, "Efficacy Study of a Test Article in Preventing Peritoneal Adhesion in Sprague-Dawley Rats," Final Report Amendment Supplement to the Final Report, Study No. 2-T35.
US Pharmacopeia XXII, 1990, pp. 1415-1497.
US Pharmacopeia XXII, 1990, pp. 1497-1500.
US Pharmacopeia XXII, 1991, Suppl. 5, pp. 2702-2703.
US Pharmacopeia XXVIII, 2004, "The Biocompatibility of Materials Used in Drug Containers," General Information, pp. 2529-2536.
Vahouny, G.V., 1983, "Comparative Effects of Chitosan and Cholestyramine on Lymphatic Absorption of Lipids in the Rat," Am. J. Clin. Nutr. 38(2):278-284.
Vandevord, P.J. et al., 2003, "The Long-term Immune Response to Chitosan Scaffolds," Society for Biomaterials 29$^{th}$ Annual Meeting Transactions, p. 165.
Vournakis, J.N. et al., 2008, "Poly-N-acetyl glucosamine nanofibers regulate endothelial cell movement and angiogenesis: dependency on integrin activation of Ets1," J Vasc Res. 45(3):222-32.
Vournakis, J.N. et al., 1994, "Isolation & Characterization of Pure Poly-N-acetylglucosamine: Controlled Enzymatic Deacetylation and Formulation for Tissue Engineering Applications," J Cell Biochem. Suppl. O(18C): 283 (Abstract PZ 313), Keystone Symposium on Tissue Engineering.
Waknine, Y., 2005, "International Approvals: Taxus Express(2), Nexstent, Chitoskin," retrieved on Feb. 12, 2007 from: http://www.medscape.com/viewartiele/503573.
Webb, M.L. and Meek, T.D., 1997, "Inhibitors of Endothelin," Medicinal Res. Rev. 17:17-67.
Weiner, M.L., 1992, "An Overview of the Regulatory Status and of the Safety of Chitin and Chitosan as Food and Pharmarceutical Ingredients," in *Advances in Chitin and Chitosan*, Brine, C.J. et al., eds., Elsevier Publishers, Ltd., pp. 663-670.
Wollina, U. et al., 2003, "Functional Textiles in Prevention of Chronic Wounds, Wound Healing and Tissue Engineering," *Textiles and the Skin. Curr. Probl. Dermatol.*, Elsner et al., eds., Basel, Karger, 31:82-97.
Yamamoto, A. et al., 2003, "Microfabrication of a Biodegradable Polymer by Ion Beam Irradiation for a New Co-Culture System of Cells," Eur. Cells Mater. 6(Suppl. 1): 77.
Yamashita, J. et al., 1991, "A Large Amount of Endothelin-1 is Present in Human Breast Cancer Tissues," Res. Comm. Chem. Pathol. Pharmacol. 74:363-369.
Yanagisawa, M. et al., 1988, "A Novel Potent Vasoconstrictor Peptide Produced by Vascular Endothelial Cells," Nature 332:411-415.
Yang, F. et al., 2002, "Performance Modification of Chitosan Membranes Induced by Gamma Irradiation," J. Biomater. Appl. 16:215-226.
Yasin, B. et al., 2004, "Theta defensins protect cells from infection by herpes simplex virus by inhibiting viral adhesion and entry," J Virol. 78(10):5147-56.
Yeo, Y. et al., 2006, "Peritoneal Application of Chitosan and UV-cross-linkable Chitosan," J. Biomed. Mater. Res. 78A:668-675.
Yohn, J.J. et al., 1994, "Human Melanoma Cells Express Functional Endothelin-1 Receptors," Biochem. Biophys. Res. Comm. 201:449-457.
Yoksan, R. et al., 2004, "γ-Ray Irradiation Practical Conditions for Low Molecular Weight Chitosan Material Production," Mat. Res. Soc. Symp. Proc. 792:R5.10.1-R5.10.6.
Yoshioka, T. et al., 1990, "Encapsulation of Mammalian Cell with Chitosan-CMC Capsule," Biotechnol. Bioeng. 35:66-72.
Zheng et al., 2003, "Study on antimicrobial activity of chitosan with different molecular weights," Carbohydrate Polymers 54:527-530.
Ziche, M. et al., 1995, "$ET_B$ Receptors Promote Proliferation and Migration of Endothelial Cells," J. Cardiovasc. Pharmacol. 26 (Suppl. 3):S284-S286.
Zielinski, B.A. and Aebischer, P., 1994, "Chitosan as a Matrix for Mammalian Cell Encapsulation," Biomaterials 15(13):1049-1056.

(56) References Cited

OTHER PUBLICATIONS

International Preliminary Report of Patentability of International Application No. PCT/US2011/032709 (published as WO 2011/130646), dated Oct. 26, 2012.
International Search Report of International Application No. PCT/US11/032709 (published as WO 2011/130646), dated Aug. 15, 2011.
Written Opinion of International Application No. PCT/US11/032709 (published as WO 2011/130646), dated Aug. 15, 2011.
International Search Report of International Application No. PCT/US2008/002172 (published as WO 2008/103345), dated Aug. 7, 2009.
Written Opinion of International Application No. PCT/US2008/002172 (published as WO 2008/103345), dated Aug. 7, 2009.
International Search Report of International Application No. PCT/US12/033782 (published as WO 2012/142581), dated Aug. 20, 2012.
Written Opinion of International Application No. PCT/US12/033782 (published as WO 2012/142581), dated Aug. 20, 2012.
International Search Report for International Application No. PCT/US2014/025623 (published as WO 2014/165302), dated Jul. 10, 2014.
Written Opinion for International Application No. PCT/US2014/025623 (published as WO 2014/165302), dated Jul. 10, 2014.
Office Action dated Apr. 2, 2013 issued in U.S. Appl. No. 13/641,015 (now U.S. Pat. No. 8,858,964) U.S. Appl. No. 13/641,015.
Office Action dated Dec. 6, 2010 issued in U.S. Appl. No. 12/033,670 (now U.S. Pat. No. 8,871,247).
Office Action dated Aug. 30, 2011 issued in U.S. Appl. No. 12/033,670 (now U.S. Pat. No. 8,871,247).
Office Action dated Sep. 17, 2014 issued in U.S. Appl. No. 13/956,012 670 (now U.S. Pat. No. 9,139,663).
Office Action dated Sep. 18, 2014 issued in U.S. Appl. No. 13/956,035 (now U.S. Pat. No. 9,139,664).
Supplementary European Search Report for European Application No. 11769676.5-1453, dated Sep. 25, 2013.
Supplementary European Search Report for European Application No. 12771138, dated Oct. 1, 2014.
Harmenberg et al., 2010, "Prevention of Ulcerative Lesions by Episodic Treatment of Recurrent Herpes Labialis: A Literature Review," Acta. Derm. Venereol 90:122-130.
Hazrati et al., 2006, "Human α- and β-Defensins Block Multiple Steps in Herpes Simplex Virus Infection," J. Immunol. 177:8658-66.
Office Action dated May 31, 2016 issued in Chinese Application No. 201280029555.8.
Pan et al., 2006, Medical Immunology, Zhejiang University Press p. 163 (cited in Office Action dated May 31, 2016 issued in Chinese Application No. 201280029555.8).
Spruance et al., 1992, "The Natural History of Recurrent Oral-Facial Herpes Simplex Virus Infection," Seminars in Dermatology 11(3):200-206.
Kazakos et al., 2007, European Society of Clinical Microbiology and Infectious Diseases 'Activity of human beta-defensin 3 against metallo-beta-lactamase-producing Pseudomonas aeruginosa strains' [online] [retrieved on Sep. 12, 2013]. Retrieved from the Internet <URL: http://www.blackwellpublishing.com/eccmid17/abstract.asp?id=56248>.
Nagatani et al., 2008, "739 Oral Chitin Administration Ameliorates Chronic Colitis in TCRα Knockout Mice by Upregulating IFN-Production and Downregulating Chitinase 3-Like-1 Expression in Mucosal Tissues," Gastroenterology 134: A-106.
Andrews et al. 1999, "The role of zinc in wound healing." Adv Wound Care. 12(3):137-8.
Barouch et al., 2003, "Viral escape from dominant Simian Immunodeficiency Virus epitope-specific cytotoxic T lymphocytes in DNA-vaccinated rhesus monkeys," J Virol. 77(13):7367-75.
Barbosa et al., 2010, "Evaluation of the effect of the degree of acetylation on the inflammatory response to 3D porous chitosan scaffolds," J Biomed Mater Res A. 93(1):20-28.

Beauman, J.G. et al., 2005, "Genital herpes: a review," Am Fam Physician, 72(8):1527-34.
Chen et al., 2004, "Transfection of mEpo gene to intestinal epithelium in vivo mediated by oral delivery of chitosan-DNA nanoparticles", World J. Gastroenterol. 10(1): 112-116.
Cho et al., Biomaterials, 1999, "Water-soluble chitin as a wound healing accelerator", Biomaterials, 20(22): 2139-2145.
Cole et al., 1997, "Characterization of a sustained-release delivery system for combined cytokine/peptide vaccination using a poly-N-acetyl glucosamine-based polymer mix", Clin. Cancer Res., 3(6): 867-873.
Fine et al., 1991, "Revised Clinical and Laboratory Criteria for Subtypes of Inherited Epidermolysis Bullosa: A Consensus Report by the Subcommittee on Diagnosis and Classification of the National Epidermolysis Bullosa Registry," Journal of the American Academy of Dermatology, 24(1):119-35.
Forrest and Pack, 2002, "On the kinetics of polyplex endocytic trafficking: implications for gene delivery vector design," Mol Ther. 6(1):57-66.
Hama et al., 2006, "Quantitative comparison of intracellular trafficking and nuclear transcription between adenoviral and lipoplex systems," Mol Ther. 13(4):786-94.
Harrington et al., 2002, "Cells as vehicles for cancer gene therapy: the missing link between targeted vectors and systemic delivery?" Hum Gene Ther. 13(11):1263-80.
Harrington et al., 2002, "Recombinant vaccinia virus-induced T-cell immunity: quantitation of the response to the virus vector and the foreign epitope," J Virol. 76(7):3329-37.
International Search Report for International App. No. PCT/US2014/025623 (published as WO 2014/165302), dated Jul. 10, 2014.
Jean et al., 2009, "Chitosan-plasmid nanoparticle formulations for IM and SC delivery of recombinant GFG-2 and PDGF-BB or generation of antibodies," Gene Therapy, 16: 1097-1110.
Kim et al., 2000, "Modulation of Antigen-Specific Humoral Responses in Rhesus Macaques by Using Cytokine cDNAs as DNA Vaccine Adjuvants," J Virol, 74(7): 3427-3429.
Klokkevold et al., 1999, "The Effect of Chitosan (poly-N-Acetyl Glucosamine) on Lingual Hemostasis in Heparanized Rabbits," J Oral Maxillofac Surg 57: 49-52.
Leff, 1998, "DNA motif gooses immune antigenicity response in mice CpG outstrips classic vaccine adjuvant 5-Fold; clinical trial to begin shortly," Bioworld Today 9(214).
Lindner et al., 2015, "pGlcNAc Nanofiber Treatment of Cutaneous Wounds Stimulate Increased Tensile Strength and Reduced Scarring via Activation of Akt1," PLoS One 10(5): e0127876. DOI: 10.1371/journal.pone.0127876.
Mansouri et al., 2004, "Chitosan-DNA nanoparticles as non-viral vectors in gene therapy: strategies to improve transfection efficacy," Eur J Pharm Biopharm. 57(1):1-8.
Mao et al., 2001, "Chitosan-DNA nanoparticles as gene carriers: synthesis, characterization and transfection efficiency," J Control Release 70(3):399-421.
Muzyczka, 1992, "Use of adeno-associated virus as a general transduction vector for mammalian cells," Curr. Top Microbiol Immunol. 158:97-129.
Premenko-Lanier et al., 2003, "DNA vaccination of infants in the presence of maternal antibody: a measles model in the primate," Virology 307(1):67-75.
Ramírez et al., 2000, "Attenuated modified vaccinia virus Ankara can be used as an immunizing agent under conditions of preexisting immunity to the vector," J Virol. 74(16):7651-5.
Ramírez et al., 2000, "Biology of attenuated modified vaccinia virus Ankara recombinant vector in mice: virus fate and activation of B- and T-cell immune responses in comparison with the Western Reserve strain and advantages as a vaccine," J Virol. 74(2):923-33.
Salem et al., 2004, "Paracrine release of IL-12 stimulates IFN-gamma production and dramatically enhances the antigen-specific T cell response after vaccination with a novel peptide-based cancer vaccine," J Immunol. 172(9):5159-67.
Salem et al., 2006, "Novel nonviral delivery approaches for interleukin-12 protein and gene systems: curbing toxicity and enhancing adjuvant activity," J Interferon Cytokine Res. 26(9):593-608.

(56) References Cited

OTHER PUBLICATIONS

Salem et al., 2008, "$T_H1/T_H2$ Cytokine Fingerprinting for Probing Diseases: From the Bench to the Clinic," J. Med. Sci. 1(2):61-67.
Salem et al., 2010, "Poly-N-acetyl glucosamine gel matrix as a non-viral delivery vector for DNA-based vaccination," Anticancer Res. 30(10):3889-3894.
Schlee et al., 2008, "Probiotic Lactobacilli and VSL#3 induce enterocyte beta-defensin 2", Clinical and Experimental Immunology, 151(3): 528-535.
Shirley et al., 2012, "Ehlers-Danlos Syndrome in Orthopaedics," Sports Health, 4(5):394-403.
Steen et al., 2001, "Improvement in Skin Thickening in Systemic Sclerosis Associated with Improved Survival," Arthritis & Rheumatism, 44(12):2828-35.
Stoute et al., 1997, "A preliminary evaluation of a recombinant circumsporozoite protein vaccine against Plasmodium falciparum malaria. RTS,S Malaria Vaccine Evaluation Group." N Engl J Med. 336(2):86-91.
Tewary et al., 2005, "A heterologous prime-boost vaccination regimen using ORFF DNA and recombinant ORFF protein confers protective immunity against experimental visceral leishmaniasis," J Infect Dis. 191(12):2130-7.
Thatte et al., 2004, "Poly-N-Acetyl Glucosamine-Mediated Red Blood Cell Interactions," J. Trauma 57:S7-S12.
Varmus, 1988, "Retroviruses," Science 240(4858):1427-35.
Vasconcelos et al., 2013, "Macrophage polarization following chitosan implantation. Biomaterials," 34(38):9952-9959.
Veleirinho et al., 2014, "Foreign body reaction associated with PET and PET/chitosan electrospun nanofibrous abdominal meshes," PLoS One. 9(4):e95293.
Vournakis et al., 2004, "Isolation, purification, and characterization of poly-N-acetyl glucosamine use as a hemostatic agent," J Trauma 57(1 Suppl):S2-6.
Wang, 2007, "Transport and Delivery System for Medicament", China Medical Science Press, p. 95.
Wasungu and Hoekstra, 2006, "Cationic lipids, lipoplexes and intracellular delivery of genes," J Control Release 116(2):255-64.
Wasungu et al., 2006, "Lipoplexes formed from sugar-based gemini surfactants undergo a lamellar-to-micellar phase transition at acidic pH. Evidence for a non-inverted membrane-destabilizing hexagonal phase of lipoplexes," Biochim Biophys Acta. 1758(10):1677-84.
Wu et al., 2005, "High efficient fabrication micropowder by combination of gamma radiation and jet pulverization," Carbohydrate Polymers, 60:61-65.
Nakamura, et al., J. Oral. Biosci, 2007, "Nicotine increases expression of beta defensin", vol. 49, Suppl., p. 135, P-105 (English translation provided).
Azuma et al., 2014, "Preparation and Biomedical Applications of Chitin and Chitosan Nanofibers," J Biomed Nanotechnol, 10:2891-2920.
Azuma et al., 2015, "Anticancer and Anti-Inflammatory Properties of Chitin and Chitosan Oligosaccharides," J Funct Biomater, 6:33-49.
Azuma et al., 2015, "Anti-Inflammatory Effects of Orally Administered Glucosamine Oligomer in an Experimental Model of Inflammatory Disease," Carbohydrate Polymers, 115:448-456.
Yousef et al., 2012, "Chitosan Oligosaccharide as Potential Therapy of Inflammatory Bowel Disease: Therapeutic Efficacy and Possible Mechanisms of Action," Pharmacological Research, 66:66-79.
Fischer et al., 2008, "Non-classical processes in surface hemostasis: mechanisms for the poly-N-acetyl glucosamine-induced alteration of red blood cell morphology and surface prothrombogenicity", Biomed Mater., 3(1):015009.
Fulco et al., 2015, "Poly-N-glucosamine nanofibers for negative-pressure wound therapies", Wound Repair Regen., 23(2):197-202.
Gorapalli et al., 2012, "Evaluation of a novel poly N-acetyl glucosamine (pGlcNAc) hydrogel for treatment of the degenerating intervertebral disc", Life Sci., 91(25-26):1328-1335.
Jayakumar et al., 2011, "Biomaterials based on chitin and chitosan in wound dressing applications", Biotechnol. Adv., 29:322-337.
Kang et al., 2005, "Arterial embolization using poly-N-acetyl glucosamine gel in a rat kidney model", Anat Rec A Discov Mol Cell Evol Biol, 284(1):454-459.
Muise-Helmericks et al., 2011, "Poly-N-acetyl glucosamine fibers activate bone regeneration in a rabbit femur injury model", J Trauma, 71(2 Suppl 1):S194-6.
Muzzarelli et al., 1999, "Biochemistry, histology and clinical uses of chitins and chitosans in wound healing", Chitin and Chitinases:251-264.
Nuss et al., 2017, "Poly-N-Acetyl Glucosamine (sNAG) Enhances Early Rotator Cuff Tendon Healing in a Rat Model", Ann Biom Eng., 45(12):2826-2836.
Salem et al., 2010, "Using poly-N-acetyl glucosamine gel matrix to deliver IL-12 with anti-schistosomasis vaccination", J. Infect Dev Countries, 4(5):318-328.
Salem et al., 2014, "Immunomodulatory effects of IL-12 released from poly-N-acetyl glucosamine gel matrix during schistosomiasis infection", Cytotechnology, 66(4):667-675.
Blatt et al. 2005 "Stimulation of skin's energy metabolism provides multiple benefits for mature human skin.", BioFactors, 25(1-4):179-85.
Extended European Search Report and European Search Opinion dated May 27, 2019 for European Patent Application No. 18207147.2 (10 pages).
Jansen et al., 2009, "Beta-defensin-2 protein is a serum biomarker for disease activity in psoriasis and reaches biologically relevant concentrations in lesional skin", PLoS One, 4(3):e4725 (9 pages).

\* cited by examiner

+ 3% DSS+control

+ 3% DSS + shortened poly-N-Acetyl Glucosamine fibers

+ 3% DSS + shortened poly-N-Acetyl Glucosamine fibers

+ 3% DSS+control

```
SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Primer Akt1 F

<400> SEQUENCE: 1
gaggccgtca gccacagtct g                                              21

<210> SEQ ID NO 2
<211> LENGTH: 21
<212> TYPE: DNA
<213> ORGANISM: Artificial Sequence
<220> FEATURE:
<223> OTHER INFORMATION: Primer Akt1 R

<400> SEQUENCE: 2
atgagcgacg tggctattgt g                                              21

<210> SEQ ID NO 3
<211> LENGTH: 19
<212> TYPE: DNA
<213> ORGANISM: Artificial Sequence
<220> FEATURE:
<223> OTHER INFORMATION: Primer Beta-Defensin3 F

<400> SEQUENCE: 3
gtggggtgaa gcctagcag                                                 19

<210> SEQ ID NO 4
<211> LENGTH: 20
<212> TYPE: DNA
<213> ORGANISM: Artificial Sequence
<220> FEATURE:
<223> OTHER INFORMATION: Primer Beta-Defensin3 R

<400> SEQUENCE: 4
tttctttctt cggcagcatt                                                20

<210> SEQ ID NO 5
<211> LENGTH: 20
<212> TYPE: DNA
<213> ORGANISM: Artificial Sequence
<220> FEATURE:
```

```
<223> OTHER INFORMATION: Primer Alpha-Defensin1 F

<400> SEQUENCE: 5
cactccaggc aagagctgat                                               20

<210> SEQ ID NO 6
<211> LENGTH: 20
<212> TYPE: DNA
<213> ORGANISM: Artificial Sequence
<220> FEATURE:
<223> OTHER INFORMATION: Primer Alpha-Defensin1 R

<400> SEQUENCE: 6
tccctggtag atgcaggttc                                               20

<210> SEQ ID NO 7
<211> LENGTH: 20
<212> TYPE: DNA
<213> ORGANISM: Artificial Sequence
<220> FEATURE:
<223> OTHER INFORMATION: Primer S26 F

<400> SEQUENCE: 7
ctccggtccg tgcctccaag                                               20

<210> SEQ ID NO 8
<211> LENGTH: 21
<212> TYPE: DNA
<213> ORGANISM: Artificial Sequence
<220> FEATURE:
<223> OTHER INFORMATION: Primer S26 R

<400> SEQUENCE: 8
cagagaatag cctgtcttca g                                             21
```

US 10,765,698 B2

TREATMENT OF DISEASE WITH POLY-N-ACETYLGLUCOSAMINE NANOFIBERS

This application is a continuation of U.S. Nonprovisional application Ser. No. 14/111,703, filed Dec. 21, 2013, which is a national stage of International Patent Application No. PCT/US2012/033782, filed Apr. 16, 2012, which claims benefit of U.S. Provisional Patent Application No. 61/476,237, filed Apr. 15, 2011, which is incorporated by reference herein in its entirety.

1. INTRODUCTION

This application relates to compositions comprising shortened fibers of poly-N-acetylglucosamine and/or a derivative thereof ("sNAG nanofibers") and the use of such compositions in the treatment of disease.

2. BACKGROUND

Defensins are small (3-4 kDa), cysteine-rich cationic peptides found in mammals, insects, and plants that are classified into different families ($\alpha$, $\beta$, and $\theta$) based on their pattern of disulfide bonding. These small peptides are important effectors of innate immunity and consequently play an important role in the body's battle against various diseases.

A number of diseases are incurable at this time or have suboptimal treatments available, due to only partial effectiveness of such treatments or side effects associated with such treatments. Such diseases include, among others, cancer, some viral diseases, some fungal diseases, inflammatory bowel diseases (e.g., Crohn's disease), and dermatological diseases such as psoriasis and dermatitis. There remains a need for an effective treatment for these diseases that can be used alone, or in combination with a standard therapy, that is safe and effective.

3. SUMMARY

In one aspect, described herein are methods for preventing and/or treating infections and/or diseases for which an increase in defensin production and/or secretion may be beneficial, comprising administering to the subject a composition comprising shortened fibers of poly-$\beta$-1→4-N-acetylglucosamine and/or derivatives thereof (referred to herein as "sNAG nanofibers"). Examples of such infections and/or diseases include, but are not limited to, solid tumor cancers, skin cancer, viral infections, yeast infections, fungal infections, inflammatory bowel disease, Crohn's disease, dermatitis and psoriasis.

In one embodiment, described herein is a method for treating a viral infection in a subject, comprising administering a composition comprising sNAG nanofibers to a subject having (e.g., diagnosed with) a viral infection (e.g., an HSV infection). In another embodiment, described herein is a method for preventing a viral disease in a human subject, comprising administering a composition comprising sNAG nanofibers to a subject at risk of developing a viral disease (e.g., a symptom of an HSV infection such as a cold sore or a lesion). In a specific embodiment, the sNAG nanofiber composition is topically administered to the subject (e.g., to the skin or mucous membrane). In specific embodiments, the subject is a human.

In another embodiment, described herein is a method for treating a solid tumor in a subject, comprising administering a composition comprising sNAG nanofibers to a subject diagnosed with a solid tumor. In a specific embodiment, all or part of the solid tumor has been removed from the subject (e.g., surgically removed), and the sNAG nanofibers are administered to the site of the solid tumor before, during, and/or after the removal of all or part of the solid tumor. In specific embodiments, the subject is a human.

In another embodiment, described herein is a method for treating a skin cancer in a subject, comprising topically administering a composition comprising sNAG nanofibers to a human subject diagnosed with a skin cancer. In a specific embodiment, all or part of the skin cancer has been removed from the subject (e.g., surgically removed), and the sNAG nanofibers are administered to the site of the skin cancer before, during, and/or after the removal of all or part of the skin cancer. In specific embodiments, the subject is a human.

In another embodiment, provided herein is a method for treating inflammatory bowel disease in a subject, comprising administering a composition comprising sNAG nanofibers to a subject with inflammatory bowel disease (e.g., diagnosed with inflammatory bowel disease). In a specific embodiment, described herein is a method for treating Crohn's disease in a subject, comprising administering a composition comprising sNAG nanofibers to a subject with Crohn's disease (e.g., a subject diagnosed with Crohn's disease). In a specific embodiment, the sNAG nanofiber composition is topically administered to the subject (e.g., rectally via a suppository). In specific embodiments, the subject is a human.

The sNAG nanofibers contemplated in the methods described herein may be of varying lengths, widths and molecular weights as described in Section 5.1, infra. In certain embodiments, the majority (and in certain embodiments, at least or more than 60%, 70%, 80%, 90%, 95% or 99%) of the sNAG nanofibers, or 100% of the sNAG nanofibers, are between about 1 to 15 m in length. In some embodiments, the majority (and in certain embodiments, at least or more than 60%, 70%, 80%, 90%, 95% or 99%) of the sNAG nanofibers, or 100% of the sNAG nanofibers, are between about 2 to 10 m, 4 to 7 μm, 4 to 10 μm, or 5 to 10 μm in length. The sNAG nanofibers of the described length can be obtained, for example, as described below in Section 5.2, infra.

In certain embodiments, the sNAG nanofibers were produced by irradiation, e.g., gamma irradiation, of poly-N-acetylglucosamine or a derivative thereof. In some embodiments, the sNAG nanofibers are produced by irradiation of the poly-$\beta$-1→4-N-acetylglucosamine in the form of dried fibers (e.g., at 500-2,000 kgy), or irradiation of the poly-$\beta$-1→4-N-acetylglucosamine in the form of wet fibers (e.g., at 100-500 kgy).

In certain embodiments, the sNAG nanofibers are derived from microalgae. In another embodiment, the sNAG nanofibers are not derived from crustaceans. In yet another embodiment, the sNAG nanofibers may be derived from microalgae, crustaceans (e.g., shrimp), fungus or any other source.

In one embodiment, the sNAG nanofibers comprise N-acetylglucosamine monosaccharides and/or glucosamine monosaccharides, wherein more than 60%, 70%, 80%, 90%, 95%, or 99% of the monosaccharides of the sNAG nanofibers are N-acetylglucosamine monosaccharides. In another embodiment, the sNAG nanofibers comprise N-acetylglucosamine monosaccharides and/or glucosamine monosaccharides, wherein more than 70% of the monosaccharides of the sNAG nanofibers are N-acetylglucosamine monosaccharides.

In certain embodiments, the sNAG nanofibers used in the methods described herein are non-reactive in a biocompatibility test or tests. For example, the sNAG nanofibers used in the methods described herein may be non-reactive when tested in an elution test, an intramuscular implantation test, an intracutaneous test, or a systemic test. In some embodiments, the compositions described herein are non-reactive when tested in an elution test, an intramuscular implantation test, an intracutaneous test, or a systemic test. In other embodiments, the sNAG nanofibers used in the methods described herein have Grade 0 or Grade 1 when tested in an elution test, an intramuscular implantation test, an intracutaneous test, or a systemic test. In yet another embodiment, the sNAG nanofibers used in the methods described herein are at most mildly reactive when tested in an elution test, an intramuscular implantation test, an intracutaneous test, or a systemic test. In one embodiment, the sNAG nanofibers or compositions comprising such nanofibers are non-reactive as determined by an intramuscular implantation test. In certain embodiments, the compositions described herein do not cause an allergenic reaction or an irritation, e.g., at the site of application. In other embodiments, the compositions described herein cause at most a mild allergenic reaction or a mild irritation, e.g., at the site of application.

In certain embodiments, the sNAG nanofibers used in the methods described herein increase the metabolic rate of serum-starved human umbilical cord vein endothelial cells in a MTT assay and/or do not rescue apoptosis of serum-starved human umbilical cord vein endothelial cells in a trypan blue exclusion test. In some embodiments, the sNAG nanofibers increase the metabolic rate of serum-starved human umbilical cord vein endothelial cells in a MTT assay and do not rescue apoptosis of serum-starved human umbilical cord vein endothelial cells in a trypan blue exclusion test.

The contemplated modes of administration of the compositions described herein are topical, e.g., topical on the skin; topical at the site of a wound, a surgery, a viral infection, a fungal infection, or a symptom of an infection (e.g., a swelling, a blister, a rash, a lesion); and topical to a body surface such as the skin, mucous membranes (e.g., vagina, anus, throat, eyes, ears), or the surface of other tissues. In certain embodiments, the sNAG nanofibers or compositions comprising such nanofibers are formulated as a dressing, a bandage, a mat, a spray, a liquid, a suspension (e.g., a thick suspension), a membrane, a powder, an ointment, a cream, a paste, a suppository, or a gel. In some embodiments, the sNAG nanofibers or compositions comprising such nanofibers are formulated as a suspension, a cream, a liquid solution, a gel, an ointment, a membrane, a powder, a spray, or a suppository. In one embodiment, the sNAG nanofibers or compositions comprising such nanofibers are formulated as a suspension (e.g., a thick suspension). In particular embodiments, compositions comprising the sNAG nanofibers are not solid or barrier-forming.

In another aspect, described herein are compositions for use in the methods described herein. In a specific embodiment, the compositions comprise sNAG nanofibers. In certain embodiments, the compositions described herein comprise sNAG nanofibers and one or more additional active ingredients useful in preventing and/or treating solid tumor cancers, skin cancer, viral infections, viral diseases, yeast infections, fungal infections, fungal diseases, inflammatory bowel disease, Crohn's disease, dermatitis and psoriasis. In certain embodiments, the compositions described herein do not comprise any additional anti-bacterial agent (e.g., an antibiotic). In a specific embodiment, the compositions described herein comprise the sNAG nanofibers as the only active ingredient and do not comprise any additional active ingredients.

In certain embodiments, the compositions described herein are administered in conjunction with one or more additional therapies. In other embodiments, the compositions described herein are not administered in conjunction with any other therapy.

3.1 Terminology

As used herein, the terms "sNAG nanofiber," "sNAG," "Taliderm," or "Talymed" (formerly known as "Taliderm") are used interchangeably to refer to shortened fibers of poly-N-acetylglucosamine and/or derivatives thereof. In a preferred embodiment, sNAG nanofibers consist entirely of shortened fibers of poly-N-acetylglucosamine and/or derivatives thereof. Taliderm or Talymed are examples of sNAG nanofibers which are membranes consisting entirely of shortened fibers of poly-N-acetylglucosamine and/or derivatives thereof.

As used herein, the term "about" means a range around a given value wherein the resulting value is the same or substantially the same (e.g., within 10%, 5% or 1%) as the expressly recited value. In one embodiment, "about" means within 10% of a given value or range. In another embodiment, the term "about" means within 5% of a given value or range. In another embodiment, the term "about" means within 1% of a given value or range.

As used herein, the terms "disease" and "disorder" are used interchangeably to refer to a condition in a subject. Exemplary diseases/disorders that can be treated or prevented in accordance with the methods described herein include, without limitation, solid tumor cancers, skin cancers, viral diseases, yeast diseases, fungal diseases, inflammatory bowel disease, and Crohn's disease, psoriasis and dermatitis. In the context of viral diseases, yeast diseases, and fungal diseases, the disease is the pathological state resulting from infection by a virus, a yeast, or a fungus, respectively.

As used herein, the term "infection" means the invasion by, multiplication and/or presence of a pathogen (e.g., a virus, yeast, or fungus) in a cell or a subject.

As used herein, the numeric term "log" refers to $\log_{10}$.

As used herein, the term "subject" and "patient" are used interchangeably to refer to an animal (e.g., cow, horse, sheep, pig, chicken, turkey, quail, cat, dog, mouse, rat, rabbit, guinea pig, etc.). In some embodiments, the subject is a mammal such as a non-primate and a primate (e.g., monkey and human). In specific embodiments, the subject is a human.

As used herein, the term "effective amount" in the context of administering a sNAG nanofiber or composition thereof to a subject refers to the amount of a sNAG nanofiber or composition thereof that results in a beneficial or therapeutic effect. In specific embodiments, an "effective amount" of a sNAG nanofiber or composition thereof refers to an amount of a sNAG nanofiber or composition thereof which is sufficient to achieve at least one, two, three, four or more of the following effects: (i) reduction or amelioration of the severity of a disease in the subject or population of subjects or a symptom associated therewith; (ii) reduction of the duration of a disease in the subject or population of subjects or a symptom associated therewith; (iii) prevention of the progression of a disease in the subject or population of subjects or a symptom associated therewith; (iv) regression of a disease in the subject or population of subjects or a symptom associated therewith; (v) prevention of the development or onset of a disease in the subject or population of subjects or a symptom associated therewith; (vi) prevention of the recurrence of a disease in the subject or population of subjects or a symptom associated therewith; (vii) prevention or reduction of the spread of a disease from the subject or population of subjects to another subject or population of subjects; (viii) reduction in organ failure associated with a disease in the subject or population of subjects; (ix) reduction of the incidence of hospitalization of the subject or population of subjects; (x) reduction of the hospitalization length of the subject or population of subjects; (xi) an increase the survival of the subject or population of subjects; (xii) elimination of a disease in the subject or population of subjects; (xiii) enhancement or improvement of the prophylactic or therapeutic effect(s) of another therapy in the subject or population of subjects; (xiv) prevention of the spread of a pathogen from a cell, tissue, organ of the subject to another cell, tissue, organ of the subject; (xv) reduction of the number of symptoms of a disease in the subject or population of subjects; (xvi) the clearance of an infection with a pathogen (e.g., a virus, a fungus, or an yeast); (xvii) the eradication of one or more symptoms associated with an infection; (xviii) the reduction of time required to clear an infection; (xix) the reduction of time required to clear an infection; (xx) the reduction or amelioration of the severity of an infection and/or one or more symptoms associated therewith; (xxi) the prevention of the recurrence of an infection and/or one or more symptoms associated there with; (xxii) the reduction or elimination of a pathogen as measured, e.g., by viral count; (xxiii) the reduction or elimination in the spread of a pathogen from one subject to another subject, or one organ or tissue to another organ or tissue; (xxiv) the prevention of an increase in the pathogen numbers as measured, e.g., by viral count; (xxv) the prevention of the development or onset of an infection or one or more symptoms associated therewith; (xxvi) the reduction in the number of symptoms associated with an infection; (xxvii) the stabilization or reduction of inflammation associated with an infection; (xxviii) the induction of the expression of one or more defensin proteins and/or defensin-like proteins; (xxix) the induction of the expression of one or more Toll-like receptors; (xxx) the induction of the expression of one or more proteins that are beneficial for clearance or reduction of a pathogen infection or one or more symptoms associated therewith; (xxxi) the reduction in organ failure associated with a pathogen infection or a disease associated therewith; (xxxii) the prevention of the onset, development or recurrence of a condition caused by or associated with a pathogen infection; (xxxiii) the reduction in mortality; (xxxiv) the inhibition of the progression of a cancer and/or one or more symptoms associated therewith; (xxxv) a reduction or elimination in the cancer cell population; (xxxvi) a reduction in the growth of a tumor or neoplasm; (xxxvii) a decrease in tumor size (e.g., volume or diameter); (xxxvii) a reduction in the formation of a newly formed tumor; (xxxviii) eradication, removal, or control of primary, regional and/or metastatic cancer; (xxxix) a decrease in the number or size of metastases; (xxxx) an increase in tumor-free survival rate of patients; (xxxxi) an increase in relapse free survival; (xxxxii) an increase in the number of patients in remission; (xxxxiii) the size of a tumor is maintained and does not increase or increases by less than the increase of a tumor after administration of a standard therapy as measured by conventional methods available to one of skill in the art, such as evaluation of PSA concentrations, digital rectal exam, ultrasound (e.g., transrectal ultrasound), bone scan, computed tomography (CT) scan, magnetic resonance imaging (MRI), dynamic contrast-enhanced MRI (DCE-MRI), or a positron emission tomography (PET) scan; (xxxxiv) an increase in the length of remission in patients; (xxxxv) an increase in symptom-free survival of cancer patients; (xxxxvi) stabilization or reduction of a tumor or peritumoral inflammation or edema; (xxxxvii) inhibition or decrease in tumor metabolism or perfusion; and/or (xxxiii) improvement in quality of life as assessed by methods well known in the art, e.g., a questionnaire. In specific embodiments, an "effective amount" of a sNAG nanofiber refers to an amount of a sNAG nanofiber composition specified herein, e.g., in Section 5.6, infra.

As used herein, the term "premature human infant" refers to a human infant born at less than 37 weeks of gestational age.

As used herein, the term "human infant" refers to a newborn to 1 year old human.

As used herein, the term "premature human infant" refers to a newborn to 1 year old year human who was born of less than 37 weeks gestational age (e.g., before 37 weeks, 36 weeks, 35 weeks, 34 weeks, 33 weeks, 32 weeks, 31 weeks, 30 weeks, 29 weeks, 28 weeks, or less than 28 weeks of pregnancy).

As used herein, the term "human toddler" refers to a human that is 1 years to 3 years old.

As used herein, the term "human child" refers to a human that is 1 year to 18 years old.

As used herein, the term "human adult" refers to a human that is 18 years or older.

As used herein, the term "elderly human" refers to a human 65 years or older.

As used herein, the term "low expression," in the context of expression of a gene (e.g., based on the level of protein or peptide produced by the gene) refers to an expression that is less than the "normal" expression of the gene. In a specific embodiment, "low expression" refers to expression of a gene that is less than 99%, less than 95%, less than 90%, less than 85%, less than 75%, less than 70%, less than 65%, less than 60%, less than 55%, less than 50%, less than 45%, less than 40%, less than 35%, less than 30%, less than 25%, or less than 20% of the "normal" expression of the gene. In another specific embodiment, "low expression" refers to expression of a gene that is about 20-fold, about 15-fold, about 10-fold, about 5-fold, about 4-fold, about 3-fold, about 2-fold, or about 1.5 fold less than the "normal" expression of the gene.

As used herein, the term "majority" refers to greater than 50%, including, e.g., 50.5%, 51%, 55%, etc.

As used herein, the terms "therapies" and "therapy" can refer to any protocol(s), method(s), compositions, formulations, and/or agent(s) that can be used in the prevention and/or treatment of an infection with a pathogen or a disease or a symptom thereof, or a disease described herein (such as Crohn's disease, inflammatory bowel disease, psoriasis, dermatitis, and solid tumor). A pathogen may be a virus, a fungus, or an yeast. In certain embodiments, the terms "therapies" and "therapy" refer to drug therapy, adjuvant therapy, radiation, surgery, biological therapy, supportive therapy, and/or other therapies useful in treatment and/or prevention of an infection with a pathogen or a disease, or a symptom thereof, or a disease described herein. In certain embodiments, the term "therapy" refers to a therapy other than a sNAG nanofiber or a pharmaceutical composition thereof. In specific embodiments, an "additional therapy" and "additional therapies" refer to a therapy other than a treatment using a sNAG nanofiber or a pharmaceutical composition thereof. In a specific embodiment, a therapy includes the use of a sNAG nanofiber as an adjuvant therapy.

For example, using a sNAG nanofiber in conjunction with a drug therapy, biological therapy, surgery, and/or supportive therapy.

4. BRIEF DESCRIPTION OF FIGURES

Figure 1B:
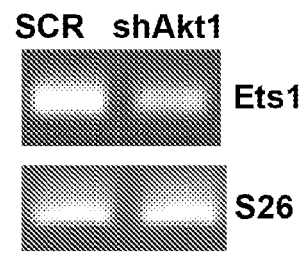
Figure 1C:
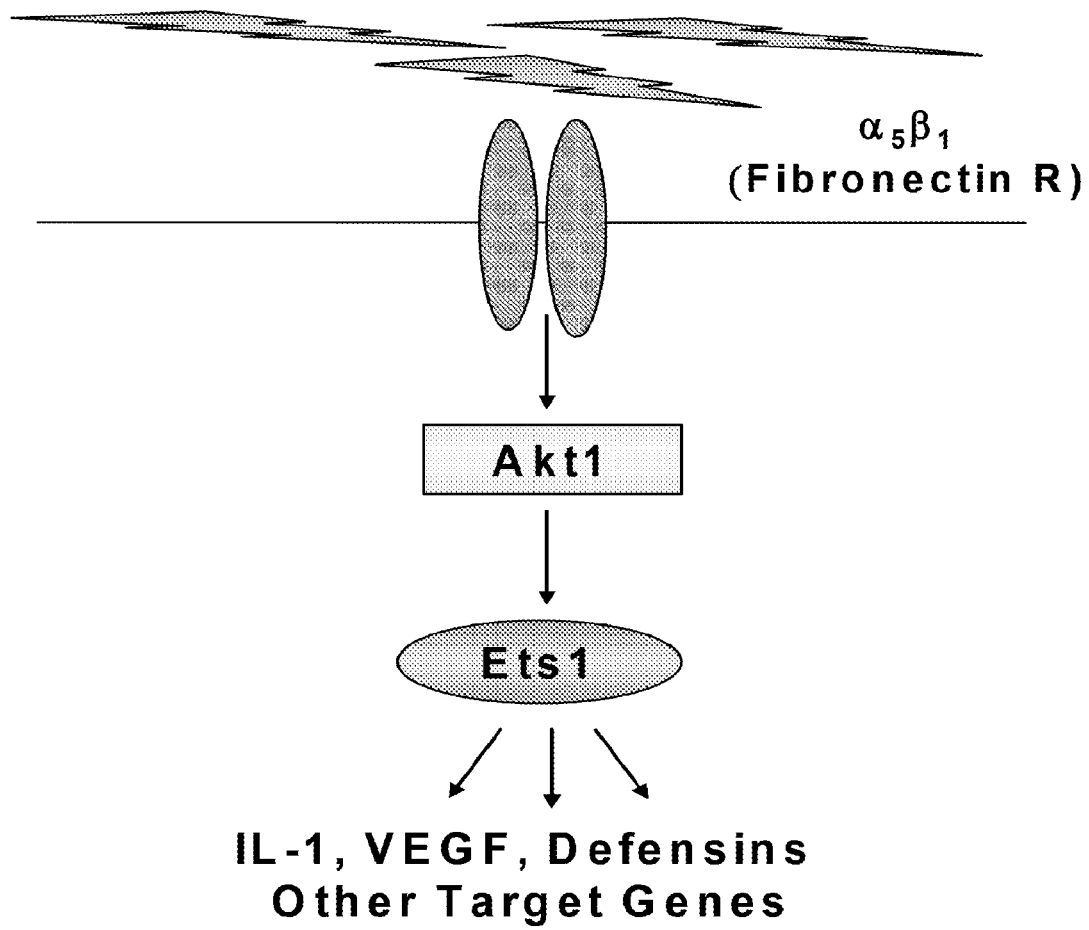

FIG. 1A-1C. Nanofibers stimulate Akt 1 activation, an upstream regulator of Ets1. FIG. 1A. Western blot analysis of phospho-Akt in response to NAG and sNAG stimulation of serum starved EC. FIG. 1B. RT-PCR analysis of EC infected either with scrambled control ("SCR") or Akt1 shRNA lentiviruses and assessed for expression of Ets1 and S26 as a loading control. FIG. 1C. Schematic of a signal transduction pathway transducing a signal from sNAG nanofibers to Akt1, Ets1 and Defensins.

Figure 2A:
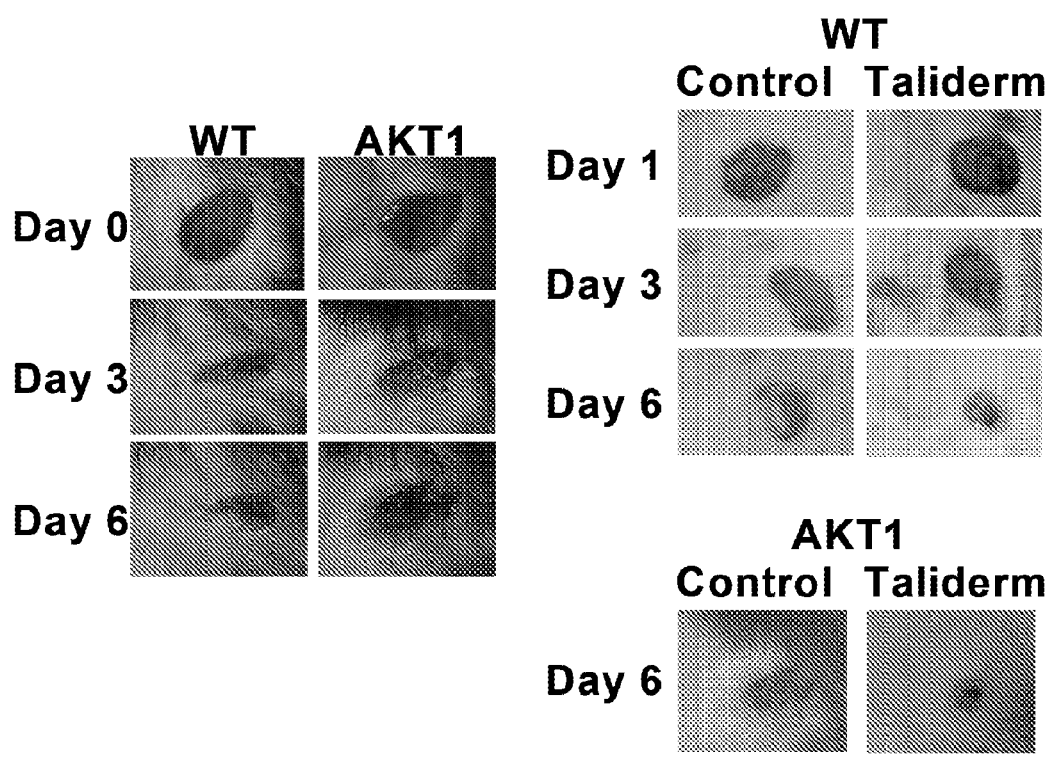
Figure 2B:
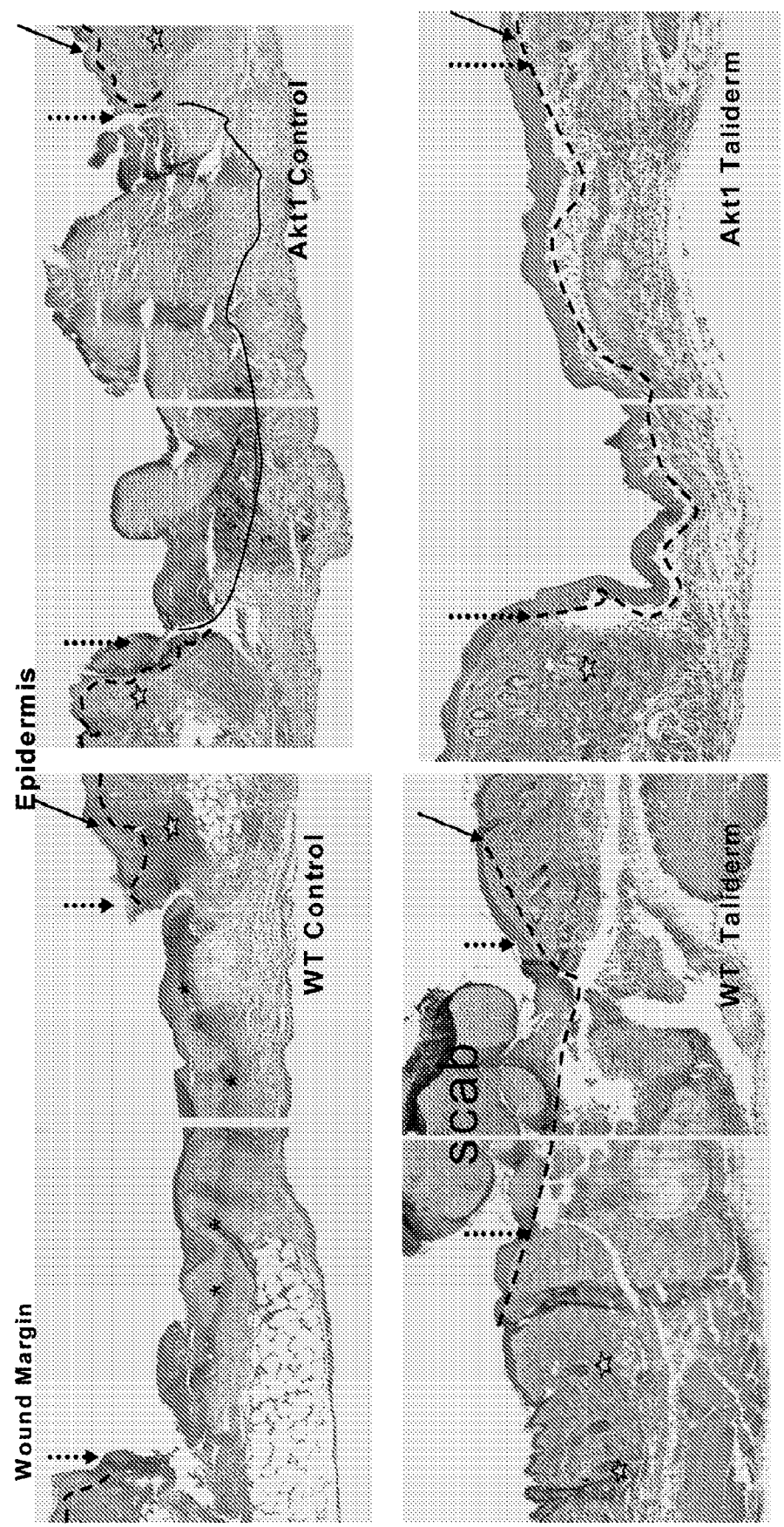

FIG. 2A-2B. Delayed wound healing in Akt1 null animals is partially rescued by Taliderm treatment. FIG. 2A. Representative images of wounded WT and AKT1 null mice with and without treatment of Taliderm. FIG. 2B. H&E staining of representative mouse skin sections from day 3 wounds.

Figure 3A:
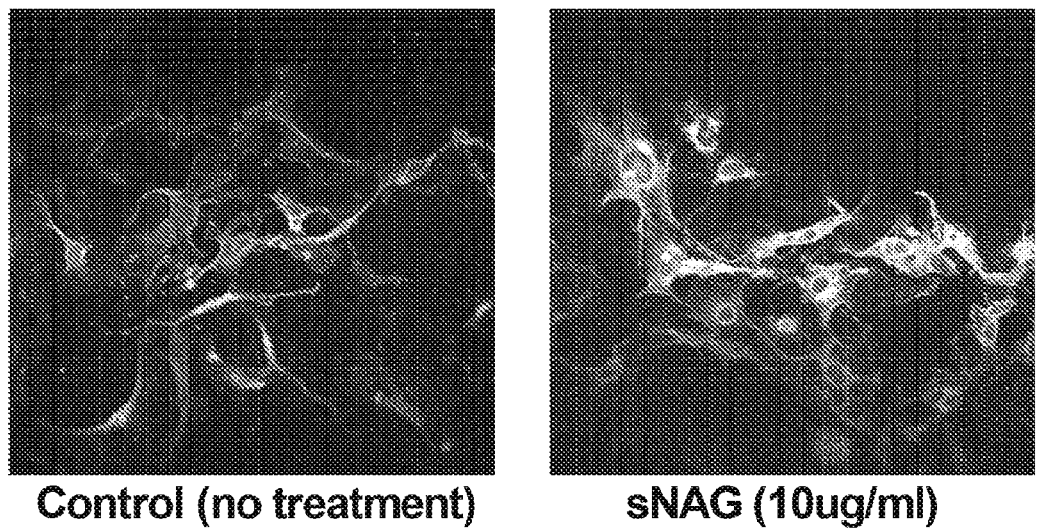
Figure 3B:
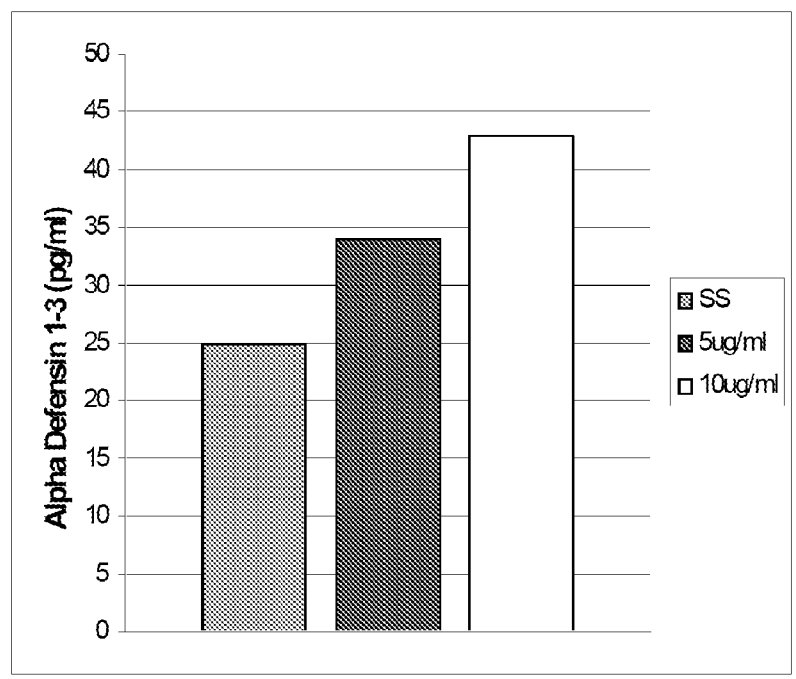

FIG. 3A-3B. sNAG nanofibers stimulate cytokine and defensin expression in primary endothelial cells. FIG. 3A. Immunohistochemisty of EC treated with or without sNAG using an antibody directed against a-defensin. FIG. 3B. ELISA showing that nanofiber treatment of EC results in the secretion of α-defensins 1-3 (serum starved, treated with 5 µg/ml or 10 µg/ml sNAG).

Figure 4A:
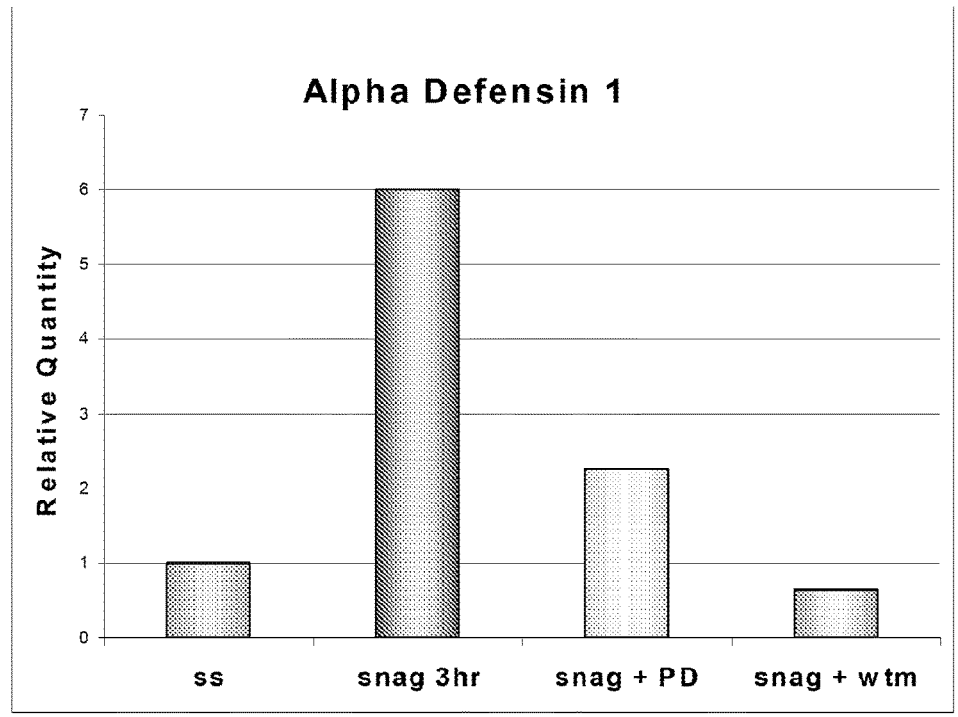
Figure 4B:
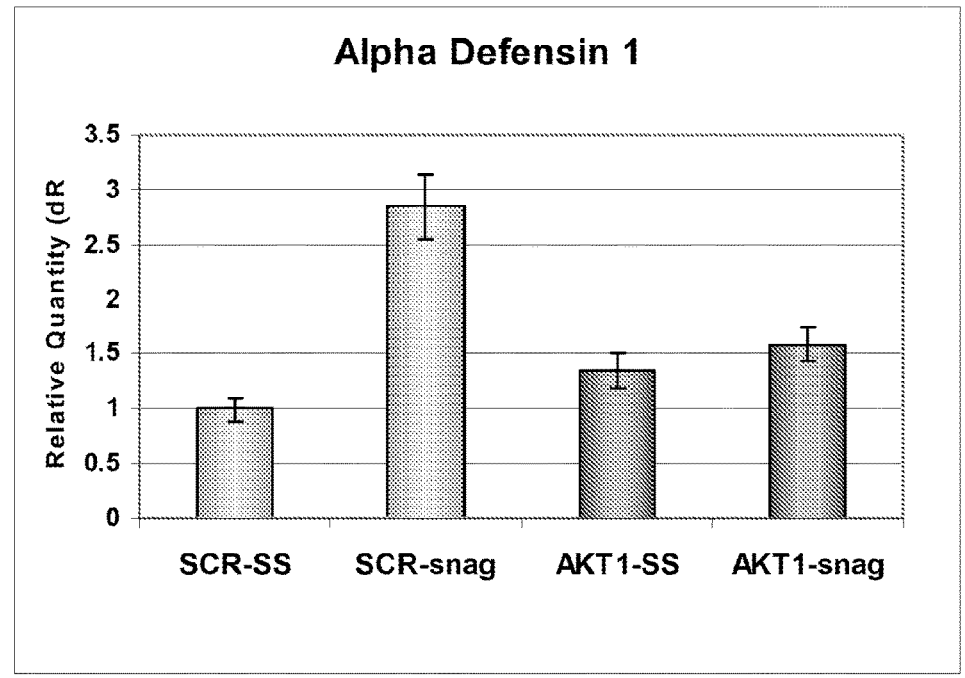

FIG. 4A-4B. sNAG nanofibers stimulate defensin expression in primary endothelial cells in an Akt1 dependent manner. FIG. 4A and FIG. 4B. Quantitative RT-PCR analyses of serum starved EC ("ss") treated with or without sNAG ("snag"), with or without PD98059 (MAPK inhibitor, "PD"), Wortmannin (PI3K inhibitor, "wtm") or infected with a scrambled control ("SCR"), or Akt1 ("AKT1") shRNA lentiviruses and assessed for expression of the genes indicated.

Figure 5A:
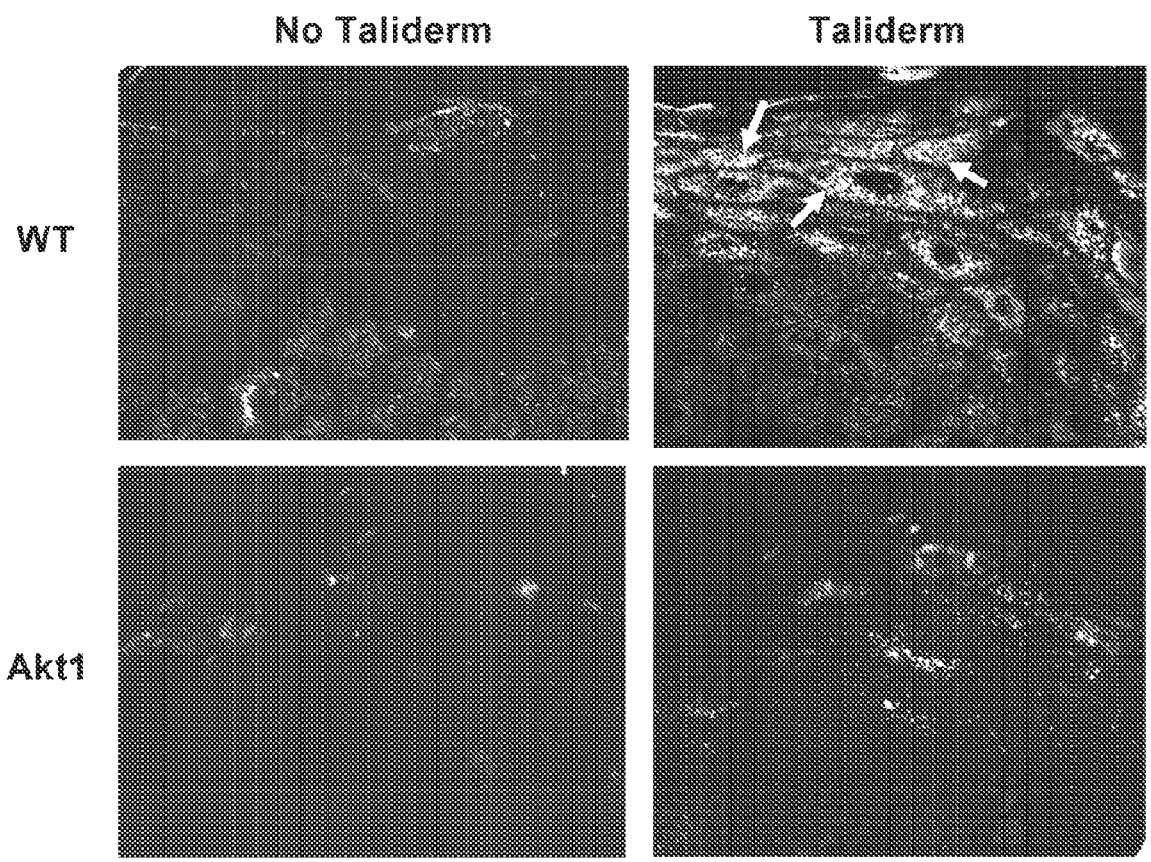
Figure 5B:
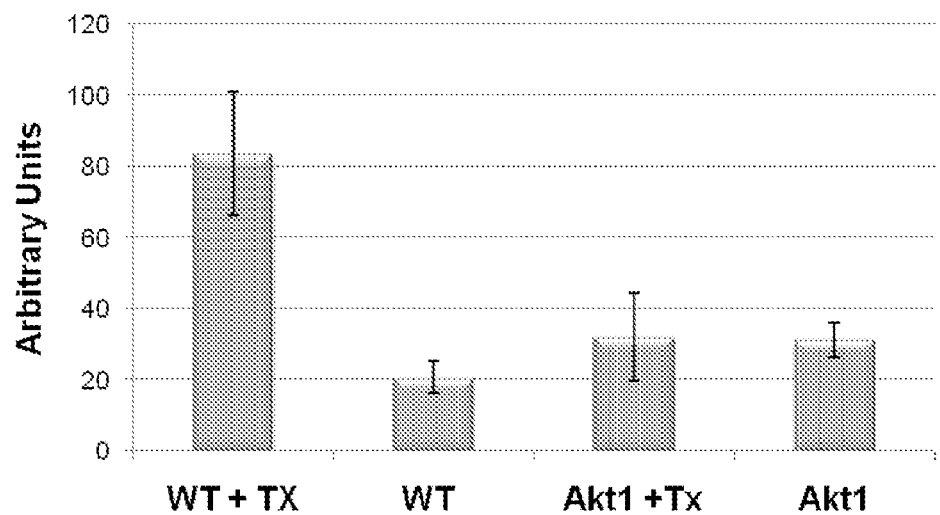
Figure 5C:
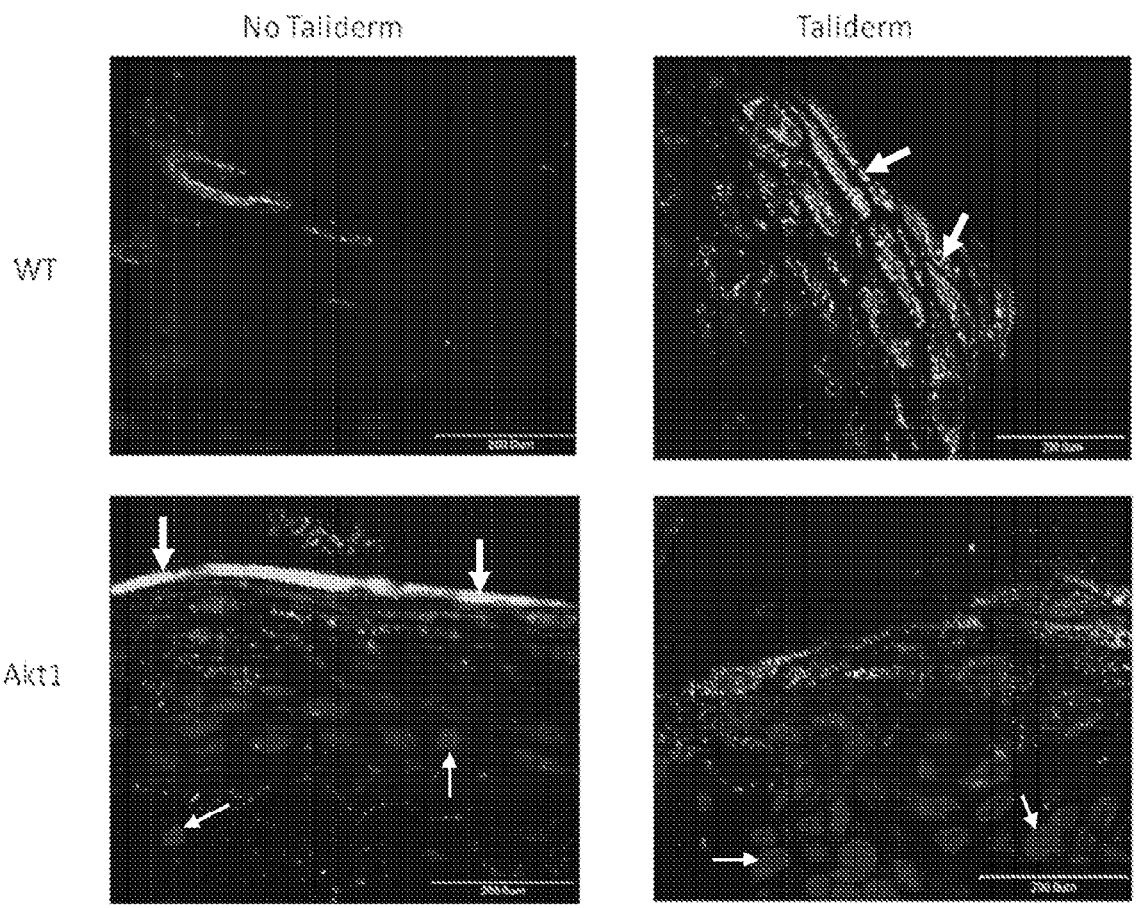

FIG. 5A-5C. sNAG nanofibers stimulate β-defensin 3 expression in mouse keratinocytes. FIG. 5A. Immunofluorescent staining with β-defensin 3 (visible as bright staining in the upper right hand panel; see, e.g., thick white arrows) and Involucrin antibodies of paraffin embedded mouse cutaneous wound sections from WT and Akt1 null animals on Day 3. FIG. 5B. Quantification of β-defensin 3 immunofluorescent staining using NIHImageJ software (TX=Taliderm; Akt1=Akt1 null). FIG. 5C. Immunofluorescent staining of WT and Akt1 null treated and untreated keratinocytes with β-Defensin 3 (visible as bright staining; see, e.g., thick white arrows) and TOPRO-3 (nuclei staining; see, e.g., thin white arrows). Notice the increase in β-Defensin 3 staining in WT and Akt1 Taliderm treated wounds.

Figure 6:
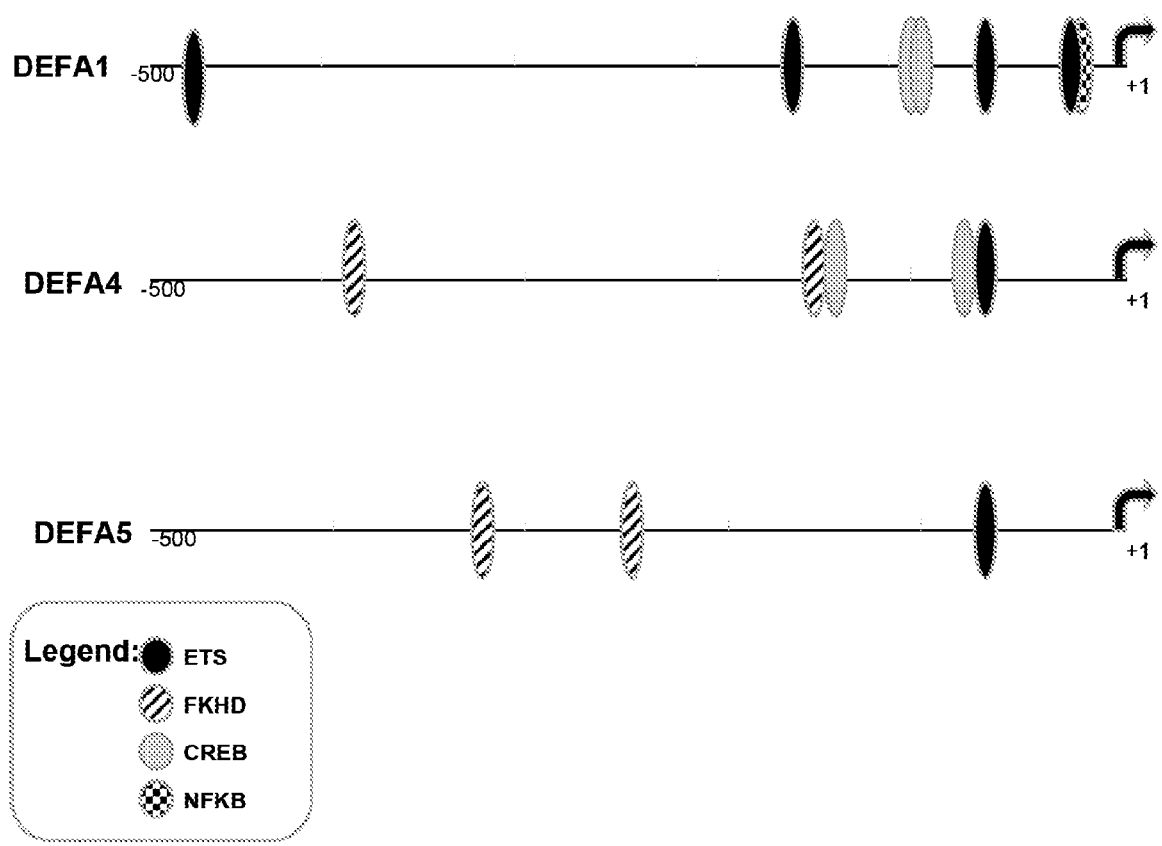

FIG. 6. Akt1 dependent transcription factor binding sites. Schematic of Akt1 dependent transcription factor binding sites. Using Genomatix software, 500 bp upstream of the transcription start site was analyzed for conserved sites on the mRNA of DEF1, 4, and 5 (ETS-black ovals; FKHD-striped ovals; CREB-white ovals; NFKB-checkered ovals).

Figure 7A:
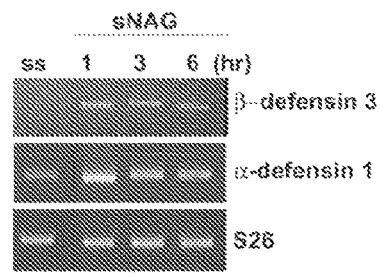
Figure 7B:
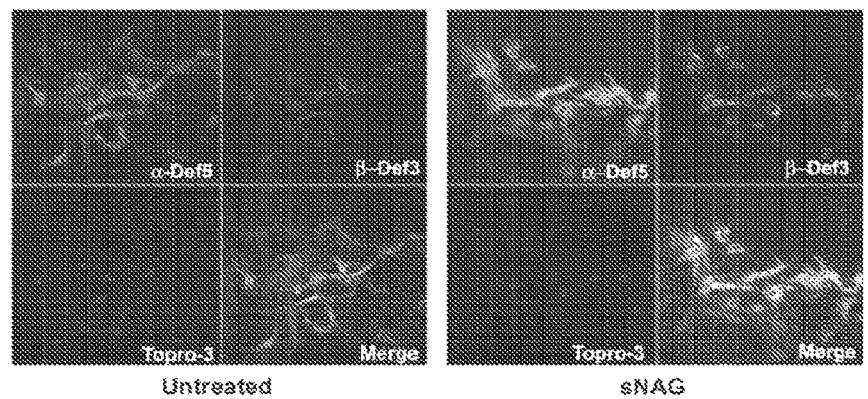
Figure 7C:
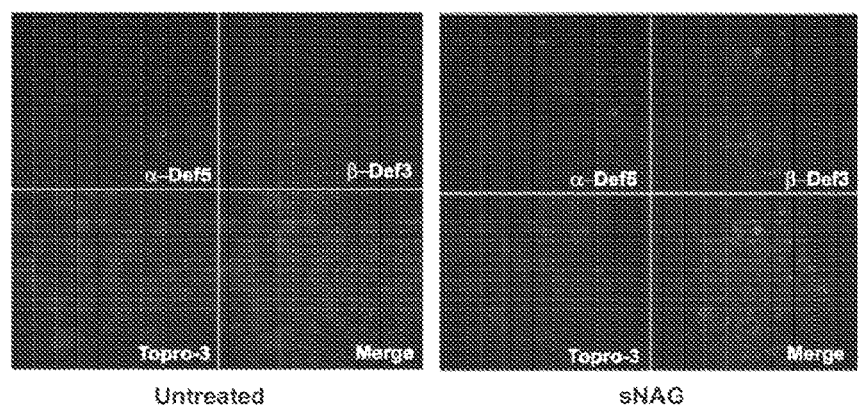

FIG. 7A-7C. sNAG treatment results in expression and secretion of defensins in vitro. FIG. 7A. RTPCR analysis of serum starved ("SS") primary endothelial cells treated with sNAG (50 µg/ml) for the times indicated and assessed for expression of β-defensin 3 and α-defensin1.

FIG. 7B. Immunofluorescent labeling of endothelial cells either serum starved (untreated) or treated with sNAG nanofibers (10 µg/ml for 5 hrs). Antibodies are directed against α-defensin 5 (FITC, upper left hand panel), β-defensin 3 (Texas Red, upper right hand panel). Nuclei are stained with TOPRO-3 (Blue, lower left hand panel). Lower right hand panel represents triple overlay. FIG. 7C. Immunofluorescent labeling of keratinocytes (HaCat) that are either serum starved (untreated) or treated with sNAG nanofibers (10 µg/ml for 5 hours). Antibodies are directed against α-defensin 5 (FITC, upper left hand panel), β-defensin 3 (Texas Red, upper right hand panel). Nuclei are stained with TOPRO-3 (Blue, lower left hand panel).

Figure 8B:
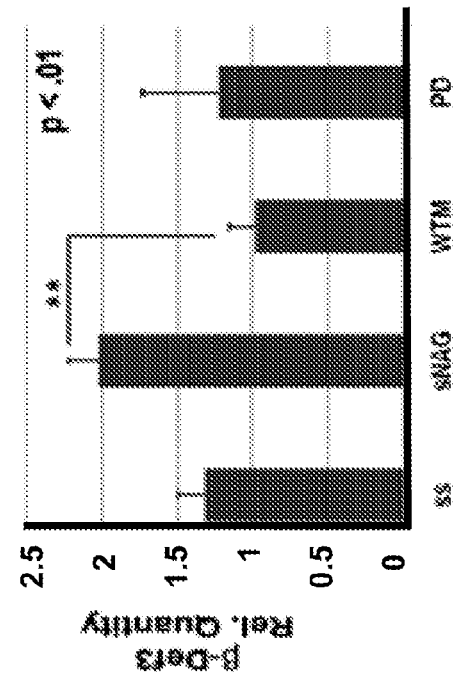
Figure 8A:
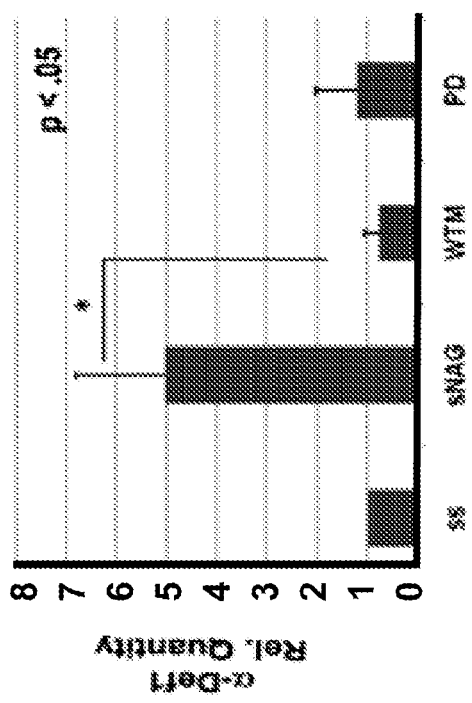
Figure 8C:
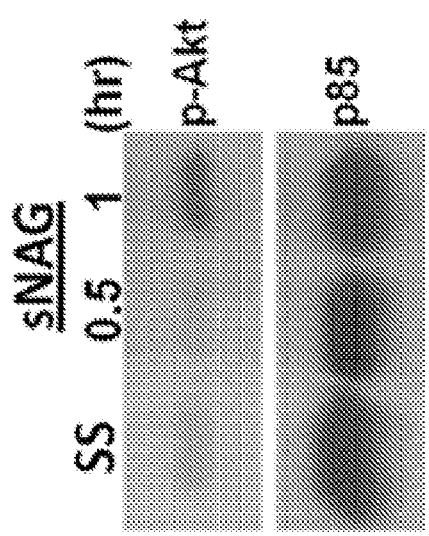
Figure 8E:
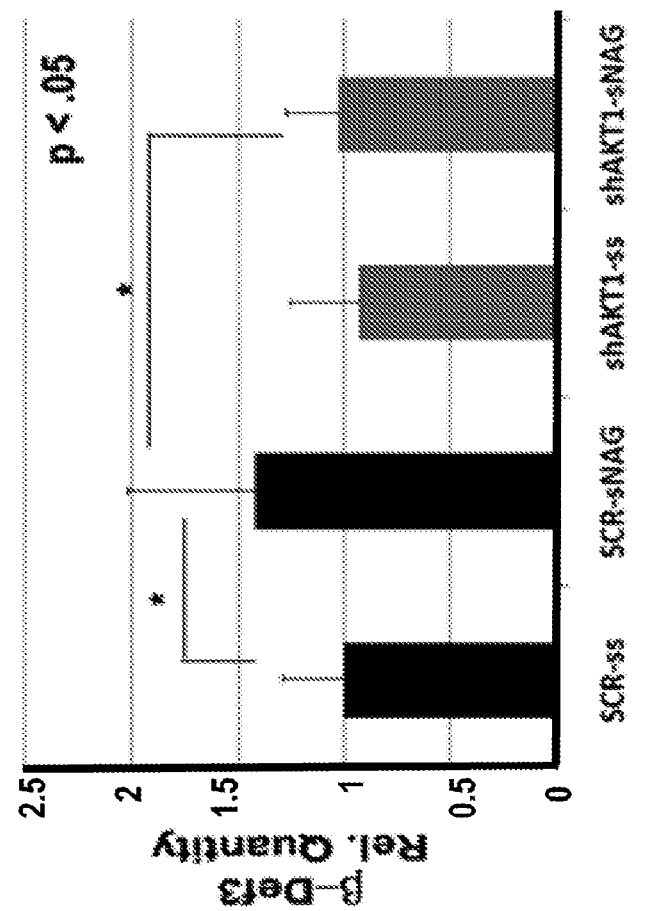

FIG. 8A-8E. sNAG induced defensin expression is dependent on Akt1. FIG. 8A. Quantitative RT-PCR analyses using primers directed against α-defensin 1 from total RNA isolated from serum starved endothelial cells treated with or without sNAG for 3 hours, with or without pretreatment with PD098059 ("PD")(50 µM), wortmannin ("WTM")(100 nm). Quantitation is relative to the S26 protein subunit. FIG. 8B. Quantitation of β-defensin 3 expression from total RNA isolated from serum starved endothelial cells treated with or without sNAG for 3 hours, with or without PD98059 (50 µm), wortmannin (100 nm) and shown as relative to S26. FIG. 8C. Western Blot analysis of phospho-Akt in serum starved endothelial cells (SS) stimulated with sNAG for the times indicated. Line indicates where lanes have been removed FIG. 8D. Quantitative RT-PCR analyses of serum starved endothelial cells infected with a scrambled control (SCR) or Akt1 shRNA lentiviruses, treated with or without sNAG and assessed for α-defensin 4 expression. Quantitation is shown relative to S26. FIG. 8E. Quantitation of β-defensin 3 expression from total RNA isolated from serum starved endothelial cells infected with a scrambled control (SCR) or Akt1 shRNA lentiviruses, treated with or without sNAG. Quantitation is shown relative to S26. All experiments were done in at least triplicate and repeated at least three independent times and p values are shown.

Figure 9A:
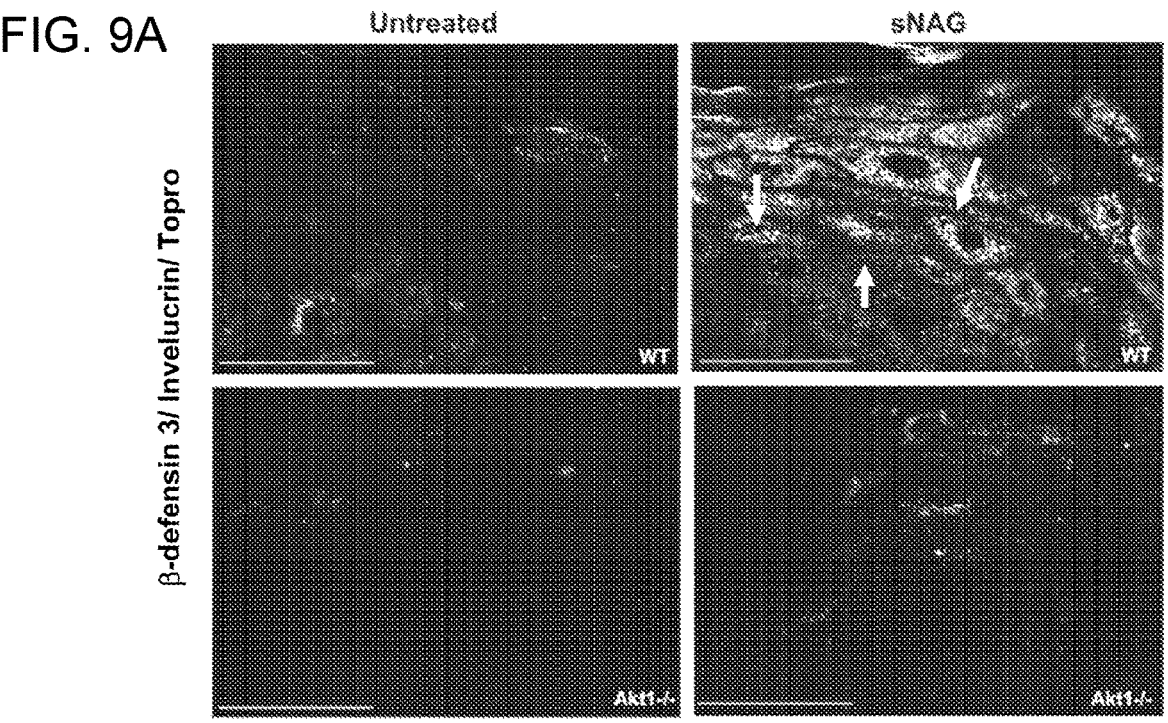
Figure 9B:
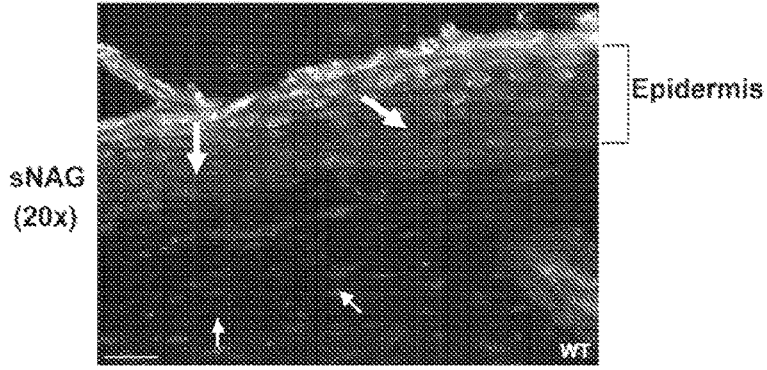
Figure 9C:
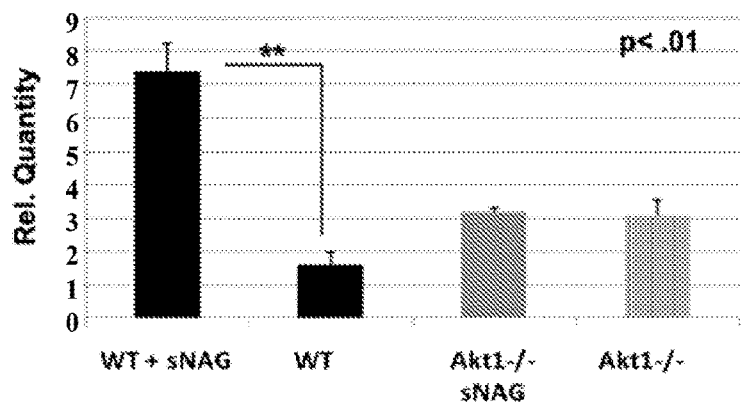

FIG. 9A-9C. sNAG induced defensin expression in vivo requires Akt1. FIG. 9A. Paraffin embedded sections of cutaneous wounds harvested on day 3 post wounding from both WT (n=3) and Akt1 mice. Wounds were either untreated or treated with sNAG membrane. Immunofluorescence was performed using antibodies directed against β-defensin 3 (green, visible as bright staining in the upper right hand panel; see, e.g., white thick arrows), Involucrin (Red), and Topro (Blue, nuclei staining; see, e.g., white thin arrows). FIG. 9B. Paraffin embedded section from WT treated with sNAG harvested on day 3. Immunofluorescence was performed using antibodies directed against β-defensin 3 (green, visible as bright staining; see, e.g., thick white arrows), Involucrin (Red), and Topro (Blue, nuclei staining; see, e.g., thin white arrows). This lower magnification (20×) is included to better illustrate the epidermal layers expressing β-defensin 3. Scale bars=50 µm. FIG. 9C. Quantitation of β-defensin 3 expression from paraffin embedded sections was performed using NIH ImageJ software. Experiments were repeated three independent times and p values are shown.

Figure 10:
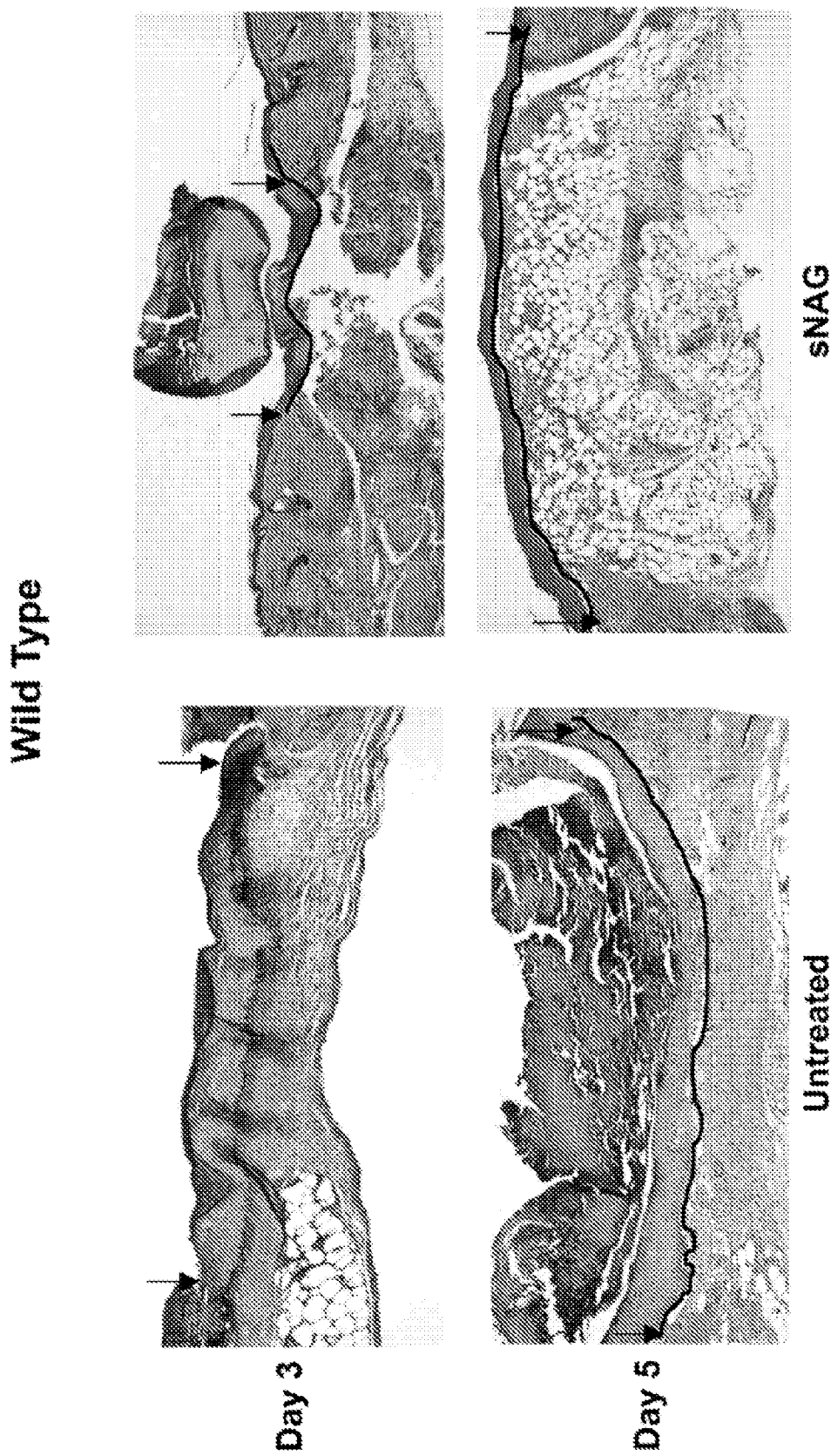

FIG. 10. sNAG treatment increases wound closure in wild type mice. H&E staining of wound tissue sections derived from C57Bl6 wild type animals either untreated or treated with sNAG membrane. The day post-wound is indicated to the left of each panel. The solid black line follows the keratinocyte cell layer indicating wound closure. Black arrows indicate the margin of the wound bed.

Figure 11A:
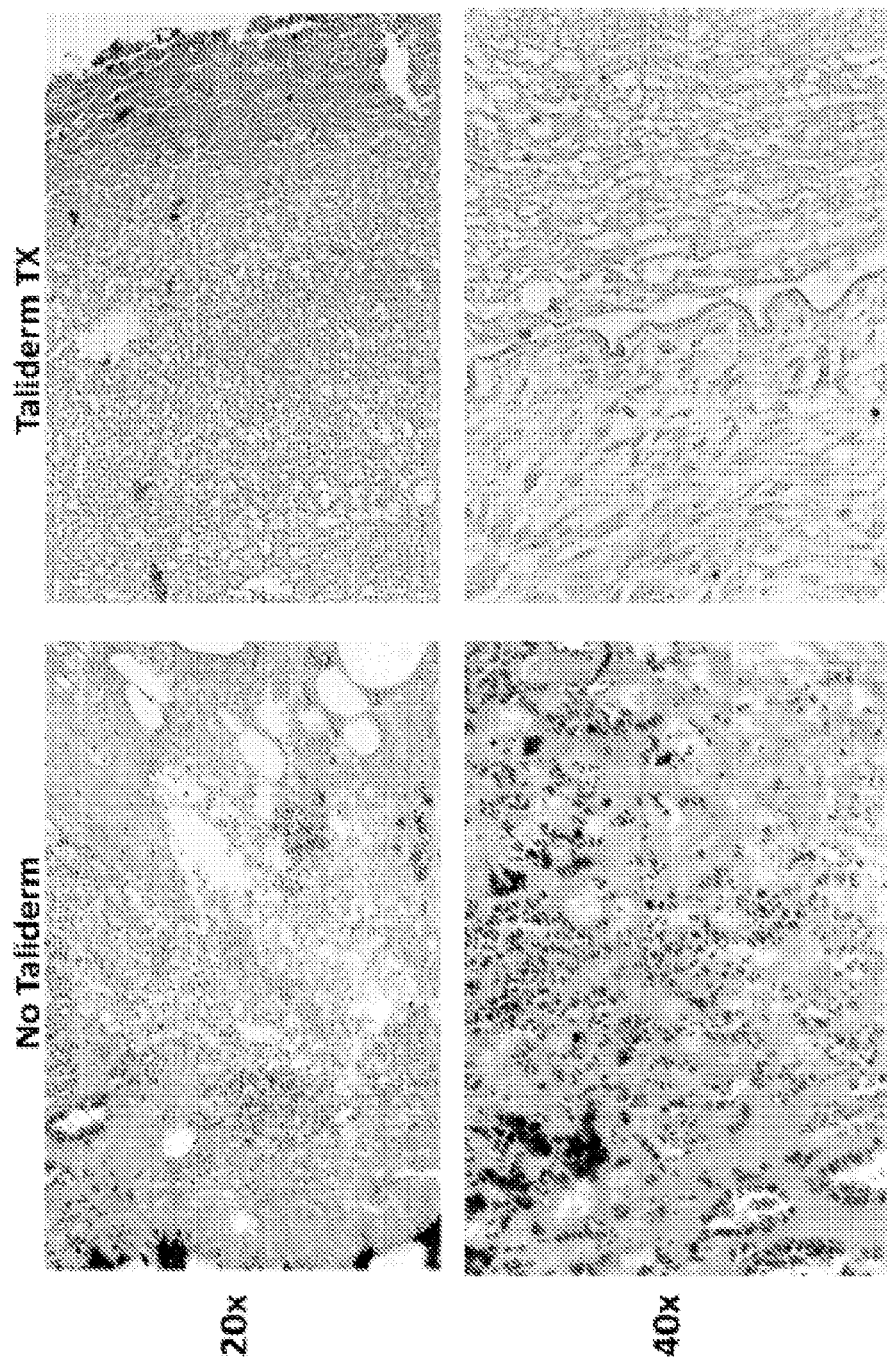
Figure 11B:
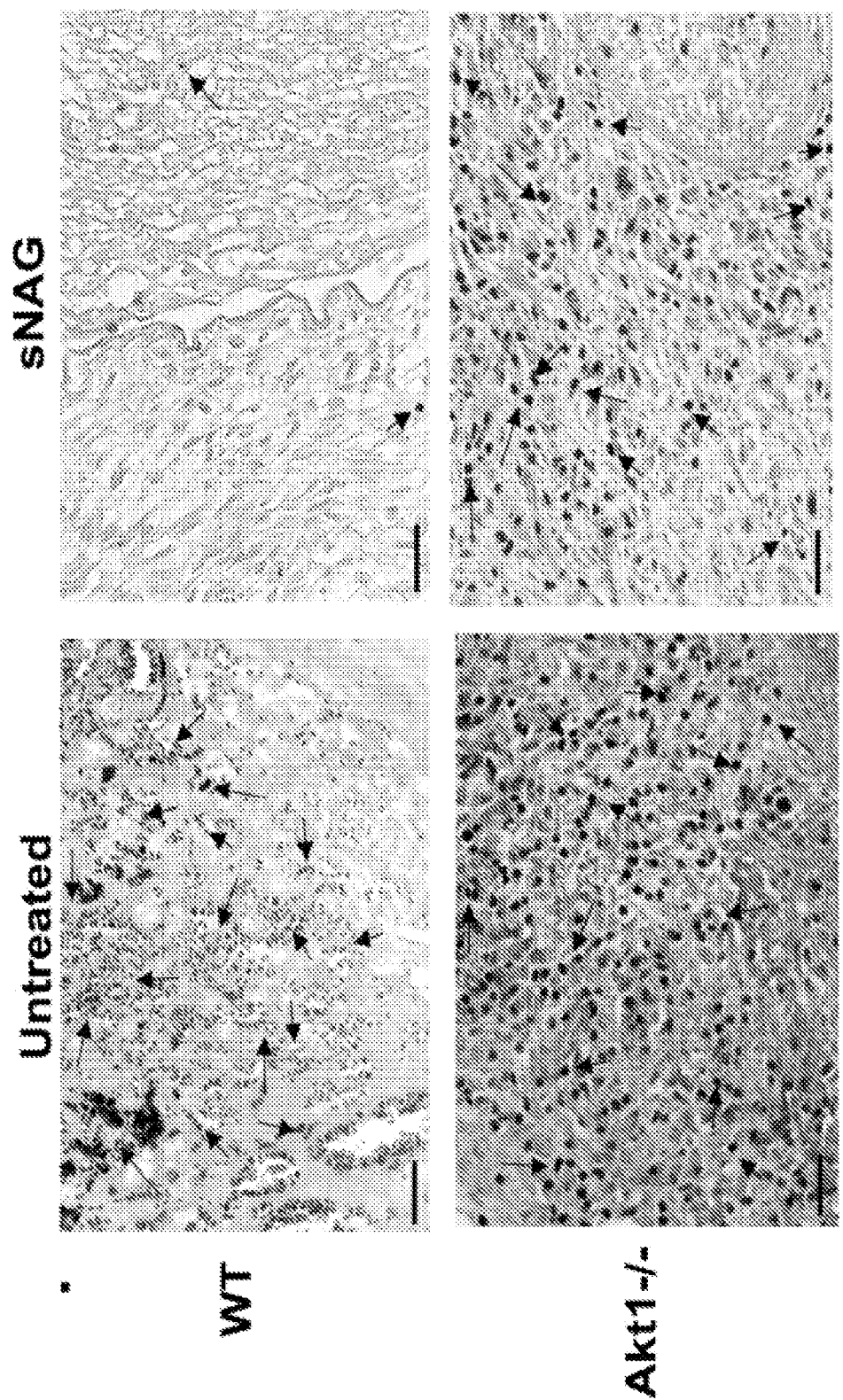
Figure 11C:
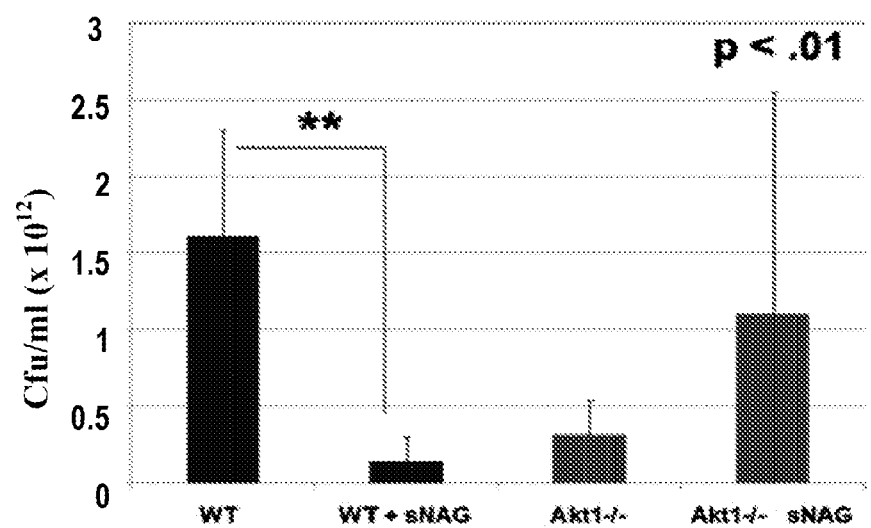
Figure 11D:
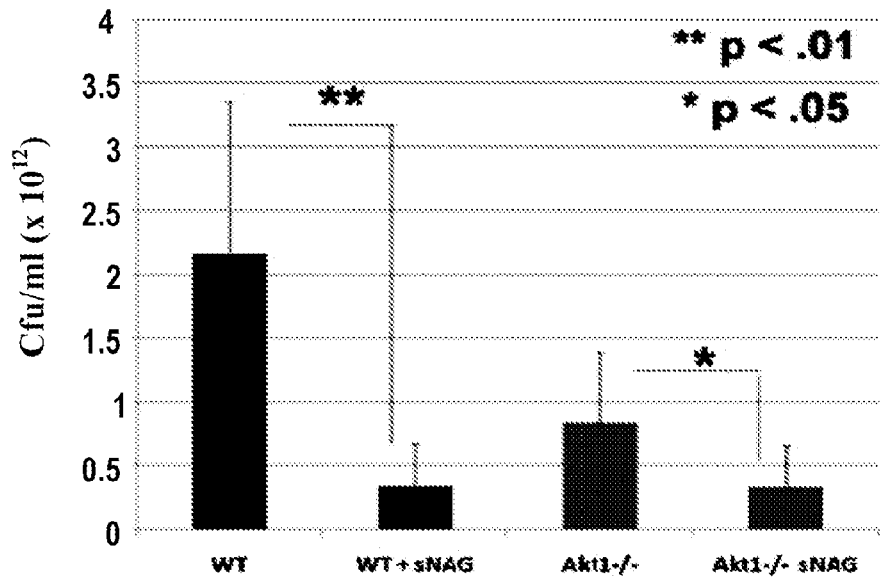
Figure 11E:
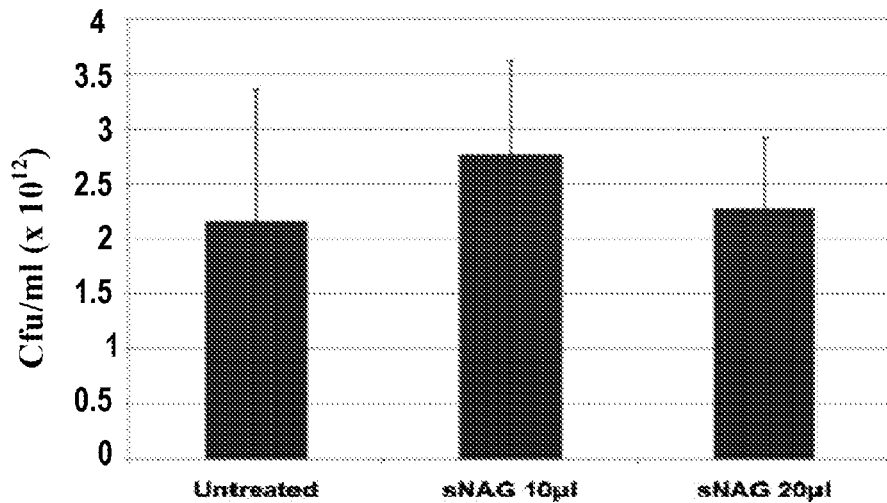
Figure 11F:
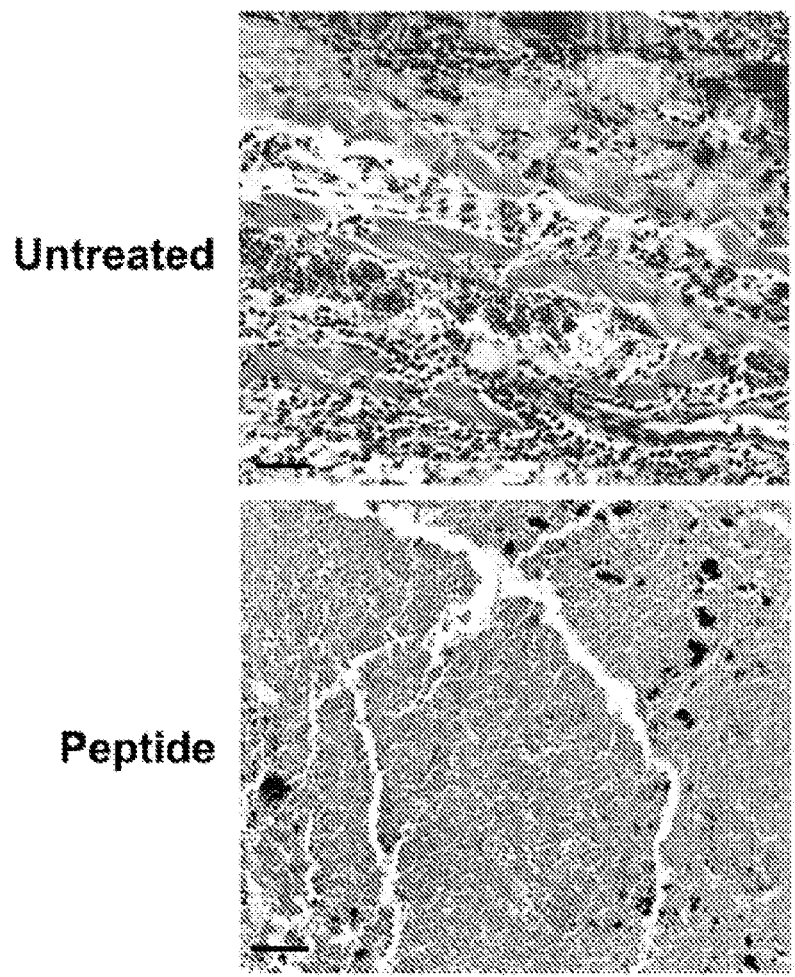
Figure 11G:
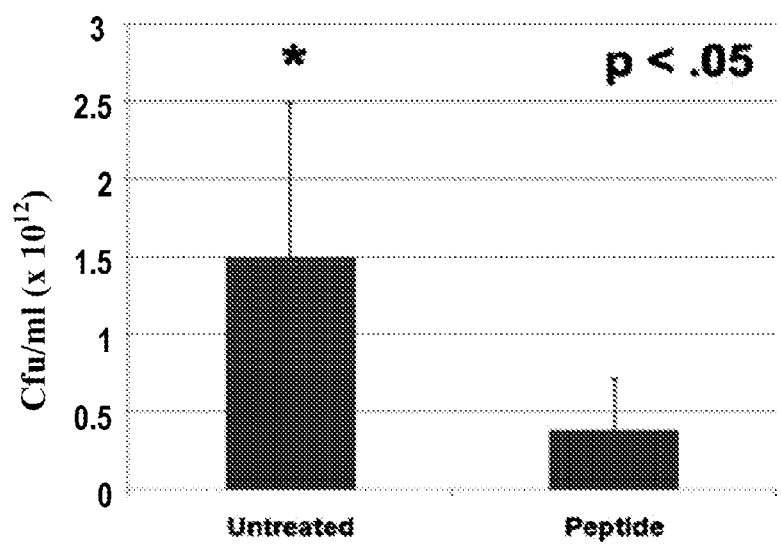

FIG. 11A-11G. sNAG treatment reduces bacterial infection in an Akt1 dependent manner. FIG. 11A. Tissue gram staining of S. aureus infected wounds from WT mice. WT mice were wounded using a 4 mm biopsy punch. Immediately after wounding mice were inoculated with 1×10$^9$ cfu/ml. 30 minutes post-infection, mice in the treated group were treated with Taliderm. Skin samples were taken 5 days post-treatment and sectioned for analysis. Tissue gram staining was performed. Dark purple staining indicates gram-positive bacteria and neutrophils that have engulfed bacteria. Sections under 20× and 40× magnification are shown. FIG. 11B. Tissue gram staining of paraffin embedded S. aureus infected wounds from WT and Akt1 null mice (n=3). Infected wounds were either untreated or treated with sNAG membrane and wound beds were harvested on day 3 and day 5 for analysis. Dark purple staining indicates the presence of gram positive bacteria in the wound bed. Black arrows indicate examples of gram positive staining. Note the accumulation of positive staining in untreated WT that is lacking in WT animals treated with sNAG. Scale bars=50 m. FIG. 11C. CFUs derived from day 5 post wounding were quantitated from S. aureus infected wounds using both treated and untreated WT (n=3) and Akt1 mice (n=3). Wild type mice that were sNAG treated show a significant (p<0.01) decrease in bacteria load in the wound beds as compared to Akt1 null animals. All experiments were repeated three independent times and the p values are shown. FIG. 11D. CFU quantitated from infected wounds at day 3 post wounding in a similar fashion described in FIG. 11C. sNAG treatment of infected wounds shows a significant decrease in CFU of both WT and Akt1 null animals on day 3, but the WT animals show an approximate 10 fold difference compared to a 2 fold difference in Akt1 animals. FIG. 11E. Quantitation of CFUs in S. aureus cultures that were either untreated or treated with various amounts of sNAG nanofibers. Each experiment was performed three independent times and p values are shown. FIG. 11F. Tissue gram staining of S. aureus infected wounds harvested on day 3 post wound from WT mice (n=3) that were treated with or without β-defensin 3 peptide (1.0 uM). Note the decrease in gram positive staining in infected wounds that were treated with β-defensin 3 peptide. FIG. 11G. Quantitation of CFUs from S. aureus infected WT mice (n=3) treated with or without β-defensin 3 peptide. Infected wounds that were treated with peptide show a significant decrease (p<0.05) in CFU. Scale bars=50 μm. Each experiment was performed three independent times and p values are shown.

Figure 12A:
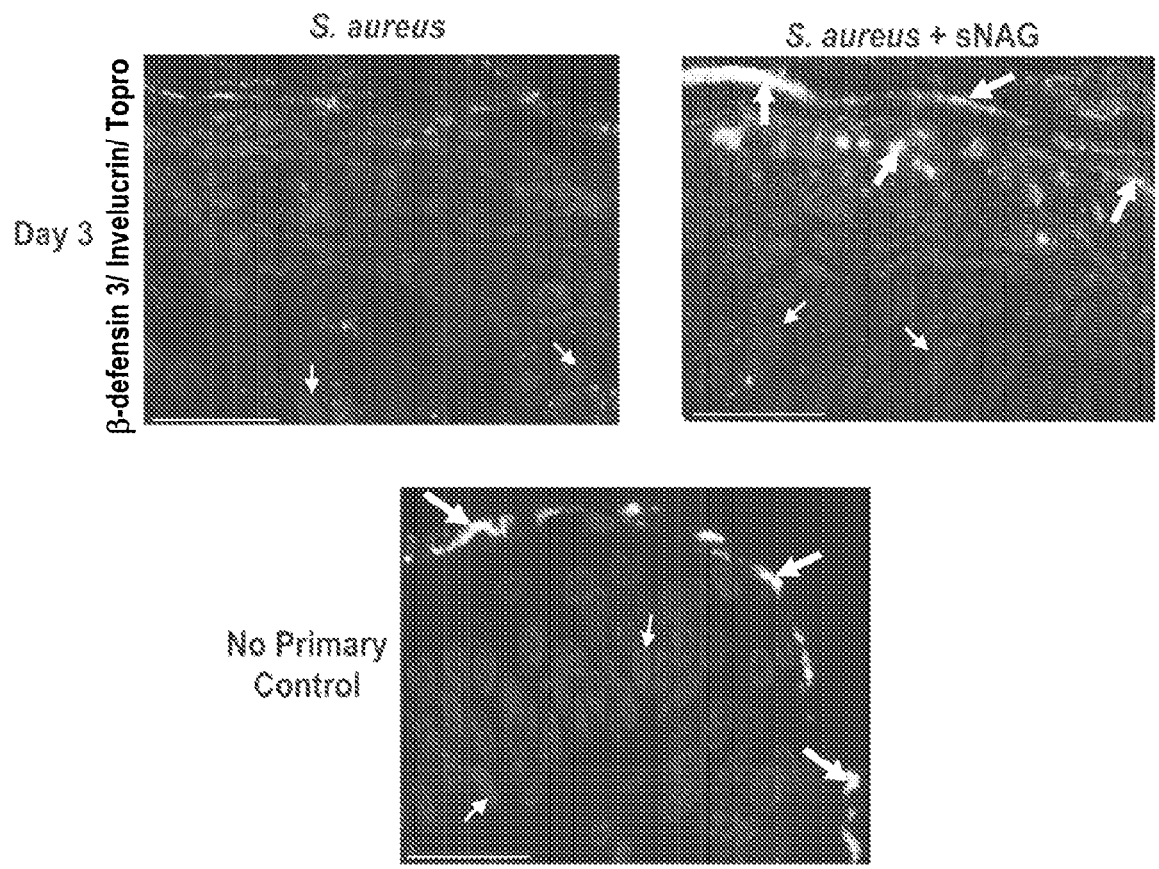
Figure 12B:
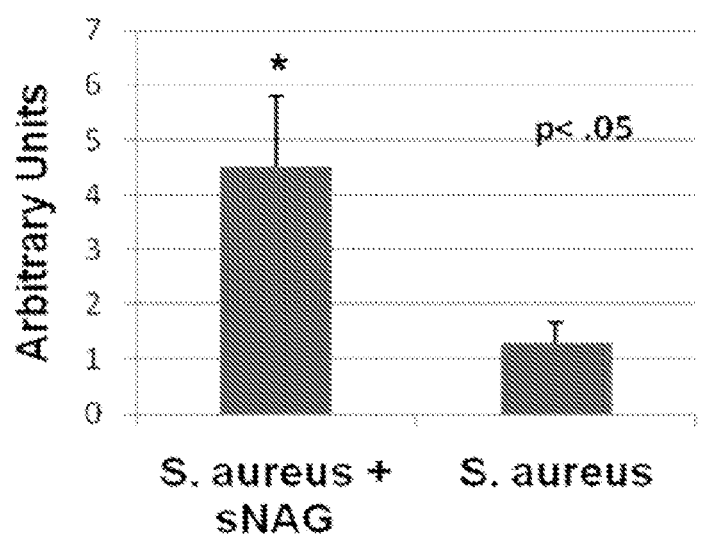

FIG. 12A-12B. Rapid induction of defensin expression by sNAG treatment of S. aureus infected wounds. FIG. 12A. Paraffin embedded tissue sections from S. aureus infected wounds, harvested on day 3, were subjected to immunofluorescence using antibodies directed against β-defensin 3 (green, visible as bright staining in the upper right hand panel and in the lower panel in the middle; see, e.g., thick white arrows), Involucrin (red) to mark the keratinocyte layer, and Topro (blue, nuclei staining; see, e.g., thin white arrows) from both sNAG treated WT (n=3) and untreated WT mice (n=3). Non specific staining of keratin is indicated by the no primary control which was stained with secondary antibody only. Scale bar=50 μm. FIG. 12B. Quantitation of β-defensin 3 expression from paraffin embedded sections using NIH ImageJ software. S. aureus infected wounds that were treated with sNAG show a significant increase (p<0.05) in β-defensin 3 staining. Experiments were repeated three independent times and p values are shown.

Figure 13A:
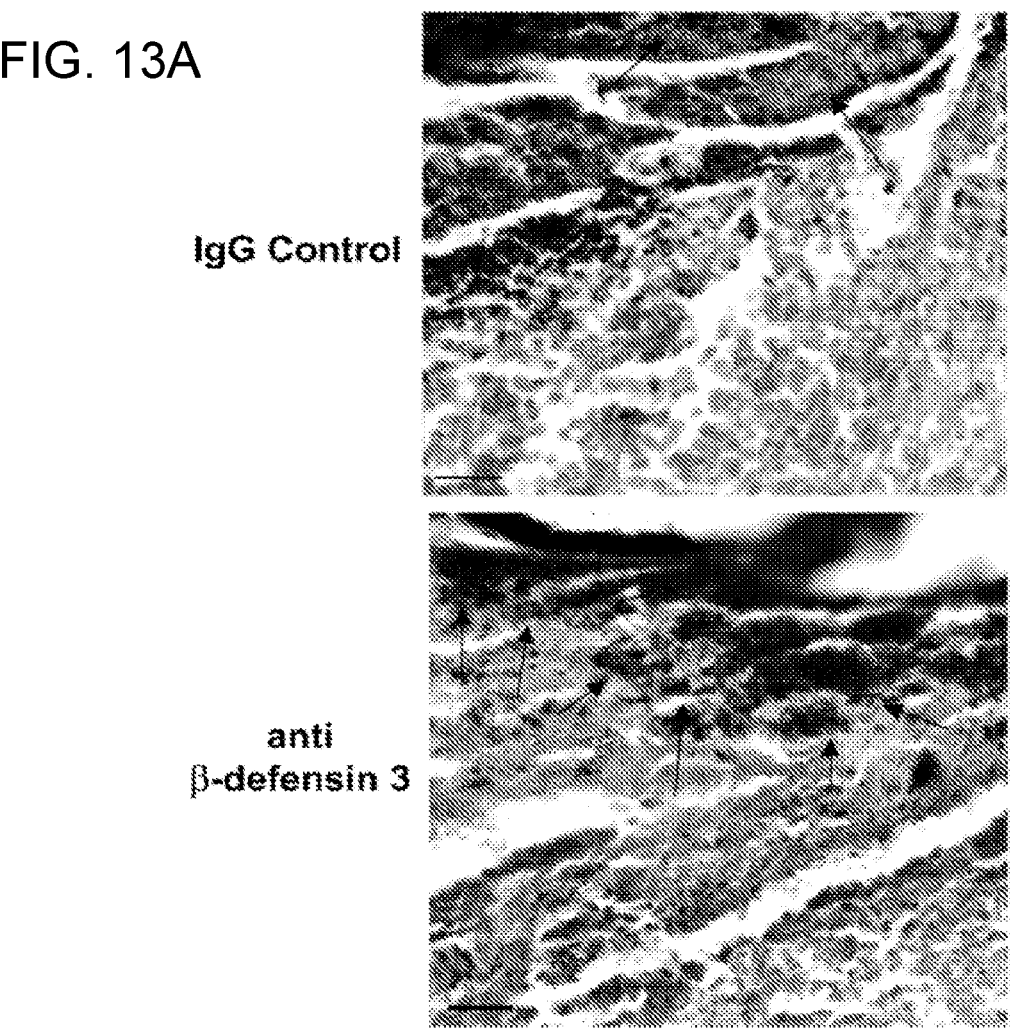
Figure 13B:
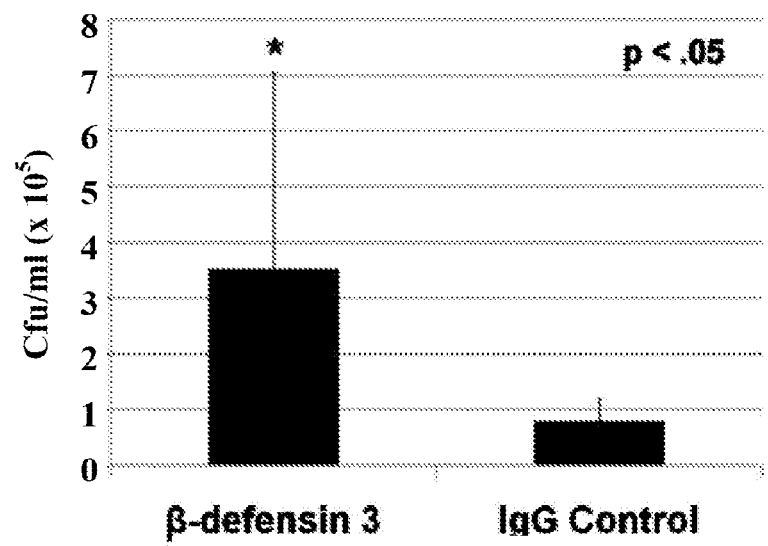

FIG. 13A-13B. Antibodies against β-defensin 3 impedes antibacterial effects of sNAG treatment. FIG. 13A. Tissue gram staining of paraffin embedded S. aureus infected wounds treated with sNAG from WT mice (n=3) that were harvested on Day 3. sNAG treated wounds were treated with either β-defensin 3 antibody or isotype control goat IgG antibody prior to sNAG treatment. Representative images show increased accumulation gram positive staining (black arrows) in the wound beds of mice treated with an antibody directed against β-defensin 3. Scale bar=20 m. FIG. 13B. Quantitation of CFUs from S. aureus infected WT mice treated either β-defensin 3 antibody (n=3) or control IgG antibody (n=3) prior to sNAG treatment. β-defensin 3 application significantly increased (p<0.05) CFU.

Figure 14A:
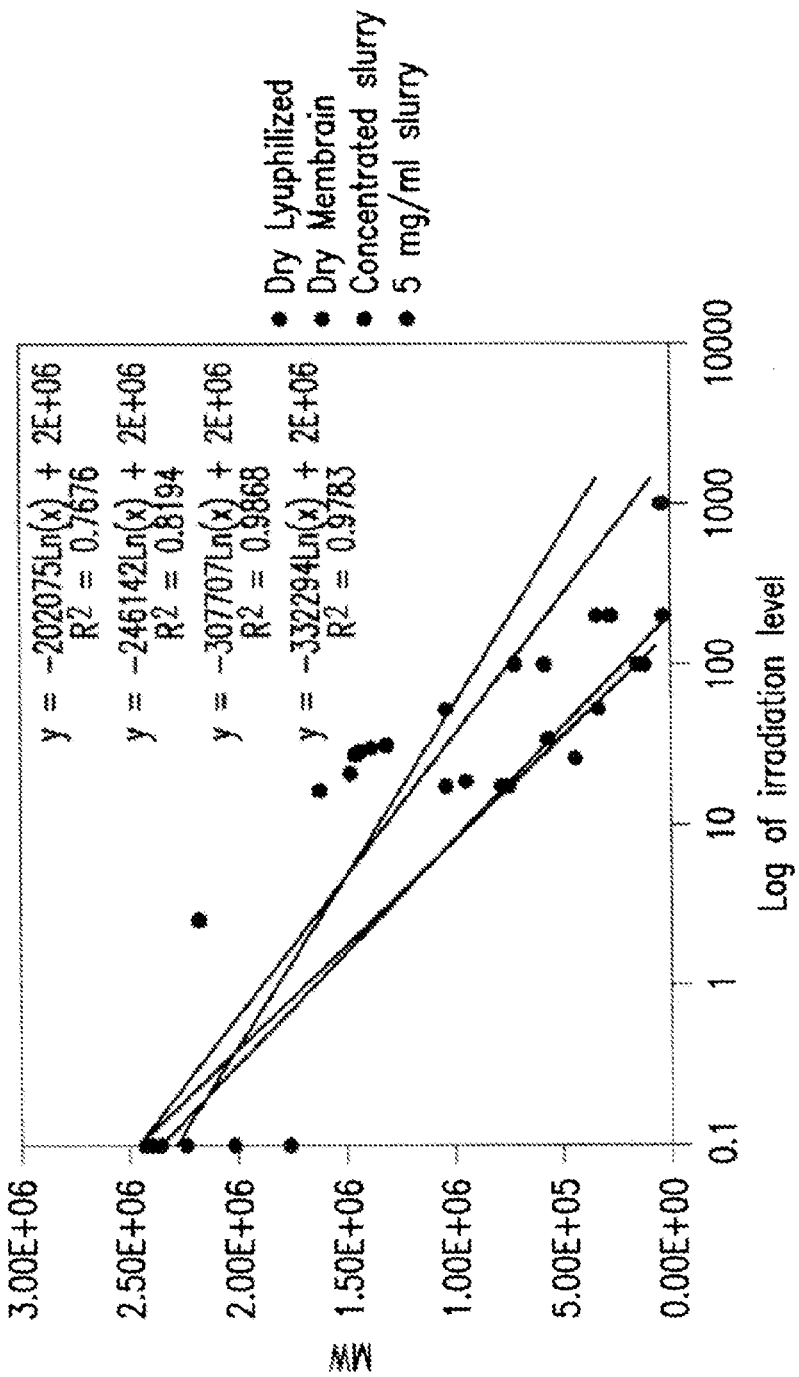
Figure 14B:
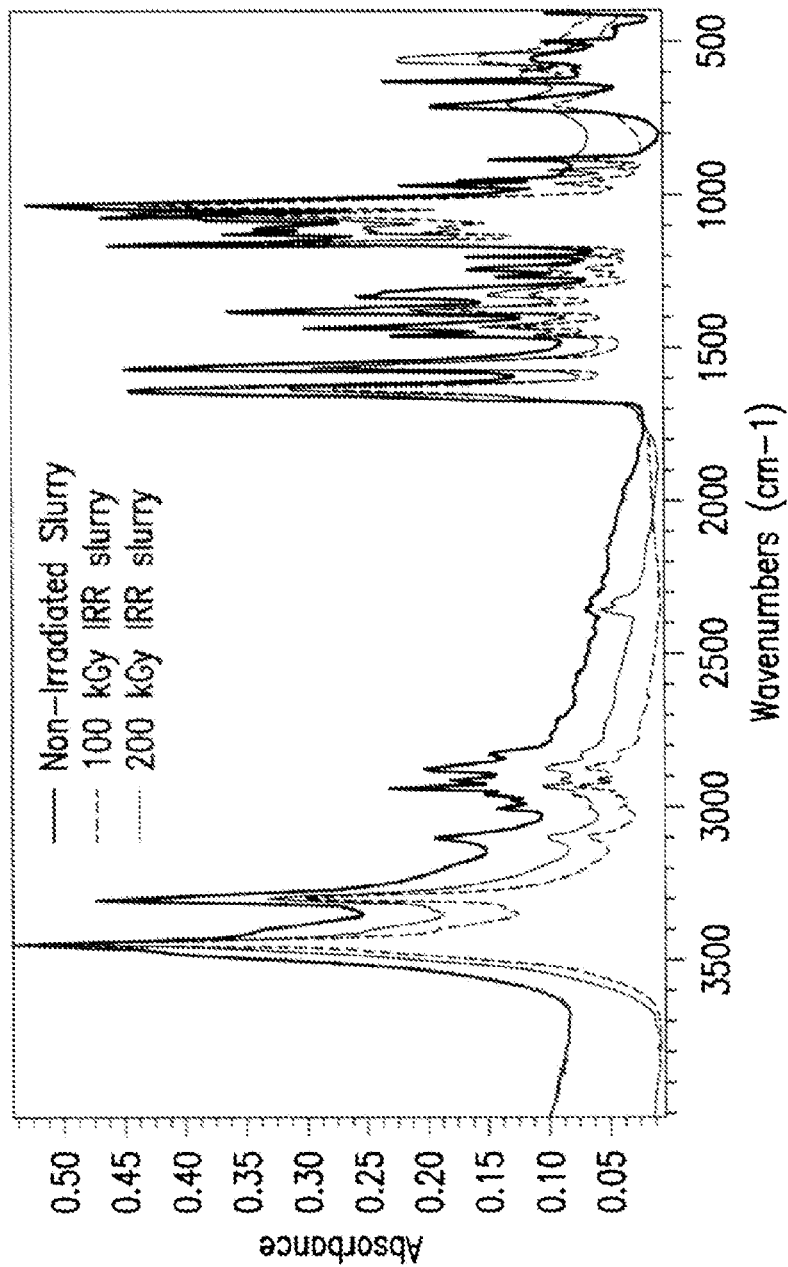
Figure 14C:
Figure 14D:
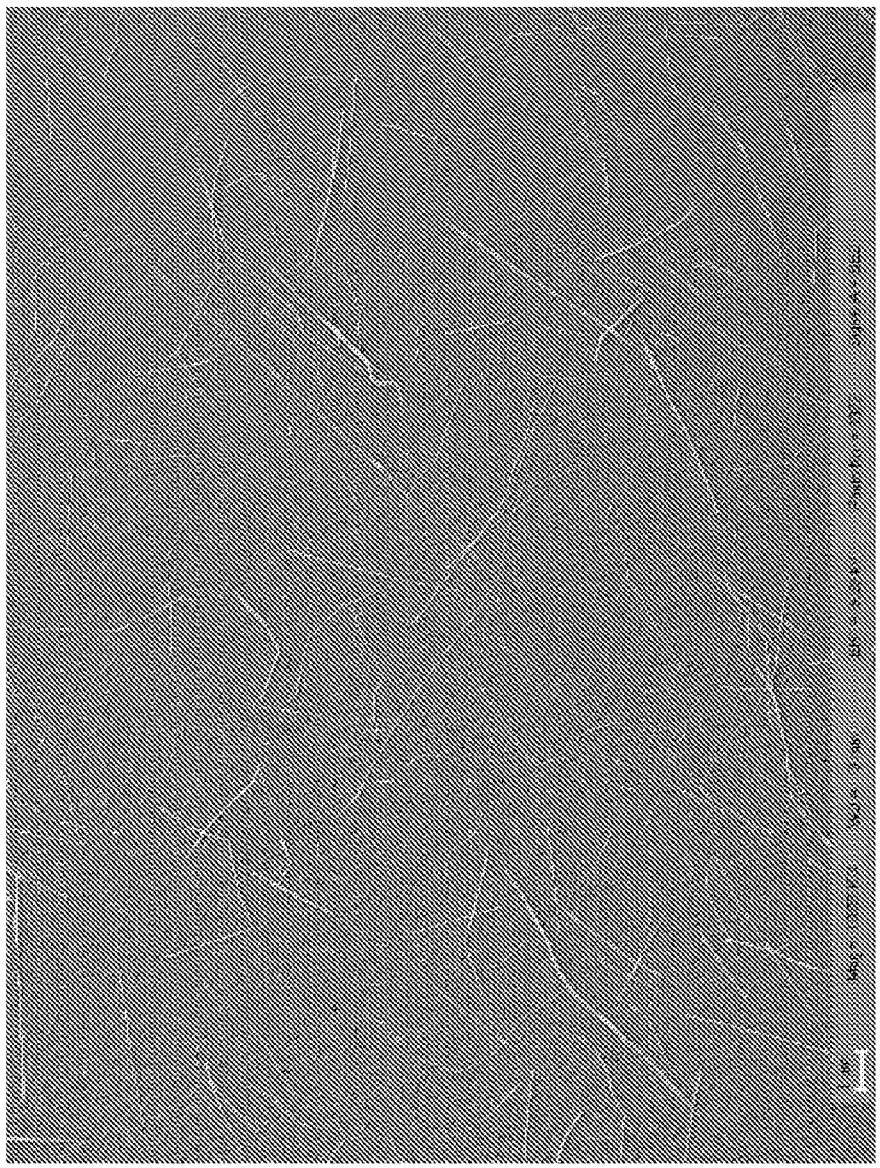

FIG. 14A-14D. Effect of irradiation on chemical and physical structure of poly-N-acetylglucosamine ("pGlcNAc") fibers. FIG. 14A. Correlation between molecular weight of pGlcNAc and irradiation level/formulation for irradiation. FIG. 14B. Infrared (IR) spectrum of non-irradiated pGlcNAc slurry (top line), pGlcNAc slurry irradiated at 100 kGy (bottom line), and pGlcNAc slurry irradiated at 200 kGy (middle line). FIG. 14C. Scanning electron microscopic (SEM) analyses of pGlcNAc. FIG. 14D. Scanning electron microscopic (SEM) analyses of sNAG.

Figure 15:
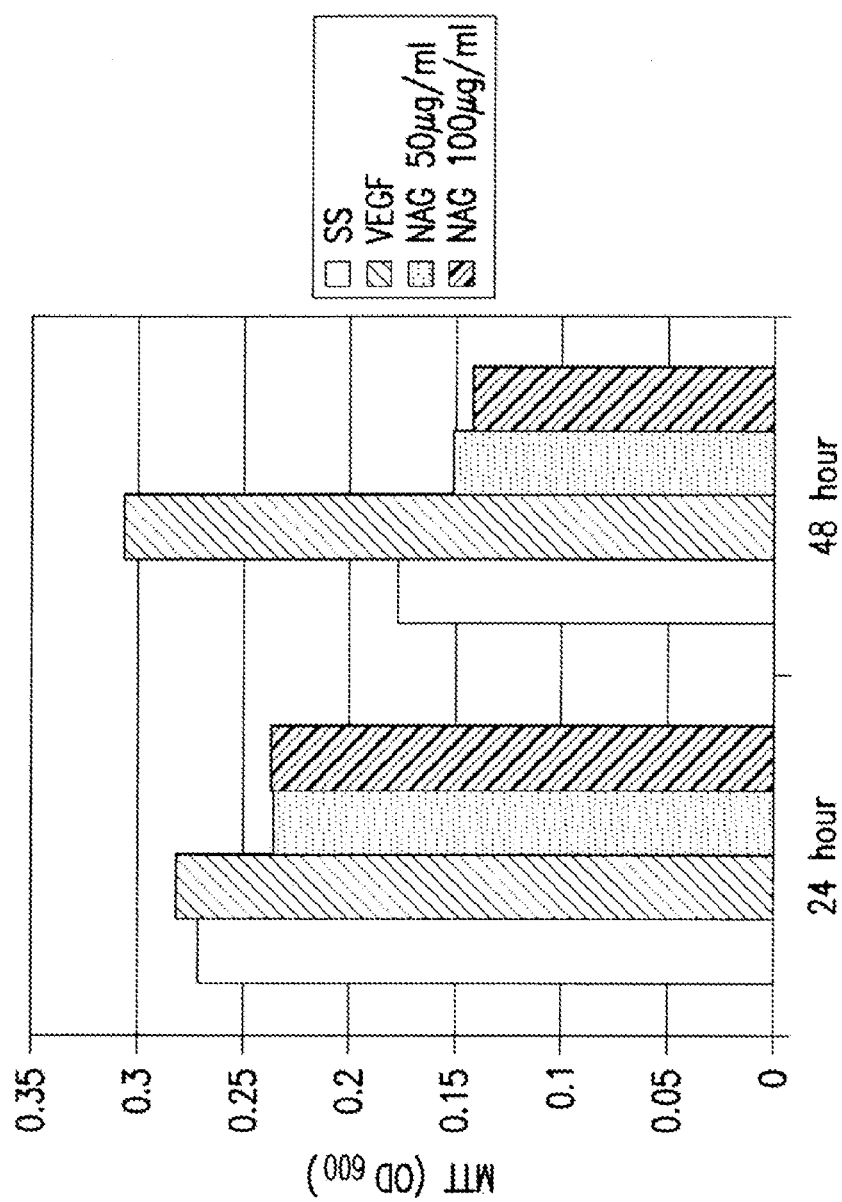

FIG. 15. pGlcNAc did not affect metabolic rate. For each time period (i.e., at 24 and 48 hours), the identity for each of the four bars (from left to right) is as follows: serum starvation (SS), VEGF, and pGlcNAc (NAG) at 50 and 100 μg/ml.

Figure 16:
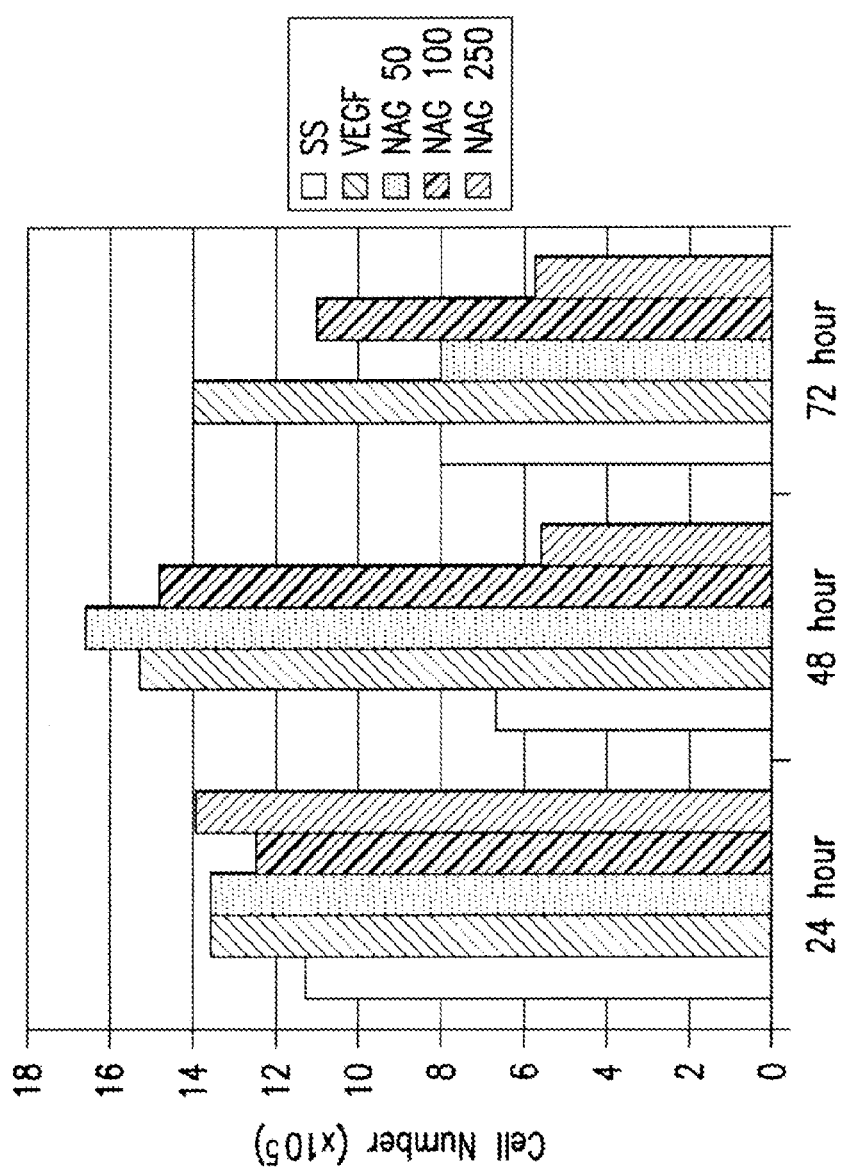

FIG. 16. pGlcNAc protected human umbilical vein endothelial cell (EC) from cell death induced by serum deprivation. For each time period (i.e., at 24, 48 and 72 hours), the identity for each of the five bars (from left to right) is as follows: serum starvation (SS), VEGF, and pGlcNAc (NAG) at 50, 100, and 250 μg/ml.

Figure 17:
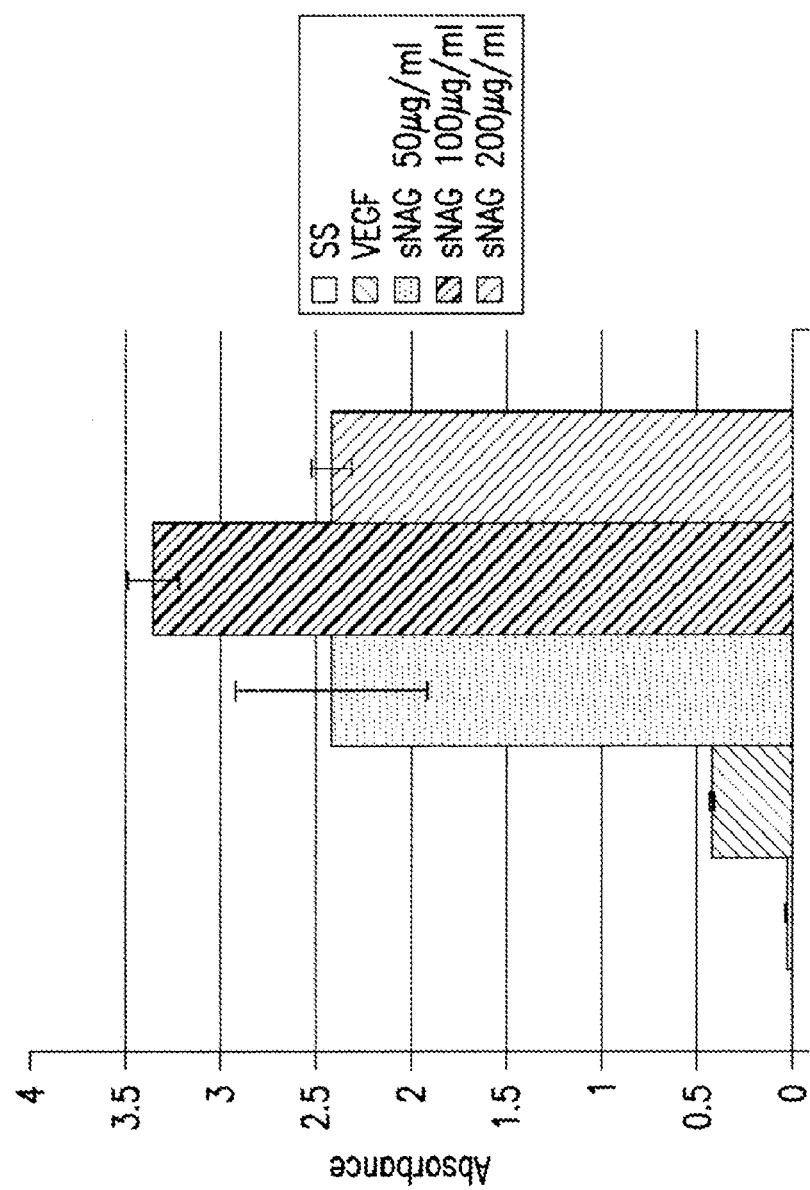

FIG. 17. sNAG induced marked increase in metabolic rate. Identity for each of the five bars (from left to right) is as follows: serum starvation (SS), VEGF, and sNAG at 50, 100 and 200 μg/ml.

Figure 18:
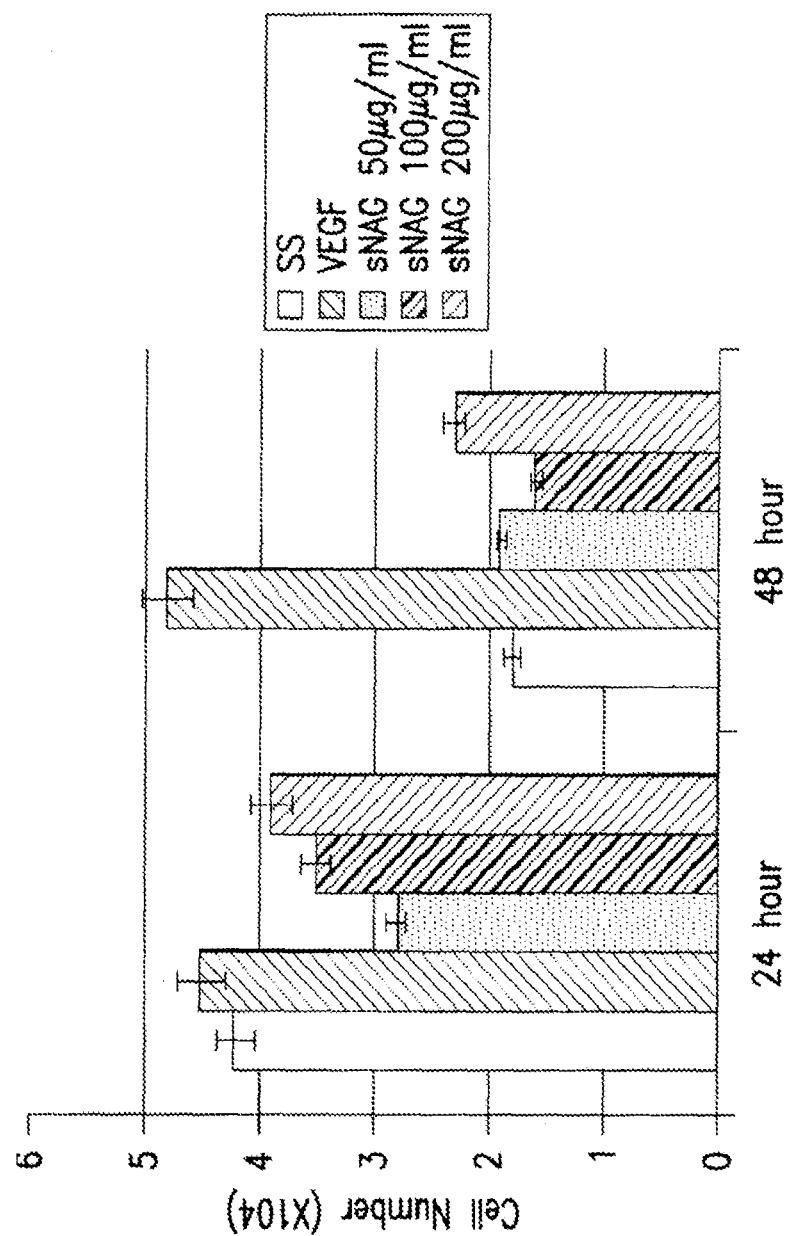

FIG. 18. sNAG did not protect EC from cell death induced by serum deprivation. For each time period (i.e., at 24 and 48 hours), the identity for each of the five bars (from left to right) is as follows: serum starvation (SS), VEGF, and sNAG at 50, 100 and 200 μg/ml.

Figure 19:
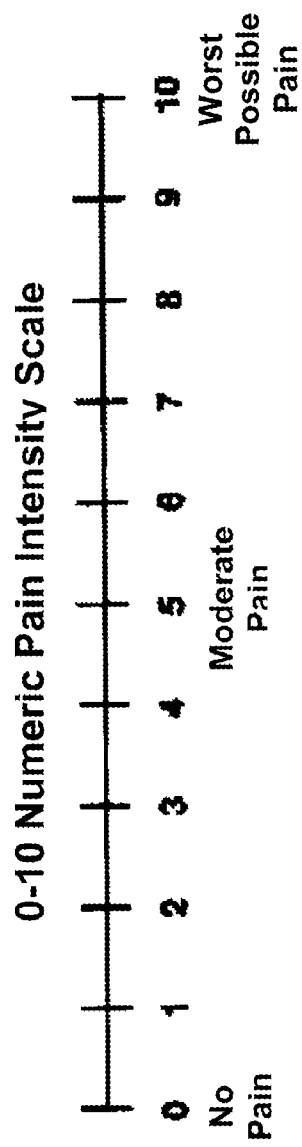

FIG. 19. Numeric Pain Intensity Scale.

Figure 20:
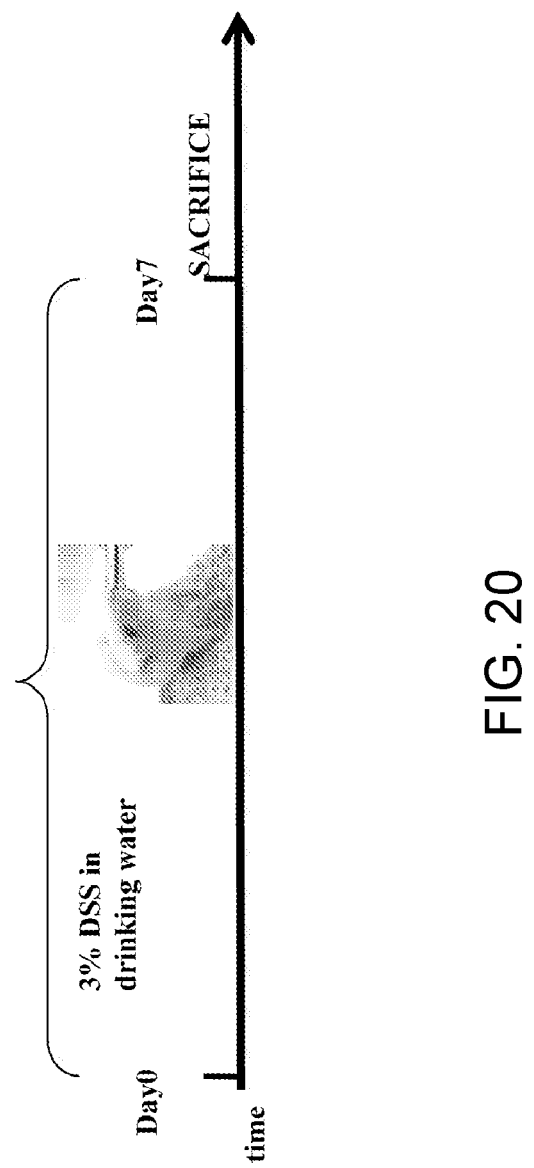

FIG. 20. Schematic showing experimental set up for the 3% DSS (dextran sodium sulphate)-induced inflammatory bowel disease (in particular, ulcerative colitis) in a mouse model.

Figure 21A:
Figure 21B:

FIG. 21A-21B. sNAG treatment decreased inflammation in an animal model of inflammatory bowel disease. FIG. 21A. H&E staining of a section of intestinal epithelium from a control group of 10 mice administered 3% DSS via drinking water for 7 days (day 0 to day 7), and saline via rectal suppository at day 0 and day 3 (100 μl). FIG. 21B. H&E staining of a section of intestinal epithelium from a test group of 10 mice administered 3% DSS via drinking water for 7 days (day 0 to day 7), and sNAG via rectal suppository at day 0 and day 3 (100 μl total with 12 μg/μl sNAG). Thin arrow and bracket point to the site of edema, and thick arrow points to the site of leukocytic infiltration.

Figure 22B:
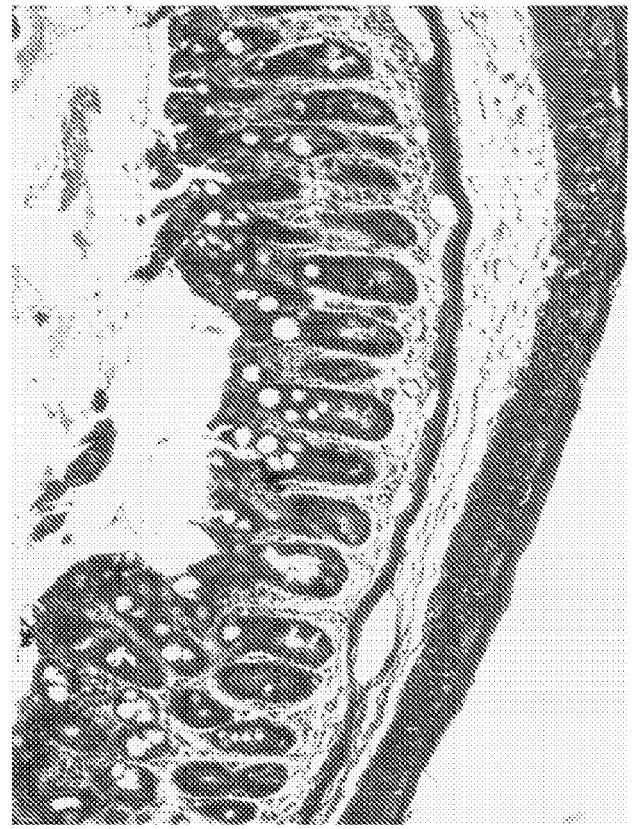
Figure 22A:
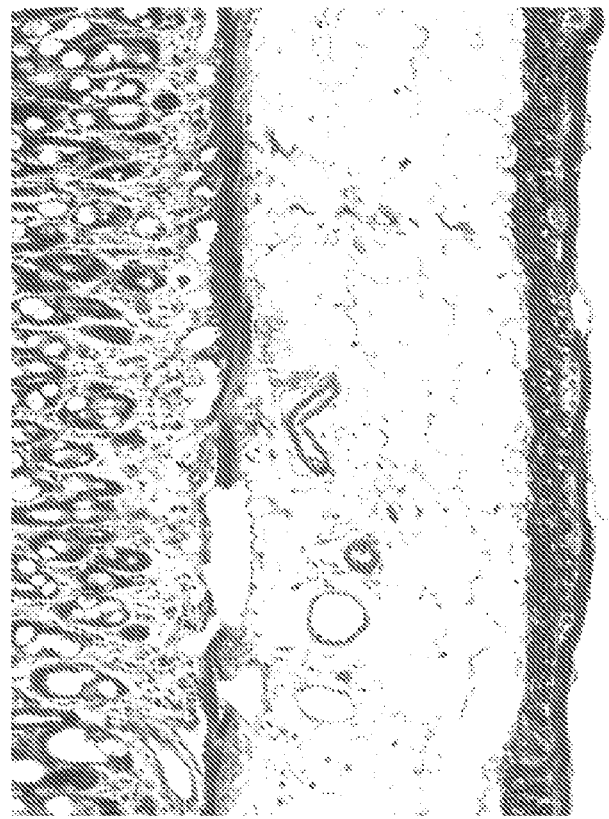

FIG. 22A-22B. sNAG treatment decreased fibrosis in an animal model of inflammatory bowel disease. FIG. 22A. Staining for fibrosis of a section of intestinal epithelium from a control group of 10 mice administered 3% DSS via drinking water for 7 days (day 0 to day 7), and saline via rectal suppository at day 0 and day 3 (100 μl). FIG. 22B. Staining for fibrosis of a section of intestinal epithelium from a test group of 10 mice administered 3% DSS via drinking water for 7 days (day 0 to day 7), and sNAG via rectal suppository at day 0 and day 3 (100 μl total with 12 μg/μl sNAG).

5. DETAILED DESCRIPTION

The inventors of the present invention have found that sNAG nanofibers can stimulate expression of defensins, which may boost the innate immune response. It is widely accepted that defensins are important players in innate immunity. As demonstrated in the examples presented in Sections 6.1 and 6.2, infra, the inventors of the present invention have found that sNAG nanofibers can increase the expression of both α- and β-type defensins in endothelial cells and β-type defensins in keratinocytes in vitro and in a wound healing model in vivo.

Further, as demonstrated in the examples presented in Sections 6.1 and 6.2, infra, but without being bound by any specific mechanism of action, Akt1 appears to be important for sNAG-dependent defensin expression in vitro and in vivo, in a wound healing model.

The inventors of this invention have also found that a number of Toll-like receptors can be up-regulated by sNAG treatment of human endothelial cells. Toll-like receptors ("TLRs" or "TLR") are highly conserved receptors that activate innate immunity. Recent work has linked human defensin expression to TLR activation, in particular, stimulation of TLRs can lead to increased defensin synthesis. Thus, without being bound by any mechanism of action, sNAG nanofibers may act as a stimulator of innate immunity.

Accordingly, described herein is the use of sNAG nanofibers as a novel method for preventing and/or treating of infections and diseases for which an increase in expression and/or secretion of one or more of defensins and Toll-like receptors may be beneficial. In certain embodiments, treatment of viral, yeast or fungal infections with sNAG nanofibers decreases the pathogen count in patients. In specific embodiments, the use of sNAG nanofibers enhances wound closure while simultaneously eradicating, decreasing or preventing a viral, a fungal or an yeast infection of the wound. In other embodiments, the sNAG nanofibers can be used in treating a dermatological condition such as dermatitis or psoriasis by, for example, alleviating one or more symptoms of such diseases. In yet another embodiment, the sNAG nanofibers can be used in treating an Inflammatory Bowel Disease (e.g., Crohn's disease) by, for example, alleviating one or more symptoms of such diseases.

The inventors have, in fact, found that sNAG nanofibers can be effective to treat viral infections. In particular, the inventors found that sNAG nanofibers are effective to treat HSV infection when administered topically to human patients. Example 8, infra, demonstrates that topical administration of sNAG nanofibers to cold sores reduces the pain associated with cold sores and reduces the duration of the cold sores in human patients. Cold sores are typically caused by HSV-1 infection, Thus, described herein are uses of sNAG nanofibers to treat viral infections, in particular, topical viral infections. In specific embodiments, described herein are uses of sNAG nanofibers to treat an HSV infection, or to treat and/or prevent a symptom associated with an HSV infection (e.g., a cold sore or a lesion) by topical administration of sNAG nanofibers to a patient (e.g., at the site of HSV infection or the site of a symptom of HSV infection, or at the site where a symptom of infection is known to occur).

The inventors have also found that sNAG nanofibers can be effective to treat inflammatory bowel disease (IBD). In particular, the inventors found that sNAG nanofibers are effective to treat IBD in an animal model of IBD when administered rectally (such as via a suppository). Example 9, infra, demonstrates that administration of sNAG nanofibers reduces inflammation and fibrosis associated with IBD in a mouse model of IBD. Thus, described herein are uses of sNAG nanofibers to treat IBD, such as ulcerative colitis and Crohn's disease. In specific embodiments, described herein are uses of sNAG nanofibers to treat IBD (e.g., ulcerative colitis, or Crohn's disease) by topical administration of sNAG nanofibers to a patient (e.g., to the anus or rectally via a suppository, a cream, a suspension, a liquid solution, a gel, or an ointment).

5.1 sNAG Nanofibers

Described herein are sNAG nanofiber compositions. The sNAG nanofibers comprise fibers of poly-N-acetylglucosamine and/or a derivative(s) thereof, the majority of which are less than 30 microns in length and at least 1 micron in length as measured by any method known to one skilled in the art, for example, by scanning electron microscopy ("SEM"). Such sNAG nanofibers may be obtained, for example, as described herein.

In certain embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers are less than about 30, 25, 20, 15, 12, 10, 9, 8, 7, 6, 5, 4, or 3 microns in length, and at least 1 micron in length as measured by any method known to one skilled in the art, for example, by SEM. In specific embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers are less than about 15 microns or less than about 12 microns in length, and at least 1 micron in length as measured by any method known to one skilled in the art, for example, by SEM. In specific embodiments, all (100%) of the sNAG nanofibers are less than about 15 microns or less than about 10 microns in length, and at least 1 micron in length as measured by any method known to one skilled in the art, for example, by SEM. In certain embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers are equal to or less than 14, 13, 12, 11, 10, 9, 8 or 7 microns in length, and at least 1 micron in length as measured by any method known to one skilled in the art, for example, by SEM. In some embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers are between 1 to 15, 2 to 15, 2 to 14, 1 to 12, 2 to 12, 1 to 10, 2 to 10, 3 to 12, 3 to 10, 4 to 12, 4 to 10, 5 to 12, 5 to 10, 1 to 9, 2 to 9, 3 to 9, 1 to 8, 2 to 8, 3 to 8, 4 to 8, 1 to 7, 2 to 7, 3 to 7, 4 to 7, 1 to 6, 1 to 5, 1 to 4, or 1 to 3 microns in length as measured by any method known to one skilled in the art, for example, by SEM.

In a specific embodiment, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers are about 8, 7, 6, 5, 4, 3 or 2 microns in length as measured by any method known to one skilled in the art, for example, by SEM. In another specific embodiment, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers are between about 2 to about 10 microns, about 3 to about 8 microns, about 4 to about 7 microns, about 4 to about 10 microns, or about 5 to about 10 microns in length as measured by any method known to one skilled in the art, for example, by SEM. In another specific embodiment, all (100%) of the sNAG nanofibers are between about 2 to about 10 microns, about 3 to about 8 microns, about 4 to about 7 microns, about 4 to about 10 microns, or about 5 to about 10 microns in length as measured by any method known to one skilled in the art, for example, by SEM.

In certain embodiments, the sNAG nanofibers fibers are in a range between 0.005 to 5 microns in thickness and/or diameter as determined by electron microscopy. In specific embodiments, the sNAG nanofibers are about 0.01, 0.02, 0.03, 0.04, 0.05, 0.06, 0.07, 0.08, 0.09, 0.1, 0.2, 0.25, 0.3, 0.35, 0.4, 0.45, 0.5, 0.55, 0.6, 0.65, 0.7, 0.75, 0.8, 0.85, 0.9, 1, 1.1, 1.2, 1.3, 1.4, 1.5, 1.6, 1.7, 1.8, 1.9, 2, 2.2, 2.4, 2.6, 2.8, 3 or 4 microns in thickness and/or diameter on average, or any range in between (e.g., 0.02 to 2 microns, 0.02 to 1 microns, 0.02 to 0.75 microns, 0.02 to 0.5 microns, 0.02 to 0.5 microns, 0.05 to 1 microns, 0.05 to 0.75 microns, 0.05 to 0.5 microns, 0.1 to 1 microns, 0.1 to 0.75 microns, 0.1 to 0.5 microns, etc.). In specific embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers have a thickness or diameter of about 0.02 to 1 microns. In other specific embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers have a thickness or diameter of about 0.05 to 0.5 microns. In specific embodiments, all (100%) of the sNAG nanofibers have a thickness or diameter of about 0.02 to 1 microns or about 0.05 to 0.5 microns. In certain embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers have a thickness or diameter of about 0.02 to 2 microns, 0.02 to 1 microns, 0.02 to 0.75 microns, 0.02 to 0.5 microns, 0.02 to 0.5 microns, 0.05 to 1 microns, 0.05 to 0.75 microns, 0.05 to 0.5 microns, 0.1 to 1 microns, 0.1 to 0.75 microns, or 0.1 to 0.5 microns.

In certain embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers are between 1 and 15 microns, or between (or in the range of) 1 to 10 microns, 2 to 10 microns, 3 to 10 microns, 4 to 10 microns, 4 to 7 microns, 5 to 10 microns, or 5 to 15 microns in length and have a thickness or diameter of about 0.02 to 1 microns.

In certain embodiments, the molecular weight of the sNAG nanofibers is less than 100 kDa, 90 kDa, 80 kDa, 75 kDa, 70 kDa, 65 kDa, 60 kDa, 55 kDa, 50 kDa, 45 kDA, 40 kDa, 35 kDa, 30 kDa, or 25 kDa. In certain embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers have a molecular weight of less than 100 kDa, 90 kDa, 80 kDa, 75 kDa, 70 kDa, 65 kDa, 60 kDa, 55 kDa, 50 kDa, 45 kDA, 40 kDa, 35 kDa, 30 kDa, or 25 kDa. In other embodiments, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers have a molecular weight between about 5 kDa to 100 kDa, about 10 kDa to 100 kDa, about 20 kDa to 100 kDa, about 10 kDa to 80 kDa, about 20 kDa to 80 kDa, 20 kDa to 75 kDa, about 25 kDa to about 75 kDa, about 30 kDa to about 80 kDa, about 30 kDa to about 75 kDa, about 40 kda to about 80 kDa, about 40 kDa to about 75 kDa, about 40 kDa to about 70 kDa, about 50 kDa to about 70 kDa, or about 55 kDa to about 65 kDa. In one embodiment, the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the sNAG nanofibers have a molecular weight of about 60 kDa.

In certain embodiments, 1% to 5%, 5% to 10%, 5% to 15%, 20% to 30% or 25% to 30% of the sNAG nanofibers are deacetylated. In some embodiments, 1%, 5%, 10%, 15%, 20%, 25%, or 30% of the sNAG nanofibers are deacetylated. In other embodiments, less than 30%, 25%, 20%, 15%, 10%, 5%, 4%, 3%, 2% or 1% of the sNAG nanofibers are deacetylated. In some embodiments, equal to or more than 1%, 5%, 10%, 15%, 20%, 25%, 30%, 35%, 40%, 45%, 50%, 55%, 60%, 65%, 70%, 75%, 80%, 85%, 90%, 95% or 99%, or all (100%), of the sNAG nanofibers are deacetylated. In other embodiments, less than 1%, 5%, 10%, 15%, 20%, 25%, 30%, 35%, 40%, 45%, 50%, 55%, 60%, 65%, 70%, 75%, 80%, 85%, 90%, 95%, 99%, or 100% of the sNAG nanofibers are deacetylated.

In certain embodiments, 70% to 80%, 75% to 80%, 75% to 85%, 85% to 95%, 90% to 95%, 90% to 99% or 95% to 100% of the sNAG nanofibers are acetylated. In some embodiments, 70%, 75%, 80%, 85%, 90%, 95%, 98%, 99% or 100% of the sNAG nanofibers are acetylated. In other embodiments, more than 70%, 75%, 80%, 85%, 90%, 95%, 97%, 98%, 99%, 99.5% or 99.9% of the sNAG nanofibers are acetylated. In some embodiments, equal to or more than 1%, 5%, 10%, 15%, 20%, 25%, 30%, 35%, 40%, 45%, 50%, 55%, 60%, 65%, 70%, 75%, 80%, 85%, 90%, 95%, 97%, 98% or 99%, or all (100%), of the sNAG nanofibers are acetylated. In other embodiments, less than 1%, 5%, 10%, 15%, 20%, 25%, 30%, 35%, 40%, 45%, 50%, 55%, 60%, 65%, 70%, 75%, 80%, 85%, 90%, 95%, 97%, 98%, 99%, or 100% of the sNAG nanofibers are acetylated.

In some embodiments, the majority (and in certain embodiments, at least 60%, 70%, 80%, 90%, 95%, 98%, 99%, 99.5%, 99.9%, or 100%) of the sNAG nanofibers are between (or in the range of) 2 to 12 microns, 2 to 10 microns, 4 to 15 microns, 4 to 10 microns, 5 to 15 microns, or 5 to 10 microns, and such sNAG nanofibers are at least 70%, 75%, 80%, 85%, 90%, 95%, 97%, 98%, 99% or 100% acetylated.

In some embodiments, the sNAG nanofibers comprise at least one glucosamine monosaccharide, and may further comprise at least 10%, 20%, 30%, 40%, 50%, 60%, 70%, 80%, 90%, 95% or 99% of the N-acetylglucosamine monosaccharides. In other embodiments, the sNAG nanofibers comprise at least one N-acetylglucosamine monosaccharide, and may further comprise at least 10%, 20%, 30%, 40%, 50%, 60%, 70%, 80%, 90%, 95% or 99% of glucosamine monosaccharides.

In one aspect, the sNAG nanofibers increase the metabolic rate of serum-starved human umbilical cord vein endothelial cells ("EC") in a MTT assay. A MTT assay is a laboratory test and a standard colorimetric assay (an assay which measures changes in color) for measuring cellular proliferation (cell growth). Briefly, yellow MTT (3-(4,5-Dimethylthiazol-2-yl)-2,5-diphenyltetrazolium bromide, a tetrazole) is reduced to purple formazan in the mitochondria of living cells. This reduction takes place only when mitochondrial reductase enzymes are active, and therefore conversion can be directly related to the number of viable (living) cells. The MTT assay is described in Example 6, infra, where it is utilized to assess the effect of sNAG nanofibers on the metabolic rate of EC cells. The metabolic rate of cells may also be determined by other techniques commonly known to the skilled artisan.

In another aspect, the sNAG nanofibers do not rescue apoptosis of serum-starved EC in a trypan blue exclusion test. A trypan blue exclusion test is a dye exclusion test used to determine the number of viable cells present in a cell suspension. It is based on the principle that live cells possess intact cell membranes that exclude certain dyes, such as trypan blue, Eosin, or propidium, whereas dead cells do not. The trypan blue assay is described in Example 6, infra, where it is utilized to assess the effect of sNAG nanofibers on cell viability of EC cells. The viability of cells may also be determined by other techniques commonly known to the skilled artisan.

In certain embodiments, compositions comprising the sNAG nanofibers are described, wherein the sNAG nanofibers increase the metabolic rate of serum-starved human umbilical cord vein endothelial cells in a MTT assay and/or do not rescue apoptosis of serum-starved human umbilical cord vein endothelial cells in a trypan blue exclusion test. In some embodiments, the sNAG nanofibers increase the metabolic rate of serum-starved human umbilical cord vein endothelial cells in a MTT assay and do not rescue apoptosis of serum-starved human umbilical cord vein endothelial cells in a trypan blue exclusion test.

In a specific embodiment, the sNAG nanofibers are biocompatible. Biocompatibility may be determined by a variety of techniques, including, but not limited to such procedures as the elution test, intramuscular implantation, or intracutaneous or systemic injection into animal subjects. Such tests are described in U.S. Pat. No. 6,686,342 (see, e.g., Example 10), which is incorporated by reference herein in its entirety. Some of the biocompatibility tests are described in Example 7, infra, which show that sNAG nanofibers are non-reactive in such tests.

In certain embodiments, the sNAG nanofibers used in the methods described herein are non-reactive in a biocompatibility test or tests. For example, the sNAG nanofibers used in the methods described herein may be non-reactive when tested in an elution test, an intramuscular implantation test, an intracutaneous test, and/or a systemic test. In other embodiments, the sNAG nanofibers used in the methods described herein have Grade 0 or Grade 1 test score when tested in an elution test, an intramuscular implantation test, an intracutaneous test, or a systemic test. In yet another embodiment, the sNAG nanofibers used in the methods described herein are at most mildly reactive when tested in an elution test, an intramuscular implantation test, an intracutaneous test, and/or a systemic test. In certain embodiments, the compositions described herein do not cause an allergenic reaction or an irritation. In other embodiments, the compositions described herein cause at most a mild allergenic reaction or a mild irritation, e.g., at the site of application. The relevant tests and evaluation of test results are described in, e.g., U.S. Pat. No. 6,686,342, which is incorporated herein by reference in its entirety, and in Section 6.8, infra.

In a specific embodiment, the sNAG nanofibers are non-reactive when tested in an intramuscular implantation test. In one aspect, an intramuscular implantation test is an intramuscular implantation test—ISO 4 week implantation, as described in Section 6.8.3, infra. In certain embodiments, the sNAG nanofibers display no biological reactivity as determined by an elution test (Elution Test Grade=0). In some embodiments, the sNAG nanofibers have a test score equal to "0" and/or are at most a negligible irritant as determined by intracutaneous injection test. In some embodiments, the sNAG nanofibers elicit no intradermal reaction (i.e., Grade I reaction) in Kligman test and/or have a weak allergenic potential as determined by Kligman test. Example 7, infra, shows that sNAG nanofibers are non-reactive in an intramuscular implantation test, an intracutaneous injection test, and Kligman test.

In certain aspects, the sNAG nanofibers are immunoneutral (i.e., they do not elicit an immune response).

In some embodiments, the sNAG nanofibers are biodegradable. The sNAG nanofibers preferably degrade within about 1 day, 2 days, 3 days, 5 days, 7 days (1 week), 8 days, 10 days, 12 days, 14 days (2 weeks), 17 days, 21 days (3 weeks), 25 days, 28 days (4 weeks), 30 days, 1 month, 35 days, 40 days, 45 days, 50 days, 55 days, 60 days, 2 months, 65 days, 70 days, 75 days, 80 days, 85 days, 90 days, 3 months, 95 days, 100 days or 4 months after administration or implantation into a patient.

In certain embodiments, the sNAG nanofibers do not cause a detectable foreign body reaction. A foreign body reaction, which may occur during wound healing, includes accumulation of exudate at the site of injury, infiltration of inflammatory cells to debride the area, and the formation of granulation tissue. The persistent presence of a foreign body can inhibit full healing. Rather than the resorption and reconstruction that occurs in wound healing, the foreign body reaction is characterized by the formation of foreign body giant cells, encapsulation of the foreign object, and chronic inflammation. Encapsulation refers to the firm, generally avascular collagen shell deposited around a foreign body, effectively isolating it from the host tissues. In one embodiment, treatment of a site (e.g., a wound or a site of a bacterial infection in a wound) with the sNAG nanofibers does not elicit a detectable foreign body reaction in 1 day, 3 days, 5 days, 7 days, 10 days or 14 days after treatment. In one such embodiment, treatment of a site (e.g., a wound) with the sNAG nanofibers does not elicit a foreign body encapsulations in 1 day, 3 days, 5 days, 7 days, 10 days or 14 days after treatment.

In some embodiments, the sNAG nanofibers (i) comprise fibers, wherein majority of the fibers are between about 1 and 15 microns in length, and (ii) (a) increase the metabolic rate of serum-starved EC in a MTT assay and/or do not rescue apoptosis of serum-starved EC in a trypan blue exclusion test, and (b) are non-reactive when tested in an intramuscular implantation test. In certain embodiments, the sNAG nanofibers (i) comprise fibers, wherein majority of the fibers are between about 1 and 12 microns in length, and (ii) (a) increase the metabolic rate of serum-starved EC in a MTT assay and/or do not rescue apoptosis of serum-starved EC in a trypan blue exclusion test, and (b) are non-reactive when tested in an intramuscular implantation test. In some embodiments, the sNAG nanofibers (i) comprise fibers, wherein majority of the fibers are between (or in the range of) 1 to 10 microns, 2 to 10 microns, 4 to 10 microns, 5 to 10 microns, or 5 to 15 microns in length, and (ii) (a) increase the metabolic rate of serum-starved EC in a MTT assay and/or do not rescue apoptosis of serum-starved EC in a trypan blue exclusion test, and (b) are non-reactive when tested in an intramuscular implantation test. In some embodiments, the sNAG nanofibers (i) comprise fibers, wherein majority of the fibers are between about 4 and 10 microns in length, and (ii) (a) increase the metabolic rate of serum-starved EC in a MTT assay and/or do not rescue apoptosis of serum-starved EC in a trypan blue exclusion test, and (b) are non-reactive when tested in an intramuscular implantation test. In certain embodiments, the sNAG nanofibers (i) comprise fibers, wherein majority of the fibers are between about 4 and 7 microns in length, and (ii) (a) increase the metabolic rate of serum-starved EC in a MTT assay and/or do not rescue apoptosis of serum-starved EC in a trypan blue exclusion test, and (b) are non-reactive when tested in an intramuscular implantation test.

In certain embodiments, the sNAG nanofibers do not have a direct effect on the growth or survival of bacteria, such as *S. aureus*, as determined by one skilled in the art. In other embodiments, sNAG nanofibers do not have a direct effect on the growth or survival of bacteria, such as *S. aureus*, as determined by the methods set forth in Section 6.2.2.5, infra. In some embodiments, the sNAG nanofibers do not have a direct effect in vitro on bacterial growth or survival. In one embodiment, the sNAG nanofibers do not have a direct effect (e.g., in vitro) on growth or survival of gram-negative bacteria. In another embodiment, the sNAG nanofibers do not have a direct effect (e.g., in vitro) on growth or survival of gram-positive bacteria. In yet another embodiment, the sNAG nanofibers do not have a direct effect (e.g., in vitro) on growth or survival of either gram-positive or gram-negative bacteria.

In some embodiments, the sNAG nanofibers (i) comprise fibers, wherein majority of the fibers are between (or in the range of) about 1 and 15 microns, 1 and 12 microns, 1 and 10 microns, 4 and 10 microns, 4 and 15 microns, 5 and 10 microns, 5 and 15 microns, or 4 and 7 microns in length, (ii) do not have an effect on bacterial growth or survival of *Staphylococcus aureus* bacterial cultures in vitro, and (iii) are non-reactive when tested in a biocompatibility test (e.g., an intramuscular implantation test).

In certain embodiments, the sNAG nanofibers induce a certain pattern of gene expression (RNA or protein expression as determined by, e.g., RT-PCR, microarray or ELISA) in a cell, tissue or organ treated with or exposed to a sNAG nanofiber composition. Specifically, in some embodiments, the sNAG nanofibers or a composition comprising the sNAG nanofibers induce expression of one or more defensin proteins, one or more defensin-like proteins, and/or one or more Toll-like receptors. In yet other embodiments, the sNAG nanofibers or a composition comprising the sNAG nanofibers induce expression of one or more proteins that are known to have an anti-bacterial effect.

In certain embodiments, the sNAG nanofibers or a composition comprising the sNAG nanofibers induce expression of one or more α-defensins (e.g., DEFA1 (i.e., α-defensin 1), DEFA1B, DEFA3, DEFA4, DEFA5, DEFA6), one or more β-defensins (e.g., DEFB1 (i.e., β-defensin 1), DEFB2, DEFB4, DEFB103A, DEFB104A, DEFB105B, DEFB107B, DEFB108B, DEFB110, DEFB112, DEFB114, DEFB118, DEFB119, DEFB123, DEFB124, DEFB125, DEFB126, DEFB127, DEFB128, DEFB129, DEFB131, DEFB136), and/or one or more θ-defensins (e.g., DEFT1P). In some embodiments, the sNAG nanofibers or a composition comprising the sNAG nanofibers induce expression of one or more of DEFA1, DEFA3, DEFA4, DEFA5, DEFB1, DEFB3, DEFB103A, DEFB104A, DEFB108B, DEFB112, DEFB114, DEFB118, DEFB119, DEFB123, DEFB124, DEFB125, DEFB126, DEFB128, DEFB129 and DEFB131. In certain embodiments, the sNAG nanofibers or a composition comprising the sNAG nanofibers induce expression of one or more Toll receptors (e.g., TLR1, TLR2, TLR3, TLR4, TLR5, TLR6, TLR7, TLR8, TLR9, TLR10, TLR11, and/or TLR12). In other embodiments, the sNAG nanofibers or a composition comprising the sNAG nanofibers induce expression of one or more of IL-1, CEACAM3, SPAG11, SIGIRR (IL1-like receptor), IRAK1, IRAK2, IRAK4, TBK1, TRAF6 and IKKi. In some embodiments, the sNAG nanofibers or a composition comprising the sNAG nanofibers induce expression of one or more of IRAK2, SIGIRR, TLR1, TLR2, TLR4, TLR7, TLR8, TLR10 and TRAF6. In one embodiment, the sNAG nanofibers or a composition comprising the sNAG nanofibers induce expression of at least one of the above-listed gene products.

In some embodiments, the sNAG nanofibers or a composition comprising the sNAG nanofibers induce expression of one or more of the above-listed genes in the amount equal to or more than about 0.25 fold, 0.5 fold, 1 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 12 fold, 15 fold or 20 fold as compared to the level of expression of the one or more of the above-listed genes in a cell, tissue or organ of a subject before treatment with the sNAG nanofibers (e.g., a known average level of expression of the one or more of the above-listed genes). In some embodiments, the sNAG nanofibers or a composition comprising the sNAG nanofibers induce expression of one or more of the above-listed genes in the amount equal to or more than about 10%, 25%, 50%, 75%, 100%, 125%, 150%, 175%, 200%, 225%, 250%, 275%, 300%, 350%, 400%, 450%, 500%, 550%, 600%, 650%, 700%, 750%, 800%, 900% or 1000% the level of expression of the one or more of the above-listed genes in a cell, tissue or organ of a subject before treatment with the sNAG nanofibers (e.g., a known average level of expression of the one or more of the above-listed genes).

In some embodiments, the sNAG nanofibers but not long poly-N-acetylglucosamine, chitin and/or chitosan induce expression of the one or more genes listed above, as determined by a method known to one skilled in the art, or described herein. In some of these embodiments, long poly-N-acetylglucosamine, chitin and/or chitosan do not induce expression of the one or more genes listed above or induce lower level (e.g., more than 1.25 fold, 1.5 fold, 2 fold, 2.5 fold, 3 fold, 3.5 fold, 4 fold, 4.5 fold, 5 fold, 6 fold, 7 fold, 8 fold, 9 fold, or 10 fold lower) of expression of the one or more genes listed above as compared to the level of expression of the one or more genes listed above induced by the sNAG nanofibers, as determined by a method known to one skilled in the art, or described herein.

In certain embodiments, the sNAG nanofibers or a composition comprising the sNAG nanofibers induce a gene expression profile that is consistent with, similar to, about the same as, or equivalent to one or more gene expression profiles demonstrated in Tables I, II, III, V, VIII and IX, Sections 6.2-6.5, infra. In some embodiments, the sNAG nanofibers or a composition comprising the sNAG nanofibers induce expression of one or more of the genes shown to be upregulated by sNAG treatment in Tables I, II, III, V, VIII and IX, Sections 6.2-6.5, infra. In some embodiments, the sNAG nanofibers or a composition comprising the sNAG nanofibers induce expression of the majority or all of the genes shown to be upregulated by sNAG treatment in Tables I, II, III, V, VIII and IX, Sections 6.2-6.5, infra. In some of these embodiments, gene expression levels are measured at 1 hour, 2 hours, 4 hours, 5 hours, 6 hours, 8 hours, 10 hours, 12 hours, 14 hours, 16 hours, 18 hours, 20 hours, 24 hours, 48 hours, 3 days or 5 days after treatment of a cell, tissue or organ with a sNAG nanofiber composition by a method known to one skilled in the art, or described herein.

In certain embodiments, the sNAG nanofibers or a composition comprising the sNAG nanofibers induce a gene expression profile that differs from the profile induced by long poly-N-acetylglucosamine polymers or fibers. In specific embodiments, a gene expression profile induced by the sNAG nanofibers is consistent with, similar to, about the same as, or equivalent to that shown in Tables I, II, III, V, VIII and IX, Sections 6.2-6.5, infra, whereas gene expression profile induced by long poly-N-acetylglucosamine polymers or fibers is consistent with, similar to, about the same with, or equivalent to that shown in Table VIII and/or IX, Section 6.5, infra. In other embodiments, the sNAG nanofibers or a composition comprising the sNAG nanofibers induce a gene expression profile that differs from the gene expression profile induced by chitin or chitosan.

In a specific embodiment, the sNAG nanofibers are obtained by irradiating poly-N-acetylglucosamine and/or a derivative thereof. See Section 5.1.1, infra, regarding poly-N-acetylglucosamine and derivatives thereof and Section 5.2, infra, regarding methods for producing the sNAG nanofibers using irradiation. Irradiation may be used to reduce the length of poly-N-acetylglucosamine fibers and/or poly-N-acetylglucosamine derivative fibers to form shortened poly-β-1→4-N-acetylglucosamine fibers and/or shortened poly-N-acetylglucosamine derivative fibers, i.e. sNAG nanofibers. Specifically, irradiation may be used to reduce the length and molecular weight of poly-N-acetylglucosamine or a derivative thereof without disturbing its microstructure. The infrared spectrum (IR) of sNAG nanofibers is similar to, about the same as, or equivalent to that of the non-irradiated poly-β-1→4-N-acetylgulcosamine or a derivative thereof.

In one embodiment, the sNAG nanofibers are not derived from chitin or chitosan. Whereas in another embodiment, the compositions described herein may be derived from chitin or chitosan, or the sNAG nanofibers may be derived from chitin or chitosan.

5.1.1 Poly-N-Acetylglucosamine and Derivatives Thereof

U.S. Pat. Nos. 5,622,834; 5,623,064; 5,624,679; 5,686,115; 5,858,350; 6,599,720; 6,686,342; 7,115,588 and U.S. Patent Pub. 2009/0117175 (each of which is incorporated herein by reference) describe the poly-N-acetylglucosamine and derivatives thereof, and methods of producing the same. In some embodiments, the poly-N-acetylglucosamine has a β-1→4 configuration. In other embodiments, the poly-N-acetylglucosamine has a α-1→4 configuration. The poly-N-acetylglucosamine and derivatives thereof may be in the form of a polymer or in the form of a fiber.

Poly-N-acetylglucosamine can, for example, be produced by, and may be purified from, microalgae, preferably diatoms. The diatoms which may be used as starting sources for the production of the poly-N-acetylglucosamine include, but are not limited to members of the *Coscinodiscus* genus, the *Cyclotella* genus, and the *Thalassiosira* genus. Poly-N-acetylglucosamine may be obtained from diatom cultures via a number of different methods, including the mechanical force method and chemical/biological method known in the art (see, e.g., U.S. Pat. Nos. 5,622,834; 5,623,064; 5,624,679; 5,686,115; 5,858,350; 6,599,720; 6,686,342; and 7,115,588, each of which is incorporated herein by reference in its entirety). In certain embodiments, the poly-N-acetylglucosamine is not derived from one or more of the following: a shell fish, a crustacean, an insect, a fungi or yeasts.

In one embodiment, poly-β-1→4-N-acetylglucosamine is derived from a process comprising a) treating a microalgae comprising a cell body and a poly-β-1→4-N-acetylglucosamine polymer fiber with a biological agent (such as hydrofluoric) capable of separating the N-acetylglucosamine polymer fiber from the cell body for a sufficient time so that the poly-β-1→4-N-acetylglucosamine polymer fiber is released from the cell body; b) segregating the poly-β-1→4-N-acetylglucosamine polymer fiber from the cell body; and c) removing contaminants from the segregated poly-β-1→4-N-acetylglucosamine polymer fiber, so that the poly-β-1→4-N-acetylglucosamine polymer is isolated and purified.

In other embodiments, the poly-β-1→4-N-acetylglucosamine may be derived from one or more of the following: a shell fish, a crustacean, an insect, a fungi or yeasts. In certain embodiments, the compositions described herein do not comprise chitin or chitosan.

One or more of the monosaccharide units of the poly-N-acetylglucosamine may be deacetylated. In certain embodiments, 1% to 5%, 5% to 10%, 5% to 15%, 20% to 30% or 25% to 30% of the poly-N-acetylglucosamine is deacetylated. In some embodiments, 1%, 5%, 10%, 15%, 20%, 25%, or 30% of the poly-N-acetylglucosamine is deacetylated. In other embodiments, less than 30%, 25%, 20%, 15%, 10%, 5%, 4%, 3%, 2% or 1% of the poly-N-acetylglucosamine is deacetylated. In some embodiments, equal to or more than 1%, 5%, 10%, 15%, 20%, 25%, 30%, 35%, 40%, 45%, 50%, 55%, 60%, 65%, 70%, 75%, 80%, 85%, 90%, 95% or 99%, or all (100%), of the poly-N-acetylglucosamine is deacetylated. In other embodiments, less than 1%, 5%, 10%, 15%, 20%, 25%, 30%, 35%, 40%, 45%, 50%, 55%, 60%, 65%, 70%, 75%, 80%, 85%, 90%, 95%, 99%, or 100% of the poly-N-acetylglucosamine is deacetylated.

In certain embodiments, a poly-N-acetylglucosamine composition comprises 70% to 80%, 75% to 80%, 75% to 85%, 85% to 95%, 90% to 95%, 90% to 99% or 95% to 100% of acetylated glucosamine (i.e., N-acetylglucosamine) monosaccharides. In some embodiments, a poly-N-acetylglucosamine composition comprises 70%, 75%, 80%, 85%, 90%, 95%, 97%, 98%, 99% or 100% of acetylated glucosamine (i.e., N-acetylglucosamine) monosaccharides. In other embodiments, a poly-N-acetylglucosamine composition comprises more than 70%, 75%, 80%, 85%, 90%, 95%, 97%, 98%, 99%, 99.5% or 99.9% of the acetylated glucosamine. In some embodiments, a poly-N-acetylglucosamine composition comprises equal to or more than 1%, 5%, 10%, 15%, 20%, 25%, 30%, 35%, 40%, 45%, 50%, 55%, 60%, 65%, 70%, 75%, 80%, 85%, 90%, 95%, 97%, 98%, or 99%, or all (100%), of the acetylated glucosamine. In other embodiments, a poly-N-acetylglucosamine composition comprises less than 1%, 5%, 10%, 15%, 20%, 25%, 30%, 35%, 40%, 45%, 50%, 55%, 60%, 65%, 70%, 75%, 80%, 85%, 90%, 95%, 99%, or 100% of the acetylated glucosamine.

In some embodiments, a poly-N-acetylglucosamine composition comprises at least one glucosamine monosaccharide, and may further comprise at least 10%, 20%, 30%, 40%, 50%, 60%, 70%, 80%, 90%, 95% or 99% of N-acetylglucosamine monosaccharides. In other embodiments, a poly-N-acetylglucosamine composition comprises at least one N-acetylglucosamine monosaccharide, and may further comprise at least 10%, 20%, 30%, 40%, 50%, 60%, 70%, 80%, 90%, 95% or 99% of glucosamine monosaccharides.

Derivatives of poly-N-acetylglucosamine may also be used in a composition described herein. Derivatives of poly-N-acetylglucosamine and methods of making such derivatives are described in U.S. Pat. No. 5,623,064 (see, e.g., Section 5.4), which is incorporated by reference herein in its entirety. Derivatives of poly-N-acetylglucosamine may include, but are not limited to, partially or completely deacetylated poly-N-acetylglucosamine, or its deacetylated derivatives. Further, poly-N-acetylglucosamine may be derivatized by being sulfated, phosphorylated and/or nitrated. Poly-N-acetylglucosamine derivatives include, e.g., sulfated poly-N-acetylglucosamine derivatives, phosphorylated poly-N-acetylglucosamine derivatives, or nitrated poly-N-acetylglucosamine derivatives. Additionally, one or more of the monosaccharide units of the poly-N-acetylglucosamine may contain one or more sulfonyl groups one or more O-acyl groups. In addition, one or more of the monosaccharides of the deacetylated poly-N-acetylglucosamine may contain an N-acyl group. One or more of the monosaccharides of the poly-N-acetylglucosamine or of its deacetylated derivative, may contain an O-alkyl group. One or more of the monosaccharide units of the poly-N-acetylglucosamine may be an alkali derivative. One or more of the monosaccharide units of the deacetylated derivative of poly-N-acetylglucosamine may contain an N-alkyl group. One or more of the monosaccharide units of the deacetylated derivative of poly-N-acetylglucosamine may contain at least one deoxyhalogen derivative. One or more of the monosaccharide units of the deacetylated derivative of poly-N-acetylglucosamine may form a salt. One or more of the monosaccharide units of the deacetylated derivative of poly-N-acetylglucosamine may form a metal chelate. In a specific embodiment, the metal is zinc. One or more of the monosaccharide units of the deacetylated derivative of poly-N-acetylglucosamine may contain an N-alkylidene or an N-arylidene group. In one embodiment, the derivative is an acetate derivative. In another embodiment, the derivative is not an acetate derivative. In one embodiment the poly-N-acetylglucosamine or deacetylated poly-N-acetylglucosamine is derivatized with lactic acid. Wherein, in another embodiment, the derivative is not derivatized with lactic acid.

5.2 Methods of Producing sNAG Nanofibers

The poly-N-acetylglucosamine polymers or fibers, and any derivatives of poly-N-acetylglucosamine polymers or fibers described above, can be irradiated as dry polymers or fibers or polymer or fiber membranes. Alternatively, poly-N-acetylglucosamine polymers or fibers, and any derivatives of poly-N-acetylglucosamine polymers or fibers described above, can be irradiated when wet. The methods of making sNAG nanofibers by irradiation and the sNAG nanofibers so produced have been described in U.S. Patent Pub. No. 2009/0117175, which is incorporated by reference herein in its entirety.

In certain embodiments, the poly-N-acetylglucosamine polymers or fibers are formulated into a suspension/slurry or wet cake for irradiation. Irradiation can be performed prior to, concurrently with or following the formulation of the polymers or fibers into its final formulation, such as a dressing. Generally, the polymer or fiber content of suspensions/slurries and wet cakes can vary, for example from about 0.5 mg to about 50 mg of polymer or fiber per 1 ml of distilled water are used for slurries and from about 50 mg to about 1000 mg of polymer or fiber per 1 ml of distilled water are use for wet cake formulations. The polymer or fiber may first be lyophilized, frozen in liquid nitrogen, and pulverized, to make it more susceptible to forming a suspension/slurry or wet cake. Also, the suspensions/slurries can be filtered to remove water such that a wet cake is formed. In certain aspects, the polymer or fiber is irradiated as a suspension comprising about 0.5 mg, 1 mg, 2 mg, 3 mg, 4 mg, 5 mg, 6 mg, 7 mg, 8 mg, 9 mg, 10 mg, 12 mg, 15 mg, 18 mg, 20 mg, 25 mg or 50 mg of polymer or fiber per ml of distilled water, or any range in between the foregoing embodiments (e.g., 1-10 mg/ml, 5-15 mg/ml, 2-8 mg/ml, 20-50 mg/ml, etc.). In other aspects, the polymer or fiber is irradiated as a wet cake, comprising about 50-1,000 mg polymer or fiber per 1 ml of distilled water. In specific embodiments, the wet cake comprises about 50, 100, 200, 300, 400, 500, 600, 700, 800, 900 or 1000 mg of polymer or fiber per 1 ml distilled water, or any range in between (e.g., 100-500 mg/ml, 300-600 mg/ml, 50-1000 mg/ml, etc.).

The irradiation is preferably in the form of gamma radiation, e-beam radiation, or x-rays. Two sources of irradiation are preferred: radioactive nuclides and electricity. In specific embodiment, the radioactive nuclides are cobalt-60 and cesium-137. Both of these nuclides emit gamma rays, which are photons containing no mass. The gamma rays have energies from 0.66 to 1.3 MeV. Using electricity, electrons are generated and accelerated to energies up to 10 MeV or higher. When irradiating polymers or fibers to reduce their size, a consideration to take into account is that the depth of penetration of materials with densities similar to water by 10 MeV electrons is limited to about 3.7 cm with one-sided exposure or about 8.6 cm with two-sided exposure. Depth of penetration decreases at lower electron energies. Electron energy can be converted to x-rays by placing a metal (usually tungsten or tantalum) target in the electron beam path. Conversion to x-rays is limited to electrons with energies up to 5 MeV. X-rays are photons with no mass and can penetrate polymers or fibers similar to gamma rays. There is only about 8% efficiency in the conversion of electron energy to x-ray energy. High powered electron beam machines are needed in x-ray production facilities to account for the low conversion efficiency.

In a specific embodiment, the irradiation is gamma irradiation.

The absorbed dose of radiation is the energy absorbed per unit weight of product, measured in gray (gy) or kilogray (kgy). For dried polymers or fibers, the preferred absorbed dose is about 500-2,000 kgy of radiation, most preferably about 750-1,250 kgy or about 900-1,100 kgy of radiation. For wet polymers or fibers, the preferred absorbed dose is about 100-500 kgy of radiation, most preferably about 150-250 kgy or about 200-250 kgy of radiation.

The dose of radiation can be described in terms of its effect on the length of the polymers or fibers. In specific embodiments, the dose of radiation used preferably reduces the length of the polymer or fiber by anywhere from about 10% to 90% of the starting length of the polymer or fiber, respectively. In specific embodiments, the average length is reduced by about 10%, by about 20%, by about 30%, by about 40%, by about 50%, by about 60%, by about 70%, by about 80%, or by about 90%, or any range in between (e.g., 20-40%, 30-70%, and so on and so forth). Alternatively, the dose of radiation used preferably reduces the length of the polymer or fiber to anywhere from 1 to 100 microns. In specific embodiments, and depending on the starting fiber length, the average length of the polymer or fiber is reduced to less than about 15 microns, less than about 14 microns, less than about 13 microns, less than about 12 microns, less than about 11 microns, less than about 10 microns, less than about 8 microns, less than about 7 microns, less than about 5 microns, less than about 4 microns, less than about 3 microns, less than about 2 microns, or less than 1 micron. In certain embodiments, the length of the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the polymers or fibers is reduced to no greater than about 20 microns, no greater than about 15 microns, no greater than about 12 microns, no greater than about 10 microns, no greater than about 8 microns, no greater than about 7 microns, or no greater than about 5 microns. In certain embodiments, irradiation of the polymers or fibers reduces the length of the majority (and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the fibers to anywhere between about 1 to 20 microns, between about 1 to 15 microns, between about 2 to 15 microns, between about 1 to 12 microns, between about 2 to 12 microns, between about 1 to 10 microns, between about 2 to 10 microns, between about 1 to 8 microns, between about 2 to 8 microns, between about 1 to 7 microns, between about 2 to 7 microns, between about 3 to 8 microns, between about 4 to 10 microns, between about 4 to 7 microns, between about 5 to 10 microns, between about 1 to 5 microns, between about 2 to 5 microns, between about 3 to 5 microns, between about 4 to 10 microns, or any ranges between the foregoing lengths, which are also encompassed.

The dose of radiation can also be described in terms of its effect on the molecular weight of the polymer or fiber. In specific embodiments, the dose of radiation used preferably reduces the molecular weight of the polymer or fiber by anywhere from about 10% to 90% of the starting weight of the polymer or fiber. In specific embodiments, the average molecular weight is reduced by about 10%, by about 20%, by about 30%, by about 40%, by about 50%, by about 60%, by about 70%, by about 80%, or by about 90%, or any range in between (e.g., 20-40%, 30-70%, and so on and so forth). Alternatively, the dose of radiation used preferably reduces the molecular weight of the polymer or fiber to anywhere from 1,000 to 1,000,000 daltons. In specific embodiments, and depending on the starting molecular weight, the average molecular weight of the polymer or fiber is reduced to less than 1,000,000 daltons, less than 750,000 daltons, less than 500,000 daltons, less than 300,000 daltons, less than 200,000 daltons, less than 100,000 daltons, less than 90,000 daltons, less than 80,000 daltons, less than 70,000 daltons, less than 60,000 daltons, less than 50,000 daltons, less than 25,000 daltons, less than 10,000 daltons, or less than 5,000 daltons. In certain embodiments, the average molecular weight is reduced to no less than 500 daltons, no less than 1,000 daltons, no less than 2,000 daltons, no less 3,500 daltons, no less than 5,000 daltons, no less than 7,500 daltons, no less than 10,000 daltons, no less than 25,000 daltons, no less than 50,000 daltons, no less than 60,000 daltons or no less than 100,000 daltons. Any ranges between the foregoing average molecular weights are also encompassed; for example, in certain embodiments, irradiation of the polymer or fiber reduces the average molecular weight to anywhere between 10,000 to 100,000 daltons, between 1,000 and 25,000 daltons, between 50,000 and 500,000 daltons, between 25,000 and 100,000 daltons, between 30,000 and 90,000 daltons, between about 40,000 and 80,000 daltons, between about 25,000 and 75,000 daltons, between about 50,000 and 70,000 daltons, or between about 55,000 and 65,000 daltons and so on and so forth. In certain embodiments, irradiation of the polymers or fibers reduces the molecular weight of the majority and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the fibers to anywhere between about 20,000 and 100,000 daltons, about 25,000 and 75,000 daltons, about 30,000 and 90,000 daltons, about 40,000 and 80,000 daltons, about 50,000 and 70,000 daltons, or about 55,000 and 65,000 daltons. In certain embodiments, irradiation of the polymers or fibers reduces the molecular weight of the majority and in certain embodiments, at least 60%, 70%, 80%, 90%, 95%, 98%, 99%, 99.5%, 99.8%, 99.9%, or 100%, or between 55% to 65%, 55% to 75%, 65% to 75%, 75% to 85%, 75% to 90%, 80% to 95%, 90% to 95%, or 95% to 99%) of the fibers to about 60,000 daltons.

Following irradiation, slurries can be filtered and dried, and wet cakes can be dried, to form compositions (e.g., dressings and other compositions described herein) that are useful in the practice of the invention.

5.3 Compositions Comprising sNAG Nanofibers

The sNAG nanofibers may be formulated in a variety of compositions for topical administration as described herein.

A composition comprising the sNAG nanofibers may be formulated as a cream, a membrane, a film, a liquid solution, a suspension (e.g., a thick suspension), a powder, a paste, an ointment, a suppository, a gelatinious composition, an aerosol, a gel, or a spray. In one embodiment, a composition comprising the sNAG nanofibers is formulated as an ultrathin membrane. In some embodiments, a composition comprising the sNAG nanofibers is formulated as a dressing, a mat, or a bandage. In particular embodiments, compositions comprising sNAG nanofibers are not solid or barrier-forming. Solid formulations suitable for solution in, or suspension in, liquids prior to administration are also contemplated. It is also possible that such compositions are incorporated in or coated on implantable devices, such as orthopedic implants (for hip, knee, shoulder; pins, screws, etc.), cardiovascular implants (stents, catheters, etc.) and the like where the antibacterial activity would be of benefit.

A composition comprising the sNAG nanofibers may include one or more of pharmaceutically acceptable excipients. Suitable excipients may include water, saline, salt solution, dextrose, glycerol, ethanol and the like, or combinations thereof. Suitable excipients also include starch, glucose, lactose, sucrose, gelatin, malt, rice, flour, chalk, silica gel, sodium stearate, glycerol monostearate, oil (including those of petroleum, animal, vegetable or synthetic origin, such as peanut oil, soybean oil, mineral oil, sesame oil and the like), talc, sodium chloride, dried skim milk, propylene, glycol and the like. In addition, a composition comprising the sNAG nanofibers may include one or more of wetting agents, emulsifying agents, pH buffering agents, and other agents. The sNAG nanofiber compositions may also be incorporated in a physiologically acceptable carrier, for example in a physiologically acceptable carrier suitable for topical application. The term "pharmaceutically acceptable" means approved by a regulatory agency of the Federal or a state government or listed in the U.S. Pharmacopeia or other generally recognized pharmacopeia for use in animals, and more particularly in humans. Examples of suitable pharmaceutical carriers are described in "Remington's Pharmaceutical Sciences" by E. W. Martin.

The final amount of the sNAG nanofibers in a composition may vary. For example, the amount of the sNAG nanofibers in a composition (e.g., prepared for administration to a patient) may be greater than or equal to about 50%, about 60%, about 70%, about 75%, about 80%, about 85%, about 90%, about 95%, about 98%, or about 99% weight by volume. In one embodiment, the amount of the sNAG nanofibers in a composition is about 95%, about 98%, about 99, or about 100%. Also, the amount of the sNAG nanofibers in a composition (e.g., prepared for administration to a patient) may be about 50%-100%, about 60%-100%, about 70%-100%, about 75%-100%, about 80%-100%, about 90%-100%, about 95%-100%, about 70%-95%, about 75%-95%, about 80%-95%, about 90%-95%, about 70%-90%, about 75%-90%, or about 80%-90% weight/volume. A composition may comprise more than 30%, 40%, 50%, 60%, 70%, 75%, 80%, 90%, 95% or 99% solution of the sNAG nanofibers.

A sNAG nanofiber composition may be formulated into a wound dressing. In certain embodiments, a sNAG nanofiber composition is formulated as a wound dressing in the form of a barrier, a membrane, or a film. Alternatively, a sNAG nanofiber composition may be added to dressing backings, such as barriers, membranes, or films. A barrier, membrane, or film can be supplied in a variety of standard sizes, which can be further cut and sized to the area being treated. The backing can be a conventional dressing material, such as a bandage or gauze to which a polymer or fiber is added or coated on, prior to application to the patient. Alternatively, the sNAG nanofibers can be formulated as a barrier, membrane, or film made out of strings, microbeads, microspheres, or microfibrils, or the composition can be formulated as a barrier-forming mat. In certain embodiments, at least 75%, at least 85%, at least 90%, or at least 95% of a dressing is composed of the sNAG nanofibers. In certain aspects, a dressing does not contain a conventional dressing material such as a gauze or bandage. In such embodiments, the sNAG nanofiber itself is formulated as a wound dressing.

A composition comprising the sNAG nanofibers may further comprise any suitable natural or synthetic polymers or fibers. Examples of suitable polymers or fibers include cellulose polymers, xanthan, polyaramides, polyamides, polyimides, polyamide/imides, polyamidehydrazides, polyhydrazides, polyimidazoles, polybenzoxazoles, polyester/amide, polyester/imide, polycarbonate/amides, polycarbonate/imides, polysulfone/amides, polysulfone imides, and the like, copolymers and blends thereof. Other suitable classes of polymers or fibers include polyvinyledene fluorides and polyacrylonitriles. Examples of these polymers or fibers include those described in U.S. Pat. Nos. RE 30,351; 4,705, 540, 4,717,393; 4,717,394; 4,912,197; 4,838,900; 4,935, 490; 4,851,505; 4,880,442; 4,863,496; 4,961,539; and European Patent Application 0 219 878, all of which are incorporated by reference. The polymers or fibers can include at least one of either of cellulose polymers, polyamides, polyaramides, polyamide/imides or polyimides. In certain embodiments, the polymers or fibers include polyaramides, polyester, urethan and polytetrafluoroethylene. In one embodiment, the compositions described herein comprise more than one type of polymer (e.g., the sNAG nanofiber and cellulose).

In certain aspects, the sNAG nanofiber is the only active ingredient in a composition.

In other embodiments, a composition comprises one or more additional active ingredients, e.g., an anti-viral agent, an anti-fungal agent, an anti-yeast agent, a chemotherapeutic agent or any other agent. In some embodiments, the additional active ingredient is one or more of an anti-viral agent, an anti-fungal agent, an anti-yeast agent, a defensin peptide, a defensin-like peptide, or a Toll-receptor-like peptide), or a growth factor. In specific embodiments, the additional active ingredient is a growth factor such as one or more of PDGF-AA, PDGF-AB, PDGF-BB, PDGF-CC, PDGF-DD, FGF-1, FGF-2, FGF-5, FGF-7, FGF-10, EGF, TGF-α, (HB-EGF), amphiregulin, epiregulin, betacellulin, neuregulins, epigen, VEGF-A, VEGF-B, VEGF-C, VEGF-D, VEGF-E, placenta growth factor (PLGF), angiopoietin-1, angiopoietin-2, IGF-I, IGF-II, hepatocyte growth factor (HGF), and macrophage-stimulating protein (MSP). In other embodiments, the additional active ingredient is an agent that boost the immune system, a pain relief agent, or a fever relief agent.

In certain embodiments, the additional active ingredient is an anti-viral agent. Any anti-viral agents well-known to one of skill in the art may be used in a sNAG nanofiber composition. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, peramivir, rimantadine, saquinavir, indinavir, ritonavir, alpha-interferons and other interferons, AZT, zanamivir (Relenza®), and oseltamivir (Tamiflu®). Other anti-viral agents include influenza virus vaccines, e.g., Fluarix® (GlaxoSmithKline), FluMist® (MedImmune Vaccines), Fluvirin® (Chiron Corporation), Flulaval® (GlaxoSmithKline), Afluria® (CSL Biotherapies Inc.), Agriflu® (Novartis) or Fluzone® (Aventis Pasteur).

In certain embodiments, the additional active ingredient is an anti-cancer agent. In a specific embodiment, the anti-cancer agent is a chemotherapeutic agent. Any anti-cancer agents known to one of skill in the art may be used in a sNAG nanofiber composition. Exemplary anti-cancer agents include: acivicin; anthracyclin; anthramycin; azacitidine (Vidaza); bisphosphonates (e.g., pamidronate (Aredria), sodium clondronate (Bonefos), zoledronic acid (Zometa), alendronate (Fosamax), etidronate, ibandomate, cimadronate, risedromate, and tiludromate); carboplatin; chlorambucil; cisplatin; cytarabine (Ara-C); daunorubicin hydrochloride; decitabine (Dacogen); demethylation agents, docetaxel; doxorubicin; EphA2 inhibitors; etoposide; fazarabine; fluorouracil; gemcitabine; histone deacetylase inhibitors (HDACs); interleukin II (including recombinant interleukin II, or rIL2), interferon alpha; interferon beta; interferon gamma; lenalidomide (Revlimid); anti-CD2 antibodies (e.g., siplizumab (MedImmune Inc.; International Publication No. WO 02/098370, which is incorporated herein by reference in its entirety)); melphalan; methotrexate; mitomycin; oxaliplatin; paclitaxel; puromycin; riboprine; spiroplatin; tegafur; teniposide; vinblastine sulfate; vincristine sulfate; vorozole; zeniplatin; zinostatin; and zorubicin hydrochloride.

Other examples of additional active ingredients that may be used in a sNAG nanofiber composition include, but are not limited to angiogenesis inhibitors; antisense oligonucleotides; apoptosis gene modulators; apoptosis regulators; BCR/ABL antagonists; beta lactam derivatives; casein kinase inhibitors (ICOS); estrogen agonists; estrogen antagonists; glutathione inhibitors; HMG CoA reductase inhibitors; immunostimulant peptides; insulin-like growth factor-1 receptor inhibitor; interferon agonists; interferons; interleukins; lipophilic platinum compounds; matrilysin inhibitors; matrix metalloproteinase inhibitors; mismatched double stranded RNA; nitric oxide modulators; oligonucleotides; platinum compounds; protein kinase C inhibitors, protein tyrosine phosphatase inhibitors; purine nucleoside phosphorylase inhibitors; raf antagonists; signal transduction inhibitors; signal transduction modulators; translation inhibitors; tyrosine kinase inhibitors; and urokinase receptor antagonists.

In some embodiments, the additional active ingredient is an anti-angiogenic agent. Non-limiting examples of anti-angiogenic agents include proteins, polypeptides, peptides, conjugates, antibodies (e.g., human, humanized, chimeric, monoclonal, polyclonal, Fvs, ScFvs, Fab fragments, F(ab)2 fragments, and antigen-binding fragments thereof) such as antibodies that specifically bind to TNF-α, nucleic acid molecules (e.g., antisense molecules or triple helices), organic molecules, inorganic molecules, and small molecules that reduce or inhibit angiogenesis. Other examples of anti-angiogenic agents can be found, e.g., in U.S. Publication No. 2005/0002934 A1 at paragraphs 277-282, which is incorporated by reference in its entirety. In other embodiments, the additional active ingredient is not an anti-angiogenic agent.

In some embodiments, the additional active ingredient is an anti-inflammatory agent. Non-limiting examples of anti-inflammatory agents include non-steroidal anti-inflammatory drugs (NSAIDs) (e.g., celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™)), steroidal anti-inflammatory drugs (e.g., glucocorticoids, dexamethasone (DECADRON™), corticosteroids (e.g., methylprednisolone (MEDROL™)), cortisone, hydrocortisone, prednisone (PREDNISONE™ and DELTASONE™), and prednisolone (PRELONE™ and PEDIAPRED™)), anticholinergics (e.g., atropine sulfate, atropine methylnitrate, and ipratropium bromide (ATROVENT™)), beta2-agonists (e.g., abuterol (VENTOLIN™ and PROVENTIL™), bitolterol (TORNALATE™), levalbuterol (XOPONEX™), metaproterenol (ALUPENT™), pirbuterol (MAXAIR™), terbutlaine (BRETHAIRE™ and BRETHINE™), albuterol (PROVENTIL™, REPETABS™, and VOLMAX™), formoterol (FORADIL AEROLIZER™), and salmeterol (SEREVENT™ and SEREVENT DISKUS™)), and methylxanthines (e.g., theophylline (UNIPHYL™, THEO-DUR™, SLO-BID™, AND TEHO-42™)).

In certain embodiments, the additional active ingredient is an alkylating agent, a nitrosourea, an antimetabolite, an anthracyclin, a topoisomerase II inhibitor, or a mitotic inhibitor. Alkylating agents include, but are not limited to, busulfan, cisplatin, carboplatin, cholormbucil, cyclophosphamide, ifosfamide, decarbazine, mechlorethamine, mephalen, and themozolomide. Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclins include but are not limited to daunorubicin, doxorubicin, epirubicin, idarubicin, and mitoxantrone. Topoisomerase II inhibitors include, but are not limited to, topotecan, irinotecan, etopiside (VP-16), and teniposide. Mitotic inhibitors include, but are not limited to taxanes (paclitaxel, docetaxel), and the vinca alkaloids (vinblastine, vincristine, and vinorelbine).

A sNAG nanofiber composition may contain collagen, although in certain aspects a sNAG nanofiber composition does not contain collagen.

In certain embodiments, a sNAG nanofiber composition does not comprise any additional therapy. In certain embodiments, a sNAG nanofiber composition does not comprise any additional anti-viral agent, anti-cancer agent, anti-fungal agent, anti-yeast agent, anti-inflammatory agent, chemotherapeutic agent, anti-angiogenic agent, a defensin peptide, a defensin-like peptide, a Toll-receptor-like peptide, or a growth factor.

In some embodiments, the additional active ingredient is not an anti-bacterial agent (e.g., an antibiotic, a defensin peptide, a defensin-like peptide, or a Toll-receptor-like peptide), or a growth factor. In specific embodiments, the additional active ingredient is not a growth factor, such as PDGF-AA, PDGF-AB, PDGF-BB, PDGF-CC, PDGF-DD, FGF-1, FGF-2, FGF-5, FGF-7, FGF-10, EGF, TGF-α, (HB-EGF), amphiregulin, epiregulin, betacellulin, neuregulins, epigen, VEGF-A, VEGF-B, VEGF-C, VEGF-D, VEGF-E, placenta growth factor (PLGF), angiopoietin-1, angiopoietin-2, IGF-I, IGF-II, hepatocyte growth factor (HGF), and macrophage-stimulating protein (MSP). In certain embodiments, the additional active ingredient is not an agents that boost the immune system, a pain relief agent, or a fever relief agent.

In certain embodiments, the additional active ingredient is not an antibiotic from one of the following classes of antibiotics: microlides (e.g., erythromycin, azithromycin), aminoglycosides (e.g., amikacin, gentamicin, neomycin, streptomycin), cephalosporins (e.g., cefadroxil, cefaclor, cefotaxime, cefepime), fluoroquinolones (e.g., ciprofloxacin, levofloxacin), penicillins (e.g., penicillin, ampicillin, amoxicillin), tetracyclines (e.g., tetracycline, doxycycline), and carbapenems (e.g., meropenem, imipenem). In some embodiments, the additional active ingredient is not vancomycin, sulfa drug (e.g., co-trimoxazole/trimethoprim-sulfamethoxazole), tetracycline (e.g., doxycycline, minocycline), clindamycin, oxazolidinones (e.g., linezolid), daptomycin, teicoplanin, quinupristin/dalfopristin (synercid), tigecycline, allicin, bacitracin, nitrofurantoin, hydrogen peroxide, novobiocin, netilmicin, methylglyoxal, bee defensin-1, tobramycin, chlorhexidine digluconate, chlorhexidine gluconate, levofloxacin, zinc, and/or silver.

In other aspects, a sNAG nanofiber composition does not comprise a significant amount of protein material. In specific embodiments, the protein content of a sNAG nanofiber composition is no greater than 0.1%, 0.5% or 1% by weight. In other embodiments, the protein content of the composition is undetectable by Coomassie staining.

In one embodiment, zinc is also included in a sNAG nanofiber composition. In addition to its antimicrobial properties, zinc also plays a role in wound healing (see Andrews et al., 1999, Adv Wound Care 12:137-8). The zinc is preferably added in the form of a salt, such as zinc oxide, zinc sulphate, zinc acetate or zinc gluconate.

5.4 Prophylactic and Therapeutic Uses

In certain embodiments, the compositions described herein can be used to prevent and/or treat infections and/or diseases for which an increase in defensin production and/or secretion is beneficial. Such diseases may be the result of a defensin deficiency or may derive benefit from increased presence of defensins.

In a specific embodiment, the compositions described herein are used to treat and/or prevent a disease which is associated with no or low level of expression of one or more defensin peptides; or a mutation/deletion/low gene copy number ("GCN") in a gene or genes encoding one or more of defensin peptides. Exemplary defensin genes that may be mutated/deleted/have low GCN/not expressed or whose expression may be low or altered include any of the known α-defensins (e.g., DEFA1, DEFA1B, DEFA3, DEFA4, DEFA5, DEFA6), any of the known β-defensins (e.g., DEFB1, DEFB2, DEFB4, DEFB103A, DEFB104A, DEFB105B, DEFB107B, DEFB108B, DEFB110, DEFB112, DEFB114, DEFB118, DEFB119, DEFB123, DEFB124, DEFB125, DEFB126, DEFB127, DEFB128, DEFB129, DEFB131, DEFB136), and any of the known θ-defensins (e.g., DEFT1P). In some embodiment, the compositions described herein are used to treat or prevent a disease or infection which is associated with no, low, or altered level of expression of or a mutation/deletion/low GCN of one or more of the above-listed genes. In a specific embodiment, the compositions described herein are used to treat or prevent a disease or infection which is associated with no, low, or altered level of expression of or a mutation/deletion/low GCN of one or more of DEFA1, DEFA3, DEFA4, DEFA5, DEFB1, DEFB3, DEFB103A, DEFB104A, DEFB108B, DEFB112, DEFB114, DEFB118, DEFB119, DEFB123, DEFB124, DEFB125, DEFB126, DEFB128, DEFB129 and DEFB131. In some embodiments, the compositions described herein are used to treat or prevent a disease or infection which is associated with no, low, or altered level of expression of or a mutation/deletion/low GCN of one or more Toll receptors (e.g., TLR1, TLR2, TLR3, TLR4, TLR5, TLR6, TLR7, TLR8, TLR9, TLR10, TLR11, and/or TLR12). In yet other embodiments, the compositions described herein are used to treat or prevent a disease or infection which is associated with no, low, or altered level of expression of or a mutation/deletion/low GCN of one or more of IL-1, CEACAM3, SPAG11, SIGIRR (IL1-like receptor), IRAK1, IRAK2, IRAK4, TBK1, TRAF6 and IKKi. In some embodiments, the compositions described herein are used to treat or prevent a disease or infection which is associated with no, low, or altered level of expression of or a mutation/deletion/low GCN of one or more of IRAK2, SIGIRR, TLR1, TLR2, TLR4, TLR7, TLR8, TLR10 and TRAF6.

A low level of expression of a gene is a level that is lower (e.g., more than 1.25 fold, 1.5 fold, 2 fold, 2.5 fold, 3 fold, 3.5 fold, 4 fold, 4.5 fold, 5 fold, 6 fold, 7 fold, 8 fold, 9 fold, 10 fold lower) than the "normal" level of expression. An altered level of expression of a gene is a level that differs (e.g., by more than 20%, 25%, 30%, 50%, 75%, 100%, 150%, 200%, 250%, 300%) from the "normal" level of expression. In certain embodiments, the expression of one or more defensin genes (e.g., above-listed defensin genes) in a patient to be administered a composition described herein may be less than less than 90%, less than 75%, less than 60%, less than 50%, less than 30% or less than 20% of the "normal" expression of one or more defensin genes. Wherein the "normal" expression of one or more defensin genes is: (i) the average expression level known to be found in subjects not displaying symptoms or not diagnosed with the disease or infection to be treated; (ii) the average expression level detected in three, five, ten, twenty, twenty-five, fifty or more subjects not displaying symptoms or not diagnosed with the disease or infection to be treated; and/or (iii) the level of expression detected in a patient to be administered a composition described herein before the onset of the disease or infection.

In another specific embodiment, the compositions described herein are used to treat a solid tumor cancer. Without being bound by any mechanism of action, the ability of sNAG nanofibers to induce alpha and beta defensins (e.g., beta-defensin 1) may contribute to the anti-cancer activity of the sNAG nanofibers. Human alpha and beta defensins (e.g., beta-defensin 1) have been shown to have anti-cancer activity. Exemplary solid tumor cancers that can be treated with the compositions described herein include, without limitation, bone and connective tissue sarcomas, brain cancer, breast cancer, ovarian cancer, kidney cancer, pancreatic cancer, esophageal cancer, stomach cancer, ovarian cancer, lung cancer (e.g., small cell lung cancer (SCLC), non-small cell lung cancer (NSCLC), throat cancer, and mesothelioma), liver cancer, and prostate cancer. In some embodiments, the compositions described herein are used to treat a cancer caused by or associated with a viral infection. In a specific embodiment, the compositions described herein are used to treat Kaposi's sarcoma. In certain embodiments, treatment of a subject having a solid tumor by administration of a composition described herein results in one or more of the following: reduction in the size of the solid tumor; prevention of the metastasis of the solid tumor; prevention of the recurrence of the solid tumor; reduction in the duration and/or severity of one or more symptoms associated with the solid tumor; reduction in the number of symptoms associated with the solid tumor; prevention of the increase in the size of the solid tumor; reduction/inhibition of proliferation of cancer cells of the solid tumor; reduction in organ failure associated with the solid tumor; reduction of the incidence of hospitalization of the subject; reduction of the hospitalization length of the subject; an increase the survival of the subject; and/or enhancement or improvement of the prophylactic or therapeutic effect(s) of another therapy in the subject.

In another specific embodiment, the compositions described herein are used to treat skin cancer. Exemplary skin cancers that can be treated with the compositions described herein include, without limitation, melanoma, basal cell carcinoma, and squamous cell carcinoma. In certain embodiments, treatment of a subject having a skin cancer by administration of a composition described herein results in one or more of the following: reduction in the size of the skin cancer; prevention of the metastasis of the skin cancer; prevention of the recurrence of the skin cancer; reduction in the duration and/or severity of one or more symptoms associated with the skin cancer; reduction in the number of symptoms associated with the skin cancer; reduction in organ failure associated with the skin cancer; reduction of the incidence of hospitalization of the subject; reduction of the hospitalization length of the subject; an increase the survival of the subject; and/or enhancement or improvement of the prophylactic or therapeutic effect(s) of another therapy in the subject.

In another specific embodiment, the compositions described herein are used to treat inflammatory bowel disease (IBD). Without being bound by any mechanism of action, the ability of sNAG nanofibers to induce alpha and beta defensins may contribute to the anti-IBD activity of the sNAG nanofibers. Alpha and beta defensins have been shown to have anti-IBD activity. IBD includes, but is not limited to, Crohn's disease and ulcerative colitis. In certain embodiments, treatment of a subject having IBD by administration of a composition described herein results in one or more of the following: prevention of the recurrence of IBD;

reduction in the duration and/or severity of one or more symptoms associated with IBD; reduction in the number of symptoms associated with the IBD; reduction of the incidence of hospitalization of the subject; reduction of the hospitalization length of the subject; and/or enhancement or improvement of the prophylactic or therapeutic effect(s) of another therapy in the subject. Some of the symptoms of IBD include abdominal pain, vomiting, diarrhea, rectal bleeding, severe internal cramps/muscle spasms in the region of the pelvis, weight loss and various associated complaints or diseases like arthritis, pyoderma gangrenosum, and/or primary sclerosing cholangitis. In some embodiments, the compositions described herein prevent the onset or development of one or more of the above-listed symptoms or other symptoms known in the art, or reduce duration and/or severity of one or more of these symptoms. In one embodiment, the compositions described herein are used to treat ulcerative colitis. Symptoms of ulcerative colitis may include above listed symptoms of IBD, and may also include defecation often mucus-like and with blood, tenesmus, and/or fever. Example 9, infra, shows that sNAG nanofibers are effective to treat IBD based on the data obtained in an animal model of IBD. A composition comprising sNAG nanofibers that can be used to treat IBD can be any sNAG composition described herein. In one embodiment, a composition comprising sNAG nanofibers that can be used to treat IBD is the same or similar to the composition described in Example 9.

In a specific embodiment, the compositions described herein are used to treat Crohn's disease (e.g., ileal Crohn's disease). Without being bound by any mechanism of action, the ability of sNAG nanofibers to induce alpha and beta defensins may contribute to the anti-Crohn's disease activity of the sNAG nanofibers. Alpha and beta defensins have been shown to have anti-Crohn's disease activity. In certain embodiments, treatment of a subject having Crohn's disease by administration of a composition described herein results in one or more of the following: prevention of the recurrence of the Crohn's disease; reduction in the duration and/or severity of one or more symptoms associated with the Crohn's disease; reduction in the number of symptoms associated with the Crohn's disease; reduction of the incidence of hospitalization of the subject; reduction of the hospitalization length of the subject; and/or enhancement or improvement of the prophylactic or therapeutic effect(s) of another therapy in the subject. Some of the symptoms of Crohn's disease include abdominal pain, vomiting, diarrhea, rectal bleeding, severe internal cramps/muscle spasms in the region of the pelvis, weight loss and various associated complaints or diseases like arthritis, pyoderma gangrenosum, and primary sclerosing cholangitis. Symptoms of Crohn's disease also may include defecation often porridge-like and sometimes steatorrhea, fever, fistulae, flatulence, bloating, perianal discomfort such itchiness and pain, fecal incontinence, aphthous ulcers of the mouth, and/or weight loss. In some embodiments, the compositions described herein prevent the onset or development of one or more of the above-listed symptoms or other symptoms known in the art, or reduce duration and/or severity of one or more of these symptoms.

In some embodiments, the compositions described herein are used to prevent and/or treat mucositis. Mucositis is the painful inflammation and ulceration of the mucous membranes lining the digestive tract (e.g., as an adverse effect of chemotherapy or radiotherapy treatment for cancer). Mucositis can occur anywhere along the gastrointestinal tract, for example, in the mouth (i.e., oral mucositis). Accordingly, in some embodiments, the compositions described herein are administered topically to a patient (e.g., a patient diagnosed with or displaying symptoms of mucositis) to treat mucositis (e.g., administered topically on the inflamed or ulcerated area of the mouth, or administered topically to the anus or rectal area such as via a cream, a suppository, a suspension, a liquid solution, a gel, or an ointment). In some embodiments, the compositions described herein are administered at the site, or in proximity to the site, of an inflammation or ulcer caused by or associated with mucositis (e.g., in the mouth). In specific embodiments, the compositions described herein can be administered daily (e.g., once or twice a day) until the symptoms of mucositis subside (e.g., for 2, 3, 4, 5, 6, 7, 8, 9, 10, 11, 12 days, 2 weeks, 3 weeks, 4 weeks, or more than 4 weeks). In certain embodiments, treatment of a subject having mucositis by administration of a composition described herein results in one or more of the following: prevention or reduction of frequency of the recurrence of the mucositis; reduction in the duration and/or severity of one or more symptoms associated with mucositis (e.g., pain, ulceration); reduction in the number of symptoms associated with mucositis; reduction of the incidence of hospitalization of the subject; reduction of the hospitalization length of the subject; and/or enhancement or improvement of the prophylactic or therapeutic effect(s) of another therapy in the subject.

In another specific embodiment, the compositions described herein are used to prevent and/or treat a viral infection or a disease caused by or associated therewith. Without being bound by any mechanism of action, the ability of sNAG nanofibers to induce beta defensins (e.g., beta-defensin 1) may contribute to the anti-viral activity of the sNAG nanofibers. Beta defensins (e.g., beta-defensin 1) have been shown to have anti-viral activity. Exemplary viruses which can cause infection or disease to be prevented and/or treated with the compositions described herein include, without limitation, respiratory syncytial virus (RSV), influenza virus (influenza A virus, influenza B virus, or influenza C virus), human metapneumovirus (HMPV), rhinovirus, parainfluenza virus, SARS Coronavirus, human immunodeficiency virus (HIV), hepatitis virus (A, B, C), ebola virus, herpes simplex virus (e.g., HSV-1, HSV-2, HSV-6, HSV-7), varicella, varicella zoster virus, human papillomavirus (HPV), parapox virus, morbilli, echovirus, adenovirus, Epstein Barr virus, Coxsackie virus, enterovirus, rubella, variola major, and variola minor. In certain embodiments, prevention of a viral infection in a subject or a disease caused by or associated therewith by administration of a composition described herein results in one or more of the following: prevention of the development or onset of a disease caused by or associated with viral infection; and/or prevention of the spread of a viral infection or a disease caused by or associated therewith from the subject to another subject or population of subjects. In certain embodiments, treatment of a subject having a viral infection or a disease caused by or associated therewith by administration of a composition described herein results in one or more of the following: prevention of the recurrence of the viral infection or a disease caused by or associated therewith; reduction in the number of symptoms associated with the viral infection or a disease caused by or associated therewith; reduction in organ failure associated with the viral infection or a disease caused by or associated therewith; reduction of the severity and/or duration of the viral infection or a disease caused by or associated therewith; reduction of the severity and/or duration of one or more symptoms of the viral infection or a disease caused by or associated therewith; reduction in viral load or count (e.g., by more than about 0.25 log, 0.5 log, 0.75 log, 1 log, 1.5 log, 2 logs, 2.5 logs, 3 logs, 4 logs, 5 logs, 6 logs, 7 logs, 8 logs, 9 logs, or 10 logs); reduction of the incidence of hospitalization of the subject; reduction of the hospitalization length of the subject; an increase the survival of the subject; enhancement or improvement of the prophylactic or therapeutic effect(s) of another therapy in the subject; prevention of the spread of a virus from a cell, tissue, organ of the subject to another cell, tissue, organ of the subject; prevention of the development or onset of a disease caused by or associated with the viral infection, or one or more symptom thereof; and/or prevention of the spread of a viral infection or a disease caused by or associated therewith from the subject to another subject or population of subjects.

In one specific embodiment, the compositions described herein are not used to prevent and/or treat an HIV infection or a disease caused by or associated with an HIV infection.

Symptoms of a viral infection may include but are not limited to fever, chills, headache, stiff neck, irritability, enlarged glands, diarrhea, nausea, vomiting, a skin or a mucous membrane abnormality associated with a viral infection (e.g, a rash, an ulceration, a cold sore, a lesion, a swelling, redness, itching, a papule, a vesicle, a pustule, a blister, a crust) and/or pain associated with such abnormality, abdominal pain, sore throat, ear pain, cough, weight loss, fatigue, body aches, and/or other flu-like symptoms. In some embodiments, the compositions described herein prevent the onset or development of one or more of the above-listed symptoms or other symptoms known in the art, or reduce duration and/or severity of one or more of these symptoms.

In another specific embodiment, the compositions described herein are used to prevent and/or treat a viral infection of a wound (e.g., an open wound such as an incision, a laceration, a penetration, an abrasion, or a burn). In another specific embodiment, the compositions described herein are not used to prevent and/or treat a viral infection of a wound. There are two types of wounds, open and closed. Open wounds are classified according to the object that caused the wound. For example, incisions or incised wounds (including surgical wounds) are caused by a clean, sharp-edged object such as a knife, a razor or a glass splinter. Lacerations are irregular wounds caused by a blunt impact to soft tissue which lies over hard tissue (e.g., laceration of the skin covering the skull) or tearing of skin and other tissues such as caused by childbirth. Abrasions or grazes are superficial wounds in which the topmost layer of the skin (the epidermis) is scraped off. Puncture wounds are caused by an object puncturing the skin, such as a nail or needle. Penetration wounds are caused by an object such as a knife entering the body. Gunshot wounds are caused by a bullet or similar projectile driving into (e.g., entry wound) and/or through the body (e.g., exit wound). In a medical context, all stab wounds and gunshot wounds are considered open wounds. Open wounds also include burn wounds induced by thermal, chemical, or electrical injury. Closed wounds include contusions (more commonly known as a bruise, caused by blunt force trauma that damages tissue under the skin), hematoma (also called a blood tumor, caused by damage to a blood vessel that in turn causes blood to collect under the skin), and crushing injuries (caused by a great or extreme amount of force applied over a long period of time).

In certain embodiments, the sNAG compositions described herein are used to prevent and/or treat a topical viral infection in a patient (e.g., in a patient diagnosed with viral infection or displaying a symptom of a viral infection). In some embodiments, the compositions described herein are used to prevent and/or treat a viral infection or a symptom of a viral infection on the skin, mucous membranes (e.g., eyes, ears, throat, vagina, anus), or the surface of other tissues. In certain embodiments, the compositions described herein are administered directly to the skin, mucous membrane (e.g., eyes, ears, throat, oral cavity, vagina, anus), or the surface of other tissues. In some embodiments, the compositions described herein are used to treat vesicular (such as a vesicle, a pustule or a blister), ulcer or crust stages of a viral infection (e.g., herpes simplex virus infection or varicella zoster infection). In other embodiments, the compositions described herein are used to treat prodrome, erythema/macule or papule/edema stages of a viral infection (e.g., herpes simplex virus infection or varicella zoster infection). In certain embodiments, the compositions described herein are administered at the site or in the proximity to the site of a viral infection or at the site or in the proximity to the site of a symptom of a viral infection (e.g., to a cold sore, lesion, blister, pustule, ulcer, rash, swelling, or crust associated with a viral infection). In some embodiments, treatment of a subject having a topical viral infection by administration of a composition described herein results in one or more of the following: reduction of the severity and/or duration of a symptom of a topical viral infection (e.g., an itching, a lesion, an ulcer, a blister, a papule, a rush, a crust, or any other symptom of a topical viral infection described herein or known in the art); reduction of pain associated with a symptom of a topical viral infection; reduction in the number of symptoms associated with a topical viral infection; prevention or reduction of frequency of the recurrence of a symptom of a topical viral infection; prevention of the spread of a topical viral infection from the subject to another subject; prevention of the onset or development of one or more of the symptoms of a topical viral infection described herein or known in the art; and/or enhancement or improvement of the prophylactic or therapeutic effect(s) of another therapy (e.g., another anti-viral therapy) in the subject. In particular embodiments, the sNAG compositions described herein are formulated in a non-barrier form for use in the treatment of topical viral infections. For example, the compositions described herein are formulated in the form of a liquid solution, a suspension (e.g., a thick suspension), a cream, or an ointment for use in the treatment of topical viral infections. In one embodiment, the sNAG compositions described herein are not in a solid form when used in the treatment of topical viral infections. In yet other embodiments, the sNAG compositions described herein are barrier-forming and/or solid for use in the treatment of topical viral infections. Example 8, infra, shows that sNAG nanofibers are effective to treat topical viral infections based on the data obtained on human patients. In particular, Example 8 shows that sNAG nanofibers are effective to treat an HSV infection, such as a cold sore caused by or associated with an HSV infection, in human patients. A composition comprising sNAG nanofibers that can be used to treat a topical viral infection can be any sNAG composition described herein. In one embodiment, a composition comprising sNAG nanofibers that can be used to treat a topical viral infection (e.g., HSV) can be the same or similar to the composition described in Example 8.

Viral infections and diseases/conditions of the skin associated with viral infections that can be topically treated using the compositions described herein include, but are not limited to, measles (morbilli), German measles (rubella), chickenpox (varicella), fifth disease (erythema infectiosum, due to parvovirus), Roseola, infectious mononucleosis or glandular fever (Epstein Barr virus), enterovirus infections, *Pityriasis rosea* (possibly caused by herpes 6 or 7), hand, foot and mouth disease (due to Coxsackie infection), Gianotto-Crosti syndrome (papular acrodermatitits occurring in children; most often caused by infectious mononucleosis due to Epstein Barr virus or hepatitis B), Laterothoracic exanthem (asymmetric periflexural exanthem of childhood or APEC), smallpox, cowpox, epidermodysplasia verruciformis, skin conditions caused by or associated with HIV infections and/or Kaposi's sarcoma, Rickettsial diseases, yellow fever (due to flavivirus infection), herpes simplex (cold sores and genital herpes), eczema herpetcum, herpes zoster (shingles), herpangina/vesicular stomatitis (oral ulcers), molluscum contagiosum, viral warts (e.g., verrucas, genital warts or condylomas, squamous cell papillomas), herpetic whitlow, herpes gladiatorum, Orf, and Milker's nodules.

In a specific embodiment, the compositions described herein are used to prevent and/or treat an infection with a herpes simplex virus (e.g., HSV-1, HSV-2), or a disease or condition caused by a herpes simplex virus (e.g., HSV-1, HSV-2). Symptoms of Herpes simplex virus type 1 (HSV-1) may include blisters or lesions in the mouth, throat, lips (e.g., peri-oral cold sores), and symptoms of herpes simplex virus type 2 (HSV-2) may include blisters or lesions (e.g., papules and/or vesicles) on the outer surface of genitals. Both types of HSV reside in a latent state in the sensory nerves of the skin. During an attack, the virus spreads down the nerves and out into the skin or mucous membranes where it multiplies, causing the clinical lesion. After each attack it recedes up the nerve fiber and becomes dormant again. During the active phase, there is considerable shedding of virus and the lesions are highly contagious. Primary infections of type 1 occur mainly in infants and young children and are usually mild or subclinical. In crowded, underdeveloped areas of the world up to 100% of children have been infected by the age of 5. Type 2 is usually sexually acquired, after puberty and is less often asymptomatic. The virus is shed in saliva and genital secretions, during a clinical attack and for some days or weeks afterwards. The amount shed from active lesions is 100 to 1,000 times greater than when it is inactive. Spread of HSV is usually by direct contact with infected secretions. Where immunity is deficient infections tend to occur more frequently and to be more pronounced and persistent. Recurrence may be triggered by: minor trauma; other infections including coryza, ultraviolet radiation (sun exposure); hormonal factors (premenstrual flares occur); emotional stress; operations or procedures performed on the face (including dentistry). Accordingly, in some embodiments, the compositions described herein are administered topically to treat HSV-1 infection or a lesion or a cold sore associated with HSV-1 infection (e.g., administered orally or peri-orally). In other embodiments, the compositions described herein are administered topically to treat HSV-2 infection or a genital lesion associated with HSV-2 infection (e.g., administered topically in the genital area, such as vaginally). In some embodiments, treatment of a subject having an HSV infection or a disease caused by or associated therewith by administration of a composition described herein results in one or more of the following: reduction of the severity and/or duration of a symptom of an HSV infection (e.g., a cold sore, a lesion, or any other symptom of an HSV infection described herein or known in the art); reduction in the number of symptoms associated with an HSV infection, reduction of pain associated with a symptom of an HSV infection (e.g., a cold sore or a lesion); prevention or reduction of frequency of the recurrence of a symptom of an HSV infection; prevention of the spread of an HSV infection from the subject to another subject; prevention of the onset of development of one or more symptoms of an HSV infection; and/or enhancement or improvement of the prophylactic or therapeutic effect(s) of another therapy in the subject. In particular embodiments, a composition described herein is administered to a human infant, a human toddler, a human child, a human adult, and/or an elderly human who has an HSV infection or a symptom of an HSV infection. In some embodiments, the compositions described herein are administered topically on a surface area (e.g., peri-oral, oral or genital area of the skin or mucous membranes) at the time when the surface area starts to tingle, itch or swell (wherein tingling, itching or swelling at the surface area is associated with an HSV infection (e.g., HSV-1 or HSV-2)). In some embodiments, the compositions described herein are administered topically at the site, or in proximity to the site, of a cold sore or lesion (e.g., a peri-oral, oral or genital lesion on the skin or on a mucous membrane) (wherein the cold sore or lesion is associated with an HSV infection (e.g., HSV-1 or HSV-2)). Example 8 shows that a sNAG nanofiber composition was effective to treat cold sores associated with HSV infection in human patients when applied topically at the site of the cold sore in a patient, and that treatment of HSV-associated cold sores with a sNAG nanofiber composition resulted in reduction of the severity and duration of the cold sores, and of the pain associated with the cold sores. In some embodiments, the compositions described herein are used to treat vesicular (such as a vesicle, a pustule or a blister), ulcer or crust stages of an HSV (e.g., HSV-1 or HSV-2) infection. In other embodiments, the compositions described herein are used to treat prodrome, erythema/macule or papule/edema stages of an HSV (e.g., HSV-1 or HSV-2) infection. In certain embodiments, compositions described herein are administered in combination with an anti-viral drug (e.g., acyclovir or any other anti-viral drug described herein or known in the art) in the treatment of an HSV infection. In specific embodiments, the compositions described herein can be administered daily (e.g., once or twice a day) until the symptoms of an HSV infection subside (e.g., for 2, 3, 4, 5, 6, 7, 8, 9, 10, 11, 12 days, 2 weeks, 3 weeks, 4 weeks, or more than 4 weeks).

In a specific embodiment, the compositions described herein are used to prevent and/or treat an infection with varicella virus, or a disease or condition caused by varicella virus (herpes zoster, shingles, or chickenpox). During varicella infection (see Shingles, Clinical Knowledge Summaries (2008)), which usually occurs in childhood, virus is seeded to nerve cells, usually sensory cells. Herpes zoster or shingles is characterized by distribution in a single dermatome. It may not affect all of the dermatome but usually it is confined to the area of one dermatome and does not therefore cross the midline. Symptoms of herpes zoster include, without limitation, a rash, which consists of macules and papules, and develops into vesicular lesions in a dermatomal distribution (most commonly on the chest), and pain. The rash tends to last 7-10 days, and healing can take 2-4 weeks. More extensive disease may occur in immune compromised patients (for example, with lymphomas and HIV). Herpes zoster can occur at any age, but it is more common in the elderly, and slightly more common in females (although chickenpox affects both sexes equally). Skin complications can include secondary infection, scarring and changes in pigmentation. The elderly are more likely to have complications due to herpes zoster (especially postherpetic neuralgia). Accordingly, in some embodiments, the compositions described herein are administered topically to treat herpes zoster infection or chickenpox (e.g., administered on the skin). In some embodiments, the compositions described herein are administered at the site, or in proximity to the site, of a rash (e.g., a macule or papule on the skin) (wherein the rash is associated with herpes zoster infection). In some embodiments, treatment of a subject having herpes zoster infection or a disease caused by or associated therewith by administration of a composition described herein results in one or more of the following: reduction of the severity and/or duration of a symptom of herpes zoster infection (e.g., a rash, or any other symptom of herpes zoster infection listed herein or known in the art); reduction in the number of symptoms associated with herpes zoster infection; reduction of pain associated with a symptom of herpes zoster infection; prevention or reduction of frequency of the recurrence of a symptom of herpes zoster infection; prevention of the spread of herpes zoster infection from the subject to another subject; prevention of the onset or development of a symptom of herpes zoster infection; and/or enhancement or improvement of the prophylactic or therapeutic effect(s) of another therapy (e.g., another anti-viral therapy) in the subject. In particular embodiments, a composition described herein is administered to a human infant, a human toddler, a human child, a human adult, and/or an elderly human who has herpes zoster infection or a symptom of herpes zoster infection. In certain embodiments, compositions described herein are administered in combination with an anti-viral drug (e.g., acyclovir or any other anti-viral drug described herein or known in the art) in the treatment of herpes zoster infection. In specific embodiments, the compositions described herein can be administered daily (e.g., once or twice a day) until the symptoms of herpes zoster infection subside (e.g., for 2, 3, 4, 5, 6, 7, 8, 9, 10, 11, 12 days, 2 weeks, 3 weeks, 4 weeks, or more than 4 weeks).

In another specific embodiment, the compositions described herein are used to prevent and/or treat molluscum contagiosum infection. Molluscum contagiosum is common and usually affects infants and young children, and, only rarely, adults (see Molluscum contagiosum. Clinical Knowledge Summaries (2008)). Symptoms of molluscum contagiosum include, but are not limited to, clusters of small papules, particularly, in the warm moist places such as the axilla, groin or behind the knees. The papules range in size from 1-6 mm and may be white, pink or brown. They often have a waxy, pinkish look and are umbilicated (a central depression of the surface). As they resolve, they may become inflamed, crusted or scabby. They may number a few or several hundred on any individual. The disease may persist for months or occasionally for a couple of years. Rarely, it may leave tiny pit-like scars (induration). Molluscum contagiosum can be spread from person to person, usually among children, by direct skin contact; and sexual contact in adults may transmit infection. Lesions tend to be more numerous and more persistent in children with atopic eczema and in HIV-infected patients. In children, lesions are common on the face and trunk. Accordingly, in some embodiments, the compositions described herein are administered topically to treat molluscum contagiosum infection (e.g., administered on the skin). In some embodiments, the compositions described herein are administered at the site, or in proximity to the site, of a rash (e.g., a macule or papule on the skin) (wherein the rash is associated with molluscum contagiosum infection). In some embodiments, treatment of a subject having molluscum contagiosum or a disease caused by or associated therewith by administration of a composition described herein results in one or more of the following: reduction of the severity and/or duration of a symptom of molluscum contagiosum (e.g., a rash, or any other symptom of molluscum contagiosum listed herein or known in the art); reduction in the number of symptoms of molluscum contagiosum; reduction of pain associated with a symptom of molluscum contagiosum; prevention or reduction of frequency of the recurrence of a symptom of molluscum contagiosum; prevention of the spread of molluscum contagiosum from the subject to another subject; prevention of the onset or development of a symptom of molluscum contagiosum; and/or enhancement or improvement of the prophylactic or therapeutic effect(s) of another therapy in the subject. In particular embodiments, a composition described herein is administered to a human infant, a human toddler, a human child, a human adult, and/or an elderly human who has molluscum contagiosum or a symptom of molluscum contagiosum. In certain embodiments, compositions described herein are administered in combination with a known therapy (e.g., squeezing, piercing, curettage, cryotherapy, wart paints such as salicylic acid and podophyllin; immunomodulatory agent such as imiquimod cream; 1% hydrocortisone cream; or fusidic acid cream 2%) in the treatment of molluscum contagiosum infection. In specific embodiments, the compositions described herein can be administered daily (e.g., once or twice a day) until the symptoms of molluscum contagiosum infection subside (e.g., for 2, 3, 4, 5, 6, 7, 8, 9, 10, 11, 12 days, 2 weeks, 3 weeks, 4 weeks, or more than 4 weeks).

In another specific embodiment, the compositions described herein are used to prevent and/or treat human papillomavirus or warts or verrucae associated with human papillomavirus. More than 80 HPV subtypes are known (see Warts and verrucae, Clinical Knowledge Summaries (June 2009)), of which 20 can affect the genital tract. The presentation and appearance of HPV infection varies according to the site of infection. For example, plantar warts occur on pressure-bearing areas and are flattened rather than raised. Warts are most common in childhood and are spread by direct contact or auto-inoculation; it may take up to 12 months for the wart to appear. HPV warts are more frequent and more troublesome in association with immunosuppression, and are more infectious when they are wet or when they bleed from trauma (e.g. scratching). HPV infection is more persistent in adults than in children. Accordingly, in some embodiments, the compositions described herein are administered topically to treat HPV infection or warts or verrucae associated with HPV infection (e.g., administered on the skin). In some embodiments, the compositions described herein are administered at the site, or in proximity to the site, of a wart or verricuae (wherein the wart or verricuae is caused by or associated with HPV). In some embodiments, treatment of a subject having HPV infection or a disease caused by or associated therewith by administration of a composition described herein results in one or more of the following: reduction of the severity and/or duration of a symptom of HPV infection (e.g., a wart, a verricuae, or any other symptom of HPV infection described herein or known in the art); reduction in the number of symptoms associated with HPV infection; reduction of pain associated with a symptom of HPV infection; prevention or reduction of frequency of the recurrence of a symptom of HPV infection; prevention of the spread of HPV infection from the subject to another subject; prevention of the onset or development of a symptom of HPV infection; and/or enhancement or improvement of the prophylactic or therapeutic effect(s) of another therapy in the subject. In particular embodiments, a composition described herein is administered to a human infant, a human toddler, a human child, a human adult, and/or an elderly human who has HPV infection or a symptom of HPV infection. In specific embodiments, the compositions described herein can be administered daily (e.g., once or twice a day) until the symptoms of HPV infection subside (e.g., for 2, 3, 4, 5, 6, 7, 8, 9, 10, 11, 12 days, 2 weeks, 3 weeks, 4 weeks, or more than 4 weeks).

In another specific embodiment, the compositions described herein are used to prevent and/or treat orf. Orf is contracted from sheep and goats (see Orf, Health Protection Agency (2010)). It is caused by a parapox virus, which infects mainly young lambs and goats that contract the infection from one another (or possibly from persistence of the virus in the pastures). Human lesions are caused by direct inoculation of infected material. It may occur in farmers, butchers, vets, children who bottle-feed lambs and possibly even children who play in pastures where sheep have grazed. The incubation period of parapox virus is 5 or 6 days. Orf lesions are usually solitary but multiple lesions do occur. Orf lesions are usually small, firm, red or reddish-blue, forming a lump that enlarges to form a flat-topped, blood-tinged pustule or blister. The fully developed lesion is usually 2 or 3 cm in diameter but may be as large as 5 cm; and although there appears to be pus under the white skin, incising this will reveal firm, red tissue underneath. The lesion is sometimes irritable during the early stages and is often tender. They usually occur on the fingers, hands or forearms, but may also occur on the face. Red lymph lines may occur on the medial side of the elbow up to the axilla. There may be a mild fever associated with orf. Accordingly, in some embodiments, the compositions described herein are administered topically to treat orf (e.g., administered on the skin). In some embodiments, the compositions described herein are administered at the site, or in proximity to the site, of a lesion, a pustule or a blister (wherein the lesion, pustule or blister is caused by or associated with orf). In some embodiments, treatment of a subject having orf by administration of a composition described herein results in one or more of the following: reduction of the severity and/or duration of a symptom of orf (e.g., a lesion, a pustule, a blister, or any other symptom of orf described herein or known in the art); reduction in the number of symptoms associated with orf, reduction of pain associated with a symptom of orf; prevention or reduction of frequency of the recurrence of a symptom of orf; prevention of the spread of orf from the subject to another subject; prevention of the onset or development of a symptom of orf; and/or enhancement or improvement of the prophylactic or therapeutic effect(s) of another therapy in the subject. In particular embodiments, a composition described herein is administered to a human infant, a human toddler, a human child, a human adult, and/or an elderly human who has orf or a symptom of orf. In specific embodiments, the compositions described herein can be administered daily (e.g., once or twice a day) until the symptoms of orf subside (e.g., for 2, 3, 4, 5, 6, 7, 8, 9, 10, 11, 12 days, 2 weeks, 3 weeks, 4 weeks, or more than 4 weeks).

In certain embodiments, the compositions described herein are used to treat viral infections that produce rashes. Examples of viral infections that produce rashes include, but are not limited to, measles (morbilli), German measles (rubella), chickenpox (varicella virus), fifth disease (erythema infectiosum, due to parvovirus), Roseola (erythema subitum, due to herpes virus 6), *Pityriasis rosea* (the cause is unknown but it may be caused by herpes virus types 6 and 7), echovirus and adenovirus infections, Epstein Barr virus of infectious mononucleosis or glandular fever, and primary HIV infection. In certain embodiments, the compositions described herein are used to treat nonspecific rashes associated with viral infections (e.g., erythematous rash such as erythematous blotchy eruption). In some embodiments, the compositions described herein are administered at the site of a rash caused by or associated with a viral infection or in proximity to the site of a rash caused by or associated with a viral infection. In certain embodiments, the compositions described herein reduce the severity of rashes, the duration of rashes, and/or pain associated with rashes caused by a viral infection.

In another specific embodiment, the compositions described herein are used to prevent and/or treat hand, foot and mouth disease or an infection caused by Coxsackie virus or enterovirus. Hand, foot and mouth disease is common, mild and brief, most often affecting young children during the summer months (see Hand, foot and mouth disease, Clinical Knowledge Summaries (March 2010)). Hand, foot and mouth disease is caused by Coxsackie virus A16, although it can also be due to enterovirus 71. Incubation period of such viruses is 3-5 days. Symptoms of hand, foot and mouth disease include small, flat blisters on the hands and feet, oral ulcers, that are sometimes painful, and the disease may be accompanied by a mild fever or a rash on the buttocks (in young children). Accordingly, in some embodiments, the compositions described herein are administered topically to treat hand, foot and mouth disease or a condition caused by or associated with Coxsackie virus or enterovirus infection (e.g., administered on the skin). In some embodiments, the compositions described herein are administered at the site, or in proximity to the site, of a blister, ulcer or rash (wherein the blister, ulcer or rash is associated with hand, foot and mouth disease or a condition caused by or associated with Coxsackie virus or enterovirus infection). In some embodiments, treatment of a subject having hand, foot and mouth disease by administration of a composition described herein results in one or more of the following: reduction of the severity and/or duration of a symptom of hand, foot and mouth disease (e.g., a rash, a blister, an ulcer or any other symptom of hand, foot and mouth disease described herein or known in the art); reduction in the number of symptoms of hand, foot and mouth disease; reduction of pain associated with a symptom of hand, foot and mouth disease; prevention or reduction of frequency of the recurrence of a symptom of hand, foot and mouth disease; prevention of the spread of hand, foot and mouth disease from the subject to another subject; prevention of the onset or development of a symptom of hand, foot and mouth disease; and/or enhancement or improvement of the prophylactic or therapeutic effect(s) of another therapy in the subject. In particular embodiments, a composition described herein is administered to a human infant, a human toddler, a human child, a human adult, and/or an elderly human who has hand, foot and mouth disease or a symptom of hand, foot and mouth disease. In specific embodiments, the compositions described herein can be administered daily (e.g., once or twice a day) until the symptoms of hand, foot and mouth disease subside (e.g., for 2, 3, 4, 5, 6, 7, 8, 9, 10, 11, 12 days, 2 weeks, 3 weeks, 4 weeks, or more than 4 weeks).

In another specific embodiment, the compositions described herein are used to prevent and/or treat Crosti-Gianotti syndrome. Crosti-Gianotti syndrome is a response of the skin to viral infection with a papular rash which lasts for several weeks. This condition is also known as papulo-vesicular acrodermatitis of childhood, papular acrodermatitis of childhood and acrodermatitis papulosa infantum.

Crosti-Gianotti syndrome can be caused by Hepatitis B virus, Epstein Barr virus, Coxsackie viruses, Echoviruses, or Respiratory syncytial virus. It affects children between 6 and 12 months. In this condition, a profuse eruption of dull red spots may develop over 3 or 4 days. They usually appear first on the thighs and buttocks, then on the outer aspects of the arms and finally on the face, often in an asymmetrical pattern (see Chuh, Cutis 68(3):207-13 (2001)). The spots may be 5-10 mm in diameter, may have a deep red color or purple color (especially on the legs, due to leakage of blood from the capillaries), and may develop into fluid-filled blisters. Accordingly, in some embodiments, the compositions described herein are administered topically to treat Crosti-Gianotti syndrome (e.g., administered on the skin). In some embodiments, the compositions described herein are administered at the site, or in proximity to the site, of a red spot, eruption or rash (wherein the red spot, eruption or rash is associated with Crosti-Gianotti syndrome or an infection caused by Hepatitis B virus, Epstein Barr virus, Coxsackie viruses, Echoviruses, or Respiratory syncytial virus). In some embodiments, treatment of a subject having Crosti-Gianotti syndrome by administration of a composition described herein results in one or more of the following: reduction of the severity and/or duration of a symptom of Crosti-Gianotti syndrome (e.g., a red spot, an eruption, a rash or any other symptom of Crosti-Gianotti syndrome described herein or known in the art); reduction in the number of symptoms associated with Crosti-Gianotti syndrome; reduction of pain associated with a symptom of Crosti-Gianotti syndrome; prevention or reduction of frequency of the recurrence of a symptom of Crosti-Gianotti syndrome; prevention of the spread of Crosti-Gianotti syndrome from the subject to another subject; prevention of the onset or development of a symptom of Crosti-Gianotti; and/or enhancement or improvement of the prophylactic or therapeutic effect(s) of another therapy in the subject. In particular embodiments, a composition described herein is administered to a human infant (particularly, to an infant between 6 and 12 months of age), a human toddler, a human child, a human adult, and/or an elderly human who has Crosti-Gianotti syndrome or a symptom thereof. In specific embodiments, the compositions described herein can be administered daily (e.g., once or twice a day) until the symptoms of Crosti-Gianotti syndrome subside (e.g., for 2, 3, 4, 5, 6, 7, 8, 9, 10, 11, 12 days, 2 weeks, 3 weeks, 4 weeks, or more than 4 weeks).

In another specific embodiment, the compositions described herein are used to prevent and/or treat herpes gladiatorum or "scrum pox." Herpes gladiatorum is primarily transmitted by direct skin-to-skin contact and abrasions may facilitate a portal of entry (see Becker et al., Am J Sports Med. 16(6):665-9 (1988)). The majority of lesions due to herpes gladiatorum occur on the head or face, followed by the trunk and extremities. Symptoms of herpes gladiatorum include, but are not limited to, prodromal itching or burning sensation, which may be followed by clustered vesicles on an erythematous base which heal with crusts over about 1 to 2 weeks. Other, less common, symptoms of herpes gladiatorum include, without limitation, headache, malaise, sore throat and fever. Recurrent episodes may follow the initial infection. Accurate diagnosis can be made by viral immunofluorescence, and cultures can be obtained by gently breaking an intact vesicle and firmly rubbing the swab tip across the base of the erosion. Accordingly, in some embodiments, the compositions described herein are administered topically to treat herpes gladiatorum infection (e.g., administered on the skin). In some embodiments, the compositions described herein are administered at the site, or in proximity to the site, of an itching, a lesion, a vesicle or a crust (wherein the site of itching, a lesion, a vesicle or a crust is caused by or associated with herpes gladiatorum infection). In certain embodiments, compositions described herein are administered in combination with an anti-viral drug (e.g., acyclovir or any other anti-viral drug described herein or known in the art) in the treatment of herpes gladiatorum infection. In some embodiments, treatment of a subject having herpes gladiatorum by administration of a composition described herein results in one or more of the following: reduction of the severity and/or duration of a symptom of herpes gladiatorum (e.g., an itching, a lesion, a vesicle, a crust, or any other symptom of HPV infection described herein or known in the art); reduction in the number of symptoms associated with herpes gladiatorum; reduction of pain associated with a symptom of herpes gladiatorum; prevention of the recurrence of a symptom of herpes gladiatorum; prevention of the spread of herpes gladiatorum from the subject to another subject; prevention of the onset or development of a symptom of herpes gladiatorum; and/or enhancement or improvement of the prophylactic or therapeutic effect(s) of another therapy in the subject. In particular embodiments, a composition described herein is administered to a human infant, a human toddler, a human child, a human adult, and/or an elderly human who has herpes gladiatorum or a symptom of herpes gladiatorum. In specific embodiments, a composition described herein is administered to an athlete (e.g., professional athlete) for a prophylactic and/or therapeutic purpose. In specific embodiments, the compositions described herein can be administered daily (e.g., once or twice a day) until the symptoms of herpes gladiatorum infection subside (e.g., for 2, 3, 4, 5, 6, 7, 8, 9, 10, 11, 12 days, 2 weeks, 3 weeks, 4 weeks, or more than 4 weeks).

In another specific embodiment, the compositions described herein are used to prevent and/or treat common warts associated with a viral infection (e.g., plantar warts, warts in calluses). In some embodiments, the compositions described herein are administered at the site, or in proximity to the site, of a wart caused by or associated with a viral infection or in proximity to the site of a wart caused by or associated with a viral infection. In certain embodiments, the compositions described herein reduce the number of warts, the severity of warts, the duration of warts and/or the pain associated with warts caused by a viral infection.

In certain embodiments, the compositions described herein are used to prevent and/or treat viral infections in immunocompromised patients (e.g., HIV-infected patients).

In some embodiments, the compositions described herein are used to treat gastroenteritis (e.g., gastroenteritis caused by or associated with a viral infection, or gastroenteritis caused by or associated with a protozoal infection). Examples of viruses that can cause gastroenteritis include but are not limited to rotavirus, noravirus, adenovirus, and astrovirus. Examples of protozoa that can cause gastroeneteritis include but are not limited to *Giardia lamblia, cryptosporidium,* and *Entamoeba histolytica.* In one embodiment, the compositions described herein are administered rectally (e.g., as a cream or suppository) to treat gastroenteritis. In certain embodiments, treatment of a subject having gastroenteritis by administration of a composition described herein results in one or more of the following: prevention of the recurrence of gastroenteritis; reduction in the duration and/or severity of one or more symptoms associated with gastroenteritis; reduction in the number of symptoms associated with gastroenteritis; reduction of the incidence of hospitalization of the subject; reduction of the hospitalization length of the subject; and/or enhancement or improvement of the prophylactic or therapeutic effect(s) of another therapy in the subject.

In another specific embodiment, the compositions described herein are used to prevent and/or treat a fungal infection or a disease caused by or associated therewith. Without being bound by any mechanism of action, the ability of sNAG nanofibers to induce beta defensins (e.g., beta-defensin 1) may contribute to the anti-fungal activity of the sNAG nanofibers. Beta defensins (e.g., beta-defensin 1) have been shown to have anti-fungal activity. Exemplary fungi which can cause infection or disease to be prevented and/or treated with the compositions described herein include, without limitation, *Blastomyces, Paracoccidioides, Sporothrix, Cryptococcus, Candida, Aspergillus, Histoplasma, Cryptococcus, Bipolaris, Cladophialophora, Cladosporium, Drechslera, Exophiala, Fonsecaea, Phialophora, Xylohypha, Ochroconis, Rhinocladiella, Scolecobasidium,* and *Wangiella*. In certain embodiments, prevention of a fungal infection in a subject or a disease caused by or associated therewith by administration of a composition described herein results in one or more of the following: prevention of the development or onset of a disease caused by or associated with fungal infection; and/or prevention of the spread of a fungal infection or a disease caused by or associated therewith from the subject to another subject or population of subjects. In certain embodiments, treatment of a subject having a fungal infection or a disease caused by or associated therewith by administration of a composition described herein results in one or more of the following: prevention of the recurrence of the fungal infection or a disease caused by or associated therewith; reduction in the number of symptoms associated with the fungal infection or a disease caused by or associated therewith; reduction in organ failure associated with the fungal infection or a disease caused by or associated therewith; reduction of the duration and/or severity of the fungal infection or a disease caused by or associated therewith; reduction of the duration and/or severity of one or more symptoms of the fungal infection or a disease caused by or associated therewith; reduction in fungal cell count; reduction of the incidence of hospitalization of the subject; reduction of the hospitalization length of the subject; an increase the survival of the subject; enhancement or improvement of the prophylactic or therapeutic effect(s) of another therapy in the subject; prevention of the spread of a fungus from a cell, tissue, organ of the subject to another cell, tissue, organ of the subject; prevention of the development or onset of a disease caused by or associated with the fungal infection, or one or more symptoms thereof; and/or prevention of the spread of a fungal infection or a disease caused by or associated therewith from the subject to another subject or population of subjects.

Symptoms of a fungal infection with jock itch may include itching in the groin are and/or a red scaly rash. Symptoms of athlete's foot may include scaling, flaking of the skin, itching of the feet and/or yelowish toenails. Symptoms of a vaginal infection may include itching and irritation, burning with urination, and/or thick vaginal discharge. Symptoms of fungal gastroenteritis may include vomiting and/or diarrhea. Symptoms of a fungal infection of the lungs may include fever, cough and/or symptoms of pneumonia. Symptoms of mouth yeast infection (thrush, Candidiasis) may include yellow-white patchy lesions/sores in the mouth or tongue. Symptoms of Candidiasis of the genitalia (e.g., vagina, vulvae, penis) include itching, burning, soreness, irritation and/or discharge. In some embodiments, the compositions described herein prevent the onset or development of one or more of the above-listed symptoms or other symptoms known in the art, or reduce duration and/or severity of one or more of these symptoms.

In some embodiments, the compositions described herein are used to prevent and/or treat Athlete's foot, jock itch, ringworm, or a fungal infection of nail, scalp or hair. These fungal infections can cause reddening, peeling, blistering, and scaling of the skin, itching, deformation and brittleness of affected nails, and/or brittle hair. They are caused by dermatophytes, a group of fungi that includes *Trichophyton, Microsporum,* and *Epidermophyton* species. Dermatophytes feed on keratin and rarely penetrate below the skin. Athlete's foot (tinea pedis) is found between the toes and sometimes covers the bottom of the foot. Jock itch (tinea cruris) may extend from the groin to the inner thigh. Scalp and hair infection (tinea capitis) affects hair shaft, primarily in children. Finger or toenail infection (tinea unguium) typically affects toenails but may also affect fingernails. Ringworm of the body (tinea corporis) can be found anywhere on the body. Barber's itch (tinea barbae) affects the bearded portion of the face. In particular embodiments, the compositions described herein are administered topically to treat any of the above-listed fungal infections (such as Athlete's foot, jock itch, nail, scalp and hair infections). In one embodiment, the compositions described herein are administered at the site, or in the proximity to the site, of reddening, peeling, blistering, or scaling of the skin, or itching, deformation or brittleness of the nail (wherein such symptoms are associated with a fungal infection). In some embodiments, treatment of a subject having one of the above-listed fungal infections by administration of a composition described herein results in one or more of the following: reduction of the severity and/or duration of a symptom of the fungal infection (e.g., itching, reddening, peeling, blistering, or any other symptom of the fungal infection described herein or known in the art); reduction in the number of symptoms of the fungal infection; reduction of pain associated with a symptom of the fungal infection; prevention of the recurrence of a symptom of the fungal infection; prevention of the spread of the fungal infection from the subject to another subject; prevention of the onset or development of a symptom of the fungal infection; and/or enhancement or improvement of the prophylactic and/or therapeutic effect(s) of another therapy (e.g., anti-fungal therapy) in the subject. In particular embodiments, a composition described herein is administered to a human infant, a human toddler, a human child, a human adult, and/or an elderly human who has one of the above-listed fungal infections or a symptom thereof. In specific embodiments, the compositions described herein can be administered daily (e.g., once or twice a day) until the symptoms of a fungal infection subside (e.g., for 2, 3, 4, 5, 6, 7, 8, 9, 10, 11, 12 days, 2 weeks, 3 weeks, 4 weeks, or more than 4 weeks).

In some embodiments, the compositions described herein are used to prevent and/or treat Sporotrichosis. Sporotrichosis is a condition caused by the fungus *Sporothrix schenckii*, which is not a dermatophyte. It is an infection of the skin and subcutaneous tissue that has been abraded by thorny plants, pine needles, and sphagnum moss where this fungus normally resides. In particular embodiments, the compositions described herein are administered topically to treat Aporotrichosis. In one embodiment, the compositions described herein are administered at the site, or in the proximity to the site, of Sporotrichosis infection. In some embodiments, treatment of a subject having Sporotrichosis by administration of a composition described herein results in one or more of the following: reduction of the severity and/or duration of a symptom of Sporotrichosis, reduction in the number of symptoms of Sporotrichosis; reduction of pain associated with a symptom of Sporotrichosis; prevention or reduction of frequency of the recurrence of a symptom of Sporotrichosis; prevention of the spread of Sporotrichosis from the subject to another subject; prevention of the onset or development of a symptom of Sporotrichosis; and/or enhancement or improvement of the prophylactic and/or therapeutic effect(s) of another therapy (e.g., anti-fungal therapy) in the subject. In specific embodiments, the compositions described herein can be administered daily (e.g., once or twice a day) until the symptoms of Sporotrichosis subside (e.g., for 2, 3, 4, 5, 6, 7, 8, 9, 10, 11, 12 days, 2 weeks, 3 weeks, 4 weeks, or more than 4 weeks).

In another specific embodiment, the compositions described herein are used to prevent and/or treat a fungal infection of a wound (e.g., an open wound such as an incision, a laceration, a penetration, an abrasion, or a burn). In another specific embodiment, the compositions described herein are not used to prevent and/or treat a fungal infection of a wound.

In another specific embodiment, the compositions described herein are used to prevent and/or treat a yeast infection or a disease caused by or associated therewith. Without being bound by any mechanism of action, the ability of sNAG nanofibers to induce beta defensins may contribute to the anti-yeast activity of the sNAG nanofibers. Beta defensins have been shown to have anti-yeast activity. Exemplary yeast which can cause infection or disease to be prevented and/or treated with the compositions described herein include, without limitation, *Aciculoconidium, Botryoascus, Brettanomyces, Bullera, Bulleromyces, Candida, Citeromyces, Clavispora, Cryptococcus, Cystofilobasidium, Debaromyces, Debaryomyces, Dekkera, Dipodascus, Endomyces, Endomycopsis, Erythrobasidium, Fellomyces, Filobasidium, Guilliermondella, Hanseniaspora, Hansenula, Hasegawaea, Hyphopichia, Issatchenkia, Kloeckera, Kluyveromyces, Komagataella, Leucosporidium, Lipomyces, Lodderomyces, Malassezia-Mastigomyces, Metschnikowia, Mrakia, Nadsonia, Octosporomyces, Oosporidium, Pachysolen, Petasospora, Phaffia, Pichia, Pseudozyma, Rhodosporidium, Rhodotorula, Saccharomyces, Saccharomycodes, Saccharomycopsis, Schizoblastosporion, Schizosaccharomyces, Schwanniomyces, Selenotila, Sirobasidium, Sporidiobolus, Sporobolomyces, Stephanoascus, Sterigmatomyces, Syringospora, Torulaspora, Torulopsis, Tremelloid, Trichosporon, Trigonopsis, Udeniomyces, Waltomyces, Wickerhamia, Williopsis, Wingea, Yarrowia, Zygofabospora, Zygolipomyces,* or *Zygosaccharomyces*. In certain embodiments, prevention of a yeast infection of a subject or a disease caused by or associated therewith by administration of a composition described herein results in one or more of the following: prevention of the development or onset of a disease caused by or associated with a yeast infection; and/or prevention of the spread of a yeast infection or a disease caused by or associated therewith from the subject to another subject or population of subjects. In certain embodiments, treatment of a subject having a yeast infection or a disease caused by or associated therewith by administration of a composition described herein results in one or more of the following: prevention of the recurrence of the yeast infection or a disease caused by or associated therewith; reduction in the number of symptoms associated with the yeast infection or a disease caused by or associated therewith; reduction in organ failure associated with the yeast infection or a disease caused by or associated therewith; reduction of the duration and/or severity of the yeast infection or a disease caused by or associated therewith; reduction of the duration and/or severity of one or more symptoms of the yeast infection or a disease caused by or associated therewith; reduction in yeast cell count; reduction of the incidence of hospitalization of the subject; reduction of the hospitalization length of the subject; an increase the survival of the subject; enhancement or improvement of the prophylactic or therapeutic effect(s) of another therapy in the subject; prevention of the spread of a yeast from a cell, tissue, organ of the subject to another cell, tissue, organ of the subject; prevention of the development or onset of a disease caused by or associated with the yeast infection, or one or more symptoms thereof; and/or prevention of the spread of a yeast infection or a disease caused by or associated therewith from the subject to another subject or population of subjects.

In some embodiments, the compositions described herein are used to prevent and/or treat Candidiasis. Candidiasis is a common yeast infection that is due primarily to the overgrowth of *Candida albicans* and other species of *Candida*, which are part of the normal flora. In the mouth, candidiasis causes redness and white patches and is called "thrush." In children, *Candida* can cause diaper rash. In women, it can cause genital itching and vaginal discharge that is referred to as a "yeast infection." Candidiasis can also cause a variety of other infections, including nail infections, and can become systemic—especially in those who are immunocompromised. It is currently the fourth most common cause of hospital-acquired septicemia in the United States. In particular embodiments, the compositions described herein are administered topically to treat Candidiasis (e.g, administered topically to the skin or topically to the genital area, such as intravaginally). In one embodiment, the compositions described herein are administered at the site, or in the proximity to the site, of redness, white patches or genital itching (wherein such symptoms are associated with Candidiasis). In some embodiments, treatment of a subject having Candidiasis by administration of a composition described herein results in one or more of the following: reduction of the severity and/or duration of a symptom of Candidiasis, reduction in the number of symptoms of Candidiasis; reduction of pain associated with a symptom of Candidiasis; prevention or reduction of frequency of the recurrence of a symptom of Candidiasis; prevention of the spread of Candidiasis from the subject to another subject; prevention of the onset or development of a symptom of Candidiasis; and/or enhancement or improvement of the prophylactic and/or therapeutic effect(s) of another therapy (e.g., anti-yeast therapy) in the subject. In specific embodiments, the compositions described herein can be administered daily (e.g., once or twice a day) until the symptoms of a *Candida* infection subside (e.g., for 2, 3, 4, 5, 6, 7, 8, 9, 10, 11, 12 days, 2 weeks, 3 weeks, 4 weeks, or more than 4 weeks).

In some embodiments, the compositions described herein are used to prevent and/or treat Tinea versicolor. Symptoms of Tinea versicolor include, but are not limited to, multicolored patches or lesions on the skin. It is a condition that is common in young adults. In particular embodiments, the compositions described herein are administered topically to treat Tinea versicolor. In one embodiment, the compositions described herein are administered at the site, or in the proximity to the site, of Tinea versicolor infection. In some embodiments, treatment of a subject having Tinea versicolor by administration of a composition described herein results in one or more of the following: reduction of the severity and/or duration of a symptom of Tinea versicolor; reduction in the number of symptoms of Tinea versicolor; reduction of pain associated with a symptom of Tinea versicolor; prevention or reduction of frequency of the recurrence of a symptom of Tinea versicolor; prevention of the spread of Tinea versicolor from the subject to another subject; prevention of the onset or development of a symptom of Tinea versicolor; and/or enhancement or improvement of the prophylactic and/or therapeutic effect(s) of another therapy (e.g., anti-yeast therapy) in the subject. In specific embodiments, the compositions described herein can be administered daily (e.g., once or twice a day) until the symptoms of a Tinea versicolor infection subside (e.g., for 2, 3, 4, 5, 6, 7, 8, 9, 10, 11, 12 days, 2 weeks, 3 weeks, 4 weeks, or more than 4 weeks).

In some embodiments, the compositions described herein are used to prevent and/or treat osteomyelitis. Osteomyelitis is an infection of the bone or bone marrow, which can be caused by a bacteria or a fungus Osteomyeltitis can be diagnosed based on radiologic results showing a lytic center with a ring of sclerosis, and culture of material can taken from a bone biopsy to identify the specific pathogen. Accordingly, in some embodiments, the compositions described herein are administered to a patient having (e.g., diagnosed with) osteomyelitis to treat osteomyelitis. In specific embodiments, the compositions described herein are used to treat osteomyelitis caused by a fungal infection. In a particular embodiment, the compositions described herein are used to treat an infection, wherein the infection is not caused by a bacteria. Yet in other embodiments, the compositions described herein are used to treat osteomyelitis caused by any infection (including, but not limited to, a bacterial infection). In specific embodiments, the compositions described herein are administered topically to a surface of a tissue (e.g., to the surface of a bone or in proximity to the surface of a bone) of a patient after surgery. For example, the compositions described herein can be administered to an area of the knee after knee replacement surgery, to an area of the hip after hip replacement surgery, or to an area of the elbow after elbow replacement surgery. In certain embodiments, treatment of a subject having osteomyelitis by administration of a composition described herein results in one or more of the following: reduction in the duration and/or severity of one or more symptoms associated with osteomyelitis (e.g., pain, inflammation); reduction in the number of symptoms associated with osteomyelitis; prevention or reduction of frequency or recurrence of osteomyelitis; reduction of the incidence of hospitalization of the subject; reduction of the hospitalization length of the subject; and/or enhancement or improvement of the prophylactic or therapeutic effect(s) of another therapy in the subject.

In another specific embodiment, the compositions described herein are used to prevent and/or treat a yeast infection of a wound (e.g., an open wound such as an incision, a laceration, a penetration, an abrasion, or a burn). In another specific embodiment, the compositions described herein are not used to prevent and/or treat a yeast infection of a wound.

In specific embodiments, a subject treated for a viral infection, a fungal infection or an yeast infection (such as any of the viral, fungal or yeast infections described herein) using the sNAG compositions described herein does not have a bacterial infection. In other embodiments, a subject treated for a viral, a fungal, or an yeast infection (such as any of the viral, fungal or yeast infections described herein) using the sNAG compositions described herein has both a bacterial infection and a viral, a fungal or an yeast infection. In some embodiments, such infections are in the same location in the subject's organism. In other embodiments, such infections are in different locations in the subject's organism.

In certain embodiments, the compositions described herein are used to treat skin diseases. Without being bound by any mechanism of action, the ability of sNAG nanofibers to induce beta defensins may contribute to the activity of the sNAG nanofibers in treatment of skin diseases. Beta defensins have been shown to have activity in skin diseases. In a specific embodiment, the compositions described herein are used to treat dermatitis (e.g., atopic dermatitis). In a specific embodiment, the compositions are used to prevent and/or treat atopic dermatitis in a premature human infant, a human infant, a human toddler, or a human child. In another specific embodiment, the compositions described herein are used to treat psoriasis (e.g., Psoriasis vulgaris, Psoriasis erythroderma, Pustular psoriasis, nail psoriasis, or guttate psoriasis). In a specific embodiment, the compositions are used to treat psoriasis in a premature human infant, a human infant, a human toddler, or a human child. In certain embodiments, treatment of a subject having a skin disease by administration of a composition described herein results in one or more of the following: prevention of the recurrence of the skin disease; reduction in the number of symptoms associated with the skin disease; reduction in the severity or duration of one or more symptoms associated with the skin disease; reduction of the incidence of hospitalization of the subject; reduction of the hospitalization length of the subject; and/or enhancement or improvement of the prophylactic or therapeutic effect(s) of another therapy in the subject.

Symptoms of dermatitis include but are not limited to rashes (e.g., a bumpy rash), blisters, redness of the skin, swelling, itching, skin lesions, oozing, and/or scarring. Such symptoms often appear on the neck, wrist, forearm, thigh or ankle; but may also appear on the genital area. Common symptoms of atopic dermatitis include but are not limited to dry, itchy, and/or red skin. Symptoms of psoriasis include but are not limited to plaques (e.g., raised areas of inflamed skin covered with silvery white scaly skin), itching, swelling, pain, pustules (e.g., raised bumps filled with noninfectious pus), smooth inflamed patches of skin, small scaly lesions, and/or thickening and discoloring of the nails. In some embodiments, the compositions described herein prevent the onset or development of one or more of the above-listed symptoms or other symptoms known in the art, or reduce duration and/or severity of one or more of these symptoms.

In a specific embodiment, a composition described herein is not used to prevent and/or treat a bacterial infection or a disease caused by or associated therewith. In one embodiment, composition described herein is not used to prevent and/or treat *S. aureus* infection or a disease caused by or associated with such infection. In another specific embodiment, a composition described herein is not used to prevent and/or treat a bacterial infection of a wound (e.g., an open wound such as an incision, a laceration, a penetration, an abrasion, or a burn).

In a specific embodiment, the disease to be treated and/or prevented by administration of a composition described herein is not a wound (e.g., an open wound such as an incision, a laceration, a penetration, an abrasion, or a burn).

5.5 Patient Populations

In certain embodiments, a composition described herein may be administered to a naïve subject, i.e., a subject that does not have a disease or infection. In one embodiment, a composition described herein is administered to a naïve subject that is at risk of acquiring a disease or infection.

In one embodiment, a sNAG nanofiber composition described herein may be administered to a patient who has been diagnosed with a disease or infection. In another embodiment, a composition described herein may be administered to a patient who displays one or more symptoms of a disease or infection. In certain embodiments, a patient is diagnosed with a disease or infection prior to administration of a composition described herein In certain embodiments, the compositions described herein are administered to patients diagnosed with an infection. For example, the compositions described herein may be administered to a patient when a pathogen (e.g., virus, fungi or yeast) is detected in a biological sample taken from the patient. In one embodiment, a biological sample is obtained from the site or area to be treated by the compositions described herein or an area to which the compositions described herein are to be administered. In one embodiment, a swab is used to collect cells or pus from the site of the suspected infection to detect an infection. In another embodiment, a fluid is aspirated from the suspected site of an infection (e.g., a wound) to detect an infection. In yet another embodiment, a tissue biopsy is performed to detect an infection. In an embodiment where the suspected site of an infection is a wound, a wound culture may be performed to detect an infection. In another embodiment, the biological sample is obtained from blood, urine, sputum or feces of the patient. In some embodiments, a blood or a urine test may be performed to detect an infection (e.g., when an infection is suspected to have spread into the blood or other tissues/organs). In some embodiments, the collected sample (e.g., cells, tissues or fluid) is tested using DNA detection methods such as PCR for presence of one or more types of bacteria. In other embodiments, immunofluorescence analysis, serology, culture (e.g., blood agar culture), or any other test known and/or practiced in the art may be used for laboratory diagnosis of an infection.

In other specific embodiments, the compositions described herein may be administered to a patient diagnosed with or displaying one or more symptoms of a disease, e.g., a cancer, an IBD, Crohn's disease, dermatitis, psoriasis or an infection (e.g., viral, yeast or fungi infection). In certain embodiments, a patient is diagnosed with a disease (e.g., one of the diseases listed above) or displays one or more symptoms of a disease prior to administration of a composition described herein. A disease may be diagnosed by any method known to a skilled artisan, including evaluation of the patient's symptoms and/or detection of a pathogen in a biological sample of the patient (e.g., as described above). In one example, the compositions described herein may be administered to a patient diagnosed with a disease by a treating physician or another medical professional. In another example, a patient may use the compositions described herein upon detection of one or more symptoms of a disease.

In certain embodiments, a subject to be administered a composition described herein is a subject with no or low level of expression of one or more defensin peptides or a mutation/deletion in a gene or genes encoding one or more defensin peptides. In some embodiments, a subject to be administered a composition described herein is a subject with no or low or altered level of expression of one or more α-defensins (e.g., DEFA1, DEFA1B, DEFA3, DEFA4, DEFA5, DEFA6), one or more β-defensins (e.g., DEFB1, DEFB2, DEFB4, DEFB103A, DEFB104A, DEFB105B, DEFB107B, DEFB108B, DEFB110, DEFB112, DEFB114, DEFB118, DEFB119, DEFB123, DEFB124, DEFB125, DEFB126, DEFB127, DEFB128, DEFB129, DEFB131, DEFB136), and/or one or more θ-defensins (e.g., DEFT1P). In some embodiment, a subject to be administered a composition described herein is a subject with no or low or altered level of expression of one or more of DEFA1, DEFA3, DEFA4, DEFA5, DEFB1, DEFB3, DEFB103A, DEFB104A, DEFB108B, DEFB112, DEFB114, DEFB118, DEFB119, DEFB123, DEFB124, DEFB125, DEFB126, DEFB128, DEFB129 and DEFB131. In certain embodiments, a subject to be administered a composition described herein is a subject with no or low or altered level of expression of one or more Toll receptors (e.g., TLR1, TLR2, TLR3, TLR4, TLR5, TLR6, TLR7, TLR8, TLR9, TLR10, TLR11, and/or TLR12). In yet other embodiments, a subject to be administered a composition described herein is a subject with no or low or altered level of expression of one or more of IL-1, CEACAM3, SPAG11, SIGIRR (IL1-like receptor), IRAK1, IRAK2, IRAK4, TBK1, TRAF6 and IKKi. In some embodiments, a subject to be administered a composition described herein is a subject with no or low or altered level of expression of one or more of IRAK2, SIGIRR, TLR1, TLR2, TLR4, TLR7, TLR8, TLR10 and TRAF6. A low level of expression of a gene is a level that is lower (e.g., more than 1.25 fold, 1.5 fold, 2 fold, 2.5 fold, 3 fold, 3.5 fold, 4 fold, 4.5 fold, 5 fold, 6 fold, 7 fold, 8 fold, 9 fold, 10 fold lower) than the normal level of expression. An altered level of expression of a gene is a level that differs (e.g., by more than 20%, 25%, 30%, 50%, 75%, 100%, 150%, 200%, 250%, 300%) from the normal level of expression. Wherein the "normal" expression of one or more defensin genes is: (i) the average expression level known to be found in subjects not displaying symptoms or not diagnosed with the disease or infection to be treated; (ii) the average expression level detected in three, five, ten, twenty, twenty-five, fifty or more subjects not displaying symptoms or not diagnosed with the disease or infection to be treated; and/or (iii) the level of expression detected in a patient to be administered a composition described herein before the onset of the disease or infection.

In certain embodiments, a composition described herein is administered to a patient who has been diagnosed with a solid tumor cancer, such as bone and connective tissue sarcomas, brain cancer, breast cancer, ovarian cancer, kidney cancer, pancreatic cancer, esophageal cancer, stomach cancer, lung cancer (e.g., small cell lung cancer (SCLC), non-small cell lung cancer (NSCLC), throat cancer, and mesothelioma), liver cancer, and prostate cancer. In a specific embodiment, a composition described herein is administered to a patient who has been diagnosed with Kaposi's sarcoma.

In certain embodiments, a composition described herein is administered to a patient who has been diagnosed with a skin cancer, such as melanoma, basal cell carcinoma, and squamous cell carcinoma.

In certain embodiments, a composition described herein is administered to a patient who has (e.g., has been diagnosed with) inflammatory bowel disease (e.g., ulcerative colitis) or displays one, two or more symptoms of inflammatory bowel disease.

In certain embodiments, a composition described herein is administered to a patient who has (e.g., has been diagnosed with) Crohn's disease (e.g., ileal Crohn's disease) or displays one or more symptoms of Crohn's disease.

In certain embodiments, a composition described herein is administered to a patient who has (e.g., has been diagnosed with) a disease caused by a virus or an infection associated with a virus (such as any disease caused by a virus or an infection associated with a virus described herein), e.g., the patient has been infected by respiratory syncytial virus (RSV), influenza virus (influenza A virus, influenza B virus, or influenza C virus), human metapneumovirus (HMPV), rhinovirus, parainfluenza virus, SARS Coronavirus, human immunodeficiency virus (HIV), hepatitis virus (A, B, C), ebola virus, herpes simplex virus (e.g., HSV-1, HSV-2), rubella, variola major, and/or variola minor. In certain embodiments, a composition described herein is administered to a patient who displays one, two or more symptoms of a disease caused by a virus or an infection associated with a virus (such as any disease caused by a virus or an infection associated with a virus described herein).

In certain embodiments, a composition described herein is administered to a patient who has (e.g., has been diagnosed with) a wound (e.g., an open wound such as an incision, a laceration, a penetration, an abrasion, or a burn) that has been infected by a virus. In a specific embodiment, a composition described herein is not administered to a patient who has been diagnosed with a wound that has been infected by a virus.

In certain embodiments, a composition described herein is administered to a patient who has (e.g., has been diagnosed with) a disease caused by a fungus or an infection associated with a fungus (any disease caused by a fungus or an infection associated with a fungus described herein), e.g., the patient has been infected by *Blastomyces, Paracoccidioides, Sporothrix, Cryptococcus, Candida, Aspergillus, Histoplasma, Cryptococcus, Bipolaris, Cladophialophora, Cladosporium, Drechslera, Exophiala, Fonsecaea, Phialophora, Xylohypha, Ochroconis, Rhinocladiella, Scolecobasidium,* and/or *Wangiella*. In certain embodiments, a composition described herein is administered to a patient who displays one, two or more symptoms of a disease caused by a fungus or an infection associated with a fungus (such as any disease caused by a virus or an infection associated with a fungus described herein).

In certain embodiments, a composition described herein is administered to a patient who has (e.g., has been diagnosed with) a wound (e.g., an open wound such as an incision, a laceration, a penetration, an abrasion, or a burn) that has been infected by a fungus. In a specific embodiment, a composition described herein is not administered to a patient who has been diagnosed with a wound that has been infected by a fungus.

In certain embodiments, a composition described herein is administered to a patient who has (e.g., has been diagnosed with) a disease caused by a yeast or an infection associated with a yeast, e.g., the patient has been infected by *Aciculoconidium, Botryoascus, Brettanomyces, Bullera, Bulleromyces, Candida, Citeromyces, Clavispora, Cryptococcus, Cystofilobasidium, Debaromyces, Debaryomyces, Dekkera, Dipodascus, Endomyces, Endomycopsis, Erythrobasidium, Fellomyces, Filobasidium, Guilliermondella, Hanseniaspora, Hansenula, Hasegawaea, Hyphopichia, Issatchenkia, Kloeckera, Kluyveromyces, Komagataella, Leucosporidium, Lipomyces, Lodderomyces, Malassezia-Mastigomyces, Metschnikowia, Mrakia, Nadsonia, Octosporomyces, Oosporidium, Pachysolen, Petasospora, Phaffia, Pichia, Pseudozyma, Rhodosporidium, Rhodotorula, Saccharomyces, Saccharomycodes, Saccharomycopsis, Schizoblastosporion, Schizosaccharomyces, Schwanniomyces, Selenotila, Sirobasidium, Sporidiobolus, Sporobolomyces, Stephanoascus, Sterigmatomyces, Syringospora, Torulaspora, Torulopsis, Tremelloid, Trichosporon, Trigonopsis, Udeniomyces, Waltomyces, Wickerhamia, Williopsis, Wingea, Yarrowia, Zygofabospora, Zygolipomyces,* and/or *Zygosaccharomyces*.

In certain embodiments, a composition described herein is administered to a patient who has (e.g., has been diagnosed with) a wound (e.g., an open wound such as an incision, a laceration, a penetration, an abrasion, or a burn) that has been infected by a yeast. In a specific embodiment, a composition described herein is not administered to a patient who has been diagnosed with a wound that has been infected by a yeast.

In certain embodiments, a composition described herein is administered to a patient who has (e.g., has been diagnosed with) a skin disease or displays one, two or more symptoms of a skin disease. In a specific embodiment, a composition described herein is administered to a patient who has been diagnosed with dermatitis (e.g., atopic dermatitis) or displays one, two or more symptoms of dermatitis. In another specific embodiment, a composition described herein is administered to a patient who has been diagnosed with psoriasis or displays one, two or more symptoms of psoriasis.

In some embodiments, a composition described herein is administered to an immunosuppressed patient, and/or a patient susceptible to acute or chronic disease or infection (e.g., an HIV positive patient, or a patient immunosuppressed as a result of cancer treatment or a transplantation procedure). In one embodiment, a composition described herein is administered to a patient diagnosed with cystic fibrosis.

In some embodiments, a composition described herein is administered to a patient with a disease or infection before symptoms of the disease or infection manifest or before symptoms of the disease or infection become severe (e.g., before the patient requires treatment or hospitalization). In some embodiments, a composition described herein is administered to a patient with a disease or infection after symptoms of the disease or infection manifest or after symptoms of the disease or infection become severe (e.g., after the patient requires treatment or hospitalization).

In some embodiments, a subject to be administered a composition described herein is an animal. In certain embodiments, the animal is a bird. In certain embodiments, the animal is a canine. In certain embodiments, the animal is a feline. In certain embodiments, the animal is a horse. In certain embodiments, the animal is a cow. In certain embodiments, the animal is a mammal, e.g., a horse, swine, mouse, or primate, preferably a human.

In certain embodiments, a subject to be administered a composition described herein is a human adult. In certain embodiments, a subject to be administered a composition described herein is a human adult more than 50 years old. In certain embodiments, a subject to be administered a composition described herein is an elderly human subject.

In certain embodiments, a subject to be administered a composition described herein is a human toddler. In certain embodiments, a subject to be administered a composition described herein is a human child. In certain embodiments, a subject to be administered a composition described herein is a human infant. In certain embodiments, a subject to be administered a composition described herein is a premature human infant.

In a specific embodiment, a composition described herein is not administered to a subject to prevent and/or treat a bacterial infection or a disease caused by or associated therewith. In one embodiment, a composition described herein is not administered to a subject to prevent and/or treat S. aureus infection or a disease caused by or associated with such infection. In another specific embodiment, a composition described herein is not administered to a subject to prevent and/or treat a bacterial infection of a wound (e.g., an open wound such as an incision, a laceration, a penetration, an abrasion, or a burn).

In a specific embodiment, a composition described herein is not administered to a subject to treat a wound (e.g., an open wound such as an incision, a laceration, a penetration, an abrasion, or a burn).

5.6 Modes of Administration

In certain embodiments, methods are described herein for treating or preventing an infection and/or a disease or a symptom thereof, wherein a composition comprising the sNAG nanofibers is topically administered to a patient in need of such treatment. In some embodiments, a sNAG nanofiber composition is applied topically to tissue or organ which has an increased risk of an infection or a disease.

In some embodiments, an effective amount of the sNAG nanofibers and/or a sNAG nanofiber composition is administered to a subject.

In some embodiments, a composition comprising the sNAG nanofibers is administered topically to the site of an infection or a disease in a patient or to the site affected by an infection or a disease. In yet other embodiments, a composition comprising the sNAG nanofibers is administered topically to the site and around the site of an infection or a disease in a patient or to the site affected by an infection or a disease. In yet other embodiments, a composition comprising sNAG nanofibers is applied in proximity to the site of an infection or disease in a patient or in proximity to the site affected by an infection or a disease. In yet another embodiment, a composition comprising the sNAG nanofibers is administered topically to the site at high risk of an infection or a disease associated with such infection.

The sNAG nanofiber compositions described herein may be administered by any of the many suitable means of topical administration which are well known to those skilled in the art, including but not limited to topically to the skin, topically to any other surface of the body (e.g., mucosal surface), by inhalation, intranasally, vaginally, rectally, buccally, or sublingually. The mode of topical administration may vary depending upon the infection or disease to be treated or prevented. The sNAG nanofiber compositions can be formulated for the various types of topical administration.

In a specific embodiment, the compositions disclosed herein are applied topically, for example to the skin of a patient in need of such treatment or to another tissue of a patient in need of such treatment. In some embodiments, the compositions may be applied directly to the site of a disease or infection and/or in the proximity to the site of a disease or infection. In some embodiments, the compositions may be applied directly to a site where a disease or infection might potentially develop (e.g., to an open wound).

In one embodiment, a composition comprising sNAG nanofibers is applied to the skin of a patient. For example, such a composition may be applied topically to the skin of a patient for treating or preventing a disease or infection of the skin.

In another embodiment, a composition described herein may be applied topically to a mucosal surface of a patient. For example, such a composition may be applied topically to the oral mucosa for treating or preventing a disease or infection of the mouth or gums.

In some embodiments, a composition described herein may be applied topically to a genital, urinal or anal surface/area of a patient. For example, such a composition may be applied topically to genital, urinal or anal surface/area for treating or preventing a genital, urinal or anal disease or infection.

The above-listed methods for topical administration may include administration of a sNAG nanofiber in the form of a suspension (e.g., a thick suspension), a cream, an ointment, a gel, a liquid solution, a membrane, a spray, a paste, a powder or any other formulation described herein or known in the art. A sNAG nanofiber may also be applied in a dressing or a bandage, for example to treat localized diseases or infections on the skin of a patient. In particular embodiments, compositions comprising sNAG nanofibers are not solid or barrier-forming.

In some embodiments, a composition described herein may be applied as a spray into the oral cavity and/or respiratory system of a patient. For example, such a composition may be applied as a spray for treating or preventing a disease or infection of the mouth, nose, gums, throat or lungs. In one such embodiment, the composition may be formulated to be administered as an inhaler.

In some embodiments, a composition described herein may be applied as a suppository in the rectum, vagina or urethra of a patient. For example, such composition may be applied as a suppository for treating or preventing a disease or infection of the digestive tract, urinary tract or reproductive tract.

In some embodiments, a composition described herein may be applied topically with a syringe or another type of applicator (e.g., a spatula, a cotton swab, a tube such as a squeeze tube) suitable for topical delivery of the composition to the patient. For example, a composition described herein formulated as a suspension (e.g., thick suspension), a liquid solution, a cream, an ointment, or a gel can be administered topically to the skin, mucous membrane or other surface tissue of a patient via an applicator (e.g., syringe).

In another embodiment, a composition described herein may be applied at the site of a surgical procedure. For example, such composition may be sprayed, applied as a cream, suspension (e.g., a thick suspension), liquid solution, ointment, gel, membrane, or powder, or coated on the surface of the tissue or organ to be subjected to a surgical procedure or that has been subjected to the surgical procedure. In one embodiment, a composition described herein is applied at the site of the surgical incision, at the site of the excised tissue, or at the site of surgical stitches or sutures. Such administration of a composition described herein may prevent a post-surgical infection or may prevent recurrence of a disease for which the surgery was indicated. For example, a composition described herein may be used during or after a surgical procedure which is known to pose high risk of a viral, yeast, or fungal infection. Surgical procedures that are known to pose high risk of an infection include bowel resection, gastrointestinal surgical procedures, kidney surgery, etc. A composition described herein may be applied at the site of any of the above-listed or other surgical procedures.

In yet other embodiments, a composition described herein may be coated on a device, for example an oral hygiene product, a catheter, a surgical instrument or another product, to be used in or inserted into a patient, in order to treat or prevent a disease or infection in a patient.

In a specific embodiment, the compositions disclosed herein are applied topically to the site of a solid tumor or skin cancer. In some embodiments, the compositions are applied directly to the solid tumor or skin cancer itself. In some embodiments, the compositions are applied directly to the site of a solid tumor or skin cancer, wherein all or part of the tumor or skin cancer has been removed (e.g., surgically removed). In some embodiments, the compositions disclosed herein are topically administered to the site and/or around the site from which a solid tumor or skin cancer has been excised or removed. In some of these embodiments, such compositions may be sprayed, applied as a suspension, liquid solution, cream, ointment, gel, membrane, or powder, or coated on the surface of an organ or tissue from which a solid tumor was excised. In specific embodiments, the compositions described herein are sprayed or coated at and around the site or sites of removed or excised solid tumor or skin cancer.

In some embodiments, methods contemplated herein include a step that includes detection/diagnosis of a disease or an infection in a patient. In some embodiments, detection/diagnosis involves a test or assay for one or more pathogen (e.g., a virus, a fungi, or an yeast) in a biological sample of the patient. In other embodiments, diagnosis involves assessing whether the patient has one or more symptoms of a disease (e.g., IBD, Crohn's disease, cancer, dermatitis, psoriasis, or a disease associated with a viral, fungal, or yeast infection).

The compositions described herein may exhibit sustained release properties and/or may be administered in a formulation resulting in a sustained release of such compositions. In some embodiments, the sNAG nanofibers biodegrade over time as described in Section 5.1, supra, and these properties of sNAG nanofibers may lead to or contribute to sustained release of the compositions described herein. In yet other embodiments, the compositions described herein are formulated to display sustained release capabilities using any methods known in the art. The compositions described herein may exhibit sustained release over a time period equal to or more than about 6 hours, 12 hours, 18 hours, 24 hours (1 day), 2 days, 3 days, 5 days, 7 days (1 week), 10 days, 14 days (2 weeks), 3 weeks or 4 weeks after administration of the composition to the patient.

Contemplated treatment regimes include a single dose or a single application of a sNAG nanofiber composition; two doses or two applications of a sNAG nanofiber composition; or a regiment of multiple doses or multiple applications of a sNAG nanofiber composition. A dose or an application may be administered hourly, daily, weekly or monthly. For example, a dose of a sNAG nanofiber composition may be administered once a day, twice a day, three times a day, four times a day, once a week, 2 times a week, 3 times a week, every other day, once in 2 weeks, once in 3 weeks, once in 4 weeks, once a month, or once in two months.

A sNAG nanofiber composition may be administered for a duration equal to or greater than 2 days, 3 days, 4 days, 5 days, 1 week, 2 weeks, 3 weeks, 1 month, 2 months, 3 months, 4 months, 5 months, 6 months, 9 months, 1 year, 1.5 years, 2 years, 2.5 years, 3 years, 4 years, 5 years, 7 years, 10 years or more. In some embodiments, a sNAG fiber composition is administered to a patient once or twice a day for a duration equal to or greater than 2 days, 3 days, 4 days, 5 days, 1 week, 2 weeks, 3 weeks, 1 month, 2 months, 3 months, 4 months, 5 months, 6 months, 9 months, or 1 year. In one such embodiment, a sNAG nanofiber composition does not cause any side effects or causes only mild side effects during the duration of the treatment. In another embodiment, a sNAG nanofiber composition does not cause irritation (e.g., moderate or severe irritation) or allergy (e.g., moderate or severe allergy).

The concentration of sNAG nanofibers in a composition may vary. In general, an effective amount of sNAG nanofibers are used in the compositions described herein to treat the diseases described herein. An effective amount may be an amount sufficient to achieve one or more of the effects described herein, for example an amount effective to treat a disease or reduce or eradicate one or more symptoms of a disease. For example, a composition may comprise about 0.2 to 20 mg/cm$^2$ of sNAG nanofibers per dose/application of the composition in a form suitable for topical delivery to a patient. In certain embodiments, a composition described herein comprises about 0.25 to 20 mg/cm$^2$, about 0.5 to 20 mg/cm$^2$, about 1 to 20 mg/cm$^2$, about 1 to 15 mg/cm$^2$, about 1 to 12 mg/cm$^2$, about 1 to 10 mg/cm$^2$, about 1 to 8 mg/cm$^2$, about 1 to 5 mg/cm$^2$, about 2 to 8 mg/cm$^2$, or about 2 to 6 mg/cm$^2$ of sNAG nanofibers per dose/application of the composition in a form suitable for topical delivery to a patient. In some embodiments, compositions described herein can comprise about 5 to 50 mg/ml of sNAG nanofibers per dose/application of the composition in a form suitable for topical delivery to a patient. In certain embodiments, a composition described herein comprises about 5 to 40 mg/ml, about 5 to 35 mg/ml, about 10 to 50 mg/ml, about 10 to 40 mg/ml, about 10 to 35 mg/ml, about 10 to 30 mg/ml, about 15 to 40 mg/ml, about 15 to 35 mg/ml, about 15 to 30 mg/ml, or about 20 to 30 mg/ml of sNAG nanofibers per dose/application of the composition in a form suitable for topical delivery to a patient. In specific embodiments, a composition described herein comprises about 10 mg/ml, 12 mg/ml, 15 mg/ml, 20 mg/ml, 25 mg/ml or 30 mg/ml of sNAG nanofibers per dose/application of the composition in a form suitable for topical delivery to a patient. In certain embodiments, compositions described herein can comprise an amount of total solution or suspension (comprising sNAG nanofibers) in the range of about 50 to 100 µl, 50 to 200 µl, 50 to 250 µl, 50 to 300 µl, 50 to 350 µl, 50 to 400 µl, 50 to 450 µl, 50 to 500 µl, 100 to 200 µl, 100 to 300 µl, 100 to 400 µl, 100 to 500 µl per 0.5 cm$^2$ or 1 cm$^2$ of the surface to be treated in a patient (e.g., skin, mucosal surface or other tissue surface). The total solution or suspension can comprise saline, buffer, solution (e.g., Hank buffer solution), or any other physiologically compatible solution.

5.7 Combination Therapy

In various embodiments, the sNAG nanofibers described herein or compositions thereof may be administered to a subject in combination with one or more other therapies. The one or more other therapies may be beneficial in the treatment or prevention of a disease or may ameliorate a symptom or condition associated with a disease. In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patent visit.

In certain embodiments, the one or more therapies is surgery. In a specific embodiment, surgery is performed to remove all or part of a solid tumor or skin cancer, and a composition described herein is administered to the site of the tumor before, during, and/or after the surgery. In certain embodiments, the one or more therapies is radiation therapy.

In certain embodiments, the one or more therapies is an anti-viral agent. Any anti-viral agents well-known to one of skill in the art may used in combination with the sNAG nanofibers described herein or compositions thereof. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, peramivir, rimantadine, saquinavir, indinavir, ritonavir, alpha-interferons and other interferons, AZT, zanamivir (Relenza®), and oseltamivir (Tamiflu®). Other anti-viral agents include influenza virus vaccines, e.g., Fluarix® (GlaxoSmithKline), FluMist® (MedImmune Vaccines), Fluvirin® (Chiron Corporation), Flulaval® (GlaxoSmithKline), Afluria® (CSL Biotherapies Inc.), Agriflu® (Novartis) or Fluzone® (Aventis Pasteur).

In certain embodiments, the one or more therapies is an anti-cancer agent. In a specific embodiment, the anti-cancer agent is a chemotherapeutic agent. Any anti-cancer agents known to one of skill in the art may used in combination with the sNAG nanofibers described herein or compositions thereof. Exemplary anti-cancer agents include: acivicin; anthracyclin; anthramycin; azacitidine (Vidaza); bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); carboplatin; chlorambucil; cisplatin; cytarabine (Ara-C); daunorubicin hydrochloride; decitabine (Dacogen); demethylation agents, docetaxel; doxorubicin; EphA2 inhibitors; etoposide; fazarabine; fluorouracil; gemcitabine; histone deacetylase inhibitors (HDACs); interleukin II (including recombinant interleukin II, or rIL2), interferon alpha; interferon beta; interferon gamma; lenalidomide (Revlimid); anti-CD2 antibodies (e.g., siplizumab (MedImmune Inc.; International Publication No. WO 02/098370, which is incorporated herein by reference in its entirety)); melphalan; methotrexate; mitomycin; oxaliplatin; paclitaxel; puromycin; riboprine; spiroplatin; tegafur; teniposide; vinblastine sulfate; vincristine sulfate; vorozole; zeniplatin; zinostatin; and zorubicin hydrochloride.

Other examples of cancer therapies include, but are not limited to angiogenesis inhibitors; antisense oligonucleotides; apoptosis gene modulators; apoptosis regulators; BCR/ABL antagonists; beta lactam derivatives; casein kinase inhibitors (ICOS); estrogen agonists; estrogen antagonists; glutathione inhibitors; HMG CoA reductase inhibitors; immunostimulant peptides; insulin-like growth factor-1 receptor inhibitor; interferon agonists; interferons; interleukins; lipophilic platinum compounds; matrilysin inhibitors; matrix metalloproteinase inhibitors; mismatched double stranded RNA; nitric oxide modulators; oligonucleotides; platinum compounds; protein kinase C inhibitors, protein tyrosine phosphatase inhibitors; purine nucleoside phosphorylase inhibitors; raf antagonists; signal transduction inhibitors; signal transduction modulators; translation inhibitors; tyrosine kinase inhibitors; and urokinase receptor antagonists.

In some embodiments, the therapy(ies) used in combination with the sNAG nanofibers described herein or compositions thereof is an anti-angiogenic agent. Non-limiting examples of anti-angiogenic agents include proteins, polypeptides, peptides, conjugates, antibodies (e.g., human, humanized, chimeric, monoclonal, polyclonal, Fvs, ScFvs, Fab fragments, F(ab)2 fragments, and antigen-binding fragments thereof) such as antibodies that specifically bind to TNF-α, nucleic acid molecules (e.g., antisense molecules or triple helices), organic molecules, inorganic molecules, and small molecules that reduce or inhibit angiogenesis. Other examples of anti-angiogenic agents can be found, e.g., in U.S. Publication No. 2005/0002934 A1 at paragraphs 277-282, which is incorporated by reference in its entirety. In other embodiments, the therapy(ies) used in accordance with the invention is not an anti-angiogenic agent.

In some embodiments, the therapy(ies) used in combination with the sNAG nanofibers described herein or compositions thereof is an anti-inflammatory agent. Non-limiting examples of anti-inflammatory agents include non-steroidal anti-inflammatory drugs (NSAIDs) (e.g., celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumetone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™)), steroidal anti-inflammatory drugs (e.g., glucocorticoids, dexamethasone (DECADRON™), corticosteroids (e.g., methylprednisolone (MEDROL™)), cortisone, hydrocortisone, prednisone (PREDNISONE™ and DELTASONE™), and prednisolone (PRELONE™ and PEDIAPRED™)), anticholinergics (e.g., atropine sulfate, atropine methylnitrate, and ipratropium bromide (ATROVENT™)), beta2-agonists (e.g., abuterol (VENTOLIN™ and PROVENTIL™), bitolterol (TORNALATE™), levalbuterol (XOPONEX™), metaproterenol (ALUPENT™), pirbuterol (MAXAIR™), terbutlaine (BRETHAIRE™ and BRETHINE™), albuterol (PROVENTIL™, REPETABS™, and VOLMAX™), formoterol (FORADIL AEROLIZER™), and salmeterol (SEREVENT™ and SEREVENT DISKUS™)), and methylxanthines (e.g., theophylline (UNIPHYL™, THEO-DUR™, SLO-BID™, AND TEHO-42™)).

In certain embodiments, the therapy(ies) used in combination with the sNAG nanofibers described herein or compositions thereof is an alkylating agent, a nitrosourea, an antimetabolite, an anthracyclin, a topoisomerase II inhibitor, or a mitotic inhibitor. Alkylating agents include, but are not limited to, busulfan, cisplatin, carboplatin, cholormbucil, cyclophosphamide, ifosfamide, decarbazine, mechlorethamine, mephalen, and themozolomide. Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclins include but are not limited to daunorubicin, doxorubicin, epirubicin, idarubicin, and mitoxantrone. Topoisomerase II inhibitors include, but are not limited to, topotecan, irinotecan, etopiside (VP-16), and teniposide. Mitotic inhibitors include, but are not limited to taxanes (paclitaxel, docetaxel), and the vinca alkaloids (vinblastine, vincristine, and vinorelbine).

In some embodiments, the therapy(ies) used in combination with the sNAG nanofibers described herein or compositions thereof is an anti-pain medication (e.g., an analgesic). In some embodiments, the therapy(ies) used in combination with the sNAG nanofibers described herein or compositions thereof is an anti-fever medication.

5.8 Kits

Also provided herein is a pharmaceutical pack or kit comprising one or more of the sNAG nanofiber compositions described herein. The pack or kit may comprise one or more containers filled with one or more ingredients comprising the compositions described herein. The composition is preferably contained within a sealed, water proof, sterile package which facilitates removal of the composition without contamination. Materials from which containers may be made include aluminum foil, plastic, or another conventional material that is easily sterilized. The kit can contain material for a single administration or for multiple administrations of the composition, preferably wherein the material for each administration is provided in a separate, waterproof, sterile package.

In another embodiment, a container having dual compartments is provided. A first compartment contains any of the above-described sNAG nanofiber compositions described herein, while the second compartment contains another active agent such as another agent to be used in combination with the sNAG nanofiber composition. In the field or the clinic, the composition in the first compartment can be readily combined with the agent in the second compartment for subsequent administration to a patient.

The kit can also contain an applicator for administration of one or more of the sNAG nanofiber compositions described herein, and/or for administration of another active agent such as another agent to be used in combination with the sNAG nanofiber composition. In one embodiment, the kit comprises an applicator for topical administration of a sNAG nanofiber composition. Examples of applicators for topical administration of a sNAG nanofiber composition include, without limitation, a syringe, a spatula, a tube (a squeeze tube), and a cotton swab.

Additionally, a kit designed for emergency or military use can also contain disposable pre-sterilized instruments, such as scissors, scalpel, clamp, tourniquet, elastic or inelastic bandages, or the like.

Optionally associated with such kit or pack can be a notice in the form prescribed by a governmental agency regulating the manufacture, use or sale of pharmaceuticals or biological products, which notice reflects approval by the agency of manufacture, use or sale for human administration. For example, a kit can comprise a notice regarding FDA approval and/or instructions for use.

The kits encompassed herein can be used in the above applications and methods.

6. EXAMPLES 6.1 Example 1: sNAG Nanofibers from a Marine Diatom Promote Wound Healing and Defensin Expression Via an Akt1/Ets1-Dependent Pathway This example demonstrates that sNAG nanofibers promote cutaneous wound healing and expression of defensins, and that the Akt1→Ets1 pathway plays a central role in the regulation of cutaneous wound healing by sNAG nanofibers.

6.1.1 Materials and Methods sNAG nanofibers (in particular, Taliderm) are produced and supplied by Marine Polymer Technologies and formed into suitable patches for wound treatment. Wildtype C57 Black and Akt1 null mice were housed at the Medical University of South Carolina animal facilities. Wildtype and Akt1 null mice, ages ranging from eight to 12 weeks, were anesthetized with 50% pure oxygen and 50% isoflurane gas. Immediately before wounding, Nair Hair Removal Lotion was applied to their dorsum to remove any unwanted hair. A dorsal 4 mm circular area of skin was removed using an excision biopsy punch. Taliderm was placed onto each wound at day 0 or wounds were left untreated. At days 1,3,5, and 7 the wounds were photographed, measured, and excised using an 8 mm biopsy punch to ensure complete removal of the wound and surrounding skin. Wildtype and Akt1 null wounds with and without Taliderm treatment were embedded in paraffin in preparation for H&E and immunofluorescent staining.

Paraffin-embedded sections were sectioned and placed on microscope slides for staining. Slides were washed with xylenes to remove paraffin and rehydrated through a series of graded alcohols. The sections were then incubated in 0.1% Triton ×100 for permeabilization. Sections were incubated in a boiling Antigen Retrival solution. 1% Animal serum was used for blocking before incubating in the primary goat antibody, β-defensin 3 1:400 dilution. The sections were then incubated in the primary antibody overnight at 4° in a humidity chamber. An immunofluorescent secondary Donkey α-goat 488 antibody 1:200 dilution was used, followed by nuclear staining with TOPRO-3. Images were captured using confocal microscopy.

Hematoxylin and eosin staining was used to visualize basic structures such as the epidermis, dermis, muscle, and blood vessels and to determine the orientation and approximate location in the wound. H&E staining was also used to begin to identify which cell types are stimulated by Taliderm in an Akt1-independent manner.

Other materials and methods are described in figure descriptions and in the results section below, and performed in accordance with the methods known in the art.

6.1.2 Results sNAG Nanofibers Stimulate Akt 1 Activation, an Upstream Regulator of Ets1 FIG. 1A shows a Western blot analysis of phospho-Akt in response to NAG and sNAG stimulation of serum starved EC. FIG. 1B shows RT-PCR analysis of EC infected either with scrambled control or Akt1 shRNA lentiviruses and assessed for expression of Ets1 and S26 as a loading control. FIG. 1C illustrates a signal transduction pathway transducing a signal from sNAG nanofibers to Akt1, Ets1 and Defensins.

Delayed Wound Healing in Akt1 Null Animals is Partially Rescued by Taliderm (sNAG) Treatment. FIG. 2A shows representative images of wounded WT and AKT1 null mice with and without treatment of Taliderm. FIG. 2B shows H&E staining of representative mouse skin sections from day 3 wounds. H&E staining of wildtype and Akt1 wound excisions indicate a Taliderm dependent increase in keratinocyte proliferation and migration. The dashed lines indicate the area of keratinocyte proliferation across the wound margin. In both the wildtype and Akt1 treated wounds there is an an evident increase in reepithelization across the wound margin compared to the wildtype and Akt1 control. This indicates that Taliderm increases kertainoctye recruitment independent of the Akt1 pathway. Although Taliderm induces a complete reepithlization of the epidermis across the wound margin, there is still substantial lack of revascularization in the underlying tissue compared to the wildtype. This is evident by substantial hemorrhaging and infiltration of red blood cells in the Akt1 aminals.

sNAG Nanofibers Stimulate Cytokine and Defensin Expression in Primary Endothelial cells. FIG. 3A shows immunohistochemisty of EC treated with or without sNAG using an antibody directed against a-defensin. FIG. 3B presents ELISA showing that nanofiber treatment of EC results in the secretion of α-defensins 1-3.

sNAG Nanofibers Stimulate Defensin Expression in Primary Endothelial Cells in an Akt1 Dependent Manner. FIGS. 4A and 4B show quantitative RT-PCR analyses of serum starved EC treated with or without sNAG, with or without PD98059 (MAPK inhibitor), Wortmannin (PI3K inhibitor) or infected with a scrambled control or Akt1 shRNA lentiviruses and assessed for expression of the genes indicated.

sNAG Nanofibers Stimulate β-Defensin 3 Expression in Mouse Keratinocytes. FIG. 5A shows immunofluorescent staining with β-defensin 3 and Involucrin antibodies of paraffin embedded mouse cutaneous wound sections from WT and Akt1 null animals on Day 3. A cutaneous wound healing model was developed in both WT and Akt1 null mice to assess the effects of Taliderm in vivo. These findings show that β-defensin 3 expression increases in Taliderm treated animals in an Akt1-dependent manner. The ability of Taliderm to increase defensin expression in a healing wound has important implications for treating and controlling wound infection. FIG. 5B shows quantification of β-defensin 3 immunofluorescent staining using NIHImageJ software. FIG. 5C shows immunofluorescent staining of WT and Akt1 null treated and untreated keratinocytes with β-Defensin 3 and TOPRO-3. Notice the increase in green β-Defensin 3 staining in WT and Akt1 Taliderm treated wounds. The immunofluorescent labeling of wound sections illustrates that Taliderm treated wounds show an increase in β-defensin 3 expression in an Akt1 dependent manner. Although the Akt1 treated wounds show a reasonable increase in β-defensin 3, the wildtype treated wounds illustrate a more remarkable increase. This indicates that β-defensin 3 expression is not only increased by application of the nanofiber, but is at least partially dependent on the Akt1 pathway. β-defensin 3 expression seems limited to the keratinocytes indicating this expression is keratinocyte specific.

Akt1 dependent transcription factor binding sites. FIG. 6 shows schematic of Akt1 dependent transcription factor binding sites. Using Genomatix software, 500 bp upstream of the transcription start site was analyzed for conserved sites on the mRNA of DEF1, 4, and 5.

6.1.3 Conclusions

The provided data show that sNAG nanofiber stimulation of Ets1 results from the activation of Akt1 by these nanofibers. Nanofiber treatment resulted in marked increases in the expression of genes involved in cellular recruitment, such as IL-1 (a known Ets1 target), VEGF and several defensins (β3, α1, α4, and α5), small anti-microbial peptides recently shown to act as chemoattractants. Both pharmacological inhibition of the PI3K/Akt1 pathway and Akt1 knockdown using shRNAs resulted in decreased expression of these chemotactic factors. Akt1 null mice exhibited a delayed wound healing phenotype that is partially rescued by Taliderm nanofibers. Taliderm treated wounds also showed an increase in defensin expression that is Akt1 dependent.

The increase of β-defensin 3 expression and keratinocyte proliferation in Taliderm treated wounds demonstrates the beneficial use of Taliderm as an effective wound healing product. Taliderm acts to increase anti-microbial peptide expression in keratinocytes in an Akt1 dependent manner suggesting the essential role of Akt1 in the function of sNAG nanofibers. This correlates with the results from other studies in the laboratory (Buff, Muise-Helmericks, unpublished) that inhibition of the PI3K/Akt1 pathway and Akt1 knockdown using shRNAs results in decreased expression of these chemotactic factors.

Although the increased expression of β-defensin 3 is Akt1-dependent, H&E staining of 8 mm wound excisions (FIG. 2B) indicated that Taliderm acts independent of Akt1 in wound reepithelization. Even though the new keratinocytes span the entire wound margin, the underlying tissue did not demonstrate the same stimulation in vascular growth. This indicates the that absence of Akt1 is responsible for leaky blood vessels and the large amount of floating red blood cells in the dermis. This suggests that Taliderm is dependent on the Akt1 pathway for an increase in vascularization.

In summary, (i) sNAG nanofibers (such as Taliderm) increase wound healing in part by stimulating angiogenesis; (ii) sNAG nanofibers treatment of endothelial cells activate an Akt1/Ets1 dependent pathway leading to changes in cell motility and cytokine secretion; (iii) Taliderm treated wounds show increased expression of β-defensin 3 in an AKT1 dependent manner; (iv) treatment of Akt1 null animals with Taliderm partially rescues the phenotype, leading to markedly increased keratinocyte proliferation/migration; and (v) bioinformatics analysis indicates that ETS1 is likely involved in the sNAG activated pathway leading to increased wound healing and cytokine secretion.

Taken together these findings suggest a central role of the Akt1→Ets1 pathway in the regulation of cutaneous wound healing by sNAG nanofibers and support the use of these nanofibers as a novel and effective method for enhancing wound healing.

6.2 Example 2: sNAG Nanofibers Increase Defensin Expression, Increase Kinetics of Wound Closure, and have an Indirect Defensin-Dependent Anti-Bacterial Effect This example demonstrates that sNAG nanofibers have a potent anti-bacterial effect against *Staphylococcus aureus* in vivo, which is indirect and defensin-dependent. This example also shows that sNAG nanofibers induce expression of defensins in vitro in keratinocytes and endothelial cells and in vivo in cutaneous wounds, in an Akt-1 dependent manner, and increase the kinetics of wound closure.

6.2.1 Materials and Methods

Tissue Culture, Pharmacological Inhibition, ELISA: Human umbilical cord vein EC (Lonza) were maintained at 37° with 5% CO2 in endothelial basal medium 2 (Lonza). Endothelial basal medium 2 (EBM2) was supplemented with EC growth medium 2 SingleQuots as described by Lonza procedures and 1% penicillin/streptomycin (Invitrogen). Serum starvation was performed at 80-90% confluency in EBM2 supplemented with 0.1% fetal calf serum (Valley Biomedical) for 24 hours followed by stimulation with highly purified pGlcNAc (50 µg/ml) nanofibers (sNAG) in sterile water (provided by Marine Polymer Technologies, Inc., Danvers, Mass., USA). The pGlcNAc diatom-derived nanofibers used in this study are short biodegradable fibers derived from a longer form (NAG), and have an average length of 4-7 µm and a polymer molecular weight of approximately 60,000 Da. For inhibition using PD098059 (50 µM) or wortmannin (100 nM), cells were pre-treated for 45 minutes prior to 3 hour stimulation with sNAG (50 µg/ml).

Statistical Analysis: Each quantitative experiment was performed at least in triplicate at least three independent times. All statistical analyses were performed using Microsoft Excel to calculate means, standard deviations and student t-test Lentiviral Infection: Mission shRNA lentiviral constructs directed against Akt1 were purchased from Sigma/Aldrich. A scrambled pLKO.1 shRNA vector was purchased from Addgene. Lentiviruses were propagated in 293T cells, maintained in DMEM supplemented as above. Lentiviral production was performed using psPAX2 and pMD2.G packaging vectors purchased from Addgene using the protocol for producing lentiviral particles from Addgene. For infection of target cells, $7.5 \times 10^5$ cells were plated on 100 mm² plates and allowed to incubate overnight. The next day, cells were transduced using a final concentration of 1 μg/ml polybrene and either scrambled control or Akt1 shRNA lentiviruses. After transduction, endothelial cells were serum starved overnight and stimulated with sNAG (50 g/ml) for 3 hours. All infections were monitored for appropriate knockdown by RT-PCR.

RT-PCR: For semi-quantitative RT-PCR, RNA was extracted with RNAsol (Teltest, Inc.) following manufacturer's instructions. cDNA was synthesized from 2 μg total RNA with a Superscript First Strand Synthesis Kit (Invitrogen), using Oligo(dT) following the manufacturer's instructions. PCR reactions contained equal amounts of cDNA and 1.25 μM of the appropriate primer pair (Sigma-Proligo, St. Louis, Mo., USA). All primer sequences used in these analyses are as follows:

| | |
|---|---|
| Akt1 F | 5' GAGGCCGTCAGCCACAGTCTG 3' (SEQ ID NO: 1) |
| Akt1 R | 5' ATGAGCGACGTGGCTATTGTG 3' (SEQ ID NO: 2) |
| β-Defensin3 F | 5' GTGGGGTGAAGCCTAGCAG 3' (SEQ ID NO: 3) |
| β-Defensin 3 R | 5' TTTCTTTCTTCGGCAGCATT 3' (SEQ ID NO: 4) |
| α-Defensin1 F | 5' CACTCCAGGCAAGAGCTGAT 3' (SEQ ID NO: 5) |
| α-Defensin1 R | 5' TCCCTGGTAGATGCAGGTTC 3' (SEQ ID NO: 6) |
| S26 F | 5' CTCCGGTCCGTGCCTCCAAG 3' (SEQ ID NO: 7) |
| S26 R | 5' CAGAGAATAGCCTGTCTTCAG 3' (SEQ ID NO: 8) |

Cycling conditions were: 94° C. for 5 min; 30-35 cycles of 94° C. for 1 min, 55-65° C. (based on primer $T_m$) for 1 min, 72° C. for 1 min; 72° C. for 7 min and cooled to 4° C. Cycle number was empirically determined to be within the linear range of the assay for each primer pair used. All semi-quantitative RT-PCR was performed with the ribosomal protein subunit S26 primers as internal controls. Products were visualized on a BioRad Molecular Imaging System (Hercules, Calif., USA). Real time PCR was performed using a Brilliant CYBR green QPCR kit in combination with an Mx3000P Real-Time PCR system both purchased from Stratagene. Primers detecting the ribosomal subunit S26 were used as internal controls.

Excisional Wound Healing Model: Wild Type C57Bl/6 and Akt1−/−[43] were used in all experiments. The Akt1 null animals were created using an insertional mutagenesis strategy at the translational start site that blocks expression of the entire protein. Wounding was performed on anesthetized adult male mice between 8-12 weeks old. Two full thickness cutaneous wounds were created using a 4 mm biopsy punch (Miltex), to create two identical wounds on each flank. Mice were anesthetized using an $O_2$/Isoflurane vaporizing anesthesia machine (VetEquip, Inc.). Isoflurane was used at 4% for induction; 2% for surgery. Prior to surgery hair was removed by depilation and the area was washed and sterilized using 70% ethanol. Wounds were either treated with sNAG membrane moistened with distilled water or left untreated. On days 3 and 5 animals were euthanized and entire wounds were harvested including the surrounding skin using an 8 mm biopsy punch (Miltex). Wounds were fixed in 4% paraformaldehyde overnight at 4°, embedded in paraffin, and sectioned for analysis.

Hematoxylin and Eosin Staining (H&E): All H&E staining was performed in the Histology Core Facility at the Medical University of South Carolina, Department of Regenerative Medicine and Cell Biology. Briefly, sections were cleared in xylene, rehydrated through a series of graded alcohols, placed in Hematoxylin followed by acid alcohol. Samples were then placed in ammonia water, rinsed in ethanol and exposed to Eosin before dehydrating through graded alcohols and clearing in xylene. Sections were mounted using Cytoseal-XYL (Richard-Allan Scientific). H&E sections were visualized using an Olympus BX40 microscope (4× objective lens, 0.13) and captured using an Olympus Camera (Model DP25) and DP2-BSW acquisition software.

Bacterial Inoculation, Tissue Gram Staining, Colony Forming Unit Quantitation: Male mice between 8-12 weeks were wounded as described above. Single colonies of *Staphylococcus aureus* (ATCC 25923) were picked and cultured overnight at 37° and adjusted to an absorbance of $OD_{600}=0.53$. One mL of *S. aureus* was spun at 10,000 rpm, re-suspended in sterile PBS, and 15 μl was used to innoculate each wound. sNAG membranes were applied to the treated group thirty minutes post inoculation. Mice were euthanized on day 3 and 5 post wounding and wounds were harvested using an 8 mm biopsy punch. One wound per animal was fixed overnight in 4% paraformaldehyde at 4° C. and the other wound was cultured and plated on LB media without antibiotic for bacterial quantitation (see below). Wounds for tissue gram staining were embedded in paraffin and sectioned. Sections were cleared in xylene and rehydrated through a series of alcohol and were stained using a tissue gram stain (Sigma-Aldrich) by procedures described by the manufacturer.

For culturing, wound sections were placed in 0.5 ml bacterial media an incubated for 30 min at 37° C. while shaking. Colony forming units (CFU) were quantitated using a dilution series plated overnight at 37° C. Number of colonies per plate/per dilution were counted and CFU/ml were calculated.

To determine CFU/ml from sNAG treated bacterial cultures, *S. aureus* cultures in solution were treated with varying concentrations of sNAG (10 μl and 20 μl of 10.8 mg/ml sNAG) for three hours. Cultures were then plated overnight at 37° and CFU/ml were determined.

β-defensin 3 Peptide Application: Three test concentrations (1.0 μM, 2.5 μM, 5.0 μM) of biologically active human β-defensin 3 peptide (Peptide Institute, Inc.) were tested for their effect on bacterial growth in the infected wound healing model described above. Each concentration negatively affected bacterial growth so the lowest concentration was chosen for analyses. After each wound was infected with *S. aureus,* 10 ul of peptide was applied. After three days, wounds were harvested, embedded for sectioning and gram staining, or cultured for CFU/ml quantitation as described above.

β-defensin 3 Antibody Blockade: Wild Type male mice were wounded and infected with 15 ul of *S. aureus* as described above. After inoculation, one wound was treated with 0.2 ug/mL of β-defensin 3 antibody (Santa Cruz) while the other was treated with 0.2 ug/mL of normal goat IgG control antibody (Santz Cruz). sNAG membranes were applied to all mice after antibody treatment on day 0. Antibody was applied every 24 hours. Mice were euthanized on day 3 and wounds were harvested using an 8 mm biopsy punch. Wounds were fixed overnight in 4% paraformaldehyde at 4° C., embedded in paraffin, sectioned, and analyzed using tissue gram stain. CFU/ml quantitation was performed from wounds harvested on day 3 as described above.

Immunofluoresence, Microscopy: Paraffin embedded tissue sections were re-hydrated through xylene and a series of graded alcohols. Sections were treated with 0.01% Triton-X100 and subjected to antigen retrieval using antigen unmasking solution (Vector Laboratories) in a pressure cooker for 5 min and allowed to cool. Skin sections were labeled with β-defensin 3 goat polyclonal antibody (Santa Cruz), involucrin rabbit polyclonal antibody (Santa Cruz), and TO-PRO 3-iodide (Molecular Probes). Sections were incubated in primary antibody overnight at 4° and appropriate secondary immunofluorescent antibodies (Invitrogen) for 1 hour at room temperature. Control sections for each antibody were stained without primary antibody. Tissue sections were visualized using an Olympus FluroView laser scanning confocal microscope (Model IX70) and captured at ambient temperature using an Olympus camera (Model FV5-ZM) and Fluoview 5.0 acquisition software. All tissue sections were imaged using 60× oil immersion lens (Olympus Immersion Oil)

HUVECs were either serum starved or treated with sNAG for 5 hours in culture and stained with antibodies directed against α-defensin 5 (FITC), β-defensin 3 (Texas Red), or TOPRO 3 (Blue). Images were taken using immunofluorescent microscopy. Cell culture defensin expression was visualized using a Zeiss Axiovert 100M confocal microscope and was captured at ambient temperature, using water as the medium, using LSM 510 camera (Zeiss Fluor 63×W/1.2A objective).

Western Blot Analysis: Endothelial cells were serum starved prior to stimulation with sNAG (50 µl/ml) for a given time course. Cells were then lysed and subjected to Western blot analysis. The antibodies used for Western blot analysis are as follows: anti-p85 subunit of PI3K and phosphospecific Akt antibody (Cell Signaling Technologies).

6.2.2 Results 6.2.2.1. Keratinocytes and Endothelial Cells Express and Secrete Defensins when Stimulated with sNAG This example demonstrates that sNAG treatment modulates the expression of defensins, small anti-microbial peptides that are part of the innate immune response.

To investigate the affect of sNAG treatment on defensin expression in vitro, primary human umbilical vein endothelial cells in culture were used. Endothelial cells express both α-type and β-type defensins when stimulated with sNAG. As shown in FIG. 7A endothelial cells treated with sNAG show an up-regulation of β-defensin 3 and α-defensin 1 mRNA expression within 1 hour of stimulation. Similar up-regulation of α-defensin 4 and 5 by sNAG treatment was also observed (data not shown). Custom gene arrays containing over 25 different defensin genes were used to confirm the expression of the α-type defensins in primary endothelial cells and the β-type defensins in keratinocytes. sNAG stimulation of endothelial cells was shown to increase the expression specifically of α-defensins 1, 4 and 5 and β-defensin 3. Additionally, sNAG stimulation of human keratinocytes increased expression of β-defensin like genes, several of which are listed in Table 1. These findings suggest that at least three α-defensin genes and β-defensin 3 are expressed in primary endothelial cells and multiple β-defensin genes are expressed in primary keratinocytes in response to sNAG stimulation.

TABLE I

Gene array analysis reveals numerous defensin genes upregulated by sNAG

| HUVEC | Gene Name | Fold Change | Keratinocyte | Gene Name | Fold Change |
|---|---|---|---|---|---|
| | α-defensin 1 | +1.36 | | β-defensin 1 | +1.4 |
| | α-defensin 4 | +2.74 | | β-defensin 126 | +1.73 |
| | α-defensin 5 | +2.46 | | β-defensin 105B | +2.55 |
| | β-defensin 1 | +2.19 | | β-defensin 123 | +1.65 |
| | β-defensin 4 | +3.06 | | β-defensin 129 | +1.46 |

To test whether the sNAG-dependent defensin expression also occurred on the protein level, sNAG stimulated endothelial cells were subjected to immunofluorescence using antibodies directed against both α and β defensins. As shown in FIG. 7B, both β-defensin 3 and α-defensin 5 are up-regulated upon sNAG stimulation in this cell type. However, stimulation of primary human keratinocytes (HaCat) with sNAG did not cause increased expression of α-defensin but does cause an increase in the expression of β-defensin 3 (FIG. 7C). Taken together, these experiments suggest that sNAG stimulation results in an up-regulation of defensin peptides in both primary keratinocytes and primary endothelial cells.

6.2.2.2. sNAG-Dependent Defensin Expression Requires Akt1

Figure 8D:
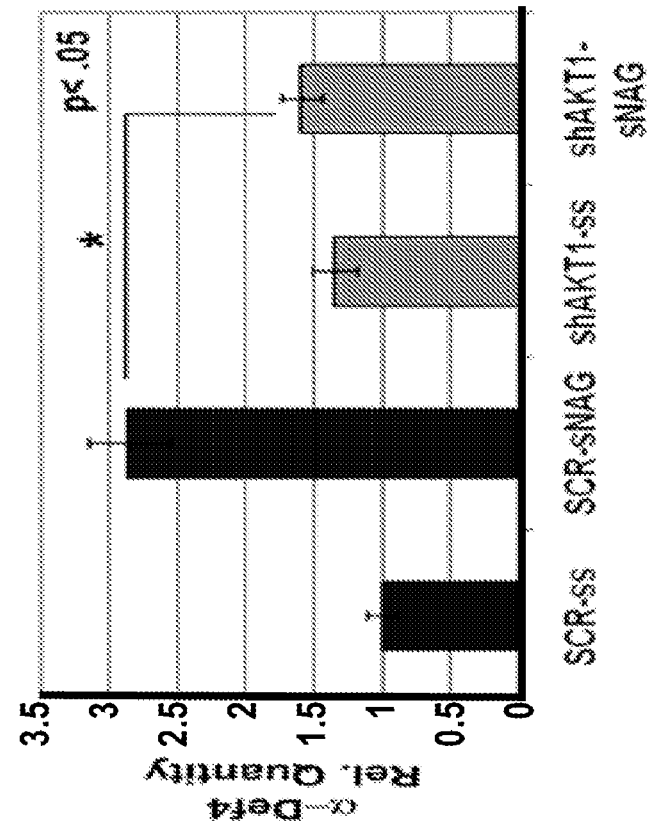

Previously published data show that sNAG stimulation of primary endothelial cells results in increased integrin activation, Ets1 expression and MAP kinase activation. (Vournakis, J. N., et al., 2008, J Vasc Res. 45(3):222-32.) Findings position Akt1 upstream of Ets1 in endothelial cells and in *Drosophila*. (Lavenburg, K. R., et al., 2003, FASEB J. 17(15): 2278-80.) To begin to determine the signaling pathway responsible for the expression of defensins, endothelial cells were serum starved and pre-treated with pharmacological inhibitors directed against PI3K (wortmannin) or MAP kinase (PD098059) prior to sNAG stimulation. Quantitative real time PCR analysis shows that α-defensin 1 mRNA levels are greatly diminished after inhibition of either the PI3K/Akt pathway or the MAP kinase pathway (FIG. 8A). RT-PCR analysis of β-defensin 3 also shows that levels are decreased by the inhibition of these pathways as well (FIG. 8B). sNAG treatment of endothelial cells for a short time course leads to phosphorylation of Akt1, a standard indicator of its activation (FIG. 8C). To confirm that Akt1 is indeed required for defensin expression, lentiviral delivery of shRNA directed against Akt1 was used. Quantitative RT-PCR of serum starved endothelial cells infected with scrambled (SCR) control or Akt1 shRNA followed with sNAG treatment confirms that Akt1 expression is required for sNAG-dependent α-defensin expression (FIG. 8D). Since β-defensins are known to be expressed in epithelial cells, lentiviral delivery of shRNA directed against Akt1 was used in human keratinocytes (HaCat). sNAG treatment of serum starved keratinocytes infected with scrambled (SCR) control leads to a significant increase in β-defensin 3 expression that is abrogated by Akt1 knockdown (FIG. 8E). These results illustrate that sNAG treatment activates Akt1 in endothelial cells and strongly suggest that sNAG-dependent defensin expression requires Akt1 in both endothelial cells and keratinocytes.

6.2.2.3. sNAG Treatment of Cutaneous Wounds Increase Defensin Expression In Vivo To confirm the dependence of Akt1 for the expression of defensins in vivo, wild type and Akt1 null animals were used in an excisional wound healing model. Although most mammalian leukocytes express α-defensins (human, rabbit, rat, and hamster), mouse leukocytes do not express α-defensins. Therefore, β-defensin expression in these mouse models was focused on. Treatment of cutaneous wounds with a dried form of sNAG, a thin biodegradable membrane, for three days results in a statistically significant increase in β-defensin 3 expression in keratinocytes of wild type animals (FIG. 9A). Involucrin (Watt, F. M., 1983, J Invest Dermatol. 81(1 Suppl):100s-3s) staining (red) was used to mark the keratinocyte cell layers and show that the expression of β-defensin 3 is confined to the epidermal layer. To assess if sNAG-dependent defensin expression is dependent on Akt1, a similar assay was performed using an Akt1 null animal model. Wounds from Akt1 null mice treated with sNAG membranes show a markedly reduced induction of β-defensin 3 expression (FIG. 9A). To better visualize the epidermal layers that are expressing β-defensin 3, FIG. 9B shows a representative image of a sNAG treated wild type wound harvested on day 3. sNAG treatment of cutaneous wounds induced β-defensin 3 expression mainly in the suprabasal layers of skin (FIG. 9B). Quantitative analyses shown in FIG. 9C shows an approximate 5-fold increase in β-defensin 3 expression in sNAG treated wild type animals and that Akt1 is required for this increase.

6.2.2.4. sNAG Treatment Increases the Kinetics of Wound Closure in WT Animals Previous results have shown an increased kinetics of wound closure in diabetic mouse models in response to sNAG treatment. sNAGs were tested for a similar affect in wild type animals. Excisional wounds were created in wild type animals which were either treated with the membrane form of sNAG or left untreated. Tissue sections were taken at 1, 3 and 5 days post wounding and subjected to H&E staining. As shown in FIG. 10, sNAG treatment of wild type wounds results in complete closure, as visualized by the solid line, at day 3 post wounding. This occurs two days earlier than in the control wounds. Akt1 null animals display a delay in wound closure; these animals do not fully close the wound until 7 days post wounding. The delay in wound closure in the Akt1 null animals is not rescued by sNAG treatment (data not shown). These findings suggest that sNAG not only induces defensin expression but also increases wound healing kinetics in wild type mice and may be a novel and effective therapeutic.

6.2.2.5. sNAG is an Effective Antimicrobial Against S. Aureus

Defensin peptides are known to possess antimicrobial properties that are active against gram-positive and gram-negative bacteria. Since treatment of endothelial cells with sNAG increases defensin expression (both α- and β-type) and treatment of cutaneous wounds with sNAG dramatically increases β-defensin 3 expression in vivo, the antimicrobial efficacy of sNAG treatment in bacterially infected wounds was assessed.

To determine if sNAG decreases bacterial load in cutaneous wounds, wild type and Akt1 null animals were subjected to cutaneous wound healing, followed by infection with Staphylococcus aureus. Infected wounds were either treated with sNAG or left untreated for 3 and 5 days post infection. As shown by the tissue gram staining in FIGS. 11A and 11B, wild type animals treated with sNAG show a significant reduction in gram positive staining by day 5 post wounding as compared with untreated wounds. In contrast, gram stained tissue derived from untreated wounds in Akt1 null animals at 5 days post wounding show an accumulation of neutrophils which stain gram positive (FIG. 11B), indicating a potential lack of bacterial clearance in these animals that is not rescued by sNAG treatment. These findings suggest that Akt1 null animals have a defect in immune clearance mechanisms which is not rescued by sNAG treatment.

To quantitate sNAG-specific bacterial changes in colony forming units (CFU), infected wounds from both wild type and Akt1 null mice either sNAG treated or untreated were harvested and cultured. As shown in FIG. 11C, at 5 days post wounding bacterial number is markedly reduced (10-fold) in wild type animals treated with sNAG. However, although the number of bacteria detected in the Akt1 null animals is reduced in comparison to wild type, sNAG treatment had a little effect on absolute bacterial number in the Akt1 null animals. At 3 days post-infection (FIG. 11D), there is a similar 10-fold decrease in CFU in sNAG treated wild type mice as compared to untreated controls. The sNAG treated Akt1 null animals show a 2-fold decrease in CFU as compared to untreated Akt1 null animals. In general, the Akt1 null animals have a lower bacterial load per wound which may be reflective of an Akt1-dependent effect on other processes in addition to defensin expression. These findings suggest that sNAG treatment results in a marked reduction in bacterial load in infected cutaneous wounds in wild type mice but not in Akt1 null mice, suggesting the possibility that defensins are mediating the anti-bacterial response.

To show that the antibacterial effect of sNAG treatment is not due to a direct effect of the nanofibers on bacterial growth or on their survival, S. aureus bacterial cultures were treated in solution with different amounts of sNAG, for 3 hours and colony forming units were determined. As shown in FIG. 11E, sNAG treatment had no direct effect on the growth of S. aureus, indicating that sNAG is not directly inhibiting bacterial growth and may then be working via the up-regulation of defensins.

6.2.2.6. Application of Defensin Peptide Mimics the sNAG Antibacterial Effect To determine whether addition of defensin peptide can block bacterial infection similarly to that shown for sNAG treatment, wild type mice were wounded and inoculated with S. aureus as described above and then treated with biologically active human β-defensin 3 peptide (1.0 μm) for three days. Tissue biopsies were stained using a tissue gram stain and CFU was quantitated. FIG. 11 F-G shows the results of these experiments. Infected mice treated with β-defensin 3 peptide have a decreased bacterial load, an approximate 7.5 fold decrease in viable bacteria (FIG. 11G), similar to that shown in wild type mice treated with sNAG.

One of the mechanisms by which defensin expression is induced is through stimulation by bacterial LPS, possibly through the activation of Toll like receptors. (Selsted, M. E. and A. J. Ouellette, 2005, Nat Immunol. 6(6):551-7.) To test whether bacterial infection alone is able to induce β-defensin expression within the time periods tested, expression of β-defensin was assessed in infected wounds from wild type animals after three days post wounding. As shown in FIG. 12A, bacterial infection alone does not induce the expression of β-defensin within 3 days of infection, as is shown with sNAG treatment. However, in wild type animals, sNAG treatment of infected wounds causes approximate 3- to 5-fold increase in the expression of β-defensin within a similar time period (FIG. 12B). These findings suggest that sNAG treatment rapidly induces the expression of defensin expression resulting in marked bacterial clearance in *S. aureus* infected wounds.

6.2.2.7. Antibodies Directed Against β-Defensin 3 Block the Antibacterial Effect of sNAG Since defensins are secreted proteins, the inventors hypothesized that antibodies directed against β-defensin 3 may be able to block the antibacterial activities. To test this hypothesis, wounds were created, infected with *S. aureus* and treated with sNAG as described above. The wounds were either treated with a β-defensin 3 antibody or an isotype control; one application each day for three days. Wound sections were obtained and stained for gram positive bacteria. As shown in FIG. 13A, sections derived from wounds treated with β-defensin antibody have more gram positive bacteria than those treated with isotype control antibodies. E ach section shown was derived from the wound area directly under the scab. Quantitation of CFU in these wounds shows that neutralization of β-defensin 3 prior to sNAG treatment in *S. aureus* infected wounds results in a significant increase in bacteria. Animals that were treated with an IgG isotype control show an approximate 5-fold reduction in viable bacteria (FIG. 13B). Taken together, these results suggest that sNAG treatment not only results in the increased kinetics of wound healing but also promotes an endogenous anti-bacterial response and supports the use of this nanofiber as novel therapy to enhance wound healing while concurrently decreasing wound infection.

6.2.3 Conclusions

The findings presented here demonstrate that a marine diatom derived nanofiber, sNAG, may be used as a novel and effective method to enhance wound healing while concurrently decreasing wound infection. The data demonstrates that this FDA approved material, which is presently used for hemostasis, stimulates the expression of both α-type and β-type defensins in primary endothelial cells and an up-regulation of the β-type in primary keratinocytes.

Defensins are an essential component of the innate immune system. These peptides possess anti-microbial properties that are active against gram-positive and negative bacteria, fungi, and many viruses. Defensins are small (3-4 kDa), cysteine-rich cationic peptides found in mammals, insects, and plants that are classified into different families (α, β, and θ) based on their pattern of disulfide bonding. α-defensins are thought to be specific to neutrophils, are found in very high concentrations (comprising approximately 5-7% of the total cellular protein) (Ganz, T. and R. I. Lehrer, 1994, Curr Opin Immunol. 6(4):584-9), and are secreted during anti-microbial responses (Ganz, T., 1987, Infect Immun. 55(3):568-71). It has also been shown that rabbit alveolar macrophages possess α-defensins in levels comparable to rabbit neutrophils. (Ganz, T., et al., 1989, J Immunol. 143(4):1358-65.) f-defensins are found in epithelial cell types such as keratinocytes, mucosal epithelial cells (Harder, J., et al., 1997, Nature 387(6636):861; and Harder, J., et al., 2001, J Biol Chem. 276(8):5707-13), oral cavity tissues and salivary secretions (Mathews, M., et al., 1999, Infect Immun. 67(6):2740-5), and kidney where they can be up-regulated in response to infectious or inflammatory stimuli (Ganz, T. and R. I. Lehrer, 1994, Curr Opin Immunol. 6(4):584-9). Human β-defensin 1 (hDEFB1) is one of the most important antimicrobial peptides in epithelial tissues. Defensin expression and secretion could be extremely important for creating wound therapeutics. The anti-microbial action by defensins is considered part of innate immunity and is non-specific and broad spectrum. Therefore acquired bacterial resistance, as seen with the overuse of antibiotics, is not an issue.

The data presented here also demonstrate that both in vitro and in vivo Akt1 is required for defensin expression. sNAG treatment decreases *Staph aureus* infection of cutaneous wounds in wild type control animals but not in similarly treated Akt1 null animals. It is also important to note that sNAG stimulation of wild type cutaneous wounds results in an increased kinetics of wound closure. Antibody blockade of β-defensin results in a reduction in the sNAG-antibacterial activity. Taken together these findings suggest a central role for Akt1 in the regulation of defensin expression that is responsible for the clearance of bacterial infection and that sNAG treatment activates these pathways in wild type animals.

The data that suggests that sNAG treatment of infected wounds could drastically decrease bacterial load in patients, at least in part, by the induction of defensin expression. *Staphylococcus aureus* is a bacterium frequently found colonizing the skin and in the nose. It is still a common cause of nosocomial infections, often causing postsurgical wound infections. *S. aureus* infections in hospitals have plagued healthcare workers for years and the widespread usage of antibiotics for treatment has lead to antibiotic resistant strains. The data presented herein shows that treatment of Staph infected wounds with sNAG dramatically decreased the bacterial load. For example, the lack of dark purple gram staining in the treated WT mice in FIGS. 11A and 11B indicates that the *S. aureus* infection has been cleared from these wounds. Both the in vitro and in vivo data provides strong evidence for the use of sNAG (in particular, Taliderm) in the treatment of wounds to decrease bacterial infection and therefore enhance wound healing.

Control experiments indicate that the antibacterial effect of sNAG is not due to a direct interaction of the material with the bacteria but is due to downstream affects such as the regulation of defensins by Akt1 activation. It is widely accepted that defensins are important players in innate immunity and function in antimicrobial activities. Most of the evidence for their function is the direct killing of bacteria by in vitro mixing experiments with purified defensin peptides (Selsted, M. E. and A. J. Ouellette, 2005, Nat Immunol. 6(6):551-7) or in similar experiments as shown in FIG. 11 with direct application of the purified active peptide. The data here show that an induction of defensin expression in wild type animals using a topical application of sNAG results in an antibacterial response. It has recently been shown that transgenic mouse models expressing the human defensin 5 gene are resistant to *S. typhimurium*, an infection that results in death of wild-type animals (Salzman, N. H., et al., 2003, Nature 422(6931):522-6) again suggesting the importance of defensins in the regulation of the antimicrobial response.

It has been accepted that the α-subtype of defensins are specifically expressed in neutrophils, whereas the β-type defensins are epithelial in origin. β-type defensin expression induced in response to sNAG in human keratinocytes both in culture and in the cutaneous wound healing model was detected. The in vivo data illustrates that β-defensin 3 is mainly expressed in the suprabasal layers after treatment with sNAG. This is consistent with previous data which localized human β-defensin 2 to the spinous and granular layers of the skin. (Oren, A., et al., 2003, Exp Mol Pathol. 74(2):180-2.) The skin is in constant contact with injury and infection and functions not only as a mechanical barrier but also maintains the ability to mount an active defense against infection. The expression of β-defensin in the outer layers of skin supports their role in cutaneous innate immunity. However, the data show that sNAG specifically stimulates the expression of three different α-defensins (1, 4 and 5) in endothelial cells. This is shown by RT-PCR, gene array analysis, immunofluorescence and ELISA (data not shown). The interaction between endothelial cells and leukocytes in tissue repair is one of the initial and most important steps in wound healing. The process of extravasation of leukocytes from the vasculature is initiated by chemotactic factors, therefore; it is interesting that α-defensins are induced by sNAG and may contribute to the necessary neutrophil/endothelial cellular interactions. More recently, it has come to light that defensins exhibit biological activities beyond the inhibition of microbial cells, including their contribution to the adaptive immune response by exhibiting chemotactic activity on dendritic (Hubert, P., et al., 2007, FASEB J. 21(11):2765-75) and T cells, monocytes, and macrophages (Garcia, J. R., et al., 2001, Cell Tissue Res. 306(2):257-64) and keratinocytes (Niyonsaba, F., et al., 2007, J Invest Dermatol. 127(3):594-604). Previous work shows that human beta defensins 1 and 2 have the ability to chemoattract immature dendritic cells and T cells through the CC-chemokine receptor 6 (CCR6) (Yang, D., et al., 1999, Science 286(5439):525-8), and that human beta defensin 2 can chemoattract TNFα treated neutrophils via the CCR6 receptor (Niyonsaba, F., H. Ogawa, and I. Nagaoka, 2004, Immunology 111(3):273-81). Human β-defensin 2 and 3 have also been shown to induce chemotaxis by interacting with CCR2, a receptor expressed on macrophages, monocytes, and neutrophils. (Rohrl, J., et al., 2010, J Immunol, 2010.) Interestingly, the data show that sNAG treatment induces both a and β-defensin expression in endothelial cells. Taken together, the recent data suggest that defensins may mediate wound healing not only by their antimicrobial properties, but also by being chemotactic for other cell types necessary for proper healing. However, application of β-defensin 3 alone did not result in an increase in wound closure (data not shown) implying that topical application of a single defensin does not sustain the cellular interactions required for increased chemo attraction, cellular recruitment and wound closure.

The in vivo data using both wild type and Akt1 knockout animals confirms the requirement for Akt1 in sNAG-induced β-defensin 3 expression. Since mouse leukocytes do not express α-defensins like most other mammalian leukocytes (Ganz, T., 2004, C R Biol. 327(6):539-49) in vivo α-defensin staining of infiltrating immune cells was not possible. Treatment of airway epithelial cells in vitro with alpha defensins 1-3 causes a dose and time-dependent increased cell migration that requires activation of PI3K and MAPK pathways. (Aarbiou, J., et al., 2004, Am J Respir Cell Mol Biol. 30(2):193-201.) sNAG stimulation of endothelial cells has been shown to result in the activation of MAPK (Vournakis, J. N., et al., 2008, J Vasc Res. 45(3):222-32) and in data presented here, pharmacological inhibition of MEK also inhibits the expression of the defensins in vitro. These findings suggest that both pathways impinge on the regulation of defensin expression by sNAG, however, Akt1 ablation results in a marked reduction of its expression both in vitro and in vivo. In myeloid cells, β-defensin 1 expression is controlled at the level of transcription, in part, by the Ets-family member PU. 1. (Yaneva, M., et al., 2006, J Immunol. 176(11):6906-17; and Ma, Y., Q. Su, and P. Tempst, 1998, J Biol Chem. 273(15):8727-40.) PU.1 is a downstream target of Akt1 in the B-cell lineage. (Rieske, P. and J. M. Pongubala, 2001, J Biol Chem. 276(11):8460-8.)

In primary endothelial cells it has been shown that Akt1 is upstream of Ets1 both in vitro and in vivo during *Drosophila* tracheal development. (Lavenburg, K. R., et al., 2003, FASEB J. 17(15):2278-80.) sNAG stimulation of endothelial cells results in increased expression of Ets1 (probably through Akt1) which is required for the migration of endothelial cells. (Vournakis, J. N., et al., 2008, J Vasc Res. 45(3):222-32.)

Thus far, sNAG treatment has resulted in a series of downstream activities; hemostasis, cell migration, cell proliferation, increased wound closure, and as described here, stimulation of the innate immune response resulting in anti-bacterial functions.

Given the dramatic increase of diabetic patients within the population who present with chronic wounds and complications due to wound infection, new clinical treatments are in high demand. Here, marine derived pGlcNAc nanofibers are described that not only increase the kinetics of wound healing but act to stimulate innate immunity thus providing anti-bacterial activity. The obvious importance of these observations is the application to nosocomial infections. Of the nosocomial infections, surgical wound infections predominate; with statistics showing up to 8% of all surgical patients. The direct cost of these types of infections is approximately 4.5 billion dollars per year. Given that defensins are part of the innate immune system, activation of these pathways will preclude the generation of resistant organisms as well as allow for the antibiotic-independent clearance of bacterial infection. Use of sNAG in a hospital setting would defray much of the cost and markedly reduce the production of antibiotic resistant species. Taken together, these findings suggest that these marine derived pGlcNAc nanofibers will be highly beneficial in the clinical arena.

6.3 Example 3: sNAG Nanofibers Upregulate Expression of a Number of Defensins and Toll Receptor Genes This example demonstrates that a number of defensins and Toll-like receptors are up-regulated by sNAG treatment of human endothelial cells.

Materials and Methods: Human Chip probes were printed on epoxy slides. HUVEC cells were cultured as described in section 6.2, and treated with sNAG nanofibers ("sNAG") for 5 hours. RNA was extracted with RNAsol (Teltest, Inc.) following manufacturer's instructions, amplified using Amino Allyl MessageAMP™ II aRNA amplification kit (Applied Biosystems), and labeled. The slides were prepared for hybridization with aRNA by soaking in blocking solution (Sigma Tris-buffered saline pH8.0, in 1000 ml dH$_2$O, 1% BSAw/v, NaN$_3$ to 0.05%) at RT O/N, then rinsed and dryed. Samples containing labeled target aRNA from sNAG-treated cells were hybridized with the slides (65 ul/slide; denatured at 95° C. for 5 min; hybridized for 48 hours at 37° C. in 0.1% SDS and 5×SSC and 1% BSA), rinsed and dryed. The slides were scanned and hybridization detected using Perkin-Elmer Scan Array equipment and ScanArray Express software V3.0, updated. To identify up-regulated genes, microarray data was analyzed using Agilent GeneSpring GX v.11 Bioinformation Data Analysis.

Genes of interest analyzed: IL-1, CEACAM3, SPAG11, defensins ("DEFA"=α-defensin, and "DEFB"=β-defensin); Toll-like receptors ("TLR"), SIGIRR (Single IG IL-1-related receptor), and TRAF6 (TNF receptor associated factor 6). Positive controls: 1433Z (Tyrosine-3-monohydrogenase/tryptophan 5 monohydrogenase acittion protein); GAPD (glyceraldehydes-3-phosphate dehydrogenase); RPL13A (Ribosomal protein L13a); UBC (Ubiquitin C); ACTB (Actin B).

Results: Results of the microarray gene chip analyses and Q-PCR validation of microarray results are presented in Tables II-VI below. Using a custom gene chip it was determined that a number of defensins and Toll-like receptors are up-regulated by sNAG treatment of human endothelial cells.

Toll-like receptors (TLRs) are highly conserved receptors that recognize specific molecular patterns of bacterial components leading to activation of innate immunity. Interestingly, *Drosophila* lack an adaptive immune system but are still resistant to microbial infections. (Imler, J. L. and J. A. Hoffmann, 2000, Curr Opin Microbiol, 3(1):16-22.) This host defense is the result of an innate immune system that provides protection by synthesizing the antimicrobial peptides dToll and 18-wheeler which are induced by TLRs. (Lemaitre, B., et al., 1996, Cell 86(6):973-83; and Williams, M. J., et al., 1997, EMBO J. 16(20):6120-30.) Recent work has also linked human defensin expression to TLR activation. Human β-defensin 2 was shown to be induced in airway epithelial cells in a TLR-2 dependent manner. (Hertz, C. J., et al., 2003, J Immunol. 171(12): p. 6820-6.) Toll-like receptor 4 has been shown to mediate human β-defensin 2 inductions in response to *Chlamydia* pneumonia in monocytes. (Romano Carratelli, C., et al., 2009, FEMS Immunol Med Microbiol. 57(2): 116-24.) Importantly, the PI3K/Akt pathway is a key component in TLR signal transduction, controlling cellular responses to pathogens. (Weichhart, T. and M. D. Saemann, 2008, Ann Rheum Dis. 67 Suppl 3:iii70-4.) Since it is known that stimulation of TLRs can lead to increased defensin synthesis, this work suggests the potential for sNAG as a stimulator of innate immunity and bacterial clearance via the activation of Akt1.

TABLE II

List of some genes up-regulated in response to sNAG stimulation

| Gene | Function |
|---|---|
| IL-1 | Pro-inflammatory cytokine involved in immune defence |
| CEACAM3 | Cell adhesion molecule which directs phagocytosis of several bacterial species |
| SPAG11 | β-defensin-3 like molecule that exhibits antimicrobial properties |
| Defensins | A series of defensins that exhibit antimicrobial activity |
| TLRs | Toll-like receptors: important for stimulation of cellular responses toward infection |

| GENE | LIGAND/FUNCTION | FOLD INDUCTION |
|---|---|---|
| TLR1 | Triacyl lipopeptides from bacteria and mycobacteria | 7.6 |
| TLR4 | LPS, viral proteins, Hsp60 (*Chlamydia*) | 5.064 |
| TLR7 | synthetic compounds | 3.271 |
| TLR8 | synthetic compounds | 2.067 |
| TRAF6 | Downstream signalling modulator | 6.167 |
| SIGRR | IL-1 receptor related TLR modulator | 5.895 |

TABLE III

Defensin Microarray Gene Expression
(HUVEC Response to sNAG 10 ug/ml 5 hours)

| Gene Name [Oligo ID] | HUVEC 10 s 48 h 37 C normalized(Fold) |
|---|---|
| D107A HUMAN [H300005354] | 4.2 (2.6 to 5.2) |
| DEFA4 [H200000646] | 4.2 (3.243 to 4.946) |
| DEFA5 [H200005803] | 4.8 (3.664 to 6.123) |
| DEFB1 [H200004191] | 2.7 (1.7 to 3.7) |
| DEFB103A [H300008014] | 9.8 (7.4 to 12.5) |
| DEFB118 [H200017001] | 2.7 (1.502 to 4.779) |
| DEFB119 [H300002796] | 6.2 (4.68 to 8.04) |
| DEFB123 [H300009262] | 8.9 (7.791 to 11.1) |
| DEFB124 [H300001942] | 3.8 (1.6 to 5.1) |
| DEFB126 [H200012496] | 9.2 (8.286 to 10) |
| DEFB129 [H300005026] | 5.2 (4.338 to 6.277) |
| ACTB HUMAN [H300006234] | 6.8 (6.603 to 7.284) |
| GAPD [H200007830] | 16.9 (12.81 to 21.13) |
| RPL13A [opHsV04TC000041] | 9.4 (7.311 to 12.01) |
| UBC [H200014214] | 7.2 (5.789 to 9.979) |
| 1433Z HUMAN [opHsV04TC000038] | 0.6 (0.4 to 0.844) |

TABLE IV

DEFCB3 Microarray Gene Validation
(AB Prism 7000; sNAG (10 ug/ml), HUVEC for 5 h)

| Sample | DEFB3 | 1433z | $\Delta$Ct = DEFB3 − 1433z | $\Delta\Delta$Ct = $\Delta$Ct treated − $\Delta$Ct untreated | Fold difference in DEFB3 relative to untreated |
|---|---|---|---|---|---|
| untreated | 37.41 ± 0.74 | 14.71 ± 0.26 | 22.7 ± 0.78 | 0.00 ± 0.78 | 1.4 (1.22-1.7) |
| treated | 40.30 ± 1.0 | 17.84 ± 0.07 | 22.46 ± 1.0 | −0.24 ± 1.0 | 1.8 (1.24-2.36) |

TABLE V

Toll-Like Receptors Microarray Gene Expression

| Gene Name [Oligo ID] | Fold Change |
|---|---|
| SIGIRR [opHsV0400002471] | 5.895 (3.916 to 7.926) |
| TLR1 [H300000701] | 7.612 (3.796 to 11.33) |
| TLR4 [H200007406] | 5.064 (1.085 to 10.66) |
| TLR7 [H200008345] | 3.271 (1.938 to 3.938) |
| TLR7 [H300006695] | 2.2 (1.5 to 2.7) |
| TLR8 [H200016515] | 2.067 (1.8 to 2.2) |
| TRAF6 [H200010465] | 6.167 (5.2 to 7) |
| 1433Z HUMAN [opHsV04TC000038] | 0.573 (0.4 to 0.844) |

TABLE VI

Real Time Q-PCR Gene Validation of TLR1 & 4
(HUVEC, 10 ug/ml sNAG for 5 h)

| Sample | Target $C_T$ ave | Target $C_T$ sd | Reference (1433z) $C_T$ ave | Reference (1433z) $C_T$ sd | $\Delta C_T$ = Target$C_T$ − 1433z$C_T$ |
|---|---|---|---|---|---|
| $TLR_1$ | | | | | |
| untreated | 31.12 | 1.2 | 17.84 | 0.34 | 13.28 |
| treated | 28.54 | 0.37 | 17.53 | 0.2 | 11.01 |
| $TLR_4$ | | | | | |
| untreated | 26.97 | 0.44 | 17.84 | 0.34 | 9.13 |
| treated | 25.04 | 0.38 | 17.53 | 0.2 | 7.51 |

| | $\Delta C_T$ sd = $(S_{target}^2 + S_{reference}^2)^{1/2}$ | $\Delta\Delta Ct$ = $\Delta Ct_{test\,sample(treated)} - \Delta Ct_{Calibrator(untreated)}$ | $\Delta\Delta Ct$ sd = $\Delta Ct$ sd | Fold up $2^{-(\Delta\Delta Ct+sd)}$ | Fold down $2^{-(\Delta\Delta Ct-sd)}$ | Fold ave |
|---|---|---|---|---|---|---|
| $TLR_1$ | | | | | | |
| untreated | 1.25 | 0 | 1.25 | 0.42 | 2.37 | 0.83 |
| treated | 0.42 | −2.27 | 0.42 | 3.60 | 6.46 | 5.03 |
| $TLR_4$ | | | | | | |
| untreated | 0.56 | 0 | 0.56 | 0.68 | 1.47 | 0.62 |
| treated | 0.43 | −1.62 | 0.43 | 2.28 | 4.14 | 3.21 |

6.4 Example 4: sNAG and Long Fiber NAG Differ in their Gene Expression Profiles

This example demonstrates that sNAG nanofibers differ from long p-GlcNAc fibers in their effect on gene expression, and specifically in their effect on expression of some of the defensins and Toll-like receptors.

Materials and Methods: Human Defensin Chip probes (concentration: 20 uM, quantity 18-20, solvent: SSC based spotting buffer) were printed on epoxy slides using standard techniques. HUVEC and HaCat cells were cultured as described in section 6.2, and treated with either long fibers ("LNAG") or sNAG nanofibers ("sNAG"), for 2 hours or 20 hours. RNA was extracted with RNAsol (Teltest, Inc.) following manufacturer's instructions, and amplified using Amino Allyl MessageAMP™ II aRNA amplification kit (Applied Biosystems). During RNA amplification, aRNA from cells treated with LNAG and aRNA from cells treated with sNAG was differentially labeled with Cy3 or Cy5 fluorescent dyes. The slides were prepared for hybridization with aRNA by soaking in blocking solution (Sigma Tris-buffered saline pH8.0, in 1000 ml dH$_2$O, 1% BSAw/v, NaN$_3$ to 0.05%) at RT O/N, then rinsed and dried. Samples containing equal amounts of differentially labeled target aRNA from LNAG and sNAG-treated cells were mixed, hybridized with the slides (65 ul/slide; denatured at 95° C. for 5 min; hybridized for 48 hours at 37° C. in 0.1% SDS and 5×SSC and 1% BSA), rinsed and dried. The following exemplary graphs in Table VII illustrate experimental set up:

TABLE VII

Labeling of aRNA

| Name | aRNA ng/ul (100 ul) | 260/280 nm | 20 ug for label (ul) | dye used | labeled conc. Pmol/ul | 260/280 | total labeled aRNA (20 ul) | |
|---|---|---|---|---|---|---|---|---|
| HaCat e14d3 ctr | 897.42 | 2.09 | 22.29 | cy3 | 851.58 | 1.34 | 17031.6 | |
| HaCat e14d3 LNAG100 | 1339.08 | 2.07 | 14.94 | cy5 | 687.01 | 1.87 | 13740.2 | |
| HaCat e14d3 sNAG100 | 1515.62 | 2.05 | 13.20 | cy5 | 519.15 | 1.93 | 10383 | |
| HUVEC e18d4 ctr | 1656.37 | 2.05 | 12.07 | cy3 | 529.11 | 1.88 | 19577.07 | 37 ul |
| HUVEC e18d4 LNAG100 | 1078.63 | 2.07 | 18.54 | cy5 | 760.26 | 1.9 | 15205.2 | |
| HUVEC e18d4 sNAG100 | 1447.87 | 2.06 | 13.81 | cy5 | 617.57 | 1.84 | 12351.4 | |

TABLE VII-continued

Labeling of aRNA

| | Sample ID | Total aRNA/slide (ng) | aRNA conc. (ng/ul) | Total vol. (ul) | 10% SDS (ul) | 20 x SSC (ul) | D H$_2$O (ul) | Total Vol (ml) | chip ID 37 C. 48 h | Chip ID 37 C. 48 h |
|---|---|---|---|---|---|---|---|---|---|---|
| HaCat | Actr | 800 | 851.58 | 0.9 | 2 | 50 | 125.9 | 200 | D1038 | D1034 |
| | ALNAG100 (Mix 1) | 800 | 687.01 | 1.2 | 0 | 0 | | | | |
| | Actr | 800 | 851.58 | 0.9 | 2 | 50 | 125.5 | 200 | D1037 | D1033 |
| | AsNAG100 (Mix 2) | 800 | 519.15 | 1.5 | 0 | 0 | | | | |
| HUVEC | VCtr | 800 | 529.11 | 1.5 | 2 | 50 | 125.4 | 200 | D1036 | D1032 |
| | VLNAG100 (Mix 3) | 800 | 760.26 | 1.1 | | | | | | |
| | Vctr | 800 | 529.11 | 1.5 | 2 | 50 | 125.2 | 200 | D1035 | D1031 |
| | VsNAG100 (Mix 4) | 800 | 617.57 | 1.3 | | | | | | |

The slides were scanned and hybridization detected using Perkin-Elmer ScanArray equipment and ScanArray Express software V3.0, updated. For each slide, Cy5, Cy3 and composite fluorescence was visualized. To identify up-regulated and down-regulated genes microarray data was analyzed using Agilent GeneSpring GX v.11 Bioinformation Data Analysis. Genes of interest analyzed: DEFA1, DEFA3, DEFA4, DEFA5, DEFA6, DEFB1, DEFB013A, DEFB104A, DEFB105B, DEFB108B, DEFB112, DEFB114, DEFB118, DEFB119, DEFB123, DEFB124, DEFB125, DEFB126, DEFB127, DEFB128, DEFB129, DEFB131, and DEFB4 ("DEFA"=α-defensin, and "DEFB"=β-defensin); TLR1, TLR10, TL2, TLR3, TLR4, TLR5, TLR6, TLR7 and TLR8 ("TLR"=Toll receptor); SIGIRR (Single IG IL-1-related receptor); IRAK2 (IL-1 receptor-associated kinase 1); TRAF6 (TNF receptor associated factor 6); D106A (β-defensin 106), D107A (β-defensin 107). Negative controls: three random sequences (1, 2, 3). Positive controls: 1433Z (Tyrosine-3-monohydrogenase/tryptophan 5 monohydrogenase action protein); GAPD (glyceraldehydes-3-phosphate dehydrogenase); RPL13A (Ribosomal protein L13a); UBC (Ubiquitin C); ACTB (Actin B).

Results: Results of the microarray gene chip analyses are presented in Tables VIII and IX below. Table VIII shows gene expression in human umbilical vein endothelial cells ("HUVEC") after 2 h or 24 h exposure to either LNAG fibers or sNAG nanofibers. Table IX shows gene expression in human keratinocyte cell line (HaCat) after 2 h or 24 h exposure to either LNAG fibers or sNAG nanofibers. The results demonstrate that gene expression profile induced by long poly-N-acetylglucosamine fibers ("LNAG") differs from the gene expression profile induced by sNAG nanofibers ("sNAG"). Specifically, LNAG and sNAG differ in their effect on expression of defensin genes and Toll receptor genes.

TABLE VIII

Microarray Defensin Gene Expression in Human Umbilical Vein Endothelial Cells (HUVEC), Fold Change

| Name | [2 h, LNAG] | [2 h, sNAG] |
|---|---|---|
| 1433Z HUMAN | 0.039 | 0.329 |
| ACTB HUMAN | -0.140 | 0.032 |
| D106A HUMAN | -1.376 | -0.195 |
| D107A HUMAN | 1.825 | 1.431 |
| DEFA1 | 0.407 | -1.107 |
| DEFA3 | 0.000 | 0.528 |
| DEFA4 | -1.007 | -0.123 |
| DEFA5 | -0.863 | 0.451 |
| DEFA6 | 1.969 | 0.805 |
| DEFB1 | 0.315 | 1.441 |
| DEFB103A | 1.426 | 1.486 |
| DEFB104A | 1.296 | 2.260 |
| DEFB105B | 0.616 | 0.667 |
| DEFB108B | 2.210 | 0.441 |
| DEFB112 | 0.000 | -0.528 |
| DEFB114 | 0.000 | 0.667 |
| DEFB118 | -0.142 | 0.631 |
| DEFB119 | 0.137 | 1.472 |
| DEFB123 | 1.664 | 1.814 |
| DEFB124 | 1.242 | 1.533 |
| DEFB125 | 1.169 | 1.969 |
| DEFB126 | -0.064 | 0.801 |
| DEFB127 | 1.723 | 0.000 |
| DEFB128 | 1.602 | -0.528 |
| DEFB129 | 1.528 | 0.407 |
| DEFB131 | -0.333 | 0.636 |
| DEFB4 | 0.406 | 0.567 |
| GAPD | 0.420 | 0.602 |
| IRAK2 | -0.035 | 1.106 |
| RPL13A | 0.671 | 1.329 |
| SIGIRR | 0.358 | 1.481 |
| TLR1 | -0.194 | 1.089 |
| TLR10 | 0.000 | -0.333 |
| TL2 | 0.653 | 2.078 |
| TLR3 | -0.528 | -0.333 |
| TLR4 | 0.613 | 2.073 |
| TLR5 | 1.723 | 1.181 |
| TLR6 | 1.333 | 0.528 |
| TLR7 | 1.839 | 1.274 |
| TLR8 | -0.033 | 0.843 |
| TRAF6 | 1.569 | 0.472 |
| UBC | -0.285 | 0.072 |

| Name | [20 h, LNAG] | [20 h, sNAG] |
|---|---|---|
| 1433Z HUMAN | -0.046 | -0.180 |
| ACTB HUMAN | 0.874 | -0.413 |
| D106A HUMAN | 1.107 | 0.522 |
| D107A HUMAN | -1.007 | 0.372 |
| DEFA1 | -0.333 | 0.384 |
| DEFA3 | 1.195 | -2.335 |
| DEFA4 | 0.496 | 2.636 |
| DEFA5 | -0.287 | -0.476 |
| DEFA6 | 0.333 | -1.402 |
| DEFB1 | 1.933 | 0.413 |
| DEFB103A | 0.628 | 1.348 |
| DEFB104A | 1.543 | 0.344 |
| DEFB105B | 0.723 | -0.162 |

TABLE VIII-continued

Microarray Defensin Gene Expression in Human Umbilical
Vein Endothelial Cells (HUVEC), Fold Change

| | | |
|---|---|---|
| DEFB108B | 0.351 | 1.895 |
| DEFB112 | −0.862 | 1.107 |
| DEFB114 | −0.862 | 1.799 |
| DEFB118 | 0.456 | 0.577 |
| DEFB119 | 0.808 | −1.530 |
| DEFB123 | 0.390 | −0.375 |
| DEFB124 | 1.113 | 1.357 |
| DEFB125 | 1.269 | −2.053 |
| DEFB126 | 1.818 | 0.385 |
| DEFB127 | 0.000 | 1.085 |
| DEFB128 | 0.805 | 2.238 |
| DEFB129 | 1.936 | −0.005 |
| DEFB131 | −0.723 | −0.608 |
| DEFB4 | 0.401 | −0.190 |
| GAPD | 0.616 | 0.324 |
| IRAK2 | 1.084 | 0.984 |
| RPL13A | 0.789 | 0.208 |
| SIGIRR | 1.870 | −0.050 |
| TLR1 | 0.196 | −0.631 |
| TLR10 | −0.528 | 0.644 |
| TLR2 | 1.848 | 4.494 |
| TLR3 | −1.484 | −1.361 |
| TLR4 | 2.616 | 0.634 |
| TLR5 | 0.723 | −0.417 |
| TLR6 | 0.246 | −0.482 |
| TLR7 | −0.160 | 0.199 |
| TLR8 | −0.371 | 1.219 |
| TRAF6 | 0.731 | 3.266 |
| UBC | −0.009 | −0.265 |

TABLE IX

Microarray Defensin Gene Expression in Human
Keratinocyte Cell Line (HaCat), Fold Change

| Name | 2 h, LNAG | 2 h, sNAG | Name | 20 h, LNAG | 20 h, sNAG |
|---|---|---|---|---|---|
| 1433Z | 0.255 | −0.282 | 1433Z | 0.000 | 0.205 |
| GAPD | 0.041 | −0.191 | GAPD | 0.000 | 0.378 |
| RPL13A | −0.532 | 0.698 | RPL13A | 0.000 | −1.187 |
| UBC | 0.136 | −0.065 | UBC | 0.834 | −0.023 |
| ACTB | 0.130 | 0.447 | ACTB | 0.333 | 0.988 |
| Negative Control | 0.000 | 0.000 | Negative Control | 0.000 | 0.000 |
| Negative Control | 0.000 | 0.000 | Negative Control | 0.000 | 0.000 |
| Negative Control | 0.000 | 0.000 | Negative Control | 0.000 | 0.000 |
| DEFB1 | −0.647 | 1.390 | DEFB1 | −0.333 | −0.426 |
| DEFB126 | 0.348 | 1.737 | DEFB126 | 1.000 | 0.744 |
| DEFB129 | 0.382 | 1.464 | DEFB129 | −0.528 | −0.931 |

6.5 Example 5: Effect of Irradiation on sNAG Membranes

Method of Preparation of sNAG Membrane. The sNAG membrane is derived from microalgal pGlcNAc fibers produced as previously described (see Vournakis et al. U.S. Pat. Nos. 5,623,064; and 5,624,679, the content of each of which is incorporated herein by reference in its entirety). Briefly, microalgae were cultured in unique bioreactor conditions using a defined growth media. Following the harvest of microalgae from high-density cultures, fibers were isolated via a stepwise separation and purification process resulting in batches of pure fibers suspended in water for injections (wfi). Fibers were formulated into patches by concentration and oven drying, and were packaged and sterilized by gamma-irradiation. Fiber dimensions average 20-50 nm×1-2 nm×~100 μm. Batches of fibers were individually quality controlled using chemical and physical test parameters, and each batch met strict purity criteria prior to release. Final batches were required to be substantially free of proteins, metal ions, and other components. The fibers were then shortened by irradiation to produce sNAG membranes. Briefly, the starting material contained 60 g of pGlcNAc slurry at a concentration of 1 mg/mL. The concentration of the pGlcNAc slurry was confirmed by filtering 5 mL into a 0.2 um filter. 15 L of pGlcNAc slurry containing 15 g pGlcNAc was filtered until formation of a wet cake. The wake cake was then transferred into a foil pouch, which is a gamma radiation compatible container, and subjected to 200 kGy gamma radiation. Other irradiation conditions were tested for their effects on pGlcNAc compositions, as reflected in FIG. 14A.

Effect of Irradiation on pGlcNAc Membranes. While irradiation reduces the molecular weight of pGlcNAc, irradiation did not disturb the microstructure of the fibers. pGlcNAc was irradiated under different conditions: as a dry, lyophilized material; as a dry membrane; as a concentrated slurry (30:70 weight by volume); and as a dilute slurry (5 mg/ml). A suitable molecular weight reduction (to a molecular weight of 500,000-1,000,000 daltons) was achieved at an irradiation dose of 1,000 kgy for dry polymer, and 200 kgy for wet polymer (FIG. 14A).

The chemical and physical structure of the fibers was maintained throughout irradiation as verified by infrared (IR) spectrum (FIG. 14B), elemental assay, and scanning electron microscopes (SEMs) analysis. Microscopic observation of irradiated fibers showed a decrease in the particle length (FIGS. 14C and 14D). The majority of the fibers are less than about 15 μm in length, with an average length of about 4 um.

6.6 Example 6: sNAG Nanofibers and Long Form p-GlcNAc Fibers Differ in their Effects on Metabolic Rate and Serum Deprivation of Umbilical Cord Vein Endothelial Cells Materials and Methods. Pooled, multiple-donor human umbilical cord vein endothelial cells (EC) (Cambrex) were maintained at 37° C. with 5% $CO_2$ in endothelial basal medium 2 (Cambrex) supplemented with EC growth medium 2 SingleQuots as described by Cambrex procedures. Serum starvation was performed at 80-90% confluency in RPMI-1640 supplemented with 0.1% fetal calf serum (Gibco BRL) for 24 h followed by stimulation with VEGF 165 (20 ng/ml, R&D Systems) or with highly purified pGlcNAc nanofibers or sNAG nanofibers in sterile water (provided by Marine Polymer Technologies, Inc., Danvers, Mass., USA) with the amounts indicated in the figure descriptions. For cellular proliferation/viability assessment, 2 different assays were used: trypan blue exclusion by direct cell counts using a hemacytometer and an MTT [3-(4,5-dimethylthiazol-2yl)-2,5-diphenyltetrazolium bromide] assay in procedures described by the manufacturer (Promega).

Results—pGlcNAc:

pGlcNAc Did not Affect Metabolic Rate. As shown in FIG. 15, pGlcNAc did not result in a higher metabolic rate as measured by MTT assays, indicating that this polymeric material was not causing marked increases in cellular proliferation.

pGlcNAc Protected EC from Cell Death Induced by Serum Starvation. To test if pGlcNAc fibers had a direct effect on EC, serum-starved EC cells were treated with VEGF or with different concentrations of pGlcNAc fibers. As shown in FIG. 16 at 48 h and 72 h after serum starvation, as compared with the total number of cells plated (control), there was about 2-fold reduction in the number of cells after 48 h or 72 h. At 48 h, this decrease in cell number was rescued by the addition of VEGF or by the addition of pGlcNAc fibers at either 50 or 100 µg/ml. At 72 h, the decrease in cell number was rescued by the addition of VEGF or largely rescued by the addition of pGlcNAc fibers at 100 µg/ml. These results indicated that like VEGF, pGlcNAc fiber treatment prevented cell death induced by serum deprivation.

Results—sNAG:

sNAG Induced Marked Increase in Metabolic Rate. As measured by MTT assays, sNAG at 50, 100 or 200 µg/ml resulted in a higher metabolic rate of EC than VEGF (FIG. 17).

sNAG Did not Protect EC from Cell Death Induced by Serum Deprivation. To test if sNAG fibers had a direct effect on EC, serum-starved EC cells were treated with VEGF or with different concentrations of sNAG fibers. As shown in FIG. 18, at 48 h after serum starvation, as compared with the total number of cells plated (control), there was about 2-fold reduction in the number of cells. This decrease in cell number was rescued by the addition of VEGF but not by the addition of sNAG fibers at 50, 100 or 200 µg/ml. These results indicated that not like VEGF, sNAG fiber treatment did not prevent cell death induced by serum deprivation.

Conclusion: The above results demonstrate that sNAG, unlike long form pGlcNAc, increases the metabolic rate of serum-starved EC in a MTT assay and does not rescue apoptosis of serum-starved EC in a trypan blue exclusion test.

6.7 Example 7. Preclinical Testing of sNAG 6.7.1 Test Article

A test article comprising sNAG produced as previously described in Section 6.2.1 supra. was utilized. The test article was supplied sterile by Marine Polymer Technologies, Inc.

6.7.2 Biocompatibility Testing—L929 MEM Elusion Test—ISO 10993-5

Biocompatibility of the test article was tested in mouse fibroblast L929 mammalian cells. No biological reactivity (Grade 0) was observed in the L929 cells at 48 hours, post exposure to the test article. The observed cellular response obtained from the positive control article (Grade 4) and negative control article (Grade 0) confirmed the suitability of the test system. Based on the criteria of the protocol, the test article is considered non-toxic and meets the requirements of the Elution Test, International Organization for Standardization (ISO) 10993-5 guidelines. See Table X below.

TABLE X

REACTIVITY GRADES

| | | | Controls | | | | | | | | |
|---|---|---|---|---|---|---|---|---|---|---|---|
| | Test Article | | | Medium | | | Negative | | | Positive | |
| Time | A | B | C | A | B | C | A | B | C | A | B | C |
| 0 Hours | 0 | 0 | 0 | 0 | 0 | 0 | 0 | 0 | 0 | 0 | 0 | 0 |
| 24 Hours | 0 | 0 | 0 | 0 | 0 | 0 | 0 | 0 | 0 | 3 | 3 | 3 |
| 48 Hours | 0 | 0 | 0 | 0 | 0 | 0 | 0 | 0 | 0 | 4 | 4 | 4 |

| Grade | Reactivity | Description of Reactivity Zone |
|---|---|---|
| 0 | None | Discrete intracytoplasmic granules; no cell lysis |
| 1 | Slight | Not more than 20% of the cells are round, loosely attached, and without intracytoplasmic granules; occasional lysed cells are present |
| 2 | Mild | Not more than 50% of the cells are round and devoid of intracytoplasmic granules; no extensive cell lysis and empty areas between cells |
| 3 | Moderate | Not more than 70% of the cell layers contain rounded cells or are lysed |
| 4 | Severe | Nearly complete destruction of the cell layers |

TABLE X-continued 6.7.3 Intramuscular Implantation Test—ISO—4 Week Implantation 6.7.3.1. Materials and Methods To evaluate the potential of the test article to induce local toxic effects, the Intramuscular Implantation Test—ISO—4 Week Implantation ("Intramuscular Implantation Test") was used. Briefly, the test article was implanted in the paravertebral muscle tissue of New Zealand White rabbits for a period of 4 weeks. The test article was then evaluated separately using two control articles: positive control Surgical (Johnson and Johnson, NJ) and negative control High Density Polyethylene (Negative Control Plastic).

Preparation of Test and Control Articles. The test article measured approximately 1 mm to in width and 10 mm in length. The two control articles were prepared. The positive control, Surgicel (C1), measured approximately 1 mm in width by 10 mm in length and was received sterile. Negative Control Plastic (C2), measured approximately 1 mm in width by 10 mm in length and was sterilized by dipping in 70% ethanol.

Pre-Dose Procedure. Each animal was weighed prior to implantation. On the day of the test, the dorsal sides of the animals were clipped free of fur and loose hair was removed by means of a vacuum. Each animal was appropriately anesthetized. Prior to implantation, the area was swabbed with a surgical preparation solution.

Dose Administration. Four test article strips were surgically implanted into each of the paravertebral muscles of each rabbit, approximately 2.5 cm from the midline and parallel to the spinal column and approximately 2.5 cm from each other. The test article strips were implanted on one side of the spine. In a similar fashion, positive control article strips (Surgicel) were implanted in the contralateral muscle of each animal. Two negative control strips (Negative Control Plastic) were implanted caudal (toward the tail) to the test article and to C1 control implant sites on either side of the spine (total of four strips). A total of at least eight test article strips and eight of each control article strips are required for evaluation.

Post-Dose Procedures. The animals were maintained for a period of 4 weeks. The animals were observed daily for this period to ensure proper healing of the implant sites and for clinical signs of toxicity. Observations included all clinical manifestations. At the end of the observation period, the animals were weighed. Each animal was sacrificed by an injectable barbiturate. Sufficient time was allowed to elapse for the tissue to be cut without bleeding.

Gross Observations. The paravertebral muscles in which the test or control articles were implanted were excised in toto from each animal. The muscle tissue was removed by carefully slicing around the implant sites with a scalpel and lifting out the tissue. The excised implant tissues were examined grossly, but without using excessive invasive procedures that might have disrupted the integrity of this tissue for histopathological evaluation. The tissues were placed in properly labeled containers containing 10% neutral buffered formalin.

Histopathology. Following fixation in formalin, each of the implant sites was excised from the larger mass of tissue.

The implant site, containing the implanted material, was examined macroscopically. Each site was examined for signs of inflammation, encapsulation, hemorrhaging, necrosis, and discoloration using the following scale:
- 0=Normal
- 1=Mild
- 2=Moderate
- 3=Marked After macroscopic observation, the implant material was left in-situ and a slice of tissue containing the implant site was processed. Histologic slides of hematoxylin and eosin stained sections were prepared by Toxikon. The slides were evaluated and graded by light microscopic examination.

Pathological Assessment of the Effects of the Implant. The following categories of biological reaction were assessed by microscopic observation for each implant site:
1. Inflammatory Responses:
   a. Polymorphonuclear leukocytes
   b. Lymphocytes
   c. Eosinophils
   d. Plasma cells
   e. Macrophages
   f. Giant cells
   g. Necrosis
   h. Degeneration
2. Healing Responses:
   a. Fibrosis
   b. Fatty Infiltrate Each category of response was graded using the following scale:
- 0=Normal
- 0.5=Very Slight
- 1=Mild
- 2=Moderate
- 3=Marked The relative size of the involved area was scored by assessing the width of the area from the implant/tissue interface to unaffected areas which have the characteristics of normal tissue and normal vascularity. Relative size of the involved area was scored using the following scale:
- 0=0 mm, No site
- 0.5=up to 0.5 mm, Very slight
- 1=0.6-1.0 mm, Mild
- 2=1.1-2.0 mm, Moderate
- 3=>2.0 mm, Marked The Intramuscular Implantation Test was conducted based upon the following references:

1. ISO 10993-6, 1994, Biological Evaluation of Medical Devices—Part 6: Tests for Local Effects After Implantation.
2. ISO 10993-12, 2002, Biological Evaluation of Medical Devices—Part 12: Sample Preparation and Reference Materials.
3. ASTM F981-04, 2004, Standard Practice for Assessment of Compatibility of Biomaterials for Surgical Implants with Respect to Effect of Materials on Muscle and Bone.
4. ASTM F763-04, 2004, Standard Practice for Short Term Screening of Implant Materials.
5. ISO/IEC 17025, 2005, General Requirements for the Competence of Testing and Calibration Laboratories.

The results of the Intramuscular Implantation Test were evaluated based upon the following criteria:
1. Calculated Rating: For each implanted site, a total score is determined. The average score of the test sites for each animal is compared to the average score of the control sites for that animal. The average difference between test and control sites for all animals is calculated and the initial Bioreactivity Rating is assigned as follows:
   - 0-1.5 No Reaction*
   - >1.5-3.5 Mild Reaction
   - >3.5-6.0 Moderate Reaction
   - >6.0 Marked Reaction

* A negative calculation is reported as zero (0).

2. Modification of the Rating: The pathology observer reviews the calculated level of bioreactivity. Based on the observation of all factors (e.g., relative size, pattern of response, inflammatory vs. resolution), the pathology observer may revise the Bioreactivity Rating. Justification for the modification to the rating is presented in the narrative report (A descriptive narrative report regarding the biocompatibility of the test material is provided by the pathology observer).

6.7.3.2. Results

The results indicated that the test article was non-reactive when implanted for 4 weeks (Bioreactivity Rating of 0.2) when compared to positive control Surgicel; and non-reactive (Bioreactivity Rating of 0.0) when compared to negative control High Density Polyethylene (Negative Control Plastic).

Clinical Observation. Table XI below shows results of the macroscopic evaluation of the test article and control implant sites indicated no significant signs of inflammation, encapsulation, hemorrhage, necrosis, or discoloration at the 4 week time period. Some test sites and the majority of the positive control, Surgicel, were not seen macroscopically and serial sections were submitted for microscopic evaluation.

TABLE XI

| | | | | | | | | | | | | | | | | |
|---|---|---|---|---|---|---|---|---|---|---|---|---|---|---|---|---|
| Macroscopic Observations 4 Week Implantation | | | | | | | | | | | | | | | | |
| Tissue Size: | T1 | T2 | T3 | T4 | Test Ave. | C1-1 | C1-2 | C1-3 | C1-4 | Control C1 Avg. | C2-1 | C2-2 | C2-3 | C2-4 | Control C2 Ave. |
| Animal No.: 60959 | | | | | | | | | | | | | | | | |
| Inflammation | 0 | NSF | 0 | NSF | 0 | NSF | NSF | NSF | NSF | N/A | 0 | 0 | 0 | 0 | 0 |
| Encapsulation | 0 | NSF | 0 | NSF | 0 | NSF | NSF | NSF | NSF | N/A | 0 | 0 | 0 | 0 | 0 |
| Hemorrhage | 0 | NSF | 0 | NSF | 0 | NSF | NSF | NSF | NSF | N/A | 0 | 0 | 0 | 0 | 0 |
| Necrosis | 0 | NSF | 0 | NSF | 0 | NSF | NSF | NSF | NSF | N/A | 0 | 0 | 0 | 0 | 0 |
| Discoloration | 0 | NSF | 0 | NSF | 0 | NSF | NSF | NSF | NSF | N/A | 0 | 0 | 0 | 0 | 0 |
| Total | 0 | N/A | 0 | N/A | | N/A | N/A | N/A | N/A | | 0 | 0 | 0 | 0 | |
| Animal No.: 60961 | | | | | | | | | | | | | | | | |
| Inflammation | NSF | NSF | NSF | NSF | N/A | NSF | NSF | NSF | NSF | N/A | 0 | 0 | NSF | 0 | 0 |
| Encapsulation | NSF | NSF | NSF | NSF | N/A | NSF | NSF | NSF | NSF | N/A | 0 | 0 | NSF | 0 | 0 |
| Hemorrhage | NSF | NSF | NSF | NSF | N/A | NSF | NSF | NSF | NSF | N/A | 0 | 0 | NSF | 0 | 0 |

TABLE XI-continued

Macroscopic Observations
4 Week Implantation

| Tissue Size: | T1 | T2 | T3 | T4 | Test Ave. | C1-1 | C1-2 | C1-3 | C1-4 | Control C1 Avg. | C2-1 | C2-2 | C2-3 | C2-4 | Control C2 Ave. |
|---|---|---|---|---|---|---|---|---|---|---|---|---|---|---|---|
| Necrosis | NSF | NSF | NSF | NSF | N/A | NSF | NSF | NSF | NSF | N/A | 0 | 0 | NSF | 0 | 0 |
| Discoloration | NSF | NSF | NSF | NSF | N/A | NSF | NSF | NSF | NSF | N/A | 0 | 0 | NSF | 0 | 0 |
| Total | N/A | N/A | N/A | N/A | | N/A | N/A | N/A | N/A | | 0 | 0 | N/A | 0 | |
| | | | | | | Animal No.: 60968 | | | | | | | | | |
| Inflammation | NSF | NSF | NSF | NSF | N/A | NSF | NSF | NSF | NSF | N/A | 0 | 0 | 0 | 0 | 0 |
| Encapsulation | NSF | NSF | NSF | NSF | N/A | NSF | NSF | NSF | NSF | N/A | 0 | 0 | 0 | 0 | 0 |
| Hemorrhage | NSF | NSF | NSF | NSF | N/A | NSF | NSF | NSF | NSF | N/A | 0 | 0 | 0 | 0 | 0 |
| Necrosis | NSF | NSF | NSF | NSF | N/A | NSF | NSF | NSF | NSF | N/A | 0 | 0 | 0 | 0 | 0 |
| Discoloration | NSF | NSF | NSF | NSF | N/A | NSF | NSF | NSF | NSF | N/A | 0 | 0 | 0 | 0 | 0 |
| Total | N/A | N/A | N/A | N/A | | N/A | N/A | N/A | N/A | | 0 | 0 | 0 | 0 | |

T = test site (representative sections were submitted for microscopic assessment)
C1 = Surgicel (Due to the nature of the material, representative sections were submitted for microscopic assessment)
C2 = Negative Control High Density Polyethylene (Negative Control Plastic)
Grading Scale
0 = no reaction
1 = mild reaction
2 = moderate reaction
3 = marked reaction
NSF = No Site Found
N/A = Not Application Implantation Site Observations (Microscopic). Table XII below shows results of the microscopic evaluation of the test article implant sites indicated no significant signs of inflammation, fibrosis, hemorrhage, necrosis, or degeneration as compared to each of the control article sites. The Bioreactivity Rating for the 4 week time period (average of three animals) was 0.2, (C1—Surgicel) and 0.0 (C2—Negative Control Plastic) indicating no reaction as compared to either of the control implant sites. The pathologist noted there was a moderate polymorphic and histiocytic (macrophages) infiltrate around the in situ test article that was not unexpected given the nature of the test material.

TABLE XII

Microscopic Observations
4 Week Implantation

Animal No.: 60959

| | Categories | | | | | | | | | | |
|---|---|---|---|---|---|---|---|---|---|---|---|
| | Test Sites** | | | Control Sites | | | | | | | |
| Reaction | T1 | T2 | T3 | C1-1 | C1-2 | C1-3 | C1-4 | C2-1 | C2-2 | C2-3 | C2-4 |
| Foreign Debris | 0.0 | 0.0 | 0.0 | 0.0 | 0.0 | 0.0 | 0.0 | 0.0 | 0.0 | 0.0 | 0.0 |
| Rel. Size of Involved area | 0.5 | 0.5 | 0.5 | 0.5 | 0.5 | 0.5 | 0.5 | 0.5 | 0.5 | 0.5 | 0.5 |
| * Polymorphs | 0.0 | 0.5 | 0.5 | 0.0 | 0.0 | 0.0 | 0.0 | 0.0 | 0.0 | 0.0 | 0.0 |
| * Lymphocytes | 0.0 | 0.0 | 0.0 | 0.0 | 0.0 | 0.0 | 0.0 | 0.0 | 0.0 | 0.0 | 0.0 |
| * Eosinophils | 0.0 | 0.0 | 0.0 | 0.0 | 0.0 | 0.0 | 0.0 | 0.0 | 0.0 | 0.0 | 0.0 |
| * Plasma cells | 0.0 | 0.0 | 0.0 | 0.0 | 0.0 | 0.0 | 0.0 | 0.0 | 0.0 | 0.0 | 0.0 |
| * Macrophages | 0.5 | 0.5 | 0.5 | 0.5 | 0.5 | 0.5 | 0.5 | 0.5 | 0.5 | 0.5 | 0.5 |
| * Giant Cells | 0.0 | 0.0 | 0.0 | 0.0 | 0.0 | 0.0 | 0.0 | 0.0 | 0.0 | 0.0 | 0.0 |
| * Degeneration | 0.5 | 0.5 | 0.5 | 0.5 | 0.0 | 0.5 | 0.0 | 0.0 | 0.0 | 0.0 | 0.0 |
| * Necrosis | 0.0 | 0.0 | 0.0 | 0.0 | 0.0 | 0.0 | 0.0 | 0.0 | 0.0 | 0.0 | 0.0 |
| * Fibrosis | 0.5 | 0.5 | 0.5 | 0.5 | 0.5 | 0.5 | 0.5 | 0.5 | 0.5 | 0.5 | 0.5 |
| * Fatty Infiltrate | 0.0 | 0.0 | 0.5 | 0.0 | 0.5 | 0.0 | 0.5 | 0.5 | 0.5 | 0.0 | 0.5 |
| Total | 1.5 | 2.0 | 2.5 | 1.5 | 1.5 | 1.5 | 1.5 | 1.5 | 1.5 | 1.0 | 1.5 |

T = Test Site
C1 = Surgicel
C2 = Negative Control High Density Polyethylene (Negative Control Plastic)
Animal Test Score(Average*) = 2.0
Animal C1 Score(Average*) = 1.5
Animal C2 Score(Average*) = 1.4
Animal Score (Average Test Score − Average C1 Score) = 0.5
Animal Score (Average Test Score − Average C2 Score) = 0.6
* Used in calculation of Bioreactivity Rating.
**No site found in T4.

TABLE XII-continued

Microscopic Observations
4 Week Implantation

Animal No.: 60961

| Reaction | Test Sites** | | | Control Sites** | | | | | |
|---|---|---|---|---|---|---|---|---|---|
| | T1 | T3 | T4 | C1-1 | C1-3 | C1-4 | C2-1 | C2-2 | C2-3 |
| Foreign Debris | 0.0 | 0.0 | 0.0 | 0.0 | 0.0 | 0.0 | 0.0 | 0.0 | 0.0 |
| Rel. Size of Involved area | 0.5 | 0.5 | 0.5 | 0.5 | 0.5 | 0.5 | 0.5 | 0.5 | 0.5 |
| * Polymorphs | 0.0 | 0.0 | 0.5 | 0.5 | 0.0 | 0.5 | 0.5 | 0.5 | 0.5 |
| * Lymphocytes | 0.0 | 0.0 | 0.0 | 0.0 | 0.0 | 0.0 | 0.0 | 0.0 | 0.0 |
| * Eosinophils | 0.0 | 0.0 | 0.0 | 0.0 | 0.0 | 0.0 | 0.0 | 0.0 | 0.0 |
| * Plasma cells | 0.0 | 0.0 | 0.0 | 0.0 | 0.0 | 0.0 | 0.0 | 0.0 | 0.0 |
| * Macrophages | 0.5 | 0.5 | 0.5 | 0.5 | 0.5 | 0.5 | 0.5 | 0.5 | 0.5 |
| * Giant Cells | 0.0 | 0.0 | 0.0 | 0.0 | 0.0 | 0.0 | 0.0 | 0.0 | 0.0 |
| * Degeneration | 0.5 | 0.5 | 0.5 | 0.5 | 0.5 | 0.5 | 0.5 | 0.5 | 0.5 |
| * Necrosis | 0.0 | 0.0 | 0.0 | 0.0 | 0.0 | 0.0 | 0.0 | 0.0 | 0.0 |
| * Fibrosis | 0.5 | 0.5 | 0.5 | 0.5 | 0.5 | 0.5 | 0.5 | 0.5 | 0.5 |
| * Fatty Infiltrate | 0.0 | 0.5 | 0.0 | 0.5 | 0.0 | 0.5 | 0.5 | 0.5 | 0.5 |
| Total | 1.5 | 2.0 | 2.0 | 2.5 | 1.5 | 2.5 | 2.5 | 2.5 | 2.5 |

T = Test Site
C1 = Surgicel
C2 = Negative Control High Density Polyethylene (Negative Control Plastic)
Animal Test Score (Average*) = 1.8
Animal C1 Score (Average*) = 2.2
Animal C2 Score (Average*) = 2.5
Animal Score (Average Test Score − Average C1 Score) = −0.4
Animal Score (Average Test Score − Average C2 Score) = −0.7
* Used in calculation of Bioreactivity Rating.
**No site found in T2, C1-2, and C2-4.

Animal No.: 60968

| Reaction | Test Sites | | | | Control Sites** | | | | | | |
|---|---|---|---|---|---|---|---|---|---|---|---|
| | T1 | T2 | T3 | T4 | C1-1 | C1-2 | C1-3 | C2-1 | C2-2 | C2-3 | C2-4 |
| Foreign Debris | 0.0 | 0.0 | 0.0 | 0.0 | 0.0 | 0.0 | 0.0 | 0.0 | 0.0 | 0.0 | 0.0 |
| Rel. Size of Involved area | 0.5 | 0.5 | 0.5 | 0.5 | 0.5 | 0.5 | 0.5 | 0.5 | 0.5 | 0.5 | 0.5 |
| * Polymorphs | 0.0 | 0.5 | 0.0 | 0.5 | 0.0 | 0.0 | 0.0 | 0.5 | 0.5 | 0.0 | 0.5 |
| * Lymphocytes | 0.0 | 0.0 | 0.0 | 0.0 | 0.0 | 0.0 | 0.0 | 0.0 | 0.0 | 0.0 | 0.0 |
| * Eosinophils | 0.0 | 0.0 | 0.0 | 0.0 | 0.0 | 0.0 | 0.0 | 0.0 | 0.0 | 0.0 | 0.0 |
| * Plasma cells | 0.0 | 0.0 | 0.0 | 0.0 | 0.0 | 0.0 | 0.0 | 0.0 | 0.0 | 0.0 | 0.0 |
| * Macrophages | 0.5 | 0.5 | 0.5 | 0.5 | 0.5 | 0.5 | 0.5 | 0.5 | 0.5 | 0.5 | 0.5 |
| * Giant Cells | 0.0 | 0.0 | 0.0 | 0.0 | 0.0 | 0.0 | 0.0 | 0.0 | 0.0 | 0.0 | 0.0 |
| * Degeneration | 0.5 | 0.5 | 0.5 | 0.5 | 0.5 | 0.5 | 0.5 | 0.5 | 0.5 | 0.5 | 0.5 |
| * Necrosis | 0.0 | 0.0 | 0.0 | 0.0 | 0.0 | 0.0 | 0.0 | 0.0 | 0.0 | 0.0 | 0.0 |
| * Fibrosis | 0.5 | 0.5 | 0.5 | 0.5 | 0.5 | 0.5 | 0.5 | 0.5 | 0.5 | 0.5 | 0.5 |
| * Fatty Infiltrate | 0.5 | 0.5 | 0.5 | 0.5 | 0.5 | 0.0 | 0.5 | 0.5 | 0.5 | 0.5 | 0.5 |
| Total | 2.0 | 2.5 | 2.0 | 2.5 | 2.0 | 1.5 | 2.0 | 2.5 | 2.5 | 2.0 | 2.5 |

T = Test Site
C1 = Surgicel
C2 = Negative Control High Density Polyethylene (Negative Control Plastic)
Animal Test Score (Average*) = 2.3
Animal C1 Score (Average*) = 1.8
Animal C2 Score (Average*) = 2.4
Animal Score (Average Test Score − Average C1 Score) = 0.5
Animal Score (Average Test Score − Average C2 Score) = −0.1
* Used in calculation of Bioreactivity Rating.
**No site found in C1-4.

|  | C1 | C2 |
|---|---|---|
| Animal Score 60759 = | 0.5 | 0.5 |
| Animal Score 60961 = | −0.4 | −0.2 |
| Animal Score 60968 = | 0.5 | −0.1 |

Bioreactivity Rating = 0.2 = No Reation
Bioreactivity Rating = −0.1 = No Reaction

6.7.4 Intracutaneous Injection Test—ISO 10993-10

USP 0.9% Sodium Chloride for Injection (NaCl) and Cottonseed Oil (CSO) extracts of the test article were evaluated for their potential to produce irritation after intracutaneous injection in New Zealand White rabbits. The test article sites did not show a significantly greater biological reaction than the sites injected with the control article. Based on the criteria of the protocol, the test article is considered a negligible irritant and meets the requirements of the ISO 10993-10 guidelines. Results are shown below in Table XIII.

TABLE XIII

Intracutaneous Test Skin Reaction Scores

| | | | Site Numbers Scoring (ER/ED) | | | | | | | | | |
|---|---|---|---|---|---|---|---|---|---|---|---|---|
| Animal # | Vehicle | Time | T-1 | T-2 | T-3 | T-4 | T-5 | C-1 | C-2 | C-3 | C-4 | C-5 |
| | | | NaCl Extract | | | | | | | | | |
| 61917 | NaCl | 0 hours† | 0/0 | 0/0 | 0/0 | 0/0 | 0/0 | 0/0 | 0/0 | 0/0 | 0/0 | 0/0 |
| | | 24 hours | 0/0 | 0/0 | 0/0 | 0/0 | 0/0 | 0/0 | 0/0 | 0/0 | 0/0 | 0/0 |
| | | 48 hours | 0/0 | 0/0 | 0/0 | 0/0 | 0/0 | 0/0 | 0/0 | 0/0 | 0/0 | 0/0 |
| | | 72 hours | 0/0 | 0/0 | 0/0 | 0/0 | 0/0 | 0/0 | 0/0 | 0/0 | 0/0 | 0/0 |
| 61919 | NaCl | 0 hours† | 0/0 | 0/0 | 0/0 | 0/0 | 0/0 | 0/0 | 0/0 | 0/0 | 0/0 | 0/0 |
| | | 24 hours | 0/0 | 0/0 | 0/0 | 0/0 | 0/0 | 0/0 | 0/0 | 0/0 | 0/0 | 0/0 |
| | | 48 hours | 0/0 | 0/0 | 0/0 | 0/0 | 0/0 | 0/0 | 0/0 | 0/0 | 0/0 | 0/0 |
| | | 72 hours | 0/0 | 0/0 | 0/0 | 0/0 | 0/0 | 0/0 | 0/0 | 0/0 | 0/0 | 0/0 |
| | Total | | | | 0.0 | | | | | 0.0 | | |
| | | | CSO Extract | | | | | | | | | |
| 61917 | CSO | 0 hours† | 0/0 | 0/0 | 0/0 | 0/0 | 0/0 | 0/0 | 0/0 | 0/0 | 0/0 | 0/0 |
| | | 24 hours | 0/0 | 0/0 | 0/0 | 0/0 | 0/0 | 0/0 | 0/0 | 0/0 | 0/0 | 0/0 |
| | | 48 hours | 0/0 | 0/0 | 0/0 | 0/0 | 0/0 | 0/0 | 0/0 | 0/0 | 0/0 | 0/0 |
| | | 72 hours | 0/0 | 0/0 | 0/0 | 0/0 | 0/0 | 0/0 | 0/0 | 0/0 | 0/0 | 0/0 |
| 61919 | CSO | 0 hours† | 0/0 | 0/0 | 0/0 | 0/0 | 0/0 | 0/0 | 0/0 | 0/0 | 0/0 | 0/0 |
| | | 24 hours | 0/0 | 0/0 | 0/0 | 0/0 | 0/0 | 0/0 | 0/0 | 0/0 | 0/0 | 0/0 |
| | | 48 hours | 0/0 | 0/0 | 0/0 | 0/0 | 0/0 | 0/0 | 0/0 | 0/0 | 0/0 | 0/0 |
| | | 72 hours | 0/0 | 0/0 | 0/0 | 0/0 | 0/0 | 0/0 | 0/0 | 0/0 | 0/0 | 0/0 |
| | Total | | | | 0.0 | | | | | 0.0 | | |

†= Immediately after injection, not used for the evaluation criteria.
Overall Mean Score* for Test Article = 0.0
Overall Mean Score* for Control Article = 0.0
Difference between Test Article and Control Article Overall Mean Score = 0.0-0.0 = 0.0
ER = Erythema; ED = Edema; T = Test Sites; C = Control Sites
*Overall Mean Score = Total erythema plus edema scores divided by 12 (2 animals × 3 scoring periods × 2 scoring categories)

6.7.5 Kligman Maximization Test—ISO 10993-10

UPS 0.9% Sodium Chloride for Injection (NaCl) and Cottonseed Oil (CSO) extracts of the test article elicited no intradermal reaction in Hartley guinea pigs at the challenge (0% sensitization), following an induction phase. Therefore, as defined by the scoring system of Kligman, this is a Grade I reaction and the test article is classified as having weak allergenic potential. Based on the criteria of the protocol, a Grade I sensitization rate is not considered significant and the test article meets the requirements of the ISO 10993-10 guidelines. Results are shown below in Table XIV.

TABLE XIV

Skin Examination Data

| Group | Animal # | Sex | Day 25 | Day 26 | Day 27 | Percent Sensitized | Allergenic Potential |
|---|---|---|---|---|---|---|---|
| Test Article | 1 | Male | 0 | 0 | 0 | 0% | Weak |
| | 2 | Male | 0 | 0 | 0 | | |
| (NaCl Extract) | 3 | Male | 0 | 0 | 0 | | |
| | 4 | Male | 0 | 0 | 0 | | |
| | 5 | Male | 0 | 0 | 0 | | |
| | 6 | Female | 0 | 0 | 0 | | |
| | 7 | Female | 0 | 0 | 0 | | |
| | 8 | Female | 0 | 0 | 0 | | |
| | 9 | Female | 0 | 0 | 0 | | |
| | 10 | Female | 0 | 0 | 0 | | |
| Test Article (CSO Extract) | 11 | Male | 0 | 0 | 0 | 0% | Weak |
| | 12 | Male | 0 | 0 | 0 | | |
| | 13 | Male | 0 | 0 | 0 | | |
| | 14 | Male | 0 | 0 | 0 | | |
| | 15 | Male | 0 | 0 | 0 | | |
| | 16 | Female | 0 | 0 | 0 | | |
| | 17 | Female | 0 | 0 | 0 | | |
| | 18 | Female | 0 | 0 | 0 | | |
| | 19 | Female | 0 | 0 | 0 | | |
| | 20 | Female | 0 | 0 | 0 | | |
| Negative Control (NaCl) | 21 | Male | 0 | 0 | 0 | 0% | Weak |
| | 22 | Male | 0 | 0 | 0 | | |
| | 23 | Female | 0 | 0 | 0 | | |
| | 24 | Female | 0 | 0 | 0 | | |
| | 25 | Female | 0 | 0 | 0 | | |
| Negative Control (CSO) | 26 | Male | 0 | 0 | 0 | 0% | Weak |
| | 27 | Male | 0 | 0 | 0 | | |
| | 28 | Female | 0 | 0 | 0 | | |
| | 29 | Female | 0 | 0 | 0 | | |
| | 30 | Female | 0 | 0 | 0 | | |

TABLE XIV-continued

Skin Examination Data

| Positive Control (DNCB) | 31 | Male | 2 | 1 | 0 | 100% | Extreme |
|---|---|---|---|---|---|---|---|
| | 32 | Male | 2 | 2 | 1 | | |
| | 33 | Female | 3 | 2 | 1 | | |
| | 34 | Female | 3 | 2 | 1 | | |
| | 35 | Female | 3 | 3 | 2 | | |

| Sensitization Rate (%) | Grade | Class |
|---|---|---|
| 0-8 | I | Weak |
| 9-28 | II | Mild |
| 29-64 | III | Moderate |
| 65-80 | IV | Strong |
| 81-100 | V | Extreme |

The test results are interpreted based upon the percentage sensitization observed.

6.8 Example 8: sNAG Nanofibers are Effective to Treat Viral Infections in Human Patients This example demonstrates that sNAG nanofibers have a potent anti-viral effect, in particular, against Herpes Simplex Virus, in vivo. Specifically, this example shows that sNAG nanofibers are effective to treat cold sores associated with HSV infection when administered topically, at the site of herpes infection, to human patients. In particular, this example demonstrates that topical treatment of human patients with compositions comprising sNAG nanofibers reduces painfulness and duration of cold sore symptoms associated with HSV infection.

Herpes Simplex Virus Infection

Herpes simplex labialis is a common infection that is estimated to affect 20% to 40% of the population (Spruance, 1992; Lowhagen, 2002). The majority of these infections are due to herpes simplex type I, with a smaller number being attributed to herpes simplex type II.

Most individuals suffer primary infection with herpes gingivostomatitis early in life. Following primary infection, the virus establishes itself in the trigeminal sensory ganglia as a chronic latent infection. Reactivation of the virus is common and typically presents as herpes labialis along the vermillion border of the lip. Primary infection with herpes simplex is marked by a long period of viral multiplication and shedding (Harmenberg, 2010). After viral replication is terminated, the lesions heal rapidly. Recurrent herpes labialis is generally cleared more rapidly than primary infection due to acquired immune response. Unfortunately, the vigorous immune response results in significant inflammation leading to clinical symptoms including pain, redness and swelling.

Recurrent herpes is marked by distinct stages (Harmenberg, 2010). The stages occur in a predictable sequence as follows: prodrome, redness, papule, vesicle, ulcer, hard crust, dry flaking residual swelling, and normal healed skin. The disease is most severe during the vesicular, ulcer and crust stages that are also referred to as the ulcerative or classical lesions.

Currently existing therapies for herpes labialis have focused principally on decreasing viral replication with either oral or topical antiviral medications. Unfortunately, since the viral replication phase is quite brief in recurrent infections these medications have only modest success, decreasing healing time of herpetic lesions by approximately 10% (Harmenberg, 2010).

Study Objectives

Primary Endpoints. The primary objective of this study was to explore the efficacy of sNAG nanofibers in the treatment of herpes labialis peri-oral lesions, and to explore the duration and intensity of pain of herpes labialis peri-oral lesions in subjects treated with sNAG nanofibers.

Inclusion Criteria

Subjects who met all of the following inclusion criteria were eligible for enrollment into the study:

1. Be a generally healthy man or woman 18 years of age or older;

2. Have recurrent herpes labialis as defined by a history of three (3) or more cold sore recurrences on the lips and/or skin surrounding the lips in the previous 12 months;

3. During ≥50% of recurrent episodes, develop a classic herpetic lesion (i.e., vesicle, ulcer, or hard crust);

4. Have the majority of their cold sore recurrences proceeded by a well defined history of prodromal symptoms including redness, pain, burning, tingling, swelling or a tight sensation of the lip at the site of the outbreak;

5. Primary cold sore recurrence for the study must be located on or within 1 cm of the lip without mucosal involvement.

Study Materials sNAG nanofibers were supplied in five white plastic tubes containing 200 microliters each (with sNAG concentration of 50 mg/mL).

Administration 10 subjects (human patients) participated in the study. The sNAG nanofibers (the majority of the sNAG nanofibers used were between about 1 to 15 microns in length) were applied to the cold sore once a night for five (5) consecutive nights, immediately prior to bedtime.

Study Assessments and Diary

Subjects participating in the study had their herpetic ulcer evaluated by the study team based upon a Cold Sore Clinical Rating scale as shown in Table XV.

TABLE XV

Cold Sore Clinical Rating

| Stage | Name | Description |
|---|---|---|
| 0 | Prodrome | Skin appears normal. Subject reports pain, burning, itching, tingling, swelling, or a tight sensation of the lip. |
| 1 | Erythema/Macule | Redness apparent. No swelling or skin elevation. |
| 2 | Papule/Edema | Firm raised area, generally slightly reddened. No visible fluid. May be more apparent by palpation than by inspection. |
| 3 | Vesicle/Pustule | Any presence of a blister-like elevation with fluid visible through the stratum corneum. |
| 4 | Ulcer/Soft Crust | Blister collapsed forming an ulcer or soft crust. Ulcer floor may be moist or contain spongy or moist crusty material. |
| 5 | Hard Crust | Ulcer dried to form a noticeable hard consolidated mass or scab or the fist scab has come off and a second or third (smaller) scab has formed. |
| 6 | Healed | Primary lesion complex has resolved. Hard crust sloughed, wound essentially re-epithelialized. Residual swelling, redness o flaking may be present |

TABLE XV-continued

Cold Sore Clinical Rating

| Stage | Name | Description |
|---|---|---|
| 7 | Aborted | Primary lesion complex did not develop beyond Stage 2 (Papule/Edema). Skin appears normal and symptoms have resolved. |

Subjects were provided instructions to record the date and time of the cold sore recurrence and time of each treatment application and severity of pain. Pain was assessed using a 10 point ordinal scale (0 to 10) where 0=no pain and 10=severe pain. FIG. 19 shows Numeric Pain Intensity Scale utilized in the study. Table XVI shows the Investigator End-of-Study Global Assessment of Therapy, including the question posed to the Investigator and the scale by which the effectiveness of therapy was measured. Table XVII shows the Subject End-of-Study Global Assessment of Therapy, including the question posed to the subject and the scale by which the effectiveness of therapy was measured. Table XVII also shows that the subjects were asked "Was this cold sore recurrence resolved faster than prior events?" and the subjects could reply "Yes" or "No" to this question.

TABLE XVI

Investigator End-of-Study Global Assessment of Therapy
Based on the clinical course of this cold sore recurrence,
what is your assessment of effectiveness of therapy?

| (0) No Response to Therapy | (1) | (2) | (3) | (4) | (5) | (6) | (7) | (8) | (9) | (10) Excellent Response to Therapy |
|---|---|---|---|---|---|---|---|---|---|---|

TABLE XVII

Subject End-of-Study Global Assessment of Therapy

Based on this cold sore recurrence, what is your
assessment of effectiveness of therapy?

| (0) No Response to Therapy | (1) | (2) | (3) | (4) | (5) | (6) | (7) | (8) | (9) | (10) Excellent Response to Therapy |
|---|---|---|---|---|---|---|---|---|---|---|

Was this cold sore recurrence resolved faster than prior events?

| No | Yes |
|---|---|

Results and Discussion

Ten patients were enrolled and completed the study described above. The research team confirmed that the cold sores in these patients conformed to the clinical rating and followed the patients throughout the prescribed therapy.

Investigator End-of-Study Global Assessment of Therapy of the 10 subjects enrolled in this study is presented in Table XVIII. At the end of the study, Investigator was asked the following question: based on the clinical course of this cold sore recurrence, what is your assessment of effectiveness of therapy? Investigator's responses are presented in Table XVIII.

TABLE XVIII

| | Investigator Assessment |
|---|---|
| Patient 1 | 7 |
| Patient 2 | 8 |
| Patient 3 | 8 |
| Patient 4 | 7 |
| Patient 5 | 10 |
| Patient 6 | 8 |
| Patient 7 | 9 |
| Patient 8 | 7 |
| Patient 9 | 8 |
| Patient 10 | 9 |
| Average | 8.1 |
| Std | 0.94 |

Accordingly, the Investigators found that topical treatment of cold sores known to be caused by a Herpes Simplex virus with sNAG nanofibers was a highly effective therapy.

Assessment of the effectiveness of therapy by the 10 subjects enrolled in this study is presented in Table XIX. The patients undertook the topical sNAG nanofiber administration (as described above) and documented treatment application and severity of pain. Patients responded the questions and reported the results. Subjects were asked the following questions: Based on this cold sore recurrence, what is your assessment of effectiveness of therapy? Was this cold sore recurrence resolved faster than prior events? Subjects' responses are presented in Table XIX.

TABLE XIX

| Patient # | Satisfaction | Faster | First Treatment Pre | First Treatment Post | Second Treatment Pre | Second Treatment Post | Third Treatment Pre | Third Treatment Post | Fourth Treatment Pre | Fourth Treatment Post | Fifth Treatment Pre | Fifth Treatment Post | Pain Reduction |
|---|---|---|---|---|---|---|---|---|---|---|---|---|---|
| Patient 1 | 7 | Y | 8 | 5 | 6 | 2 | 3 | 0 | 2 | 0 | | | 3.0 |
| Patient 2 | 8 | Y | 5 | 2 | 2 | 0 | | | | | | | 2.5 |
| Patient 3 | 10 | Y | 7 | 2 | 3 | 0 | | | | | | | 4.0 |
| Patient 4 | 9 | Y | 6 | 2 | 4 | 1 | 2 | 0 | | | | | 3.0 |
| Patient 5 | 9 | Y | 5 | 2 | 3 | 0 | | | | | | | 3.0 |
| Patient 6 | 8 | Y | 7 | 5 | 6 | 3 | 4 | 1 | 2 | 0 | 1 | 0 | 2.5 |
| Patient 7 | 9 | Y | 8 | 3 | 6 | 2 | | | | | | | 4.5 |
| Patient 8 | 10 | Y | 9 | 4 | 6 | 2 | 3 | 0 | | | | | 4.0 |
| Patient 9 | 7 | Y | 6 | 4 | 3 | 1 | 3 | 0 | 2 | 0 | | | 2.3 |

TABLE XIX-continued

| Patient Satisfaction # | Faster | First Treatment Pre | Post | Second Treatment Pre | Post | Third Treatment Pre | Post | Fourth Treatment Pre | Post | Fifth Treatment Pre | Post | Pain Reduction |
|---|---|---|---|---|---|---|---|---|---|---|---|---|
| Patient 10 | 9 | Y | 7 | 2 | 4 | 1 | 3 | 0 | | | | | 3.7 |
| Average | 8.6 ± 1.02 | | | | | | | | | | | |

Y means "yes," when the patient responded "yes" to the question "Was this cold sore recurrence resolved faster than prior events?"
Patient Overall Satisfaction was assessed based on Subjects' End of Study Global Assessment of Therapy (see Table XVII).
"Pre" assessment is assessment of pain according to Numeric Pain Intensity Scale (see FIG. 19) before treatment with sNAG nanofibers.
"Post" assessment is assessment of pain according to Numeric Pain Intensity Scale (see FIG. 19) within about 1 hour after treatment with sNAG nanofibers.

The results of the study demonstrate that application of sNAG nanofibers reduced the duration and pain associated with recurrent herpes labialis. Both investigators and patients reported that the therapy was highly effective in treating the condition.

The results from this study apply not only to herpes labialis but indicate the potential of treating ulcerations caused by viruses including but not limited to genital herpes and herpes zoster.

Next, effectiveness of topical application of sNAG nanofibers is to be evaluated in a placebo-controlled study, using sNAG nanofibers at a concentration of 25 mg/ml.

REFERENCES

Spruance S L. The natural history of recurrent oral-facial herpes simplex virus infection. Semin Dermatol 1992; 11: 200-206.

Löwhagen G B, Bonde E, Eriksson B, Nordin P, Tunbäck P, Krantz I. Self-reported herpes labialis in a Swedish population. Scand J Infect Dis 2002; 34: 664-667.

Harmenberg J, Oberg B, Spruance S. Prevention of ulcerative lesions by episodic treatment of recurrent herpes labialis: A literature review. Acta Derm Venereol. 2010 March; 90(2):122-30.

Hull C, McKeough M, Sebastian K, Kriesel J, Spruance S. Valacyclovir and topical clobetasol gel for the episodic treatment of herpes labialis: a patient-initiated, double-blind, placebo-controlled pilot trial. J Eur Acad Dermatol Venereol. 2009 March; 23(3):263-7.

6.9 Example 9: sNAG Nanofibers are Effective to Treat Inflammatory Bowel Disease In Vivo This example shows that sNAG nanofibers are effective to treat and/or prevent the development of inflammatory bowel disease. In particular, this example shows that rectal administration of sNAG nanofibers is effective to treat and/or prevent inflammation associated with chemically-induced inflammatory bowel disease in an animal model of the disease.

Inflammatory Bowel Disease

One of the common chronic inflammatory diseases with significant impact in morbidity and quality of life is inflammatory bowel disease (IBD) including Crohn's disease and ulcerative colitis (UC). There are two main questions associated with the pathophysiology of this disease, i.e. what is the primary trigger and how the disease progresses towards chronic inflammation, ineffective repair of the injured tissue and compromised healing. Increasing interest in the second question lately is associated with the impact new findings can have in the effective treatment of the disease and the improvement the quality of life.

Materials and Methods

The model used in this study is the DSS-induced ulcerative colitis that consists of administration of 3% DSS (dextran sodium sulphate) via drinking water for 7 days to a mouse. The peak of the inflammatory reaction is observed on day 7 and is followed by a period of repair of the injured colonic tissue and ultimately regeneration or progression to chronic disease and development of fibrosis.

The Chart showing experimental set up is presented in FIG. 20. At Days 0 through 7 DSS was administered via drinking water to all of the animals (mice) used in the study. One group of animals (N=10) was administered 100 µl of sNAG nanofibers (at a concentration of 12 mg/ml; the majority of sNAG nanofibers used were between about 1 to 15 microns in length), rectally, at Day 0 and Day 3 of the study (test group). Second group of animals (N=10) was administered saline control, rectally, at Day 0 and Day 3 of the study (control group). All mice were sacrificed at day 7, and their inflammatory response was evaluated by histological analysis of intestinal epithelium. Histological analysis was performed via staining of the sections of intestinal epithelium, such as H&E staining.

Protocol for H&E staining of intestinal epithelium sections. For deparafinization, sections were initially incubated in xylene for 30 min followed by decreasing concentrations of ethanol (100%×2 for 3 min, 95% for 3 min, 75% for 3 min, 50% for 3 min). The sections remained in running water for 5 min to remove excess ethanol. Then, sections were immersed in hematoxylin for 20 sec and washed with 1-2 immersions in clean water. Sections were subsequently incubated in eosin for 45 sec and washed again in clean water. Then, sections were incubated in increasing concentrations of ethanol (80% for 30 sec, 90% for 30 sec and 100% for 2 min), followed by incubation in xylene for 9 min. Subsequently, sections were mounted with DPX mounting medium and placed under a coverslip.

Results and Discussion

FIGS. 21 and 22 show that in the DSS-induced mouse model of inflammatory bowel disease, treatment with sNAG nanofibers resulted in: significant reduction in the inflammatory reaction (as judged by published histological criteria) compared to the control mice; and protective effects in the subacute phase of DSS-colitis, acting in concert with repair mechanisms to support tissue remodeling including the intestinal epithelium.

Specifically, FIG. 21 shows improved histological findings related to the inflammatory process in the mice administered sNAG nanofibers but not in control mice. In particular, sNAG-treated group mice but not control mice displayed decreased edema (see FIGS. 21A and 21B; the area of edema is indicated by a thin arrow and a bracket), and reduced leukocytic infiltration (see FIGS. 21A and 21B; the leukocytic infiltration is indicated by a thick arrow).

FIG. 22 shows staining for fibrosis in sections from mice treated with sNAG nanofibers and from control mice. The differences in the inflammatory response between sNAG-treated mice and control mice are evident. In particular, the control group shows signs of increased fibrosis (see FIG. 22A), whereas sNAG-treated group does not (see FIG. 22B).

The presented data show that sNAG nanofibers are effective to treat and/or prevent inflammation associated with inflammatory bowel disease in an animal model of the disease. These findings demonstrate the potential therapeutic application of sNAG nanofibers in the treatment of IBD patients. In addition, advantageously, sNAG nanofibers can be applied locally by topical application (such as rectally via a suppository), and thus avoid systemic side-effects (common to systemically-administered drugs).

7. INCORPORATION BY REFERENCE

The disclosures of all references such as publications, patents and patent applications cited in this specification are hereby incorporated by reference herein in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating atopic dermatitis in a human subject, comprising topically administering a composition comprising shortened poly-N-acetylglucosamine fibers ("sNAG nanofibers") to the skin of a human subject in need thereof, wherein the sNAG nanofibers comprise 70%, or more than 70%, of N-acetylglucosamine monosaccharides, wherein more than 50% of the sNAG nanofibers are between 1 to 15 μm in length, and wherein the sNAG nanofibers are the only active ingredient in the composition.

2. The method of claim 1, wherein the human subject is a human infant, human toddler, or elderly human.

3. The method of claim 1, wherein the sNAG nanofibers comprise more than 90% of N-acetylglucosamine monosaccharides.

4. The method of claim 1, wherein the sNAG nanofibers were produced by irradiation of poly-N-acetylglucosamine fibers comprising N-acetylglucosamine monosaccharides, and wherein (i) the poly-N-acetylglucosamine was irradiated in the form of dry fibers at the dose of irradiation of 500-2,000 kgy, or (ii) the poly-N-acetylglucosamine was irradiated in the form of wet fibers at the dose of irradiation of 100-500 kgy.

5. The method of claim 1, wherein the sNAG nanofibers were produced from a microalgal poly-N-acetylglucosamine.

6. The method of claim 1, wherein the infrared spectrum ("IR") of the sNAG nanofibers is about the same as or equivalent to that of non-irradiated microalgal poly-N-acetylglucosamine.

7. A method for reducing the severity or duration of one or more symptoms associated with atopic dermatitis in a human subject, comprising topically administering a composition comprising shortened poly-N-acetylglucosamine fibers ("sNAG nanofibers") to the skin of a human subject in need thereof, wherein the sNAG nanofibers comprise 70%, or more than 70%, of N-acetylglucosamine monosaccharides, wherein more than 50% of the sNAG nanofibers are between 1 to 15 μm in length, and wherein the sNAG nanofibers are the only active ingredient in the composition.

8. The method of claim 7, wherein the human subject is a human infant, human toddler, or elderly human.

9. The method of claim 7, wherein one or more of the symptoms associated with atopic dermatitis is dry, itchy, or red skin.

10. The method of claim 7, wherein the sNAG nanofibers comprise more than 90% of N-acetylglucosamine monosaccharides.

11. The method of claim 7, wherein the sNAG nanofibers were produced by irradiation of poly-N-acetylglucosamine fibers comprising N-acetylglucosamine monosaccharides, and wherein (i) the poly-N-acetylglucosamine was irradiated in the form of dry fibers at the dose of irradiation of 500-2,000 kgy, or (ii) the poly-N-acetylglucosamine was irradiated in the form of wet fibers at the dose of irradiation of 100-500 kgy.

12. The method of claim 7, wherein the sNAG nanofibers were produced from a microalgal poly-N-acetylglucosamine.

13. The method of claim 7, wherein the infrared spectrum ("IR") of the sNAG nanofibers is about the same as or equivalent to that of non-irradiated microalgal poly-N-acetylglucosamine.

14. A method for treating inflammatory bowel disease in a human subject, comprising topically administering a composition comprising shortened poly-N-acetylglucosamine fibers ("sNAG nanofibers") to a human subject in need thereof, wherein the sNAG nanofibers comprise 70%, or more than 70%, of N-acetylglucosamine monosaccharides, wherein more than 50% of the sNAG nanofibers are between 1 to 15 μm in length, and wherein the sNAG nanofibers are the only active ingredient in the composition.

15. The method of claim 14, wherein the inflammatory bowel disease is ulcerative colitis.

16. The method claim 14, wherein the amount of the sNAG nanofibers is effective to achieve one or more of the following: (i) reduce the severity of the inflammatory bowel disease or one or more symptoms thereof, (ii) reduce the duration of the inflammatory bowel disease or one or more symptoms thereof, (iii) reduce the number of symptoms associated with the inflammatory bowel disease.

17. The method of claim 14, wherein the composition comprising sNAG nanofibers is administered to the anus of the subject or rectally.

18. The method of claim 14, wherein the sNAG nanofibers comprise more than 90% of N-acetylglucosamine monosaccharides.

19. The method of claim 14, wherein the sNAG nanofibers were produced by irradiation of poly-N-acetylglucosamine fibers comprising N-acetylglucosamine monosaccharides, and wherein (i) the poly-N-acetylglucosamine was irradiated in the form of dry fibers at the dose of irradiation of 500-2,000 kgy, or (ii) the poly-N-acetylglucosamine was irradiated in the form of wet fibers at the dose of irradiation of 100-500 kgy.

20. The method of claim 14, wherein the sNAG nanofibers were produced from a microalgal poly-N-acetylglucosamine.

21. The method of claim 14, wherein the infrared spectrum ("IR") of the sNAG nanofibers is about the same as or equivalent to that of non-irradiated microalgal poly-N-acetylglucosamine.

22. The method of claim 1, wherein more than 95% of the sNAG nanofibers are between 1 to 15 μm in length.

23. The method of claim 7, wherein more than 95% of the sNAG nanofibers are between 1 to 15 μm in length.

24. The method of claim 14, wherein more than 95% of the sNAG nanofibers are between 1 to 15 μm in length.

25. The method of claim 1, wherein the average length of the sNAG nanofibers is from about 4 to 7 μm.

26. The method of claim 7, wherein the average length of the sNAG nanofibers is from about 4 to 7 μm.

27. The method of claim 14, wherein the average length of the sNAG nanofibers is from about 4 to 7 μm.

28. The method of claim 1, wherein more than 50% of the sNAG nanofibers are between about 1 to less than 10 μm in length.

29. The method of claim 7, wherein more than 50% of the sNAG nanofibers are between about 1 to less than 10 μm in length.

30. The method of claim 14, wherein more than 50% of the sNAG nanofibers are between about 1 to less than 10 μm in length.

31. The method of claim 1, wherein the length of the fibers is determined by scanning electron microscopic (SEM) analysis.

32. The method of claim 7, wherein the length of the fibers is determined by scanning electron microscopic (SEM) analysis.

33. The method of claim 14, wherein the length of the fibers is determined by scanning electron microscopic (SEM) analysis.

34. The method of claim 1, wherein the poly-N-acetylglucosamine has a (β-1→4) configuration.

35. The method of claim 7, wherein the poly-N-acetylglucosamine has a (β-1→4) configuration.

36. The method of claim 14, wherein the poly-N-acetylglucosamine has a (β-1→4) configuration.

37. The method of claim 14, wherein the inflammatory bowel disease is Crohn's disease.

* * * * *

UNITED STATES PATENT AND TRADEMARK OFFICE
CERTIFICATE OF CORRECTION

PATENT NO. : 10,765,698 B2
APPLICATION NO. : 15/457576
DATED : September 8, 2020
INVENTOR(S) : John N. Vournakis and Sergio Finkielsztein It is certified that error appears in the above-identified patent and that said Letters Patent is hereby corrected as shown below:

In the Claims

In Column 99, Claim 1, Line 47, insert -- ; and wherein the composition is not administered to treat an open wound -- after "composition."

In Column 100, Claim 7, Line 47, insert -- ; and wherein the composition is not administered to treat an open wound -- after "composition."

In Column 102, Claim 34, Line 33, remove -- ( -- after "a"

In Column 102, Claim 35, Line 35, remove -- ( -- after "a"

In Column 102, Claim 36, Line 37, remove -- ( -- after "a"

Signed and Sealed this
Twenty-ninth Day of December, 2020

Andrei Iancu
*Director of the United States Patent and Trademark Office*